(12) United States Patent
Chen et al.

(10) Patent No.: US 9,884,919 B2
(45) Date of Patent: Feb. 6, 2018

(54) METHODS OF TREATMENT WITH BISPECIFIC ANTIBODIES BINDING TO BETA-KLOTHO AND FIBROBLAST GROWTH FACTOR RECEPTOR 1

(71) Applicant: GENENTECH, INC., South San Francisco, CA (US)

(72) Inventors: Yongmei Chen, South San Francisco, CA (US); James Ernst, South San Francisco, CA (US); Hok Seon Kim, South San Francisco, CA (US); Junichiro Sonoda, South San Francisco, CA (US); Christoph Spiess, South San Francisco, CA (US); Scott Stawicki, South San Francisco, CA (US); Yan Wu, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/214,160

(22) Filed: Jul. 19, 2016

(65) Prior Publication Data

US 2016/0319038 A1 Nov. 3, 2016

Related U.S. Application Data

(62) Division of application No. 14/582,100, filed on Dec. 23, 2014.

(60) Provisional application No. 61/920,396, filed on Dec. 23, 2013, provisional application No. 62/081,435, filed on Nov. 18, 2014.

(51) Int. Cl.
*A61K 39/395* (2006.01)
*C07K 16/40* (2006.01)
*C07K 14/71* (2006.01)
*C07K 16/28* (2006.01)
*A61K 39/00* (2006.01)

(52) U.S. Cl.
CPC ............ *C07K 16/40* (2013.01); *C07K 14/71* (2013.01); *C07K 16/2863* (2013.01); *A61K 2039/505* (2013.01); *C07K 2317/24* (2013.01); *C07K 2317/31* (2013.01); *C07K 2317/33* (2013.01); *C07K 2317/34* (2013.01); *C07K 2317/40* (2013.01); *C07K 2317/41* (2013.01); *C07K 2317/524* (2013.01); *C07K 2317/56* (2013.01); *C07K 2317/565* (2013.01); *C07K 2317/567* (2013.01); *C07K 2317/71* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,474,893 A | 10/1984 | Reading |
| 4,676,980 A | 6/1987 | Segal et al. |
| 4,881,175 A | 11/1989 | Ladner |
| 5,013,653 A | 5/1991 | Huston et al. |
| 5,091,513 A | 2/1992 | Huston et al. |
| 5,132,405 A | 7/1992 | Huston et al. |
| 5,258,498 A | 11/1993 | Huston et al. |
| 5,260,203 A | 11/1993 | Ladner et al. |
| 5,455,030 A | 10/1995 | Ladner et al. |
| 5,476,786 A | 12/1995 | Huston |
| 5,482,858 A | 1/1996 | Huston et al. |
| 5,731,168 A | 3/1998 | Carter et al. |
| 5,837,243 A | 11/1998 | Deo et al. |
| 5,922,845 A | 7/1999 | Deo et al. |
| 6,579,850 B1 | 6/2003 | Nabeshima et al. |
| 7,531,304 B2 | 5/2009 | Bange et al. |
| 7,537,903 B2 | 5/2009 | Kuro-o et al. |
| 8,293,241 B2 | 10/2012 | Desnoyers et al. |
| 8,372,952 B2 | 2/2013 | Smith et al. |
| 2003/0119910 A1 | 6/2003 | Kamiya et al. |
| 2006/0025576 A1 | 2/2006 | Miller et al. |
| 2007/0248604 A1 | 10/2007 | Desnoyers et al. |
| 2007/0293430 A1 | 12/2007 | Frye et al. |
| 2007/0299007 A1 | 12/2007 | Frye et al. |
| 2009/0098603 A1 | 4/2009 | Botstein et al. |
| 2010/0158914 A1 | 6/2010 | Desnoyers |
| 2010/0184665 A1 | 7/2010 | Suzuki et al. |
| 2012/0059047 A1 | 3/2012 | Prins et al. |
| 2012/0121609 A1 | 5/2012 | Sun et al. |
| 2012/0294861 A1 | 11/2012 | Sonoda et al. |
| 2014/0363435 A1 | 12/2014 | Desnoyers |
| 2015/0132309 A1 | 5/2015 | Desnoyers |

FOREIGN PATENT DOCUMENTS

| | | |
|---|---|---|
| JP | 2001-72607 | 3/2001 |
| JP | 2003-334088 | 11/2003 |
| JP | 2006-158339 | 6/2006 |
| KR | 2003-0031998 A | 4/2003 |
| WO | WO 93/08829 | 5/1993 |

(Continued)

OTHER PUBLICATIONS

U.S. Appl. No. 14/670,358, filed Mar. 26, 2015, Genentech, Inc.
Arrese et al., "βKlotho: A New Kid on the Bile Acid Biosynthesis Block," Hepatology, 43(1):191-3 (Jan. 2006).
Ashida et al., "AP-1 and colorectal cancer," Inflammopharmacology 13(1-3):113-25 (2005).
Atwell et al., "Stable Heterodimers From Remodeling the Domain Interface of a Homodimer Using a Phage Display Library," J. Mol. Bio. 270(1): 26-35 (1997).
Berglund et al., "Fibroblast growth factor 21 controls gylcemia via regulation of hepatic glucose flux and insulin sensitivity," Endocrinology 150(9):4084-4093 ( 2009).

(Continued)

*Primary Examiner* — Chritine J Saoud
(74) *Attorney, Agent, or Firm* — Baker Botts L.L.P.

(57) ABSTRACT

The presently disclosed subject matter provides antibodies that bind KLB and FGFR1, and methods of using the same. In certain embodiments, an antibody of the present disclosure includes a bispecific antibody that binds to an epitope present on FGFR1 and binds to an epitope present on KLB.

16 Claims, 43 Drawing Sheets

(56) References Cited

FOREIGN PATENT DOCUMENTS

| WO | WO 99/027100 | 6/1999 |
|---|---|---|
| WO | WO 01/04160 | 1/2001 |
| WO | WO 01/18210 A1 | 3/2001 |
| WO | WO 01/20031 | 3/2001 |
| WO | WO 02/18608 A2 | 3/2002 |
| WO | WO 2005/037235 | 4/2005 |
| WO | WO 2005/066211 A2 | 7/2005 |
| WO | WO 2007/136893 A2 | 11/2007 |
| WO | WO 2009/009173 | 1/2009 |
| WO | WO 2009/035786 A1 | 3/2009 |
| WO | WO 2009/089004 A1 | 7/2009 |
| WO | WO 2010/042747 | 4/2010 |
| WO | WO 2011/071783 | 6/2011 |
| WO | WO 2011/130417 | 10/2011 |
| WO | WO 2012/158704 | 11/2012 |

OTHER PUBLICATIONS

Bowie et al., "Deciphering the message in protein sequences: tolerance to amino acid substitutions," Science 247:1306-1310 (1990).
Brennan et al., "Preparation of bispecific antibodies by chemical recombination of monoclonal immunoglobulin G1 fragments," Science, 229: 81 (1985).
Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol. 111:2129-2138, 1990.
Cappellen et al., "Frequent activating mutations of FGFR3 in human bladder and cervix carcinomas," Nat Genet. 23(1):18-20 (Sep. 1999).
Chan et al., "Therapeutic antibodies for autoimmunity and inflammation," Nature Reviews. Immunology 10, 301-316 (2010).
Chau et al., "Fibroblast growth factor 21 regulates energy metabolism by activating the AMPK-SIRT1-PGC-1δ pathway," PNAS 107(28):12553-12558 (2010).
Chiang, "Regulation of bile acid synthesis: pathways, nuclear receptors, and mechanisms," J Hepatol 40(3):539-51 (Mar. 2004).
Choi et al., "Identification of a hormonal basis for gallbladder filling," Nat Med. 12(11):1253-5 (Nov. 2006).
Coskun et al., "Fibroblast growth factor 21 corrects obesity in mice," Endocrinology 149, 6018-6027 (2008).
Desnoyers et al., "Targeting FGF19 inhibits tumor growth in colon cancer xenograft and FGF19 transgenic hepatocellular carcinoma models," Oncogene 27(1):85-97 (Jan. 2008).
Drueke et al., "Klotho spins the thread of life—what does Klotho do to the receptors of fibroblast growth factor-23 (FGF23)?," Nephrol Dialysis Transplantation 22(6):1524-6 (Jun. 2007).
Eswarakumar et al., "Cellular signaling by fibroblast growth factor receptors," Cytokine Growth Factor Rev. 16(2):139-149 (Apr. 2005).
Fisher et al., "FGF21 regulates PGC-1α and browning of white adipose tissues in adaptive thermogenesis," Genes & Development 26, 271-281 (2012).
Foltz et al., "Treating Diabetes and Obesity with an FGF21-Mimetic Antibody Activating the βKlotho/FGFR1c Receptor Complex," Sci. Transl. Med. 4:162ra153 (2012).
Fon Tacer et al., "Research resource: Comprehensive expression atlas of the fibroblast growth factor system in adult mouse," Mol. Endocrinol 24(10):2050-2064 (2010).
French et al., "Targeting FGFR4 inhibits hepatocellular carcinoma in preclinical mouse models," PLoS One 7, e36713 (2012).
Fu L. et al., "Fibroblast growth factor 19 increases metabolic rate and reverses dietary and leptin-deficient diabetes," Endocrinology 145, 2594-2603 (2004).
Fujimori, T. et al., "New polynucleotide with cholesterol metabolism promoter activity for inhibiting expression of beta klotho gene, enhancing cholesterol 7 alpha hydroxylase expression, and promoting bile acid synthesis (Univ. Kyoto)," Database WPI Section Ch, Thomson Scientific (Jun. 22, 2006).
Goetz et al., "Exploring mechanisms of FGF signalling through the lens of structural biology," Nature Reviews, Molecular Cell Biology vol. 14, No. 3, 166-180 (2013).
Goetz et al., "Klotho coreceptors inhibit signaling by paracrine fibroblast growth factor 8 subfamily ligands," Molecular Cell Biology 32(10): 1944-54 (2012).
Goetz et al., "Molecular insights into the klotho-dependent, endocrine mode of action of fibroblast growth factor 19 subfamily members," Molecular Cell Biol. 27(9):3417-28 (May 2007).
Gowardhan et al., "Evaluation of the fibroblast growth factor system as a potential target for therapy in human prostate cancer," British J Cancer 92(2):320-7 (Jan. 2005).
Gruber et al., "Efficient Tumor Cell Lysis Mediated by a Bispecific Single Chain Antibody Expressed in *Escherichia coli*," J. Immunol., 152:5368 (1994).
Gutierrez et al., "Bile acids decrease hepatic paraoxonase 1 expression and plasma high-density lipoprotein levels via FXR-mediated signaling of FGFR4," Arterioscler Thromb Vasc Biol. 26(2):301-306 (Feb. 2006).
Harmer et al., "The Crystal Structure of Fibroblast Growth Factor (FGF) 19 Reveals Novel Features of the FGF Family and Offers a Structural Basis for its Unusual Receptor Affinity," Biochemistry 43(3):629-640 (Jan. 27, 2004).
Hart et al., "Attenuation of FGF signaling in mouse β-cells lead to diabetes," Nature 408:864 (2000).
Hess et al., "AP-1 subunits: quarrel and harmony among siblings," J Cell Sci. 117(Pt 25):5965-73 (Dec. 2004).
Holland et al., "An FGF21-Adiponectin-Ceramide Axis Controls Energy Expenditure and Insulin Action in Mice," Cell Metab. 17, 790-797 (2013).
Hollinger et al., "Diabodies: Small Bivalent and Bispecific Antibody Fragments," Proc. Natl. Acad. Sci. USA, 90:6444-6448 (1993).
Holt et al., "Definition of a novel growth factor-dependent signal cascade for the suppression of bile acid biosynthesis," Genes Dev. 17(13):1581-1591 (Jul. 1, 2003).
Hondares et al., "Hepatic FGF21 Expression is Induced at Birth via PPARα in Response to Milk Intake and Contributes to Thermogenic Activation of Neonatal Brown Fat," Cell Metabolism, 11:206-212 (2010).
Inagaki et al., "Fibroblast growth factor 15 functions as an enterohepatic signal to regulate bile acid homeostasis," Cell Metabolism, 24(4):217-25 (Oct. 2005).
Inagaki et al., "Inhibition of growth hormone signaling by the fasting-induced hormone FGF21," Cell Metabolism, 8:77-83 (2008).
International Search Report dated Apr. 10, 2015 in International Application No. PCT/US14/072245.
Ito et al., "Impaired negative feedback suppression of bile acid synthesis in mice lacking βKlotho," J. Clin Invest., 115(8):2202-8 (Aug. 2005).
Ito et al., "Molecular cloning and expression analyses of mouse βklotho, which encodes a novel Klotho family protein," Mech Dev., 98(1-2):115-9 (Nov. 2000).
Jaakkola et al., "Amplification of fgfr4 gene in human breast and gynecological cancers," Int. J. Cancer, 54(3):378-382 (May 28, 1993).
Jang et al., "Mutations in fibroblast growth factor receptor 2 and fibroblast growth factor receptor 3 genes associated with human gastric and colorectal cancers," Cancer Res 61(9):3541-3 (May 2001).
Jeffers et al., "Fibroblast growth factors in cancer: therapeutic possibilities," Expert Opin. Ther. Targets, 6(4):469-482 (Aug. 2002).
Jelinek et al., "Cloning and regulation of cholesterol 7 alpha-hydroxylase, the rate-limiting enzyme in bile acid biosynthesis," J Biol Chem., 266(14):8190-7 (May 1990).
Jones et al., "Mini-review: endocrine actions of fibroblast growth factor 19," Mol Pharm., 5(1):42-8 (Jan.-Feb. 2008).
Kato et al., "Establishment of the anti-Klotho monoclonal antibodies and detection of Klotho protein in kidneys," Biochemical and

(56) References Cited

OTHER PUBLICATIONS

Biophysical Research Communications, Academic Press Inc. Orlando, FL, US, vol. 267, No. 2, Jan. 19, 2000, pp. 597-602.

Keler et al., "Bispecific antibody-dependent cellular cytotoxicity of HER2/neu-overexpressing tumor cells by Fcγ receptor type I—expressing effector cells," Cancer Res., 57:4008-4014 (1997).

Kharitonenkov et al., "FGF-21 as a novel metabolic regulator," J. Clin. Invest., 115(6): 1627-35 (2005).

Kharitonenkov et al., "FGF21 reloaded: challenges of a rapidly growing field," Trends in Endocrinology and Metabolism, 22(3):81 (2011).

Kharitonenkov et al., "FGF-21/FGF-21 receptor interaction and activation is determined by betaKlotho," J Cell Physiol., 215(1):1-7 (Apr. 2008).

Kostelny et al., "Formation of a Bispecific Antibody by the Use of Leucine Zippers," J. Immunol., 148(5):1547-1553 (1992).

Kranz, "Restricted reassociation of heavy and light chains from hapten-specific monoclonal antibodies," Proc. Natl. Acad. Sci. USA 78:5807 (1981).

Kuro-o, "Klotho as a regulator of fibroblast growth factor signaling and phosphate/calcium metabolism," Current Opinion in Nephrology and Hypertension, 15(4):437-41 (Jul. 2006).

Kurosu et al., "Regulation of fibroblast growth factor-23 signaling by klotho," J Biol Chem. 281(10):6120-3 (Mar. 2006).

Kurosu et al., "The Klotho gene family as a regulator of endocrine fibroblast growth factors," Mol Cell Endocrinol. 299(1):72-8 (Feb. 2009).

Kurosu et al., "Tissue-specific expression of βKlotho and fibroblast growth factor (FGF) receptor isoforms determines metabolic activity of FGF19 and FGF21," J Biol Chem 282(37):26687-95 (Sep. 2007).

Lazar et al. "Transforming Growth Factor ox: Mutation of Aspartic Acid 47 and Leucine 48 Results in Different Biological Activities," Mol. Cell. Biol., 8:1247-1252, 1988.

Li et al., "Inhibition of lipolysis may contribute to the acute regulation of plasma FFA and glucose by FGF21 in ob/ob mice" FEBS Letters 583:3230-3234 (2009).

Li et al., "Regulation of cholesterol 7 alpha-hydroxylase in the liver. Cloning, sequencing, and regulation of cholesterol 7 alpha-hydroxylase mRNA," J Biol Chem. 265(20):12012-9 (Jul. 1990).

Lin et al. Endocrine FGFs and Klothos, Chapter 12 "FGF19 and Cancer" Makoto Kuro-o, Landes Bioscience and Springer Science+Business Media:183 (2012).

Lin et al., "Adiponectin Mediates the Metabolic Effects of FGF21 on Glucose Homeostasis and Insulin Sensitivity in Mice," Cell Metab. 17(5), 779-789 (2013).

Lin et al., "Liver-specific activities of FGF19 require Klotho beta," J Biol Chem. 282(37):27277-84 (Sep. 2007).

Lundasen et al., "Circulating intestinal fibroblast growth factor 19 has a pronounced diurnal variation and modulates hepatic bile acid synthesis in man," J Intern Med. 260(6):530-6 (Dec. 2006).

Luo et al., "Metabolic Regulator beta Klotho Interact with Fibroblast Growth Factor Receptor 4 (FGFR) to Induce Apoptosis and Inhibit Tumor Cell Proliferation," J. Biol Chem 285(39):30069-30078 (2010).

Manetti et al., "Small-molecule inhibitors of fibroblast growth factor receptor (FGFR) tyrosine kinases (TK)," Curr Pharm Des. 9(7):567-81 (2003).

Marsh et al., "Increased expression of fibroblast growth factor 8 in human breast cancer," Oncogene 18(4):1053-60 (Jan. 1999).

Mattila et al., "FGF-8b increases angiogenic capacity and tumor growth of androgen regulated S115 breast cancer cells," Oncogene 20(22):2791-804 (May 17, 2001).

Mikula et al., "The proto-oncoprotein c-Fos negatively regulates hepatocellular turmorigenesis," Oncogene 22:6725-6738 (2003).

Milstein et al., "Hybrid hybridomas and their use in immunohistochemistry," Nature 305:537 (1983).

Morimoto et al., "Single nucleotide polymorphism in fibroblast growth factor receptor 4 at codon 388 is associated with prognosis in high-grade soft tissue sarcoma," Cancer 98(10):2245-50 (2003).

Moschetta and Kliewer, "Weaving betaKlotho into bile acid metabolism," J Clin Invest. 115(8):2075-7 (Aug. 2005).

Nicholes et al., "Animal Model: A mouse model of hepatocellular carcinoma, ectopic expression of fibroblast growth factor 19 in skeletal muscle of transgenic mice," American Journal of Pathology 160(6):2295-2307 (Jun. 2002).

Ogawa Y. et al., "BetaKlotho is required for metabolic activity of fibroblast growth factor 21," Proc. Natl. Acad. Sci. USA 104(18): 7432-37 (2007).

Ornitz et al., "Fibroblast growth factors," Genome Biol (Reviews3005), 2(3):1-12 (2001).

Pai et al., "Inhibition of fibroblast growth factor 19 reduces tumor growth by modulating beta-catenin signaling," Cancer Research 68(13):5086-95 (Jul. 2008).

Plotnikov et al., "Structural basis for FGF receptor dimerization and activation," Cell 98(5): 641-50 (1999).

Poh et al., "Klotho-beta overexpression as a novel target for suppressing proliferation and fibroblast growth factor receptor-4 signaling in hepatocellular carcinoma," Molecular Cancer 11(14):1-10 (2012).

Potthoff et al., "FGF21 induces PGC-1α and regulates carbohydrate and fatty acid metabolism during the adaptive starvation response," PNAS 106(26):10853-10858 (2009).

Powers et al., "Fibroblast growth factors, their receptors and signaling," Endocr Relat Cancer, 7(3):165-97 (Sep. 2000).

Qian et al., "Cytoplasmic expression of fibroblast growth factor receptor-4 in human pituitary adenomas: relation to tumor type, size, proliferation, and invasiveness," J Clin Endocrinol Metab. 89(4):1904-1911 (Apr. 2004).

Ruohola et al., "Enhanced invasion and tumor growth of fibroblast growth factor 8b-overexpressing MCF-7 human breast cancer cells," Cancer Research 61(10):4229-37 (May 2001).

Russell, "The enzymes, regulation, and genetics of bile acid synthesis," Annu Rev Biochem 72:137-74 (2003).

Saito et al., "In Vivo klotho Gene Delivery Protects Against Endothelial Dysfunction in Multiple Risk Factor Syndrome," Biochemical and Biophysical Research Communications 276:767-772 (2000).

Schlessinger et al., "Crystal structure of a ternary FGF-FGFR-heparin complex reveals a dual role for heparin in FGFR binding and dimerization," Mol Cell. 6(3):743-50 (Sep. 2000).

Schlessinger, "Common and distinct elements in cellular signaling via EGF and FGF receptors," Science 306(5701):1506-1507 (Nov. 26, 2004).

Shaulian et al., "AP-1 as a regulator of cell life and death," Nat Cell Biol. 4(5):E131-6 (May 2002).

Shimokawa et al., "Involvement of the FGF18 gene in colorectal carcinogenesis, as a novel downstream target of the beta-catenin/T-cell factor complex," Cancer Research 63(19):6116-20 (Oct. 2003).

Sleeman et al., "Identification of a new fibroblast growth factor receptor, FGFR5," Gene 271:171-82 (2001).

Smith et al., "FGF21 Can Be Mimicked In Vitro and In Vivo by a Novel Anti-FGFR1c/[beta]—Klotho Bispecific Protein," PLOS One, vol. 8, No. 4, Apr. 22, 2013, p. e61432.

Somasundaram et al., "Development of a trispecific antibody conjugate that directs two distinct tumor-associated antigens to CD64 on myeloid effector cells," Hum. Antibodies 9(1):47-54 (1999).

Spinola et al., "Functional FGFR4 Gly388Arg polymorphism predicts prognosis in lung adenocarcinoma patients," J Clin Oncol. 23(29):7307-7311 (Oct. 10, 2005).

Streit et al., "Involvement of the FGFR4 Arg388 allele in head and neck squamous cell carcinoma," Int J Cancer 111(2):213-217 (Aug. 20, 2004).

Sugiyama et al., "Fibroblast growth factor receptor 4 regulates tumor invasion by coupling fibroblast growth factor signaling to extracellular matrix degradation," Cancer Research 70(20):7851-7861 (2010).

Sun et al., "Monoclonal antibody antagonists of hypothalamic FGFR1 cause potent but reversible hypophagia and weigh loss in rodents and monkeys," Am. J. Physiol. Endocrinol. Metab. 292:E964-E976 (2007).

(56) References Cited

OTHER PUBLICATIONS

Suzuki et al., "βKlotho is required for fibroblast growth factor (FGF) 21 signaling through FGF receptor (FGFR) 1c and FGFR3c," Mol Endocrinol. 22(4):1006-14 (Apr. 2008).
Tohyama et al., "Klotho is a novel β-glucuronidase capable of hydrolyzing steroid β-glucuronides," J Biol Chem. 279(11):9777-84 (Mar. 2004).
Tomiyama et al., "Relevant use of Klotho in FGF19 subfamily signaling system in vivo," Proc Natl Acad Sci U S A. 107(4):1666-71 (Jan. 2010).
Tomlinson et al., "Transgenic mice expressing human fibroblast growth factor-19 display increased metabolic rate and decreased adiposity," Endocrinology 143, 1741-1747 (2002).
Traunecker et al., "Bispecific single chain molecules (Janusins) target cytotoxic lymphocytes on HIV infected cells," EMBO J. 10:3655 (1991).
Trauner and Boyer, "Cholestatic syndromes," Curr Opin Gastroenterol. 20(3):220-30 (May 2004).
Triantis et al., "Glycosylation of Fibroblast Growth Factor Receptor 4 is a Key Regulator of Fibroblast Growth Factor 19-Mediated Down-Regulation of Cytochrome P450 7A1," Hepatology 52(2):656-666 (2010).
Tutt et al., "Trispecific F(ab')3 Derivatives that Use Cooperative Signaling via the TCR/CD3 Complex and CD2 to Activate and Redirect Resting Cytotoxic T Cells," J. Immunol. 147:60 (1991).
Urakawa et al., "Klotho converts canonical FGF receptor into a specific receptor for FGF23," Nature 444(7120):770-4 (Dec. 2006).
Wang et al., "Fibroblast growth factor receptors have different signaling and mitogenic potentials," Molecular & Cellular Biology 14(1):181-188 (Jan. 1994).
Wente et al., "Fibroblast growth factor-21 improves pancreatic β-Cell function and survival by activation of extracellular signal-regulated kinase 1/2 and Akt signaling pathways," Diabetes 55:2470 (2006).
Winer et al., "Development and validation of real-time quantitative reverse transcriptase-polymerase chain reaction for monitoring gene expression in cardiac myocytes in vitro," Analytical Biochem 270(1):41-9 (May 1999).
Wu et al., "Amelioration of Type 2 Diabetes by Antibody-Mediated Activation of Fibroblast Growth Factor Receptor 1," Science Translational Med. 3(113): 1-10 (2011).
Wu et al., "Antibody-Mediated Activation of FGFR1 Induces FGF23 Production and Hypophosphatemia," PLoS One 8, e57322 (2013).
Wu et al., "FGF19-induced Hepatocyte Proliferation is Mediated Through FGFR4 Activation," Journal of Biological Chemistry 285(8):5165-5170 (Feb. 2010).
Wu X. et al., "Co-receptor requirements for fibroblast growth factor-19 signaling," J. Biol. Chem, 282(40): 29069-29072 (2007).
Xiao, "Klotho is a serum factor related to human aging," Chinese Medical Journal, vol. 117, No. 5, Jan. 1, 2004, pp. 742-747.
Xie et al., "FGF-19, a novel fibroblast growth factor with unique specificity for FGFR4," Cytokine 11(10):729-735 (Oct. 1999).
Xu et al., "Acute glucose-lowering and insulin-sensitizing action of FGF21 in insulin-resistant mouse models—association with liver and adipose tissue effects," American Journal of Physiology—Endocrinology and Metabolism 297:E1105-E1114 (2009).
Xu et al., "Fibroblast growth factor 21 reverses hepatic steatosis, increases energy expenditure, and improves insulin sensitivity in diet-induced obese mice," Diabetes 58:250 (2009).
Yahata et al., "'Molecular cloning and expression of a novel klotho-related protein'," J. Mol. Med. 78:389-394 (2000).
Yamada et al., "Fibroblast growth factor receptor (FGFR) 4 correlated with the malignancy of human astrocytomas," Neurol Res. 24(3):244-248 (Apr. 2002).
Ye et al., "βKlotho Suppresses Tumor Growth in Hepatocellular Carcinoma by Regulating Akt/GSK-3β/Cyclin D1 Signaling Pathway," PLOS One 8(1):e55615 (Jan. 2013).
Yie et al., "FGF21 N- and C-termini play different roles in receptor interaction and activation," FEBS Lett. 583(1): 19-24 (2009).
Yie et al., "Understanding the Physical Interactions in the FGF21/FGFR/β-Klotho Complex: Structural Requirements and Implications in FGF21 Signaling," Chemical Biology Drug Design 79, 398-410 (2012).
Yu et al., "Boosting brain uptake of a therapeutic antibody by reducing its affinity for a transcytosis target," Sci. Transl. Med. 3, 84ra44 (2011).
Yu et al., "Elevated cholesterol metabolism and bile acid synthesis in mice lacking membrane tyrosine kinase receptor FGFR4", J Biol Chem. 275(20):15482-15489 (May 19, 2000).
Zeidler, "Simultaneous activation of T cells and accessory cells by a new class of intact bispecific antibody results in efficient tumour cell killing," J. Immunol. 163:1246-1252 (1999).
European Search Report dated Dec. 20, 2012 in EP Application No. 12179244.
International Preliminary Report on Patentability dated Oct. 6, 2009 in International Application No. PCT/US2008/059032.
International Search Report dated Aug. 24, 2009 in International Application No. PCT/US2008/059032.
Song, Mi-Kyung et al., "Light chain of natural antibody plays a dominant role in protein antigen binding", Biochem Bioph Res Co 268:390-394 (2000).
Thio et al., "Antigen Binding Characteristics of Immunoglobulin Free Light Chains: Crosslinking by Antigen is Essential to Induce Allergic Inflammation" PLos One 7(7):e40986 (2012).
Brown et al., "Tolerance of Single, but Not Multiple, Amino Acid Replacements in Antibody VH CDR 2: a Means of Minimizing B Cell Wastage from Somatic Hypermutation?" J Immunol 156:3285-3291 (1996).
Fisher et al., "Obesity Is a Fibroblast Growth Factor 21 (FGF21)-Resistant State," Diabetes 59:2781-2789 (2010).
Vajdos et al., "Comprehensive Functional Maps of the Antigen-binding Site of an Anti-ErbB2 Antibody Obtained with Shotgun Scanning Mutagenesis," J. Mol. Biol. 320:415-428 (2002).
Woo et al., "Fibroblast Growth Factor 21 as an emerging metabolic regulator: clinical perspectives," Clin Endocrinol 78:489-496 (2013).
U.S. Appl. No. 13/472,352 (now U.S. Pat. No. 9,085,626), filed May 15, 2012, (Jul. 21, 2015).
U.S. Appl. No. 14/302,895 (US 2014/0363435), filed Jun. 12, 2014, (Dec. 11, 2014).
U.S. Appl. No. 14/582,100 (US 2015/0218276), filed Dec. 23, 2014 (Aug. 6, 2015).
U.S. Appl. No. 14/754,229 (US 2015/0376283, filed Jun. 29, 2015 (Dec. 31, 2015).
U.S. Appl. No. 13/472,352, dated Jun. 12, 2015 Issue Fee Payment.

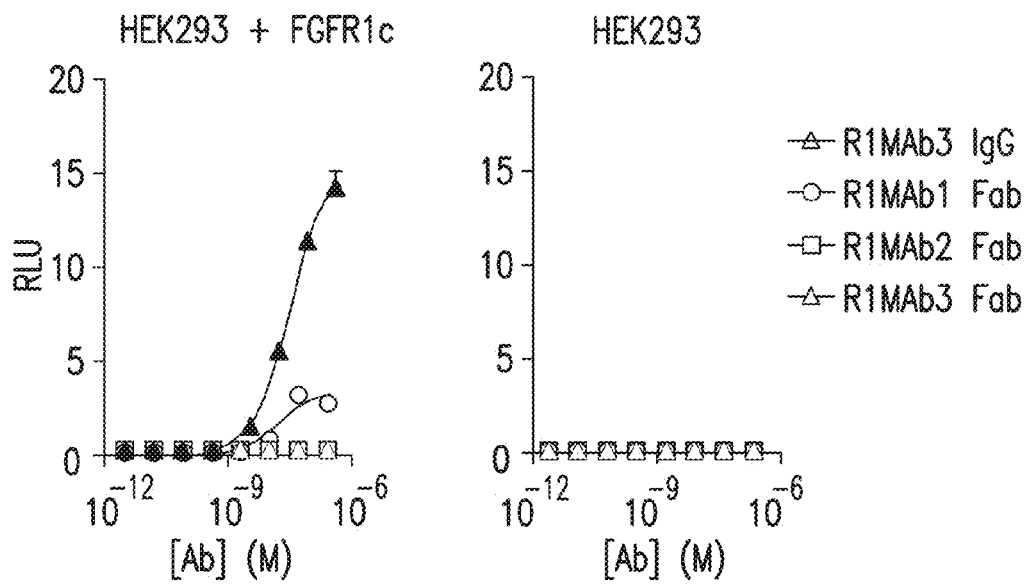
FIG. 1A
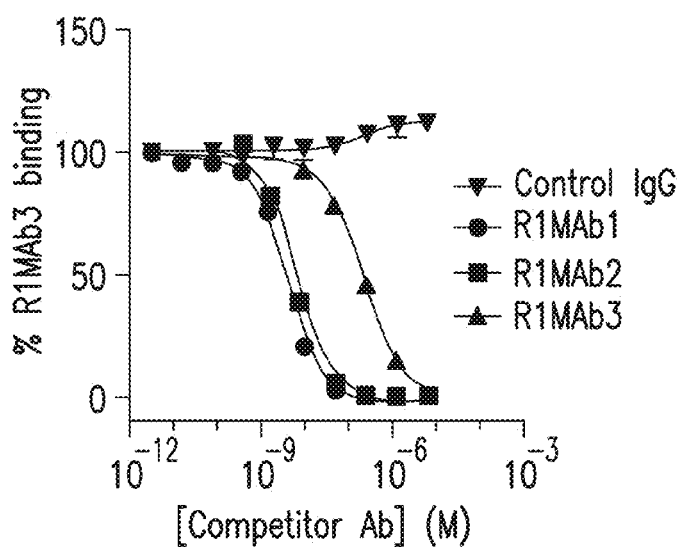
FIG. 1B
```
161       170       180       190       200       212
 |         |         |         |         |         |
...MEKKLHAVPAAKTVKFKCPSSGTPNPTLRWLKNGKEFKPDHRIGGYKVRYATW...
...MEKKLHAVPAAKTVKFKCPSSGTPNPTLRWLKNGKEFKPDHRIGGYKVRYATW...
   KLHAVPAAKTVKFKCP (P26)            FKPDHRIGGYKVRY(P28)
```
FIG. 1C

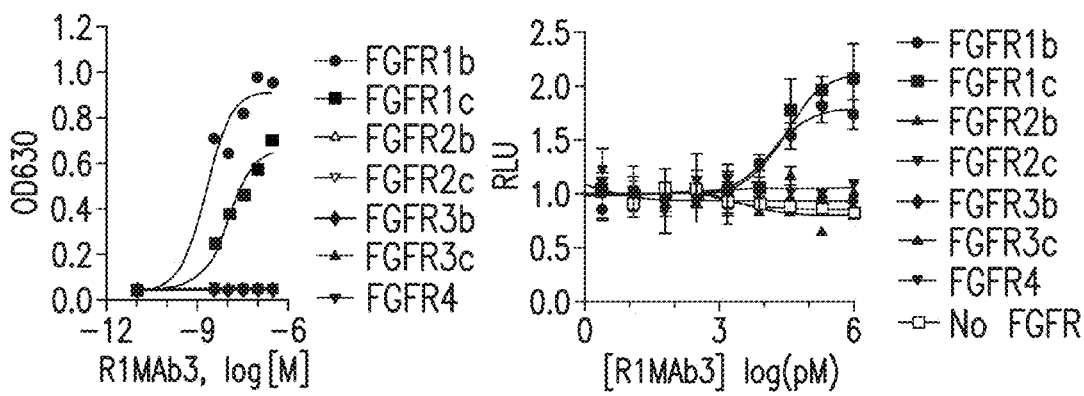
FIG. 2A
FIG. 2B
FIG. 2C
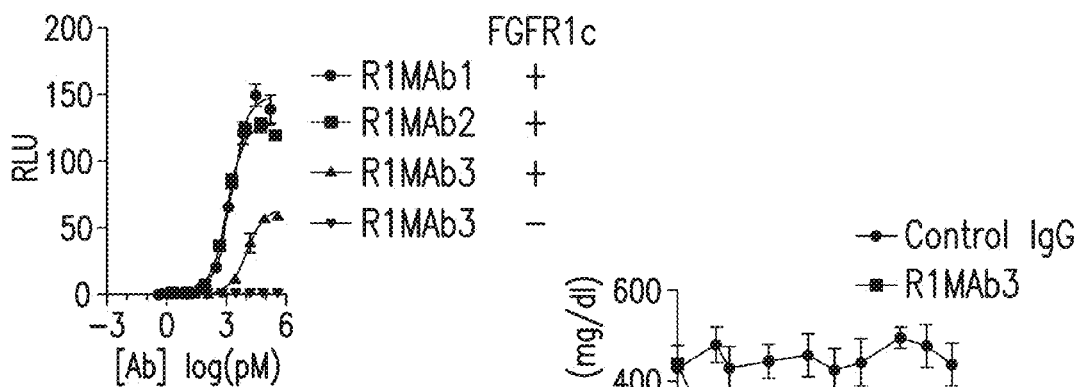
FIG. 2D
FIG. 2E

Heavy chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 11F1 | E | V | Q | L | V | E | S | G | G | G | L | V | K | P | G | G | S | L | K | L | S | C | A | A | S | G | F | T | F | S | S | Y | G | I | S | . | . | W | V | R | Q | A |
| 6012 | E | V | Q | L | V | E | S | G | G | E | L | V | R | P | G | A | L | V | R | L | S | C | T | V | S | G | F | S | L | K | D | Y | Y | M | N | . | . | W | V | R | Q | P |
| 11D4 | Q | V | Q | L | Q | Q | S | G | A | E | L | V | R | P | G | Q | S | L | K | L | T | C | T | A | S | G | F | N | I | K | N | Y | Y | V | S | . | . | W | I | R | Q | P |
| 8E1 | E | V | Q | L | V | E | S | G | G | E | L | V | K | P | G | A | S | V | K | L | S | C | T | A | S | G | F | N | I | . | S | Y | Y | I | H | . | . | W | V | K | Q | R |
| 46C3 | E | V | Q | L | V | E | S | G | A | E | L | V | K | P | G | A | S | V | R | L | S | C | T | A | S | G | Y | S | F | T | S | Y | W | I | T | . | . | W | V | K | Q | R |
| 8H7 | Q | V | Q | L | Q | Q | S | G | A | E | L | V | K | P | G | A | S | V | K | L | S | C | K | A | S | G | F | N | I | Q | S | Y | W | I | H | . | . | W | V | K | Q | R |
| 21H3 | E | V | Q | L | V | E | S | G | A | E | L | V | K | P | G | A | S | V | R | L | S | C | K | A | S | G | Y | T | F | T | S | Y | F | M | N | . | . | W | V | K | Q | R |
| 25F7 | E | V | Q | L | V | E | S | G | G | E | L | V | K | P | G | A | S | V | R | L | S | C | T | A | S | G | Y | T | F | T | E | Y | I | I | H | . | . | W | V | K | Q | R |
| 14E6 | Q | V | Q | L | Q | Q | S | G | A | E | L | V | R | P | G | A | S | V | K | L | S | C | K | A | S | G | Y | I | F | S | S | Y | W | M | N | . | . | W | V | K | Q | R |
| 14C6 | E | V | Q | L | V | E | S | G | A | E | L | V | K | P | G | A | S | V | R | L | S | C | K | A | S | G | Y | I | F | T | D | Y | E | I | H | . | . | W | V | K | Q | R |
| 24A1 | Q | V | Q | L | Q | Q | S | G | A | E | L | V | R | P | G | A | S | V | K | L | S | C | T | A | S | G | F | N | I | K | S | Y | W | M | H | . | . | W | V | K | Q | R |
| 5F8 | E | V | Q | L | V | E | S | G | A | E | L | V | K | P | G | A | S | V | K | L | S | C | A | V | S | G | F | D | F | S | S | R | Y | W | M | . | . | W | V | R | Q | A |
| 6C1 | Q | V | K | L | L | E | S | G | T | E | L | V | K | P | G | E | T | A | K | I | S | C | K | A | S | G | N | I | L | S | N | Y | G | I | S | . | . | W | I | K | Q | P |
| 12A11 | Q | V | Q | L | V | E | S | G | D | G | L | V | K | P | G | G | S | L | R | L | S | C | S | F | S | G | F | D | F | S | S | Y | A | M | N | . | . | W | V | R | Q | A |
| 12B8 | Q | V | Q | L | V | E | S | G | G | G | L | V | Q | P | G | G | S | L | S | V | . | C | T | V | S | G | F | S | L | S | N | Y | G | M | G | . | G | W | I | R | Q | P |
| 14C10 | Q | V | K | L | K | E | S | G | P | G | L | V | Q | P | S | Q | T | L | S | L | T | C | S | F | S | G | F | D | L | S | S | Y | W | I | N | . | . | W | V | R | Q | P |
| 8C5 | G | V | V | L | V | Q | S | G | P | G | L | V | . | P | S | Q | S | A | S | V | A | C | T | V | S | G | F | S | L | T | T | Y | G | V | H | . | . | V | R | R | Q | S |

CDR H1 – Contact  
CDR H1 – Kabat

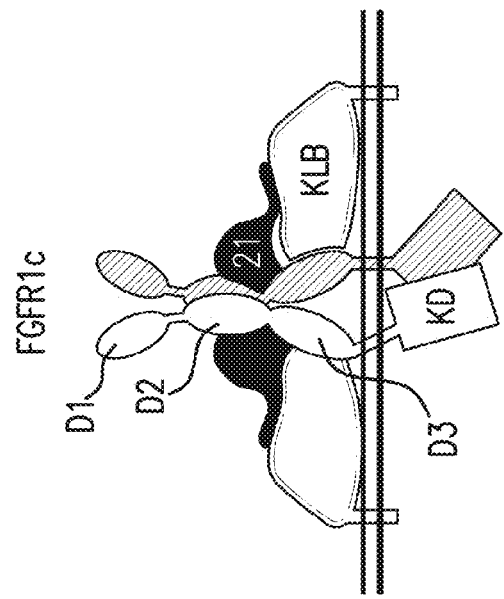
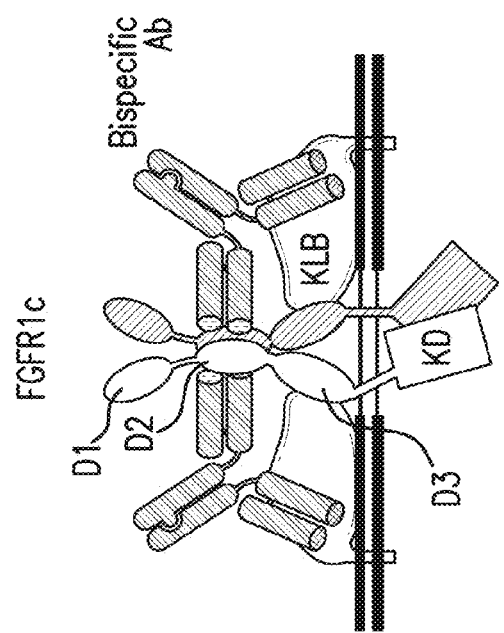
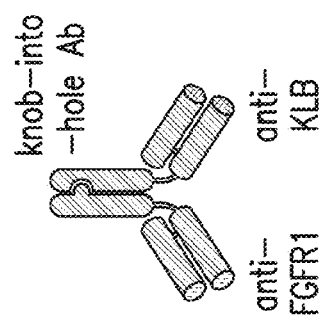
FIG. 6A
FIG. 6B

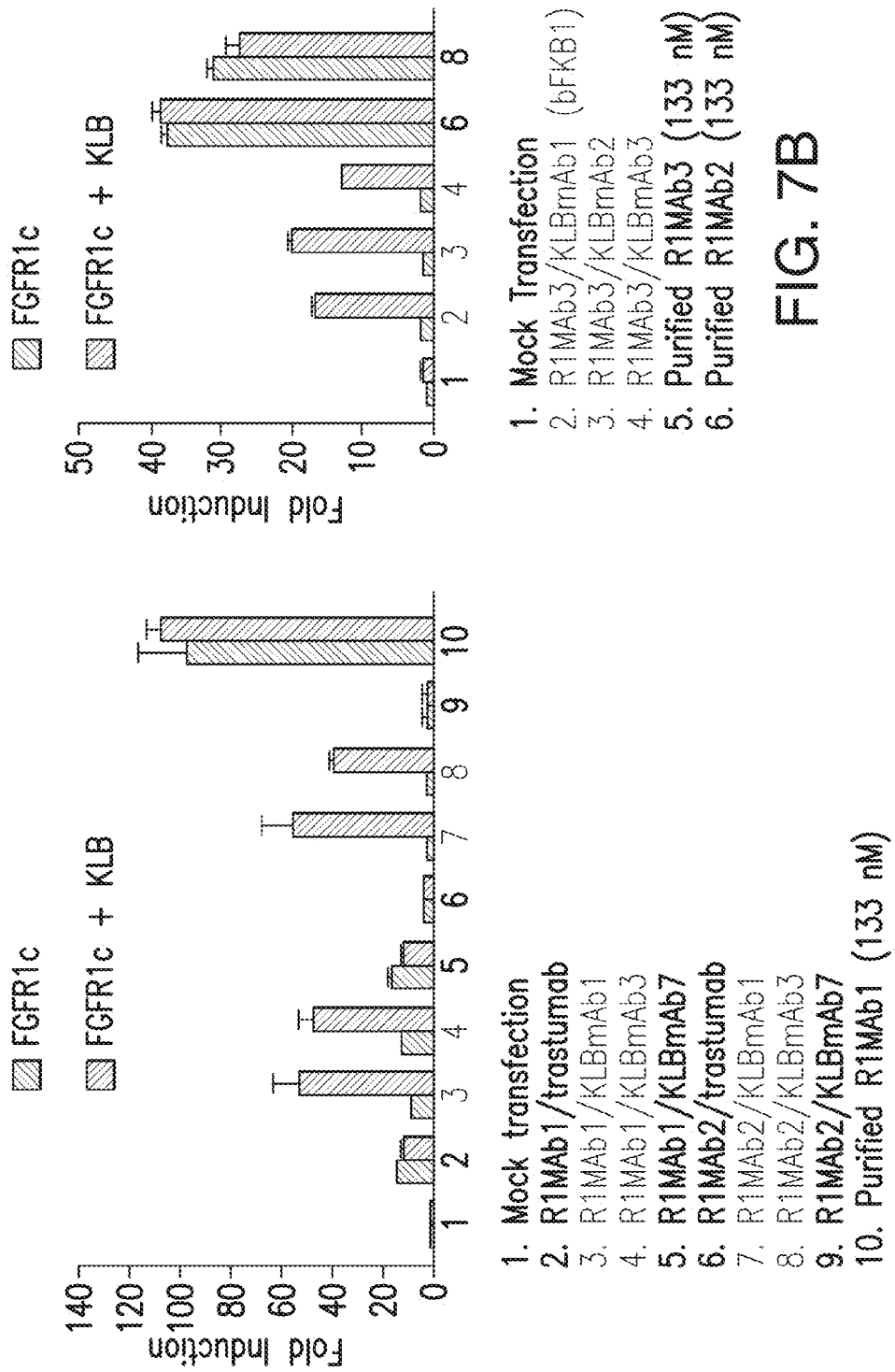

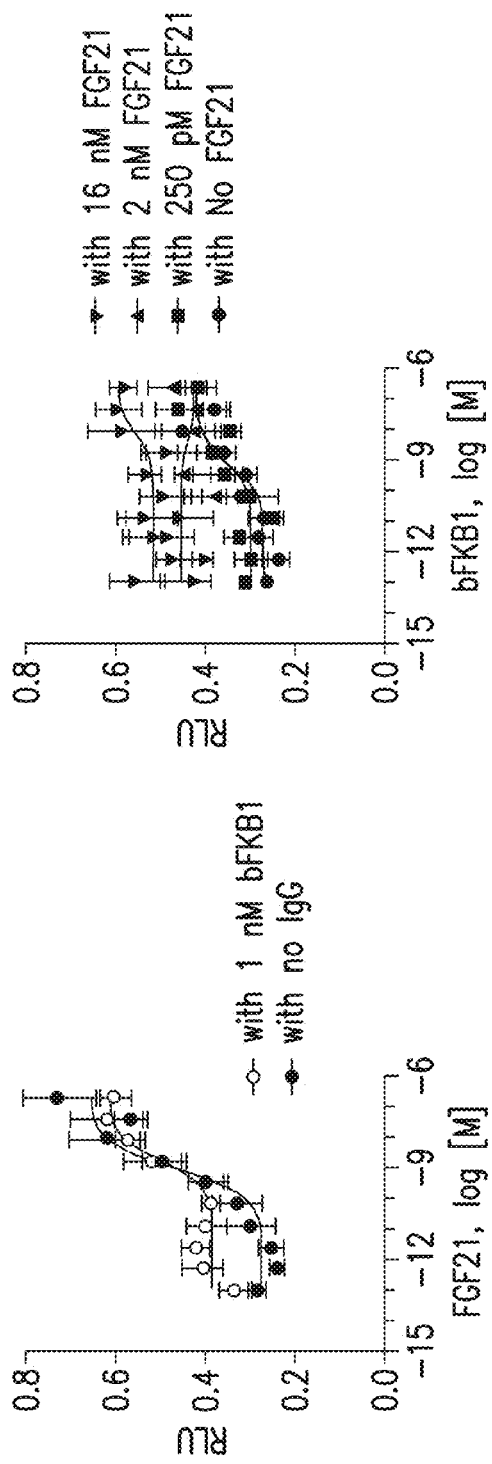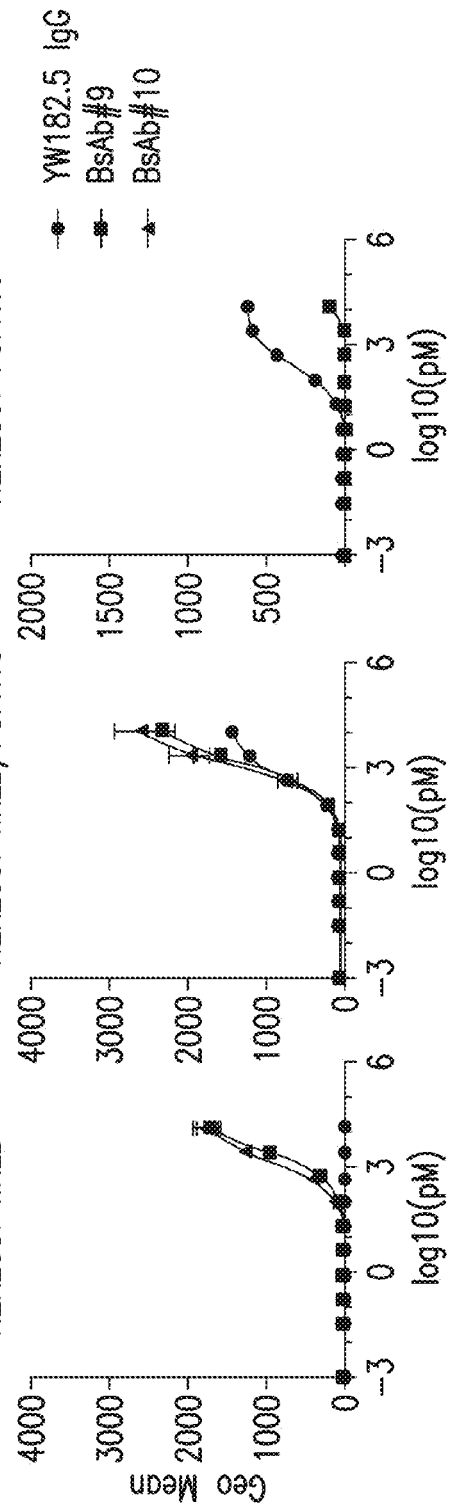
FIG. 9B
FIG. 9C
FIG. 9D

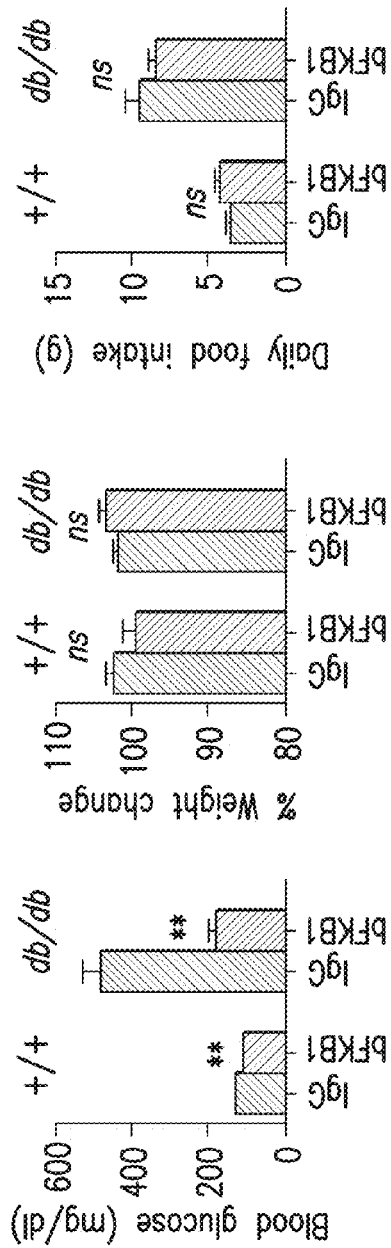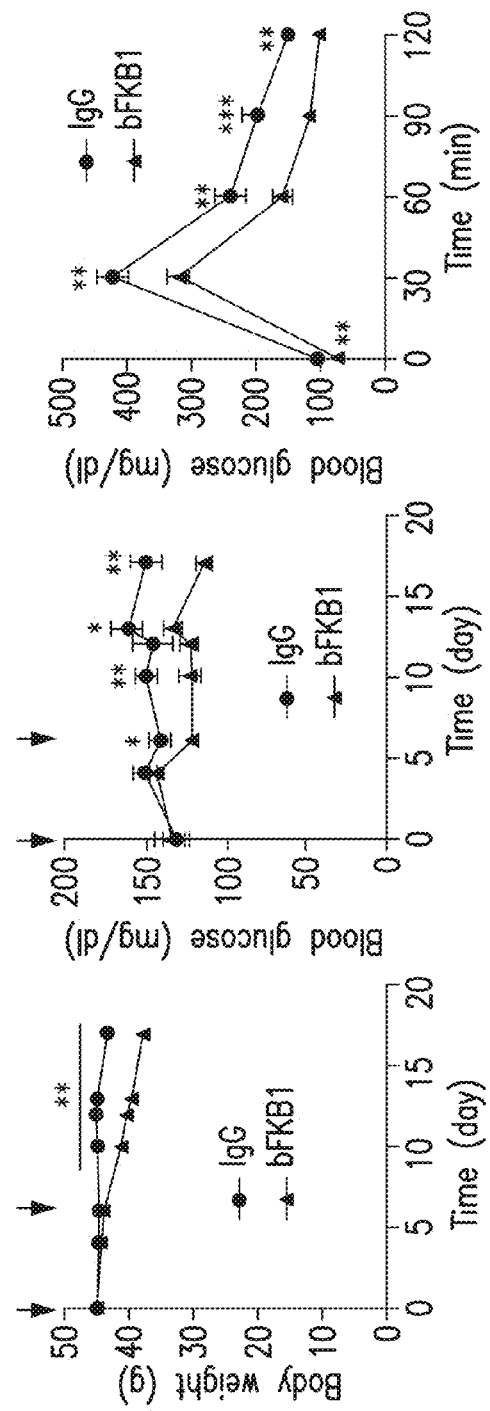
FIG. 15A
FIG. 15B
FIG. 15C

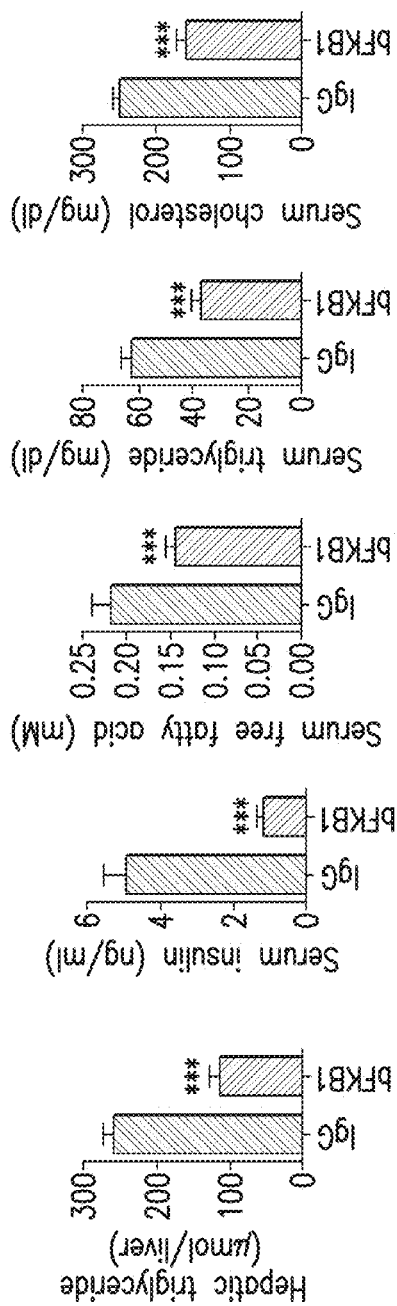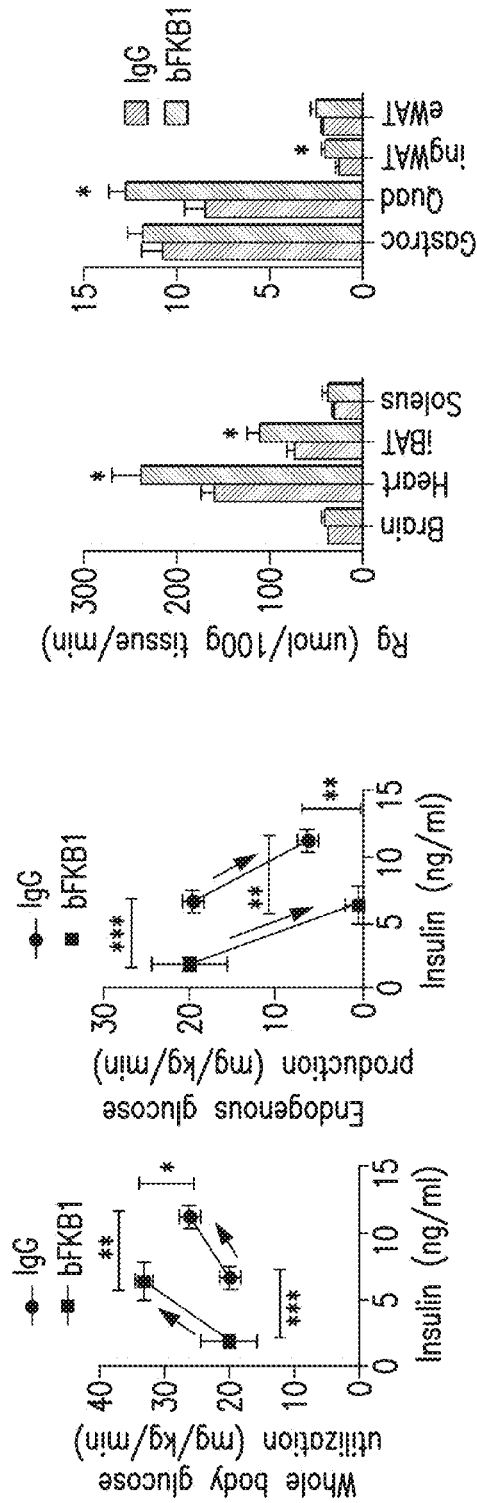
FIG. 15D, FIG. 15E, FIG. 15F, FIG. 15G wt: F S G D G K A I W D K K Q Y V S P ...
ko: F S E T G K Q Y G I K N S T *
FIG. 16A
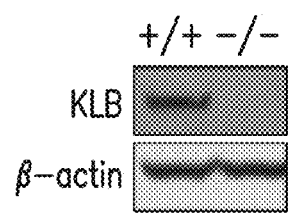
FIG. 16B
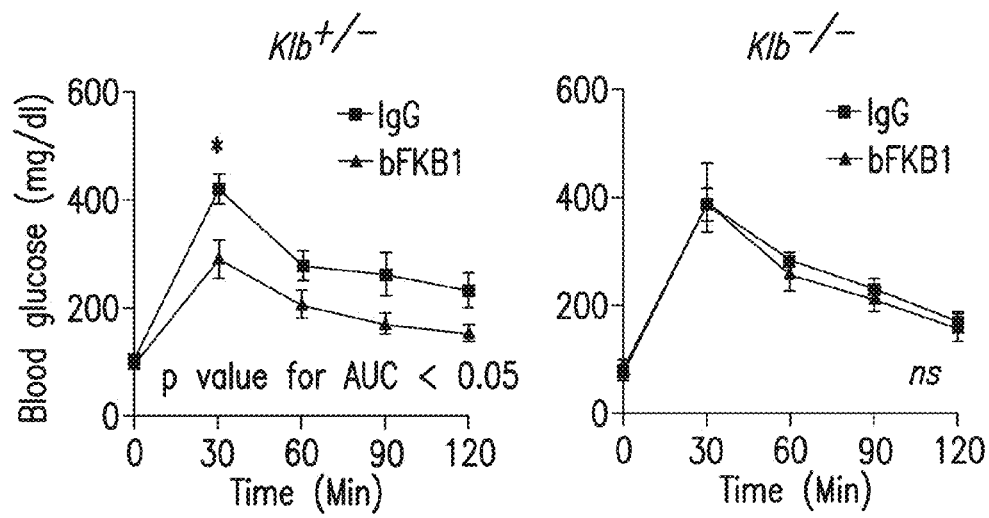
FIG. 16C
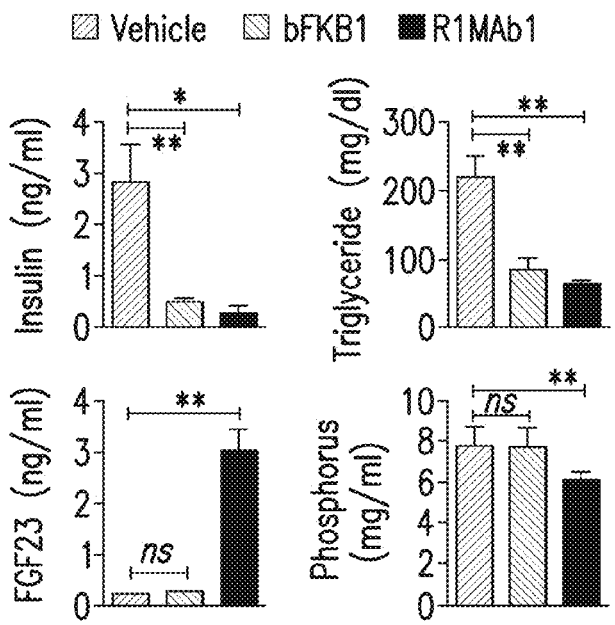
FIG. 16D

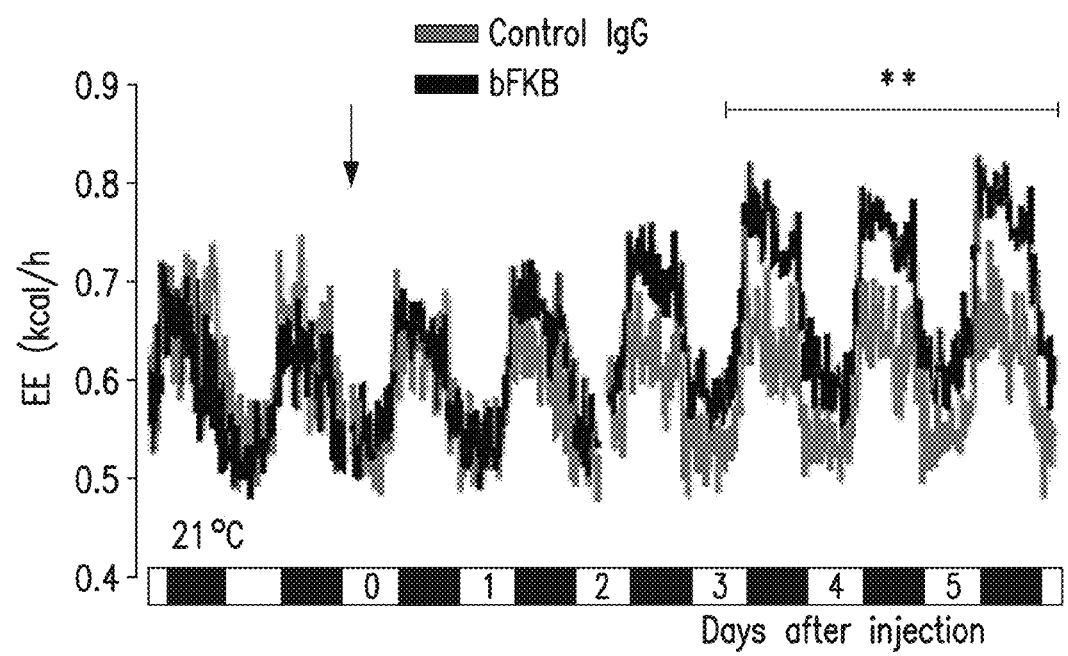
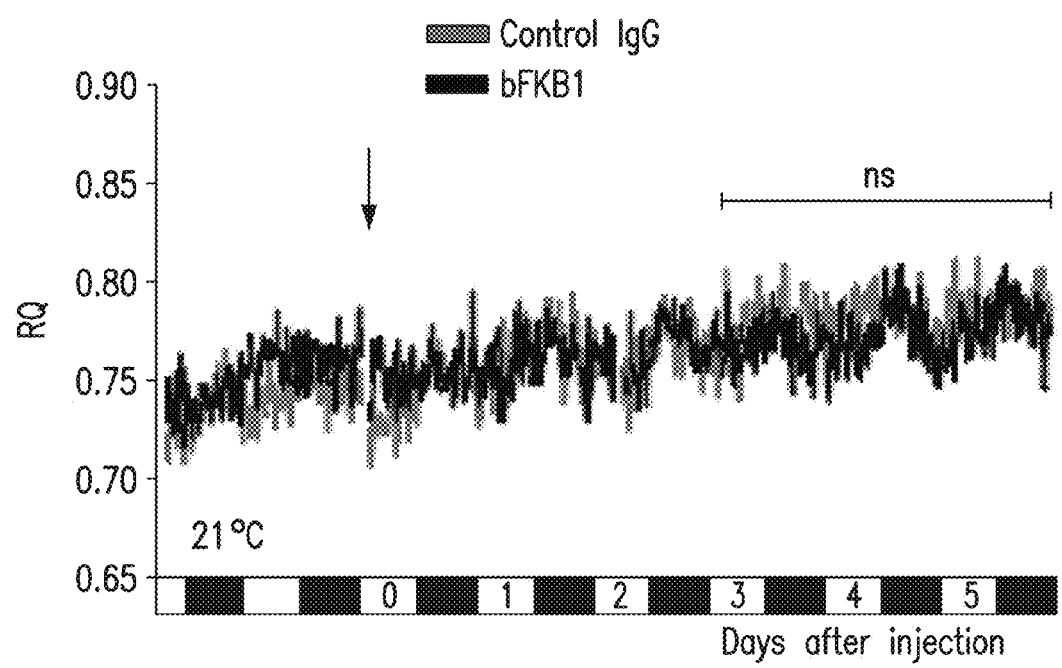
FIG. 19A

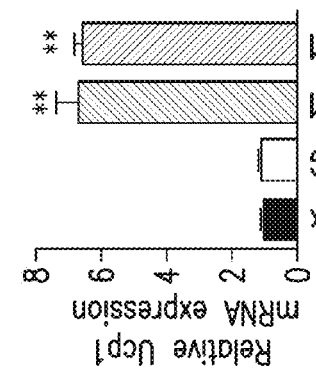
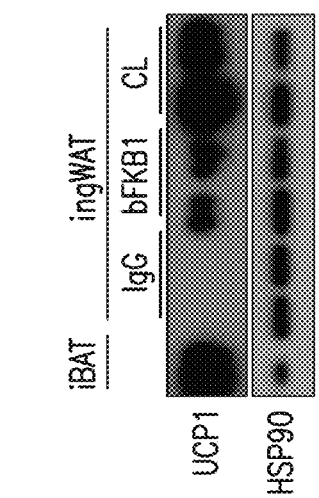
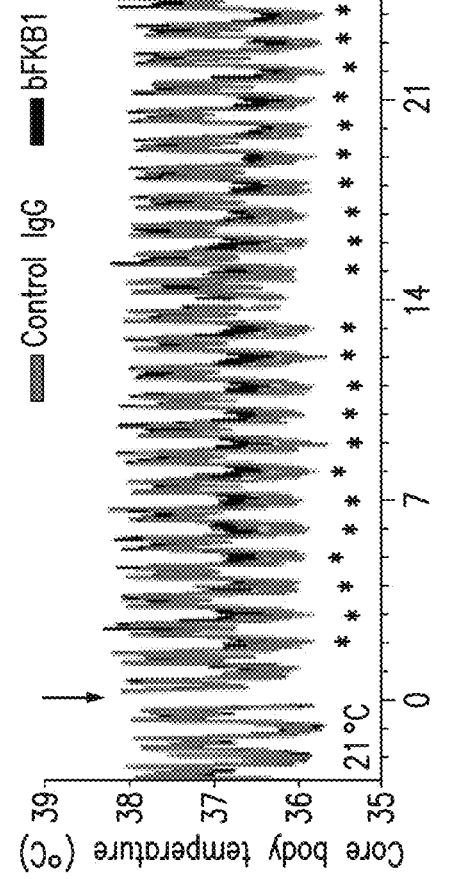
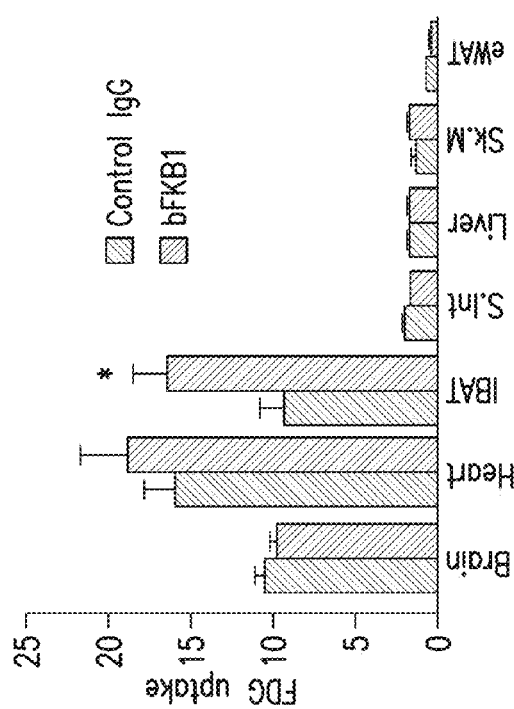
FIG. 19C
FIG. 19D
FIG. 19E
FIG. 19F

FIG. 23

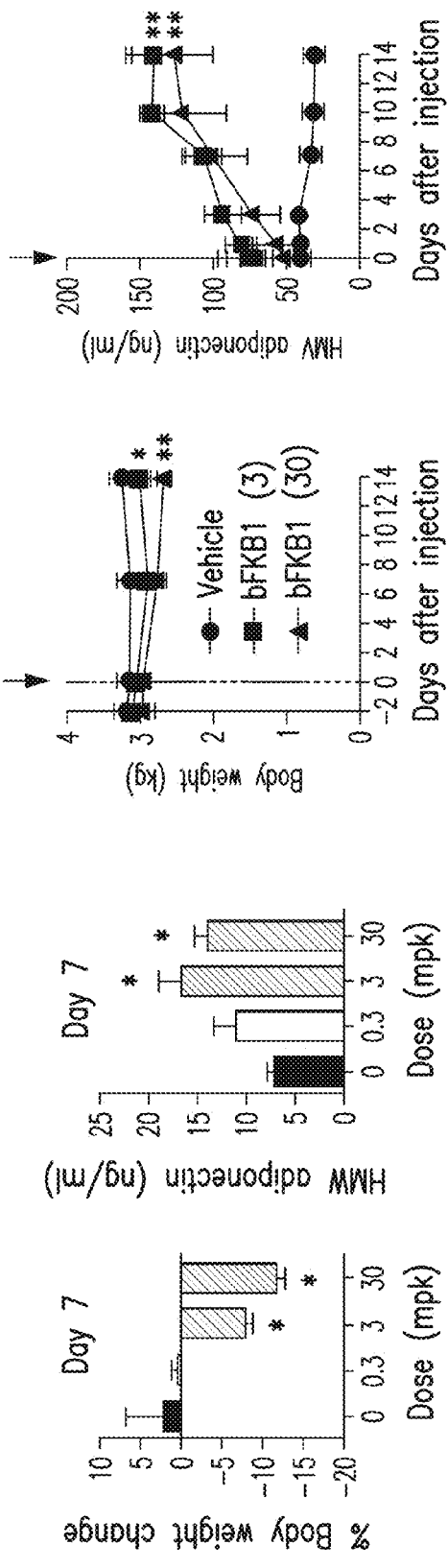
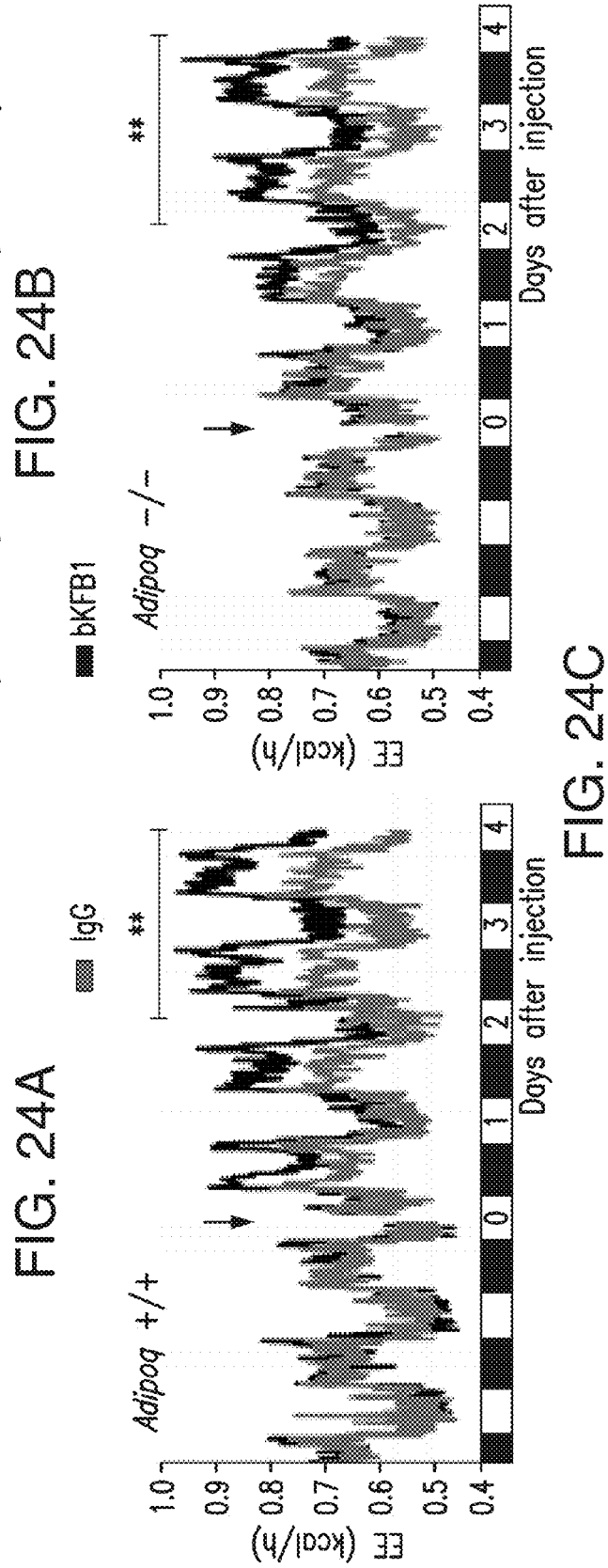
FIG. 24A
FIG. 24B
FIG. 24C

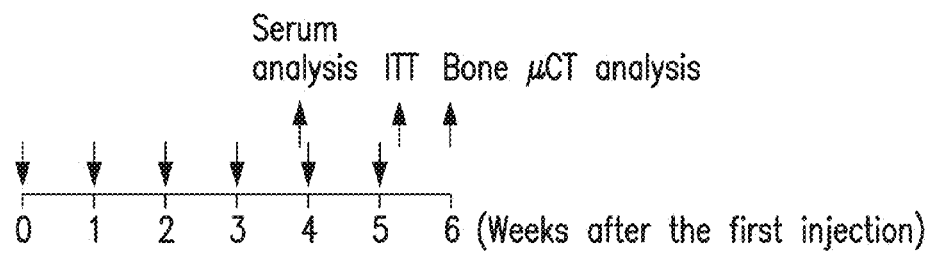

FIG. 28A

| | Control IgG | bFKB1 (1 mpk) | bFKB1 (3 mpk) | Lean control |
|---|---|---|---|---|
| Body weight change (%) | 112.8 ± 1.1 | 116.6 ± 1.1 | 102.3 ± 4.7 * | |
| ITT AUC (h*mg/kg) | 226 ± 18 | 153 ± 15 * | 156 ± 23 * | |
| Serum analysis | | | | |
| Insulin (ng/ml) | 3.87 ± 0.42 | 2.00 ± 0.54 * | 1.37 ± 0.65 * | 0.59 ± 0.60 *** |
| FGF21 (pg/ml) | 824 ± 67 | 754 ± 65 | 696 ± 62 § | 690 ± 60 * |
| Leptin (pg/ml) | 46.5 ± 2.3 | 45.6 ± 2.1 | 32.9 ± 1.9 * | 3.20 ± 1.8 *** |
| HMW Adiponectin (ng/ml) | 2802 ± 202 | 4174 ± 199 | 5667 ± 299 * | 2745 ± 321 * |
| Total cholesterol (mg/dl) | 240.6 ± 9.3 | 200.7 ± 9.4 ** | 177.4 ± 9.7 *** | 74.6 ± 9.6 *** |
| Triglyceride (mg/dl) | 41.3 ± 2.7 | 44.8 ± 2.8 | 31.9 ± 2.9 § | 57.69 ± 2.8 ** |
| FFA (mM) | 1.01 ± 0.04 | 1.04 ± 0.04 | 0.81 ± 0.04 ** | 0.77 ± 0.03 ** |
| Trabecular bone μCT analysis | | | | |
| BV/TV | 0.107 ± 0.006 | 0.114 ± 0.006 | 0.117 ± 0.010 | 0.136 ± 0.004 * |
| Bone Density (mg HA/ccm) | 1028 ± 3 | 1026 ± 6 | 1033 ± 3 | 975 ± 6 *** |
| Bone Volume (mm3) | 0.286 ± 0.026 | 0.327 ± 0.025 | 0.330 ± 0.033 | 0.390 ± 0.017 * |
| Total Volume (mm3) | 2.65 ± 0.09 | 2.86 ± 0.07 | 2.80 ± 0.10 | 2.87 ± 0.09 |
| Tb.N (mm-1) | 4.11 ± 0.04 | 4.08 ± 0.09 | 4.22 ± 0.13 | 4.73 ± 0.07 *** |
| Tb.Th (mm) | 0.0517 ± 0.0009 | 0.0526 ± 0.0008 | 0.0528 ± 0.0014 | 0.0477 ± 0.0002 * |
| Tb.Sp (mm) | 0.234 ± 0.003 | 0.235 ± 0.006 | 0.228 ± 0.008 | 0.202 ± 0.003 *** |
| Bone surface area (mm2) | 13.6 ± 1.0 | 15.5 ± 1.0 | 15.3 ± 1.2 | 19.5 ± 0.9 ** |
| BS/BV(mm-1) | 52.6 ± 1.7 | 51.3 ± 1.1 | 51.2 ± 2.1 | 53.5 ± 0.4 |
| Cortical bone μCT analysis | | | | |
| BV/TV | 0.404 ± 0.005 | 0.391 ± 0.005 | 0.391 ± 0.006 | 0.393 ± 0.007 |
| Bone Density (mg HA/cm3) | 1236 ± 2 | 1239 ± 3 | 1240 ± 22 | 1243 ± 2 * |
| Bone Volume (mm3) | 2.55 ± 0.06 | 2.57 ± 0.06 | 2.46 ± 0.07 | 2.56 ± 0.09 |
| Total Volume (mm3) | 6.33 ± 0.17 | 6.6 ± 0.23 | 6.33 ± 0.26 | 6.52 ± 0.26 |
| Bone Thickness (mm) | 0.119 ± 0.001 | 0.116 ± 0.001 | 0.115 ± 0.001 § | 0.115 ± 0.002 |
| Marrow Volume (mm3) | 3.79 ± 0.12 | 4.05 ± 0.17 | 3.88 ± 0.22 | 3.98 ± 0.18 |

FIG. 28B

METHODS OF TREATMENT WITH BISPECIFIC ANTIBODIES BINDING TO BETA-KLOTHO AND FIBROBLAST GROWTH FACTOR RECEPTOR 1

PRIORITY CLAIM

This application is a divisional application of U.S. patent application Ser. No. 14/582,100, filed Dec. 23, 2014, which claims priority to U.S. Provisional Patent Application Ser. No. 61/920,396, filed Dec. 23, 2013, and U.S. Provisional Patent Application Ser. No. 62/081,435, filed Nov. 18, 2014, and the contents of each of the above-listed applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 19, 2016, is named 00B206_0267_SL.txt and is 152,372 bytes in size.

FIELD OF THE INVENTION

The present invention relates to antibodies that bind to beta-Klotho (KLB), Fibroblast Growth Factor Receptor 1 (FGFR1), or both, and methods of using the same.

BACKGROUND

Fibroblast growth factor 21 (FGF21) and its closest homologue FGF19 are members of the FGF superfamily. FGF21 signaling requires FGF-receptor (FGFR) isoforms and the membrane-bound coreceptor Klotho-beta (KLB) (Ogawa et al. Proc. Natl. Acad. Sci. USA 104(18): 7432-37 (2007); US2010/0184665). FGF19 has also been shown to signal through FGFR isoforms complexed with KLB (Wu et al. J. Biol. Chem. 282(40): 29069-29072 (2007)). Of the 7 primary isoforms of FGFR encoded by mammalian species (1b, 2b, 3b, 1c, 2c, 3c, and 4), only three isoforms, FGFR1c, 2c and 3c, can transduce signaling by both FGF19 and FGF21 when bound by coreceptor KLB, which is predominantly expressed in the liver, adipose tissue, and pancreas (Goetz and Mohammadi, Nature reviews. Molecular Cell Biology 14, 166-180 (2013)). Of these receptors, FGFR1c appears to play a predominant role in mediating the metabolic effect of FGF21. Without being bound to a particular theory, it is believed that FGF21 acts by inducing homodimerization of FGFR isoforms in the presence of the membrane-bound co-receptor KLB. Unlike other FGF ligands, FGF21 exhibits very low affinity to any individual FGFR. However, high affinity binding to KLB through the C-terminal tail region recruits FGF21 to the FGFR/KLB complex, allowing FGF21 to interact with FGFRs despite the low affinity to FGFRs alone.

FGF21 was identified as a potent disease-modifying protein agent to reverse obesity and type 2 diabetes in animal disease models (Kharitonenkov et al. J. Clin. Invest. 115(6): 1627-35 (2005)). Recombinant FGF21 has been shown to reduce hepatic lipids, improve insulin sensitivity, and normalize glycemic control in leptin-signaling-deficient (ob/ob or db/db) mice or high-fat diet (HFD)-fed mice. Reduction in blood glucose and improvements in various cardiovascular risk factors have also been observed in obese and diabetic rhesus monkeys treated daily with recombinant FGF21. FGF21 and FGF19 have both been shown to activate the thermogenic function of uncoupling protein 1 (UCP1)-positive adipose tissues (brown and beige adipose tissues; BAT) in obese rodents (Fu et al., Endocrinology 145, 2594-2603 (2004); Coskun et al., Endocrinology 149, 6018-6027 (2008); Fisher et al., Genes & Development 26, 271-281 (2012)).

Although clinical applications of recombinant FGF21 or FGF19 analogs are currently being tested for the treatment of metabolic disease, their development for therapeutic intervention has proven challenging. For example, the serum half-life of FGF21, ~2 hours in non-human primates, is too short for practical clinical application and the remaining FGF21 protein in circulation can be rapidly inactivated by proteolytic cleavage. Efforts have been made to improve these properties through protein engineering, but such modifications could increase immunogenicity and other modification-specific adverse effects. Another significant challenge is a possibility of long-term adverse effects from chronic FGF21-mediated therapy. For example, FGF21 has been reported to induce hepatic growth hormone resistance via induction of SOCS2, an inhibitor of growth hormone receptor signaling (Inagaki et al., Cell Metab. 8: 77-83 (2008)). In humans, growth hormone resistance or deficiency is associated with low bone mass in children and adults and transgenic overexpression of FGF21 or two weeks treatment of mice with recombinant FGF21 leads to a dramatic loss of bone mineral density. It has not yet been demonstrated that the bone-related adverse effects of FGF21 can be de-linked from the beneficial metabolic effects. Further, transgenic overproduction of FGF19 can lead to hepatocellular carcinogenesis via activation of FGF Receptor (FGFR) 4 (Fu et al., Endocrinology 145, 2594-2603 (2004); Tomlinson et al., Endocrinology 143, 1741-1747 (2002); French et al., PLoS One 7, e36713 (2012)).

Recombinant monoclonal antibodies (Abs) can act as a powerful therapeutic modality as they can provide excellent target selectivity, pharmacokinetic profile, and other properties important for a pharmaceutical agent (Chan and Carter, Nature reviews. Immunology 10, 301-316 (2010)). For example, an antibody antagonist specific for FGFR1c was reported to induce weight loss in mice and monkeys (WO2005/037235) and agonistic antibody-mediated selective activation of FGFR1c is sufficient to recapitulate the insulin sensitization by FGF21 in diabetic mice (WO2012/158704; Wu et al. Science Translational Med. 3(113): 1-10 (2011)). Antibodies that bind to the KLB/FGFR1c complex have been proposed as activators/therapeutic agents (U.S. Pat. No. 7,537,903; WO2011/071783; WO2012/158704). Others have investigated two alternative approaches to selectively activate the FGFR1c/KLB complex, such as a high affinity anti-KLB antibody called mimAb1 (Foltz et al. Sci. Transl. Med. 4: 162ra153 (2012)) and bispecific anti-FGFR1/KLB Avimer polypeptide C3201 linked to human serum albumin (HSA) (U.S. Pat. No. 8,372,952).

Given the significant role for FGF19 and FGF21 in glucose metabolism, there remains a need in the art for the development of therapeutic molecules and methods to modulate FGF19 or FGF21-mediated activities.

SUMMARY

The present disclosure provides antibodies that bind to KLB, antibodies that bind to FGFR1, and bispecific antibodies that bind to both KLB and FGFR1, and methods of using the same. The invention is based, in part, on the discovery of bispecific antibodies that bind to both KLB and FGFR1, which selectively activate the FGFR1c/KLB receptor complex and induce the beneficial metabolic changes expected from the FGF21-like activity, including weight loss and improvement in glucose and lipid metabolism, without a significant impact on the liver and without a loss in bone mass.

In certain embodiments, the antibody is a bispecific antibody. For example, and not by way of limitation, an isolated antibody of the present invention can bind to both beta-Klotho (KLB) and Fibroblast Growth Factor Receptor 1 (FGFR1), wherein the antibody binds to the C-terminal domain of KLB. For example and not by way of limitation, an isolated antibody of the present disclosure binds to both KLB and FGFR1c. In certain embodiments, the antibody binds to a fragment of KLB including the amino acid sequence SSPTRLAVIPWGVRKLLRWVRRNYGDMDIYITAS (SEQ ID NO: 142). In certain embodiments, the antibody binds to an epitope within a fragment of FGFR1 including the amino acid sequence KLHAVPAAKTVKFKCP (SEQ ID NO: 143) or FKPDHRIGGYKVRY (SEQ ID NO: 144).

In certain embodiments, an antibody of the present disclosure activates the KLB/FGFR1c complex. In certain embodiments, an antibody of the present disclosure reduces blood glucose levels in vivo. In certain embodiments, the antibody does not significantly affect bone density. In certain embodiments, an antibody of the present disclosure does not have a significant impact on the liver. In certain embodiments, the antibody induces ERK and MEK phosphorylation in the liver at significantly lower levels than FGF21 induces. In certain embodiments, the antibody binds to KLB with a $K_d$ from $10^{-8}$ M to $10^{-13}$ M. In certain embodiments, an antibody of the present disclosure can bind to a FGFR1 protein with a $K_d$ from $10^{-8}$ M to $10^{-13}$ M. In certain embodiments, an antibody of the present disclosure can bind to FGFR1c with a $K_d$ from $10^{-8}$ M to $10^{-13}$ M. In certain embodiments, the antibody binds to KLB with a $K_d$ of <10 nM and to FGFR1c with a $K_d$ of >300 nM. In certain embodiments, an anti-KLB/anti-FGFR1 bispecific antibody can include an anti-FGFR1 arm that has a $K_d$ of about 10 nM to about 10 μM.

In certain embodiments, an antibody of the present disclosure binds to an epitope present on KLB. For example, and not by way of limitation, the present disclosure provides an anti-KLB antibody that binds the same epitope as an antibody shown in FIGS. 3A and B. In certain embodiments, an anti-KLB antibody of the present disclosure binds the same epitope as the 12A11 or the 8C5 antibody. In certain embodiments, the anti-KLB antibody binds to an epitope within the C-terminal domain of KLB. In certain embodiments, the anti-KLB antibody binds to a fragment of KLB consisting of the amino acid sequence SSPTRLAVIPWGVRKLLRWVRRNYGDMDIYITAS (SEQ ID NO: 142).

In certain embodiments, an anti-KLB/anti-FGFR1 bispecific antibody of the present disclosure includes a first antibody, or antigen binding portion thereof, that includes a heavy chain variable region and a light chain variable region, where the heavy chain variable region includes amino acids having a sequence that is at least 95% identical to the sequence set forth in SEQ ID NO: 128, and the light chain variable region includes amino acids having a sequence that is at least 95% identical to the sequence set forth in SEQ ID NO: 130. In certain embodiments, the second antibody, or antigen binding portion thereof, includes a heavy chain variable region and a light chain variable region, where the heavy chain variable region includes amino acids having a sequence that is at least 95% identical to the sequence set forth in SEQ ID NO: 132, and the light chain variable region includes amino acids having a sequence that is at least 95% identical to the sequence set forth in SEQ ID NO: 134.

In certain embodiments, an anti-KLB/anti-FGFR1 bispecific antibody of the present disclosure includes a first antibody, or antigen binding portion thereof, which includes a heavy chain region and a light chain region, where the heavy chain region includes amino acids having a sequence that is at least 95% identical to the sequence set forth in SEQ ID NO: 129, and the light chain region includes amino acids having a sequence that is at least 95% identical to the sequence set forth in SEQ ID NO: 131. In certain embodiments, the second antibody, or antigen binding portion thereof, includes a heavy chain region and a light chain region, where the heavy chain region includes amino acids having a sequence that is at least 95% identical to the sequence set forth in SEQ ID NO: 133, and the light chain region includes amino acids having a sequence that is at least 95% identical to the sequence set forth in SEQ ID NO: 135.

The present disclosure further provides an anti-KLB antibody that includes: (a) HVR-H3 comprising an amino acid sequence selected from the group consisting of SEQ ID NOs: 1-15, (b) HVR-L3 comprising an amino acid sequence selected from the group consisting of SEQ ID NOs: 79-93, and (c) HVR-H2 comprising an amino acid sequence selected from the group consisting of SEQ ID NOs: 16-31.

In certain embodiments, the anti-KLB antibody comprises (a) HVR-H1 comprising an amino acid sequence selected from the group consisting of SEQ ID NOs: 1-15, (b) HVR-H2 comprising an amino acid sequence selected from the group consisting of SEQ ID NOs: 16-31, and (c) HVR-H3 comprising an amino acid sequence selected from the group consisting of SEQ ID NOs: 32-47.

In certain embodiments, the anti-KLB antibody further comprises (a) HVR-L1 comprising an amino acid sequence selected from the group consisting of SEQ ID NOs: 48-62, (b) HVR-L2 comprising an amino acid sequence selected from the group consisting of SEQ ID NOs: 63-78, and (c) HVR-L3 comprising an amino acid sequence selected from the group consisting of SEQ ID NOs: 79-93.

In certain embodiments, the anti-KLB antibody comprises (a) HVR-H1 comprising the amino acid sequence of SEQ ID NO: 12, (b) HVR-H2 comprising the amino acid sequence of SEQ ID NO: 28, (c) HVR-H3 comprising the amino acid sequence of SEQ ID NO: 44, (d) HVR-L1 comprising the amino acid sequence of SEQ ID NO: 59, (e) HVR-L2 comprising the amino acid sequence of SEQ ID NO: 75, and (f) HVR-L3 comprising the amino acid sequence of SEQ ID NO: 90.

In certain embodiments, the anti-KLB antibody comprises (a) HVR-H1 comprising the amino acid sequence of SEQ ID NO: 15, (b) HVR-H2 comprising the amino acid sequence of SEQ ID NO: 31, (c) HVR-H3 comprising the amino acid sequence of SEQ ID NO: 47, (d) HVR-L1 comprising the amino acid sequence of SEQ ID NO: 62, (e) HVR-L2 comprising the amino acid sequence of SEQ ID NO: 78, and (f) HVR-L3 comprising the amino acid sequence of SEQ ID NO: 93.

In certain embodiments, the anti-KLB antibody comprises (a) a heavy chain variable region comprising the amino acid sequence of SEQ ID NO: 128 and (b) a light chain variable region comprising the amino acid sequence of SEQ ID NO: 130. In certain embodiments, the antibody comprises (a) a heavy chain comprising the amino acid sequence of SEQ ID NO: 129 and (b) a light chain comprising the amino acid sequence of SEQ ID NO: 131.

In another aspect, the present disclosure provides an anti-KLB antibody comprising (a) a heavy chain variable region having at least 95% sequence identity to the amino acid sequence of SEQ ID NO: 128; (b) a light chain variable region having at least 95% sequence identity to the amino acid sequence of SEQ ID NO: 130; and (c) a heavy chain variable region as in (a) and a light chain variable region as in (b).

The present disclosure further provides antibodies that bind to FGFR1, e.g., FGFR1c. For example, and not by way of limitation, an antibody of the present disclosure comprises a variable domain that binds to FGFR1. In certain embodiments, the antibody binds to a fragment of FGFR1 consisting of the amino acid sequence KLHAVPAAKTVK-FKCP (SEQ ID NO: 143) or FKPDHRIGGYKVRY (SEQ ID NO: 144). In certain embodiments, the antibody comprises (a) HVR-H1 comprising the amino acid sequence of SEQ ID NO: 136, (b) HVR-H2 comprising the amino acid sequence of SEQ ID NO: 137, (c) HVR-H3 comprising the amino acid sequence of SEQ ID NO: 138, (d) HVR-L1 comprising the amino acid sequence of SEQ ID NO: 139, (e) HVR-L2 comprising the amino acid sequence of SEQ ID NO: 140, and (f) HVR-L3 comprising the amino acid sequence of SEQ ID NO: 141. In certain embodiments, the antibody comprises (a) a heavy chain variable region comprising the amino acid sequence of SEQ ID NO: 132 and (b) a light chain variable region comprising the amino acid sequence of SEQ ID NO: 134. In certain embodiments, the antibody comprises (a) a heavy chain comprising the amino acid sequence of SEQ ID NO: 133 and (b) a light chain comprising the amino acid sequence of SEQ ID NO: 135. In certain embodiments, an antibody of the present disclosure binds to a fragment of FGFR1c consisting of the amino acid sequence KLHAVPAAKTVKFKCP (SEQ ID NO: 143) or FKPDHRIGGYKVRY (SEQ ID NO: 144).

In certain embodiments, an antibody of the present disclosure is a monoclonal antibody. In certain embodiments, the antibody is a human, humanized, or chimeric antibody. In certain embodiments, the antibody has reduced effector function.

In another aspect, the present disclosure provides an isolated nucleic acid encoding an antibody of the present disclosure. In certain embodiments, the present disclosure provides a host cell comprising a nucleic acid of the present disclosure. In certain embodiments, the present disclosure provides a method of producing an antibody comprising culturing a host cell of the present disclosure so that the antibody is produced. In certain embodiments, this method further comprises recovering the antibody from the host cell.

The present disclosure further provides a pharmaceutical formulation that includes one or more antibodies of the invention and a pharmaceutically acceptable carrier. In certain embodiments, the pharmaceutical formulation comprises an additional therapeutic agent.

In another aspect, the present disclosure provides an antibody of the invention for use as a medicament. In certain embodiments, the antibody is for use in treating metabolic disorders, e.g., polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY). In certain embodiments, the antibody is for use in treating type 2 diabetes. In certain embodiments, the antibody is for use in treating obesity. In certain embodiments, the present disclosure provides an antibody for use in treating Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Börjeson-Forssman-Lehman syndrome. In certain embodiments, the present disclosure provides an antibody for use in activating a KLB/FGFR1 receptor complex, e.g., a KLB/FGFR1c receptor complex.

In another aspect, the present disclosure provides the use of an antibody, disclosed herein, in the manufacture of a medicament for treatment of metabolic disorders, e.g., polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY), and aging and related diseases such as Alzheimer's disease, Parkinson's disease and ALS. In certain embodiments, the metabolic disorder is type 2 diabetes. In certain embodiments, the metabolic disorder is obesity. In certain embodiments, the manufacture is of a medicament for activating a KLB/FGFR1c receptor complex.

In another aspect, the present disclosure provides a method of treating an individual having a disease selected from the group consisting of polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY), and aging and related diseases such as Alzheimer's disease, Parkinson's disease and ALS, the method comprising administering to the individual an effective amount of one or more antibodies of the present disclosure. In certain embodiments, the disease is diabetes, e.g., type 2 diabetes. In certain embodiments, the disease is obesity. In certain embodiments, the present disclosure provides a method of treating an individual having a disease and/or disorder selected from the group consisting of Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Börjeson-Forssman-Lehman syndrome. In certain embodiments, the method further includes administering an additional therapeutic agent to the individual. In certain embodiments, a method using one or more antibodies of the present disclosure does not affect liver function in an individual. In certain embodiments, the present disclosure provides a method for inducing weight loss comprising administering to an individual an effective amount of one or more antibodies of the present disclosure.

In another aspect, the present disclosure provides a method of activating a KLB-FGFR1c receptor complex in an individual comprising administering to the individual an effective amount of an antibody of the present disclosure.

BRIEF DESCRIPTION OF THE FIGURES

FIG. 1A depicts agonistic activity of anti-FGFR1 antibodies and antibody fragments.

FIG. 1B depicts results of binding competition experiments using anti-FGFR1 antibodies.

FIG. 1C depicts amino acid residues in FGFR1 important for binding by anti-FGFR1 antibodies of the presently disclosed subject matter. FIG. 1C discloses SEQ ID NOs: 159, 159, 143 and 144, respectively, in order of appearance.

FIG. 2A depicts the affinities of two anti-FGFR1 antibodies for FGFR1b and FGFR1c.

FIG. 2B depicts binding of an anti-FGFR1 antibody to various FGFRs.

FIG. 2C depicts an anti-FGFR1 antibody that acted as a specific agonist for FGFR1 in GAL-ELK1 (ETS-like transcription factor 1) based luciferase assay in L6 cells.

FIG. 2D depicts that an anti-FGFR1 antibody acted as a specific agonist for FGFR1 in GAL-ELK1 based luciferase assay in HEK293 cells.

FIG. 2E depicts that an anti-FGFR1 antibody normalized blood glucose levels when injected into diabetic ob/ob mice.

FIG. 3A depicts the light chain variable region sequences for 17 anti-KLB antibodies. The CDR L1 sequences are, in order, SEQ ID NOs: 48-62; the CDR L2 sequences are, in order, SEQ ID NOs: 63-78; and the CDH L3 sequences are, in order, SEQ ID NOs: 79-93. The light chain variable region sequences are, in order, SEQ ID NOs: 111-127.

FIG. 3B depicts the heavy chain variable region sequences for 17 anti-KLB antibodies. The CDR H1 sequences for the antibodies are, in order (11F1-8C5), SEQ ID NOs: 1-15; the CDR H2 sequences are, in order, SEQ ID NOs: 16-31; the CDR H3 sequences are, in order, SEQ ID NOs: 32-47. The heavy chain variable region sequences for the antibodies are, in order, SEQ ID NOs: 94-110.

FIG. 6A is a schematic diagram representing antibodies of the presently disclosed subject matter and a model for KLB/FGFR1c bispecific Ab complex formation for signal activation.

FIG. 6B depicts a model for FGFR1c-KLB-FGF21 complex formation for signal activation.

FIG. 7A depicts induction by various bispecific antibodies with anti-FGFR1 and anti-KLB arms in a GAL-ELK1 based luciferase assay. Note that bispecific Abs with R1MAb1 arm exhibited significant KLB-independent activity, presumably due to the agonistic activity of R1MAb1 Fab. No such activity was observed with bispecific Abs with R1MAb2 or R1MAb3 arm.

FIG. 7B depicts that induction of signaling by various bispecific antibodies with anti-FGFR1 and anti-KLB arms is dependent on both FGFR1c and KLB.

FIG. 9B depicts similar GAL-ELK1 luciferase assays as shown in FIG. 9A. Transfected L6 cells were treated with combinations of FGF21 and BsAb17 as indicated. N=4.

FIG. 9C depicts similar GAL-ELK1 luciferase assays as shown in FIG. 9A. Transfected L6 cells were treated with combinations of FGF21 and BsAb17 as indicated. N=4.

FIG. 9D depicts the binding of an anti-FGFR1 antibody and the anti-KLB/anti-FGFR1 bispecific antibodies, BsAB9 and BsAb10, to cells expressing KLB, FGFR1c or both.

FIG. 13B discloses SEQ ID NOs: 160-164, respectively, in order of appearance.

FIG. 15A depicts the blood glucose levels (day 7), % body weight change (day 7) and daily food intake (day 0-3) of lean C57BL/6 and db/db mice (n=7) after a single intraperitoneal (i.p.) injection of BsAb17 or control IgG at 3 mg/kg (lean) or 5 mg/kg (db/db).

FIG. 15B depicts the body weight and blood glucose levels of Diet Induced Obesity (DIO) mice, which received i.p. injections of the indicated IgG (BsAb20) at 3 mg/kg on day 0 and 6 (arrows). N=9.

FIG. 15C depicts the results of the glucose tolerance test with the same mice and antibody used in 15B on day 14.

FIG. 15D depicts the amount of hepatic triglycerides, and serum markers in animals shown in 15B-C on day 17.

FIG. 15E depicts whole body glucose utilization, measured during hyperinsulinaemic-euglycaemic clamps with DIO mice 5 days after a single i.p. injection of the indicated IgG (BsAb17) at 10 mg/kg (N=12). The horizontal axis represents serum insulin levels. The arrows indicate the direction of changes from basal to insulin-stimulated states. $p<0.05$ (*), $<0.005$ (), $<0.0001$ (*) vs control.

FIG. 15F depicts endogenous glucose production, measured during hyperinsulinaemic-euglycaemic clamps with DIO mice 5 days after a single i.p. injection of the indicated IgG (BsAb17) at 10 mg/kg (N=12). The horizontal axis represents serum insulin levels. The arrows indicate the direction of changes from basal to insulin-stimulated states. $p<0.05$ (*), $<0.005$ (), $<0.0001$ (*) vs control.

FIG. 15G depicts insulin-stimulated tissue glucose uptake, measured during hyperinsulinaemic-euglycaemic clamps with DIO mice 5 days after a single i.p. injection of the indicated IgG (BsAb17) at 10 mg/kg (N=12). $p<0.05$ (*), $<0.005$ (), $<0.0001$ (*) vs control.

FIG. 16A shows the N-terminal amino acid sequence of mouse KLB protein (SEQ ID NO: 165), and the corresponding amino acid sequence encoded by the Klb allele in the KO mice (SEQ ID NO: 166) are shown. A missense mutation in Klb gene results in a frame-shift after the second amino acid in the KO allele, as shown with red letters.

FIG. 16B shows KLB protein expression in epididymal white adipose tissue in wildtype (+/+) and KLB knockout (−/−) mice.

FIG. 16C shows that KLB is important for BsAb20 to affect glucose metabolism. Glucose tolerance test (GTT) in DIO mice that received four weekly injections of BsAb20 or control IgG at 3 mpk. GTT was conducted on day 23, three days after the last injection. The mice were on HFD for 20 weeks prior to GTT. *$p<0.05$.

FIG. 16D depicts the serum parameters in DIO mice on day 7 after an i.p. injection of an anti-KLB/anti-FGFR1 bispecific antibody or R1MAb1 at 50 mg/kg or vehicle. N=6.

FIG. 19A depicts the energy expenditure (EE) (left) and Respiratory quotient (RQ) (right) of DIO mice that received a single i.p. injection of 10 mg/kg IgG at the indicated time at 21-22° C. N=7.

FIG. 19C depicts the tissue fludeoxyglucose (FDG) uptake in DIO mice at 40 hr after single i.p. injection of indicated IgG at 10 mg/kg. N=8. Mice were overnight fasted before FDG-uptake was measured.

FIG. 19D depicts the Western blot analysis of ingWAT harvested on day 7 after single i.p. injection (BsAb17 or control IgG at 10 mg/kg) and surgical implantation of an osmotic pump (CL316,243 (0.75 nmol/h) or vehicle).

FIG. 19E depicts the expression of Ucp1 mRNA in primary human subcutaneous adipocytes treated with indicated protein at 30 nM for 48 hr. N=3.

FIG. 19F depicts the core body temperature of DIO mice that received 10 mg/kg of BsAb17 or control IgG. N=7~8.

FIG. 23 depicts the FGF21 and BsAb20-induced ERK and MEK phosphorylation to a similar extent in epididymal fat, inguinal fat, and interscapular brown fat, and pancreas. Tissues were harvested at 1 h (liver, pancreas and epididymal white adipose tissue (eWAT)) or 2 h (iBAT or ingWAT) after i.p. injection of lean C57BL/6 mice at 10 mg/kg (BsAb20) or 1 mg/kg (FGF21). Total ERK and MEK serve as loading controls.

FIG. 24A depicts the body weight changes and serum HMW adiponectin levels in DIO mice (N=6) that received single i.p. of BsAb17 at the indicated dose (mg/kg).

FIG. 24B depicts the body weight changes and serum HMW adiponectin levels in cynomolgus monkeys (N=3) that received a single i.v. injection of BsAb17 at the indicated dose (mg/kg).

FIG. 24C depicts the EE of DIO mice (left: wt and right: adipoq KO) that received single i.p. injection of indicated IgG (BsAb17) at 10 mg/kg (arrow). N=5~6.

FIG. 28A is a schematic representation of the experiment shown in FIG. 28B. DIO mice received BsAb20 (1 or 3 mg/kg/week) or control IgG (1 mg/kg/week) for 6 weeks as indicated. Control lean C57BL/6 mice did not receive treatment.

FIG. 28B depicts the bone phenotype after BsAb20 treatment. Femur and tibia were dissected and subjected to μCT analysis. (N=7~8). Note that no negative effect was observed in various bone parameters in trabecular and cortical bones with the possible exception of cortical bone thickness, which showed a decreasing trend with 3 mg/kg/week BsAb20 treatment although statistical significance was not reached. Since a reduction in cortical bone thickness without an effect in trabecular bone density in calorie restricted mice has been reported (11), the observed effect may be related to weight loss. p<0.001 (*), <0.01 (), <0.05 (*), <0.1 (#), <0.2 ($) vs DIO mice treated with control IgG. N=7~8.

DETAILED DESCRIPTION

Figure 1D:
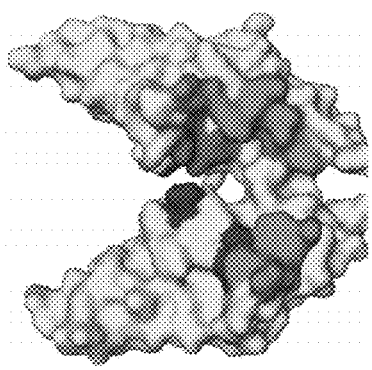
FIG. 1D depicts the results of site-specific mutagenesis to determine amino acid residues important for binding by anti-FGFR1 antibodies of the presently disclosed subject matter.

For clarity and not by way of limitation the detailed description of the presently disclosed subject matter is divided into the following subsections:
 I. Definitions;
 II. Antibodies;
 III. Methods of Use;
 IV. Pharmaceutical Formulations; and
 V. Articles of Manufacture.

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In certain embodiments, the number of amino acid changes are 10 or less, 9 or less, 8 or less, 7 or less, 6 or less, 5 or less, 4 or less, 3 or less, or 2 or less. In certain embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

"Klotho-beta," "KLB" and "beta-Klotho," as used herein, refers to any native beta-Klotho from any vertebrate source, including mammals such as primates (e.g., humans) and rodents (e.g., mice and rats), unless otherwise indicated. The term encompasses "full-length," unprocessed KLB as well as any form of KLB that results from processing in the cell. The term also encompasses naturally occurring variants of KLB, e.g., splice variants or allelic variants. A non-limiting example of a human KLB amino acid sequence targeted by an antibody of the present disclosure, excluding the signal sequence, is as follows:

(SEQ ID NO: 145)
FSGDGRAIWSKNPNFTPVNESQLFLYDTFPKNFFWGIGTGALQVEGSWKK

DGKGPSIWDHFIHTHLKNVSSTNGSSDSYIFLEKDLSALDFIGVSFYQFS

ISWPRLFPDGIVTVANAKGLQYYSTLLDALVLRNIEPIVTLYHWDLPLAL

QEKYGGWKNDTIIDIFNDYATYCFQMFGDRVKYWITIHNPYLVAWHGYGT

GMHAPGEKGNLAAVYTVGHNLIKAHSKVWHNYNTHFRPHQKGWLSITLGS

HWIEPNRSENTMDIFKCQQSMVSVLGWFANPIHGDGDYPEGMRKKLFSVL

PIFSEAEKHEMRGTADFFAFSFGPNNFKPLNTMAKMGQNVSLNLREALNW

IKLEYNNPRILIAENGWFTDSRVKTEDTTAIYMMKNFLSQVLQAIRLDEI

RVFGYTAWSLLDGFEWQDAYTIRRGLFYVDFNSKQKERKPKSSAHYYKQI

IRENGFSLKESTPDVQGQFPCDFSWGVTESVLKPESVASSPQFSDPHLYV

WNATGNRLLHRVEGVRLKTRPAQCTDFVNIKKQLEMLARMKVTHYRFALD

WASVLPTGNLSAVNRQALRYYRCVVSEGLKLGISAMVTLYYPTHAHLGLP

EPLLHADGWLNPSTAEAFQAYAGLCFQELGDLVKLWITINEPNRLSDIYN

RSGNDTYGAAHNLLVAHALAWRLYDRQFRPSQRGAVSLSLHADWAEPANP

YADSHWRAAERFLQFEIAWFAEPLFKTGDYPAAMREYIASKHRRGLSSSA

LPRLTEAERRLLKGTVDFCALNHFTTRFVMHEQLAGSRYDSDRDIQFLQD

ITRLSSPTRLAVIPWGVRKLLRWVRRNYGDMDIYITASGIDDQALEDDRL

RKYYLGKYLQEVLKAYLIDKVRIKGYYAFKLAEEKSKPRFGFFTSDFKAK

SSIQFYNKVISSRGFPPFENSSSRCSQTQENTECTVCLFLVQKKPLIFLGC

CFFSTLVLLLSIAIFQRQKRRKFWKAKNLQHIPLKKGKRVVS.

In certain embodiments, a KLB protein can include a N-terminal signal sequence having the amino acid sequence (SEQ ID NO: 157)
MKPGCAAGSPGNEWIFFSTDEITTRYRNTMSNGGLQRSVILSALILRAVT

G.

The term "C-terminal domain of KLB" refers to the carboxy-terminal glycosidase-like domain of KLB. For example, the C-terminal domain of the exemplary KLB protein shown in SEQ ID NO: 145 comprises the following amino acid sequence:

(SEQ ID NO: 155)
FPCDFSWGVTESVLKPESVASSPQFSDPHLYVWNATGNRLLHRVEGVRLK

TRPAQCTDFVNIKKQLEMLARMKVTHYRFALDWASVLPTGNLSAVNRQAL

RYYRCVVSEGLKLGISAMVTLYYPTHAHLGLPEPLLHADGWLNPSTAEAF

QAYAGLCFQELGDLVKLWITINEPNRLSDIYNRSGNDTYGAAHNLLVAHA

LAWRLYDRQFRPSQRGAVSLSLHADWAEPANPYADSHWRAAERFLQFEIA

WFAEPLFKTGDYPAAMREYIASKHRRGLSSSALPRLTEAERRLLKGTVDF

CALNHFTTRFVMHEQLAGSRYDSDRDIQFLQDITRLSSPTRLAVIPWGVR

KLLRWVRRNYGDMDIYITASGIDDQALEDDRLRKYYLGKYLQEVLKAYLI

DKVRIKGYYAFKLAEEKSKPRFGFFTSDFKAKSSIQFYNKVISSRGFPFE

NSSSR.

The terms "anti-KLB antibody" and "an antibody that binds to KLB" refer to an antibody that is capable of binding KLB with sufficient affinity such that the antibody is useful as a diagnostic and/or therapeutic agent in targeting KLB. In one embodiment, the extent of binding of an anti-KLB antibody to an unrelated, non-KLB protein is less than about 10% of the binding of the antibody to KLB as measured, e.g., by a radioimmunoassay (RIA). In certain embodiments, an antibody that binds to KLB has a dissociation constant ($K_d$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-KLB antibody binds to an epitope of KLB that is conserved among KLB from different species. In certain embodiments, an anti-KLB antibody binds to an epitope on KLB that is in the C-terminal part of the protein.

The term "Fibroblast Growth Factor Receptor 1" or "FGFR1," as used herein, refers to any native FGFR1 from any vertebrate source, including mammals such as primates (e.g., humans) and rodents (e.g., mice and rats), unless otherwise indicated. The term encompasses "full-length," unprocessed FGFR1 as well as any form of FGFR1 that results from processing in the cell. The term also encompasses naturally occurring variants of FGFR1, e.g., splice variants or allelic variants, including FGFR1c. A non-limiting example of a human FGFR1c amino acid is shown below:

(SEQ ID NO: 146)
MWSWKCLLFWAVLVTATLCTARPSPTLPEQAQPWGAPVEVESFLVHPGDL

LQLRCRLRDDVQSINWLRDGVQLAESNRTRITGEEVEVQDSVPADSGLYA

CVTSSPSGSDTTYFSVNVSDALPSSEDDDDDDSSSEEKETDNTKPNPVA

```
PYWTSPEKMEKKLHAVPAAKTVKFKCPSSGTPNPTLRWLKNGKEFKPDHR

IGGYKVRYATWSIIMDSVVPSDKGNYTCIVENEYGSINHTYQLDVVERSP

HRPILQAGLPANKTVALGSNVEFMCKVYSDPQPHIQWLKHIEVNGSKIGP

DNLPYVQILKTAGVNTTDKEMEVLHLRNVSFEDAGEYTCLAGNSIGLSHH

SAWLTVLEALEERPAVMTSPLYLEIIIYCTGAFLISCMVGSVIVYKMKSG

TKKSDFHSQMAVHKLAKSIPLRRQVTVSADSSASMNSGVLLVRPSRLSSS

GTPMLAGVSEYELPEDPRWELPRDRLVLGKPLGEGCFGQVVLAEAIGLDK

DKPNRVTKVAVKMLKSDATEKDLSDLISEMEMMKMIGKHKNIINLLGACT

QDGPLYVIVEYASKGNLREYLQARRPPGLEYCYNPSHNPEEQLSSKDLVS

CAYQVARGMEYLASKKCIHRDLAARNVLVTEDNVMKIADFGLARDIHHID

YYKKTTNGRLPVKWMAPEALFDRIYTHQSDVWSFGVLLWEIFTLGGSPYP

GVPVEELFKLLKEGHRMDKPSNCTNELYMMMRDCWHAVPSQRPTFKQLVE

DLDRIVALTSNQEYLDLSMPLDQYSPSFPDTRSSTCSSGEDSVFSHEPLP

EEPCLPRHPAQLANGG LKRR.
```

The terms "anti-FGFR1c antibody" refers to an antibody that is capable of binding FGFR1c with sufficient affinity such that the antibody is useful as a diagnostic and/or therapeutic agent in targeting FGFR1c. In one embodiment, the extent of binding of an anti-FGFR1c antibody to an unrelated, non-FGFR1c protein is less than about 10% of the binding of the antibody to FGFR1c as measured, e.g., by a radioimmunoassay (RIA). In certain embodiments, an antibody that binds to FGFR1c has a dissociation constant ($K_d$) of ≤1 M, ≤100 mM, ≤10 mM, ≤1 mM, ≤100 μM, ≤10 μM, ≤1 μM, ≤100 nM, ≤10 nM, ≤1 nM, ≤0.1 nM, ≤0.01 nM, or ≤0.001 nM. In certain embodiments, the $K_d$ of an antibody that binds to FGFR1c, disclosed herein, can be $10^{-3}$ M or less, or $10^{-8}$ M or less, e.g., from $10^{-8}$ M to $10^{-13}$ M, e.g., from $10^{-9}$ M to $10^{-13}$ M. In certain embodiments, an anti-FGFR1c antibody binds to an epitope of FGFR1c that is conserved among FGFR1c from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that competes for binding" with a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is described in "Antibodies," Harlow and Lane (Cold Spring Harbor Press, Cold Spring Harbor, N.Y.).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{53}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result. For example, and not by way of limitation, an "effective amount" can refer to an amount of an antibody, disclosed herein, that is able to alleviate, minimize and/or prevent the symptoms of the disease and/or disorder, prolong survival and/or prolong the period until relapse of the disease and/or disorder.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" as used interchangeably herein, refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), Vols. 1-3. In certain embodiments, for the VL, the subgroup is subgroup kappa I as in Kabat et al., supra. In certain embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Unless otherwise indicated, HVR residues and other residues in the variable domain (e.g., FR residues) are numbered herein according to Kabat et al., supra. Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Figure 3A:
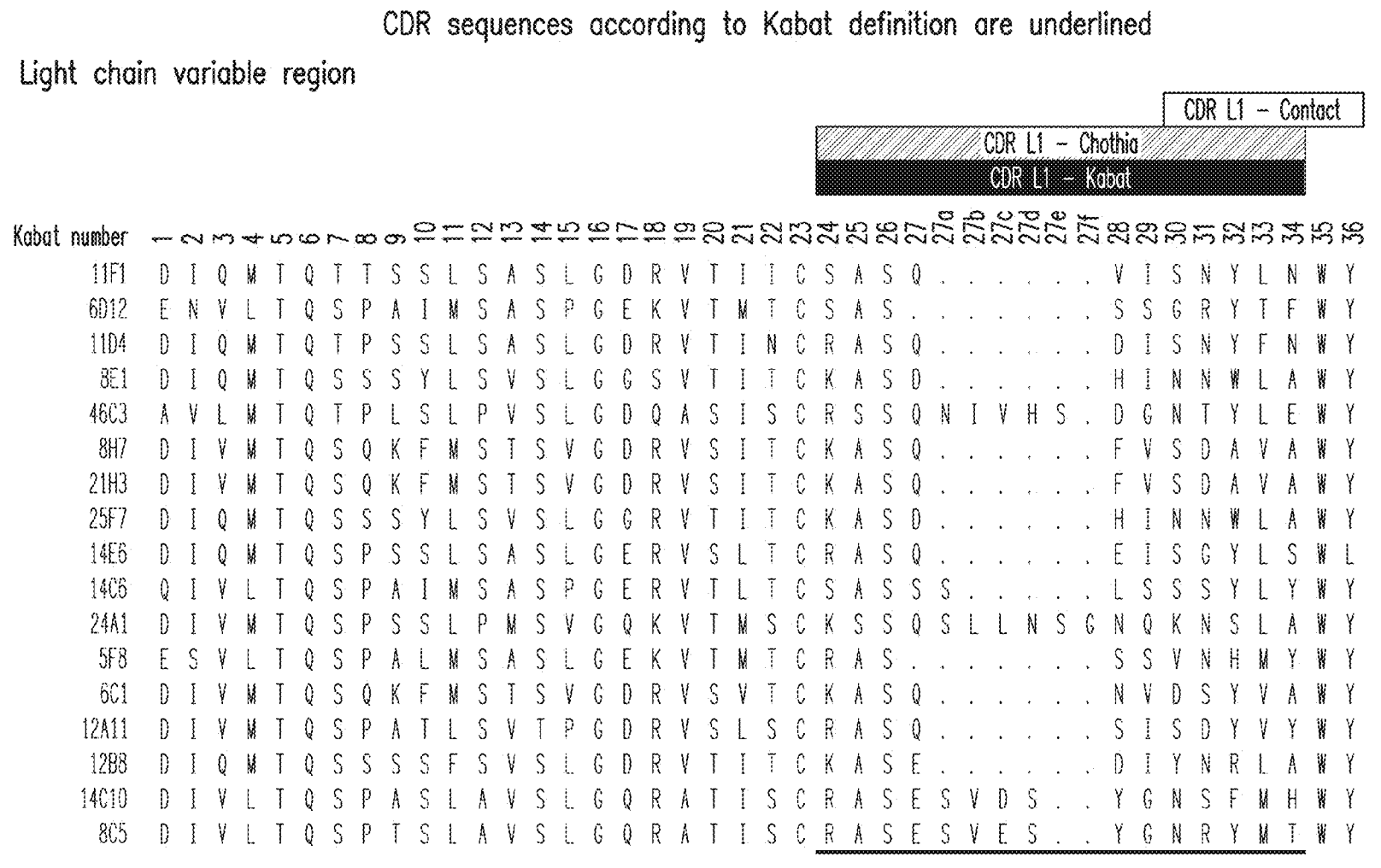
Figure 3A:
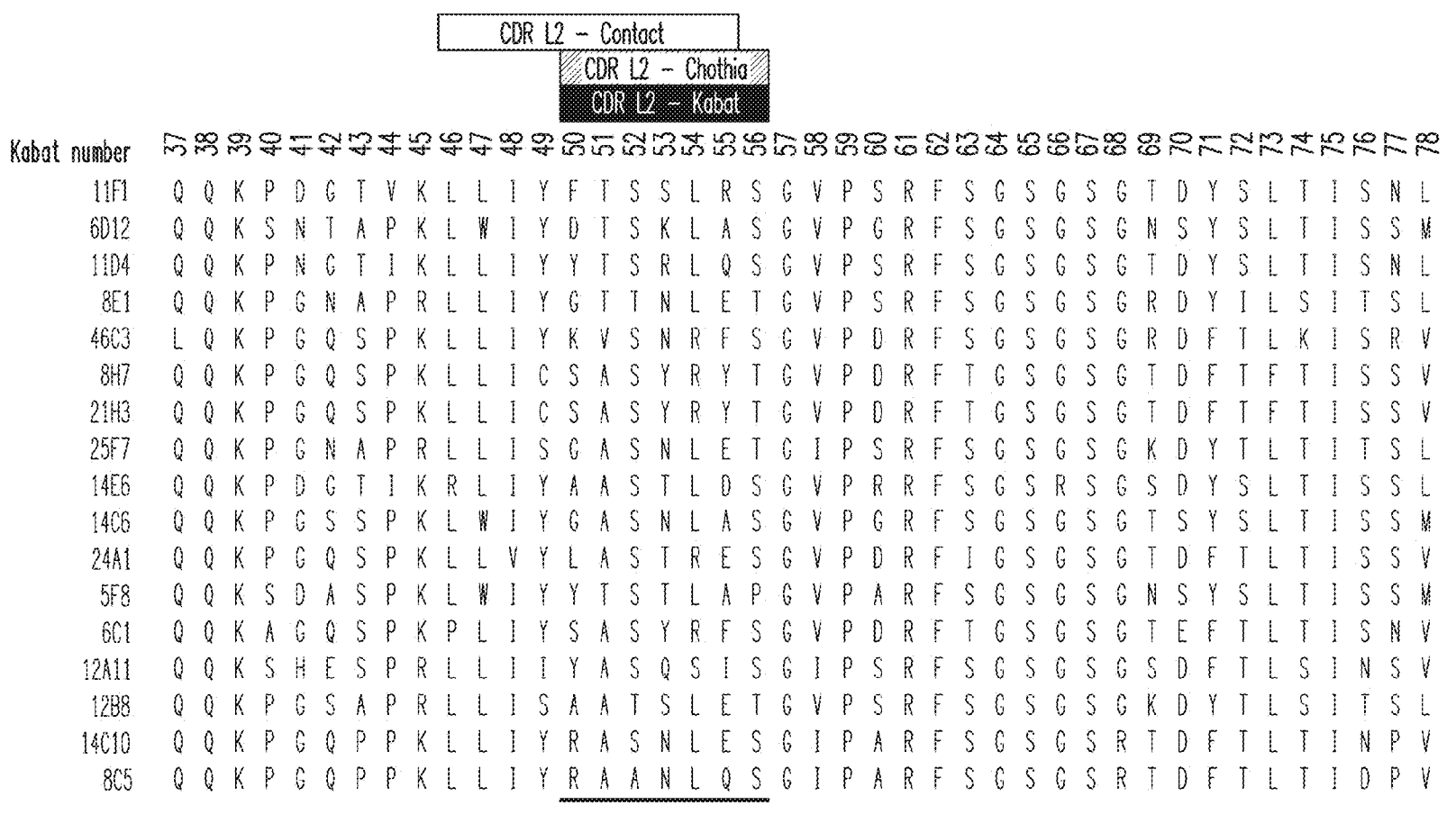
Figure 3A:
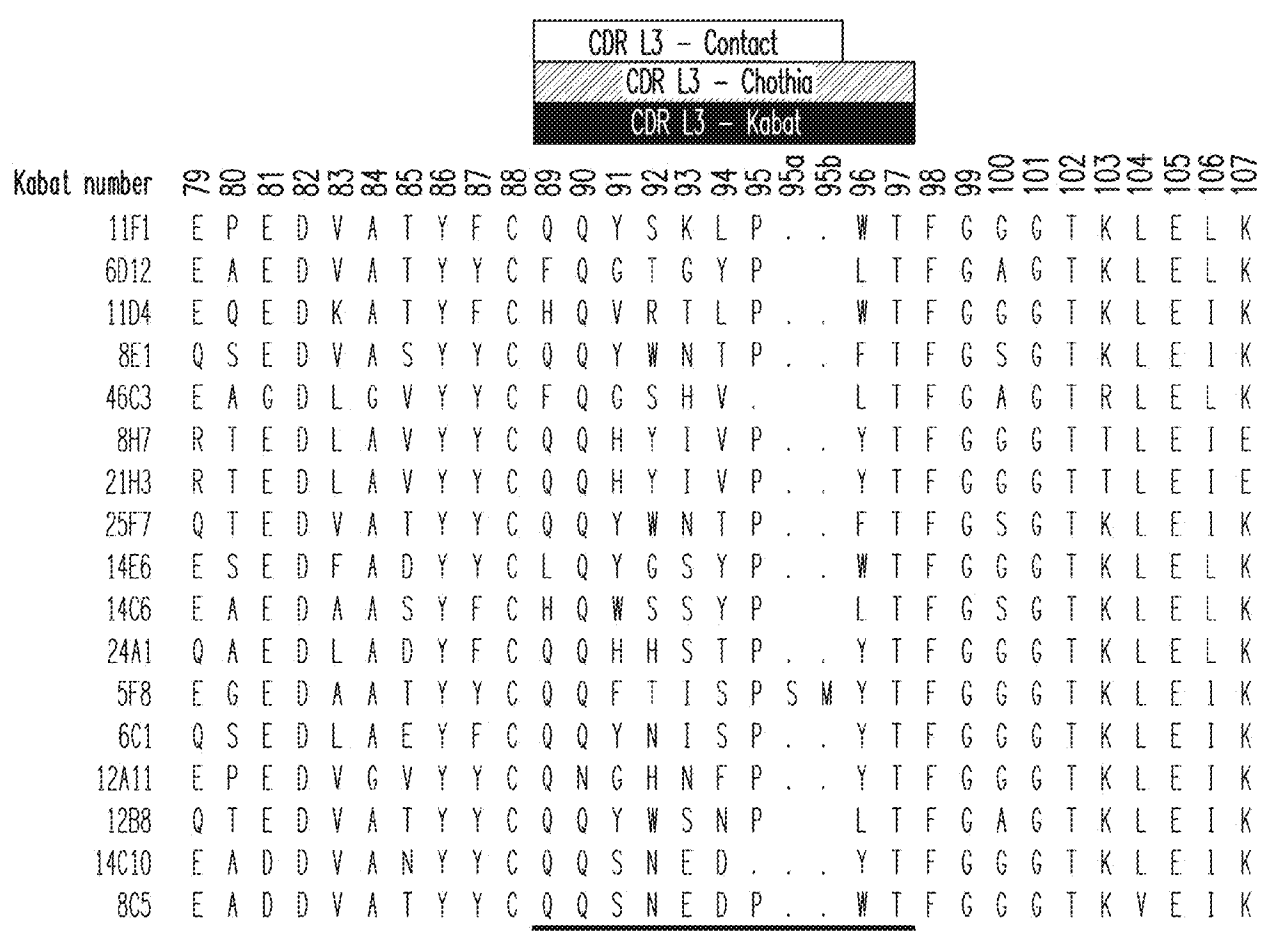
Figure 3B:
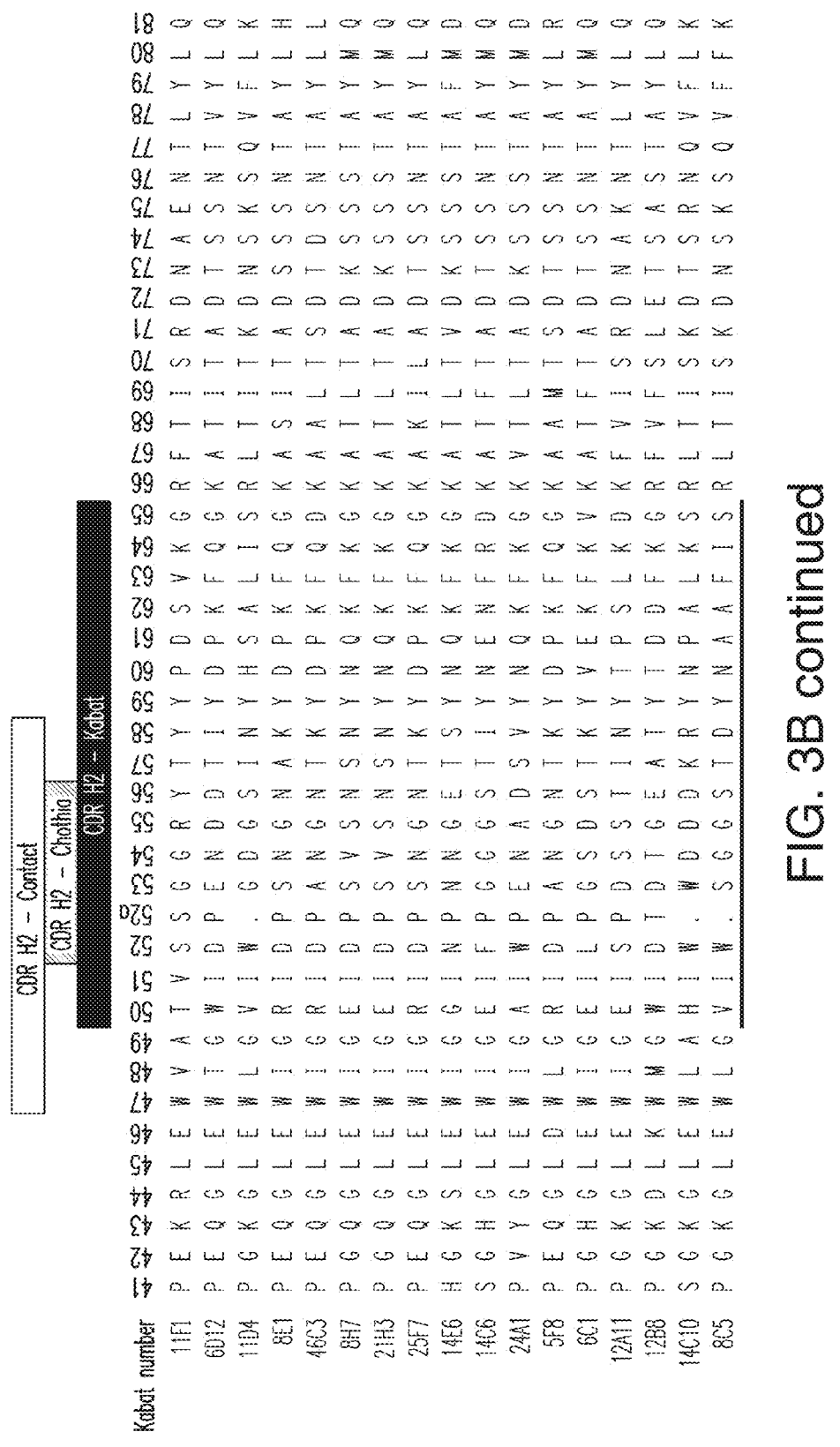
Figure 3B:
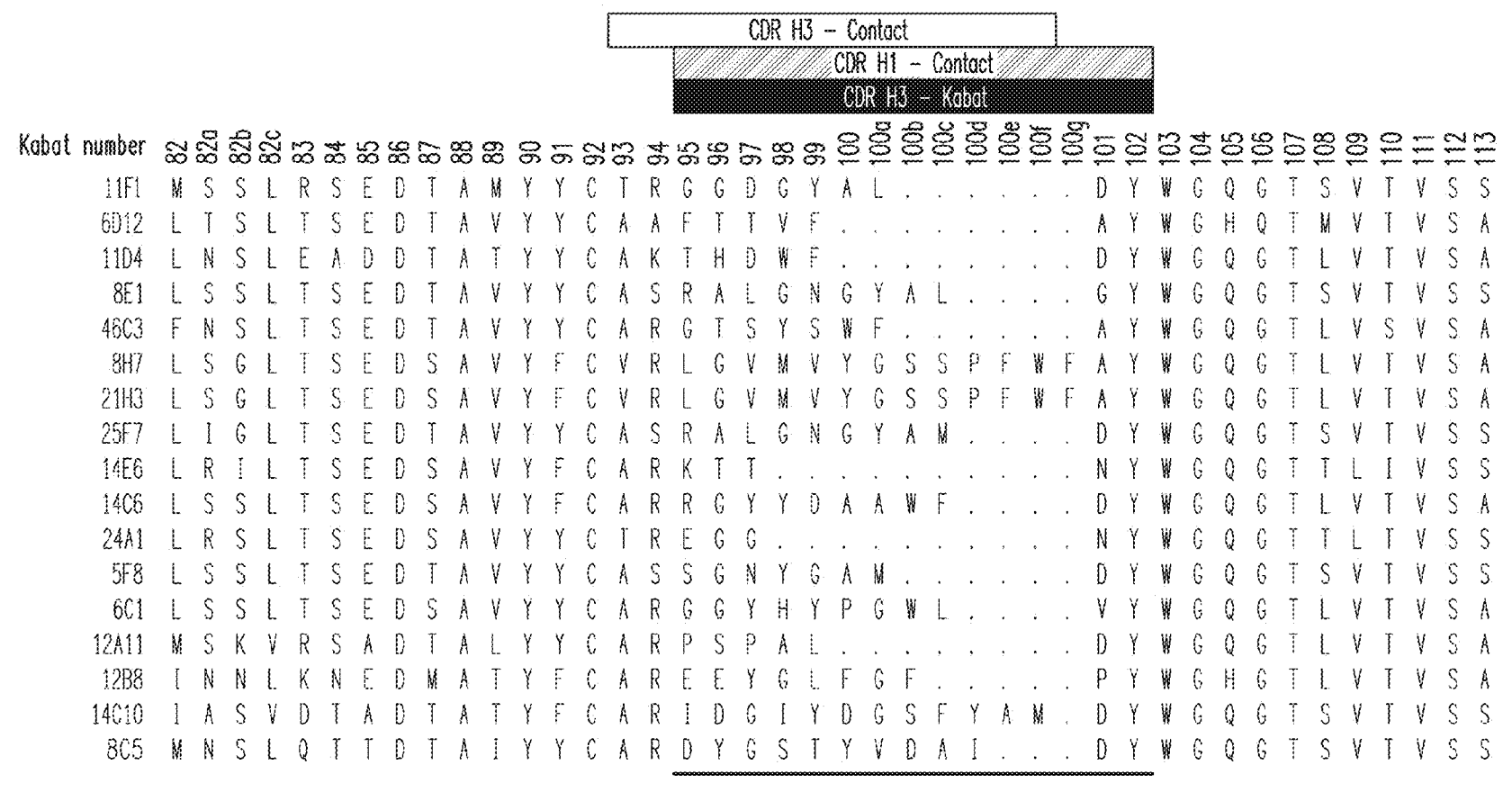

In certain embodiments, HVR residues comprise those identified in FIG. 3A or FIG. 3B or elsewhere in the specification.

An "immunoconjugate" refers to an antibody conjugated to one or more heterologous molecule(s), including but not limited to a cytotoxic agent.

An "individual" or "subject," as used interchangeably herein, is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" (including references to a specific antibody, e.g., an anti-KLB antibody) refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert," as used herein, refers to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier," as used herein, refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the present disclosure can be used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Antibodies

In one aspect, the invention is based, in part, on the discovery of bispecific antibodies that bind to both KLB and FGFR1c and selectively activate the FGFR1c/KLB receptor complex and induce the beneficial metabolic changes expected from the FGF21-like activity, including weight loss, and improvement in glucose and lipid metabolism, without a significant impact on the liver and without loss in bone mass.

In certain embodiments, antibodies that bind to KLB are provided. The present disclosure further provides anti-FGFR1 antibodies, e.g., anti-FGFR1c antibodies. The present disclosure further provides bispecific antibodies that bind to both KLB and FGFR1 (referred to herein as anti-KLB/anti-FGFR1 bispecific antibodies). In certain embodiments, an anti-KLB/anti-FGFR1 bispecific antibody of the present disclosure binds to both KLB and FGFR1c. In certain embodiments, the antibodies of the present disclosure include antibodies that do not block binding and/or interaction of the FGF ligands, e.g., FGF19 and FGF21, to the KLB/FGFR1c complex.

In certain embodiments, an antibody of the present disclosure does not have a significant impact on the liver, e.g., liver function. Without being limited to a particular theory, an antibody of the present disclosure does not result in the activation of the FGFR1c/KLB receptor complex in the liver. In certain embodiments, an antibody of the present disclosure does not modulate the activity of an FGFR/KLB receptor complex in the liver as compared to the modulation of an FGFR/KLB receptor complex in the liver by an FGF21 protein. In certain embodiments, an antibody of the present disclosure does not result in the inhibition of the FGFR4/KLB complex and/or does not result in the elevation of liver enzymes such as, but not limited to, ALT, AST, ALP and GLDH. In certain embodiments, an antibody of the present disclosure does not function as an agonist of the FGFR2c/KLB complex and/or the FGFR3c/KLB complex in the liver, which can lead to activated MAPK signaling and/or altered expression of Spry4 and Dusp6 in the liver. In certain embodiments, an antibody of the present disclosure does not result in the activation of MAPK signaling in the liver as compared to the activation of MAPK signaling by an FGF21 protein. In certain embodiments, an antibody of the present disclosure does not function as an agonist of the FGFR4/KLB complex in the liver.

In certain embodiments, an antibody of the present disclosure can be humanized. In certain embodiments, an antibody of the present disclosure comprises an acceptor human framework, e.g., a human immunoglobulin framework or a human consensus framework.

In certain embodiments, an antibody of the present disclosure can be a monoclonal antibody, including a chimeric, humanized or human antibody. In certain embodiments, an antibody of the present disclosure can be an antibody fragment, e.g., a Fv, Fab, Fab', scFv, diabody, or F(ab')$_2$ fragment. In certain embodiments, the antibody is a full length antibody, e.g., an intact IgG1 antibody, or other antibody class or isotype as defined herein. In a certain embodiments, an antibody of the present disclosure can incorporate any of the features, singly or in combination, as described in Sections 1-7, detailed below.

Antibodies of the present disclosure are useful, e.g., for the diagnosis or treatment of metabolic disorders. Non-limiting examples of metabolic disorders include polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), maturity onset diabetes of the young (MODY), and aging and related diseases such as Alzheimer's disease, Parkinson's disease and ALS.

A. Exemplary Anti-KLB Antibodies

In one aspect, the present disclosure provides isolated antibodies that bind to a KLB protein. In certain embodiments, an anti-KLB antibody of the present disclosure binds to the C-terminal domain of KLB. In certain embodiments, an anti-KLB antibody of the present disclosure binds to a fragment of KLB that comprises the amino acid sequence SSPTRLAVIPWGVRKLLRWVRRNYGDMDIYITAS (SEQ ID NO: 142). In certain embodiments, the antibody binds to the same epitope as an anti-KLB antibody, e.g., 8C5, described herein.

In certain embodiments, an anti-KLB antibody of the present disclosure comprises at least one, two, three, four, five, or six HVRs selected from (a) HVR-H1 comprising an amino acid sequence of any one of SEQ ID NOs: 1-15, e.g., 12 or 15; (b) HVR-H2 comprising an amino acid sequence of any one of SEQ ID NOs: 16-31, e.g., 28 or 31; (c) HVR-H3 comprising an amino acid sequence of any one of SEQ ID NOs: 32-47, e.g., 44 or 47; (d) HVR-L1 comprising an amino acid sequence of any one of SEQ ID NOs: 48-62, e.g., 49 or 62; (e) HVR-L2 comprising an amino acid sequence of any one of SEQ ID NOs: 63-78, e.g., 75 or 78; and (f) HVR-L3 comprising an amino acid sequence of any one of SEQ ID NOs: 79-93, e.g., 90 or 93.

In certain embodiments, the present disclosure provides an anti-KLB antibody comprising at least one, two, three, four, five, or six HVRs selected from (a) HVR-H1 comprising SEQ ID NO: 12; (b) HVR-H2 comprising SEQ ID NO: 28; (c) HVR-H3 comprising SEQ ID NO: 44; (d) HVR-L1 comprising SEQ ID NO: 49; (e) HVR-L2 comprising SEQ ID NO: 75; and (f) HVR-L3 comprising SEQ ID NO: 90. In certain embodiments, the present disclosure provides an anti-KLB antibody comprising at least one, two, three, four, five, or six HVRs selected from (a) HVR-H1 comprising SEQ ID NO: 15; (b) HVR-H2 comprising SEQ ID NO 31; (c) HVR-H3 comprising SEQ ID NO: 47; (d) HVR-L1 comprising SEQ ID NO 62; (e) HVR-L2 comprising SEQ ID NO: 78; and (f) HVR-L3 comprising SEQ ID NO: 93.

The present disclosure further provides an anti-KLB antibody that comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 128. In certain embodiments, a VH sequence having at least 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-KLB antibody comprising that sequence retains the ability to bind to KLB. In certain embodiments, a total of 1 to 10 amino acids have been substituted, inserted and/or deleted in SEQ ID NO: 128. In certain embodiments, substitutions, insertions, or deletions occur in regions outside the HVRs (i.e., in the FRs). Alternatively or additionally, the anti-KLB antibody comprises the VH sequence in SEQ ID NO: 128, including post-translational modifications of that sequence as disclosed below. In certain embodiments, the VH comprises one, two or three HVRs selected from: (a) HVR-H1 comprising the amino acid sequence of SEQ ID NO: 15, (b) HVR-H2 comprising the amino acid sequence of SEQ ID NO: 31, and (c) HVR-H3 comprising the amino acid sequence of SEQ ID NO: 47.

In another aspect, the present disclosure provides an anti-KLB antibody, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 130. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLB antibody comprising that sequence retains the ability to bind to KLB. In certain embodiments, a total of 1 to 10 amino acids have been substituted, inserted and/or deleted in SEQ ID NO: 130. In certain embodiments, the substitutions, insertions, or deletions occur in regions outside the HVRs (i.e., in the FRs). Alternatively or additionally, the anti-KLB antibody comprises the VL sequence in SEQ ID NO: 130, including post-translational modifications of that sequence. In certain embodiments, the VL comprises one, two or three HVRs selected from (a) HVR-L1 comprising the amino acid sequence of SEQ ID NO: 62; (b) HVR-L2 comprising the amino acid sequence of SEQ ID NO: 78; and (c) HVR-L3 comprising the amino acid sequence of SEQ ID NO: 93.

The present disclosure further provides an anti-KLB antibody, wherein the antibody comprises a VH as in any of the embodiments provided above, and a VL as in any of the embodiments provided above. In certain embodiments, the antibody comprises the VH and VL sequences in SEQ ID NO: 128 and SEQ ID NO: 130, respectively, including post-translational modifications of those sequences.

In certain embodiments, an anti-KLB antibody binds to a fragment of KLB consisting of the amino acid sequence SSPTRLAVIPWGVRKLLRWVRRNYGDMDIYITAS (SEQ ID NO: 142).

B. Exemplary Anti-FGFR1 Antibodies

In one aspect, the present disclosure provides isolated antibodies that bind to a FGFR1 protein. In certain embodiments, an anti-FGFR1 antibody of the present disclosure binds to FGFR1c. In certain embodiments, the present disclosure provides an anti-FGFR1 antibody comprising at least one, two, three, four, five, or six HVRs selected from (a) HVR-H1 comprising SEQ ID NO: 136; (b) HVR-H2 comprising SEQ ID NO: 137; (c) HVR-H3 comprising SEQ ID NO: 138; (d) HVR-L1 comprising SEQ ID NO: 139; (e) HVR-L2 comprising SEQ ID NO: 140; and (f) HVR-L3 comprising SEQ ID NO: 141.

In certain embodiments, an anti-FGFR1 antibody of the present disclosure comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 132. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR1 antibody comprising that sequence retains the ability to bind to FGFR1. In certain embodiments, a total of 1 to 10 amino acids have been substituted, inserted and/or deleted in SEQ ID NO: 132. In certain embodiments, substitutions, insertions, or deletions occur in regions outside the HVRs (i.e., in the FRs). Alternatively or additionally, the anti-FGFR1 antibody comprises the VH sequence in SEQ ID NO: 132, including post-translational modifications of that sequence. In certain embodiments, the VH comprises one, two or three HVRs selected from: (a) HVR-H1 comprising the amino acid sequence of SEQ ID NO: 136, (b) HVR-H2 comprising the amino acid sequence of SEQ ID NO: 137, and (c) HVR-H3 comprising the amino acid sequence of SEQ ID NO: 138.

The present disclosure further provides an anti-FGFR1 antibody, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 134. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR1 antibody comprising that sequence retains the ability to bind to FGFR1. In certain embodiments, a total of 1 to 10 amino acids have been substituted, inserted and/or deleted in SEQ ID NO: 134. In certain embodiments, the substitutions, insertions, or deletions occur in regions outside the HVRs (i.e., in the FRs). Alternatively or additionally, the anti-FGFR1 antibody comprises the VL sequence in SEQ ID NO: 134, including post-translational modifications of that sequence. In a particular embodiment, the VL comprises one, two or three HVRs selected from (a) HVR-L1 comprising the amino acid sequence of SEQ ID NO: 139; (b) HVR-L2 comprising the amino acid sequence of SEQ ID NO: 140; and (c) HVR-L3 comprising the amino acid sequence of SEQ ID NO: 141.

In another aspect, an anti-FGFR1 antibody is provided, wherein the antibody comprises a VH as in any of the embodiments provided above, and a VL as in any of the embodiments provided above. In certain embodiments, the anti-FGFR1 antibody comprises the VH and VL sequences in SEQ ID NO: 132 and SEQ ID NO: 134, respectively, including post-translational modifications of those sequences.

In certain embodiments, an FGFR1 antibody of the present disclosure binds to a fragment of FGFR1c consisting of the amino acid sequence KLHAVPAAKTVKFKCP (SEQ ID NO: 143) or FKPDHRIGGYKVRY (SEQ ID NO: 144).

C. Exemplary Anti-KLB/Anti-FGFR1 Bispecific Antibodies

The present disclosure further provides bispecific antibodies that bind to both KLB and FGFR1 (i.e., anti-KLB/anti-FGFR1 bispecific antibodies). A bispecific antibody has two different binding specificities, see, e.g., U.S. Pat. Nos. 5,922,845 and 5,837,243; Zeilder (1999) J. Immunol. 163: 1246-1252; Somasundaram (1999) Hum. *Antibodies* 9:47-54; Keler (1997) *Cancer Res.* 57:4008-4014. For example, and not by way of limitation, the presently disclosed subject matter provides bispecific antibodies having one binding site (e.g., antigen binding site) for a first epitope present on KLB and a second binding site for a second epitope present on FGFR1. For example, and not by way of limitation, the present disclosure provides an antibody where one arm binds KLB and comprises any of the anti-KLB antibody sequences described herein and the second arm binds to FGFR1 and comprises any of the anti-FGFR1 antibody sequences described herein. In certain embodiments, an anti-KLB/anti-FGFR1 bispecific antibody of the present disclosure has one binding site for a first epitope present on KLB and a second binding site for a second epitope present on FGFR1c.

In certain embodiments, an anti-KLB/anti-FGFR1 bispecific antibody disclosed herein refers to an antibody that modulates KLB/FGFR1c complex activity. For example, the bispecific anti-KLB/anti-FGFR1 bispecific antibody can function as an agonist and activate the KLB/FGFR1c complex. In certain embodiments, an anti-KLB/anti-FGFR1 bispecific antibody is an antibody that increases the activity of the KLB/FGFR1c complex by at least 10%, 20%, 30%, 40%, 50%, 60%, 70%, 80%, 90%, 99% or 99.9%. In certain embodiments, the anti-KLB/anti-FGFR1 bispecific can be an antibody that results in the phosphorylation of the downstream targets of the KLB/FGFR1c complex, e.g., MAPK and/or ERK.

In certain embodiments, an anti-KLB/anti-FGFR1 bispecific antibody disclosed herein refers to an antibody that modulates KLB/FGFR1c complex activity and does not block the interaction and/or binding of the native FGF ligands, e.g., FGF19 and FGF21, to the KLB/FGFR1c complex. In certain embodiments, an anti-KLB/anti-FGFR1 bispecific antibody disclosed herein refers to an antibody that does not block the activity and/or binding of native FGF ligands to a FGF receptor in the absence of KLB. For example, and not by way of limitation, an anti-KLB/anti-FGFR1 bispecific antibody of the present disclosure does not block the interaction of native FGF ligands with the FGFR1/KLA complex and/or FGFR1 alone. In certain embodiments, an anti-KLB/anti-FGFR1 bispecific antibody disclosed herein refers to an antibody that does not block the activity and/or binding of native FGF ligands to KLB in the absence of FGFR1. For example, and not by way of limitation, an anti-KLB/anti-FGFR1 bispecific antibody of the present disclosure does not block the interaction of native FGF ligands with the FGFR4/KLB complex, the FGFR2c/KLB complex and/or the FGFR3c/KLB complex.

In certain embodiments, an anti-KLB/anti-FGFR1 bispecific antibody, e.g., an anti-KLB/anti-FGFR1c bispecific antibody, or an antigen-binding portion thereof, includes a heavy chain and a light chain region. In certain embodiments, the full length heavy chain includes amino acids having a sequence that is at least 90%, 91%, 92%, 93%, 94%, 95%, 96%, 97%, 98%, 99%, or 100% identical to the sequence set forth in SEQ ID NO: 129. In certain embodiments, the full length light chain includes amino acids having a sequence that is at least 90%, 91%, 92%, 93%, 94%, 95%, 96%, 97%, 98%, 99%, or 100% identical to the sequence set forth in SEQ ID NO: 131. In certain embodiments, the full length heavy chain includes amino acids having the sequence set forth in SEQ ID NO: 129. In certain embodiments, the full length light chain includes amino acids having the sequence set forth in SEQ ID NO: 131.

In certain embodiments, an anti-KLB/anti-FGFR1 bispecific antibody, e.g., an anti-KLB/anti-FGFR1c bispecific antibody, or an antigen-binding portion thereof, includes a heavy chain variable region and a light chain variable region. In certain embodiments, the heavy chain variable region includes amino acids having a sequence that is at least 90%, 91%, 92%, 93%, 94%, 95%, 96%, 97%, 98%, 99%, or 100% identical to the sequence set forth in SEQ ID NO: 128. In certain embodiments, the light chain variable region includes amino acids having a sequence that is at least 90%, 91%, 92%, 93%, 94%, 95%, 96%, 97%, 98%, 99%, or 100% identical to the sequence set forth in SEQ ID NO: 130. In certain embodiments, the heavy chain variable region includes amino acids having the sequence set forth in SEQ ID NO: 128. In certain embodiments, the light chain variable region includes amino acids having the sequence set forth in SEQ ID NO: 130.

In certain embodiments, an anti-KLB/anti-FGFR1 bispecific antibody comprises at least one, two, three, four, five, or six HVRs selected from (a) HVR-H1 comprising an amino acid sequence of any one of SEQ ID NOs: 1-15, e.g., 12 or 15; (b) HVR-H2 comprising an amino acid sequence of any one of SEQ ID NOs: 16-31, e.g., 28 or 31; (c) HVR-H3 comprising an amino acid sequence of any one of SEQ ID NOs: 32-47, e.g., 44 or 47; (d) HVR-L1 comprising an amino acid sequence of any one of SEQ ID NOs: 48-62, e.g., 49 or 62; (e) HVR-L2 comprising an amino acid sequence of any one of SEQ ID NOs: 63-78, e.g., 75 or 78; and (f) HVR-L3 comprising an amino acid sequence of any one of SEQ ID NOs: 79-93, e.g., 90 or 93.

In certain embodiments, an anti-KLB/anti-FGFR1 bispecific antibody, e.g., an anti-KLB/anti-FGFR1c bispecific antibody, comprises at least one, two, three, four, five, or six HVRs selected from (a) HVR-H1 comprising SEQ ID NO: 12; (b) HVR-H2 comprising SEQ ID NO: 28; (c) HVR-H3 comprising SEQ ID NO: 44; (d) HVR-L1 comprising SEQ ID NO: 49; (e) HVR-L2 comprising SEQ ID NO: 75; and (f) HVR-L3 comprising SEQ ID NO: 90. In certain embodiments, the present disclosure provides an anti-KLB antibody comprising at least one, two, three, four, five, or six HVRs selected from (a) HVR-H1 comprising SEQ ID NO: 15; (b) HVR-H2 comprising SEQ ID NO: 31; (c) HVR-H3 comprising SEQ ID NO: 47; (d) HVR-L1 comprising SEQ ID NO: 62; (e) HVR-L2 comprising SEQ ID NO: 78; and (f) HVR-L3 comprising SEQ ID NO: 93.

In certain embodiments, an anti-KLB/anti-FGFR1 bispecific antibody, e.g., an anti-KLB/anti-FGFR1c bispecific antibody, includes a heavy chain variable region that comprises CDR1, CDR2, and CDR3 domains, and a light chain variable region that comprises CDR1, CDR2, and CDR3 domains. In certain embodiments, the heavy chain variable region CDR1 domain includes an amino acid sequence having a sequence set forth in SEQ ID NO: 1-15. In certain embodiments, the heavy chain variable region CDR2 domain includes an amino acid sequence a sequence set forth in SEQ ID NO: 16-31. In certain embodiments, the heavy chain variable region CDR3 domain includes an amino acid sequence having a sequence that is at least 90%, 91%, 92%, 93%, 94%, 95%, 96%, 97%, 98%, 99%, or 100% identical to SEQ ID NO: 32-47. In certain embodiments, the light chain variable region CDR1 domain includes an amino acid sequence having a sequence that is at least 90%, 91%, 92%, 93%, 94%, 95%, 96%, 97%, 98%, 99%, or 100% identical to SEQ ID NO: 48-62. In certain embodiments, the light chain variable region CDR2 domain includes an amino acid sequence having a sequence that is at least 90%, 91%, 92%, 93%, 94%, 95%, 96%, 97%, 98%, 99%, or 100% identical to SEQ ID NO: 63-78. In certain embodiments, the light chain variable region CDR3 domain includes an amino acid sequence having a sequence that is at least 90%, 91%, 92%, 93%, 94%, 95%, 96%, 97%, 98%, 99%, or 100% identical to SEQ ID NO: 79-93.

In certain embodiments, an anti-KLB/anti-FGFR1 bispecific antibody, e.g., an anti-KLB/anti-FGFR1c bispecific antibody, includes a heavy chain variable region that comprises CDR1, CDR2, and CDR3 domains, and a light chain variable region that comprises CDR1, CDR2, and CDR3 domains. In certain embodiments, the heavy chain variable region CDR1 domain includes an amino acid sequence having a sequence set forth in SEQ ID NO: 1-15. In certain embodiments, the heavy chain variable region CDR2 domain includes an amino acid sequence having a sequence set forth in SEQ ID NO: 16-31. In certain embodiments, the heavy chain variable region CDR3 domain includes an amino acid sequence having a sequence set forth in SEQ ID NO: 32-47. In certain embodiments, the light chain variable region CDR1 domain includes an amino acid sequence having a sequence set forth in SEQ ID NO: 48-62. In certain embodiments, the light chain variable region CDR2 domain includes an amino acid sequence having a sequence set forth in SEQ ID NO: 63-78. In certain embodiments, the light chain variable region CDR3 domain includes an amino acid sequence having a sequence set forth in SEQ ID NO: 79-93.

In certain embodiments, an anti-KLB/anti-FGFR1 bispecific antibody, e.g., an anti-KLB/anti-FGFR1c bispecific antibody, includes a heavy chain variable region CDR1 having the sequence set forth in SEQ ID NO: 15; a heavy chain variable region CDR2 having the sequence set forth in SEQ ID NO: 31; a heavy chain variable region CDR3 having the sequence set forth in SEQ ID NO: 47; a light chain variable region CDR1 having the sequence set forth in SEQ ID NO: 62; a light chain variable region CDR2 having the sequence set forth in SEQ ID NO: 78; and a light chain variable region CDR3 having the sequence set forth in SEQ ID NO: 93.

In certain embodiments, an anti-KLB/anti-FGFR1 bispecific antibody includes a first antibody, or antigen binding portion thereof, and includes a second antibody, or antigen binding portion thereof, where the first antibody, or antigen binding portion thereof, binds to an epitope present on KLB, and the second antibody, or antigen binding portion thereof, bind to an epitope present on FGFR1, e.g., FGFR1c. For example, and not by way of limitation, the first antibody, or antigen binding portion thereof, can include a heavy chain variable region and a light chain variable region; and the second antibody, or antigen binding portion thereof, can include a heavy chain variable region and a light chain variable region. In certain embodiments, the heavy chain variable region of the first antibody, or antigen binding portion thereof, includes amino acids having a sequence that is at least 90%, 91%, 92%, 93%, 94%, 95%, 96%, 97%, 98%, 99%, or 100% identical to the sequence set forth in SEQ ID NO: 128. In certain embodiments, the light chain variable region of the first antibody, or antigen binding portions thereof, includes amino acids having a sequence that is at least 90%, 91%, 92%, 93%, 94%, 95%, 96%, 97%, 98%, 99%, or 100% identical to the sequence set forth in SEQ ID NO: 130. In certain embodiments, the heavy chain variable region of the second antibody or antigen binding portion thereof includes amino acids having a sequence that is at least 90%, 91%, 92%, 93%, 94%, 95%, 96%, 97%, 98%, 99%, or 100% identical to the sequence set forth in SEQ ID NO: 132. In certain embodiments, the light chain variable region of the second antibody, or antigen binding portions thereof, includes amino acids having a sequence that is at least 90%, 91%, 92%, 93%, 94%, 95%, 96%, 97%, 98%, 99%, or 100% identical to the sequence set forth in SEQ ID NO: 134.

In certain embodiments, an anti-KLB/anti-FGFR1 bispecific antibody that binds to the same epitope as an anti-KLB antibody is provided herein. For example, in certain embodiments, an anti-KLB/anti-FGFR1 bispecific antibody is provided that binds to the same epitope as an anti-KLB antibody comprising the VH sequence of SEQ ID NO: 128 and a VL sequence of SEQ ID NO: 130. In certain embodiments, an anti-KLB/anti-FGFR1 bispecific antibody is provided that binds to a fragment of KLB consisting of the amino acid sequence SSPTRLAVIPWGVRKLLRWVRRNYGDMDI-YITAS (SEQ ID NO: 142).

In certain embodiments, an anti-KLB/anti-FGFR1 bispecific antibody is provided that binds to a fragment of KLB having an amino acid sequence that is at least 90%, 91%, 92%, 93%, 94%, 95%, 96%, 97%, 98%, 99%, or 100% identical to the sequence set forth in SEQ ID NO: 142.

In certain embodiments, an anti-KLB/anti-FGFR1 bispecific antibody binds to the same epitope as an anti-KLB antibody is provided herein. For example, in certain embodiments, an anti-KLB/anti-FGFR1 bispecific antibody is provided that binds to the same epitope as an anti-KLB antibody comprising the full length heavy chain sequence of SEQ ID NO: 129 and a full length light chain sequence of SEQ ID NO: 131.

In certain embodiments, the present disclosure provides an anti-KLB/anti-FGFR1 bispecific antibody that binds to the same epitope as an anti-FGFR1 antibody provided herein. For example, in certain embodiments, an anti-KLB/anti-FGFR1 bispecific antibody is provided that binds to the same epitope as an anti-FGFR1 antibody comprising the VH sequence of SEQ ID NO: 132 and a VL sequence of SEQ ID NO: 134. In certain embodiments, an anti-KLB/anti-FGFR1 bispecific antibody is provided that binds to a fragment of FGFR1c comprising amino acid sequence KLHAVPAAK-TVKFKCP (SEQ ID NO: 143) or FKPDHRIGGYKVRY (SEQ ID NO: 144).

In certain embodiments, the present disclosure provides an anti-KLB/anti-FGFR1 bispecific antibody that binds to the same epitope as an anti-FGFR1 antibody provided herein. For example, in certain embodiments, an anti-KLB/anti-FGFR1 bispecific antibody is provided that binds to the same epitope as an anti-FGFR1 antibody comprising the heavy chain sequence of SEQ ID NO: 133 and a light chain sequence of SEQ ID NO: 135.

In certain embodiments, an anti-KLB/anti-FGFR1 bispecific antibody of the present disclosure binds to a fragment of FGFR1c having an amino acid sequence that is at least 90%, 91%, 92%, 93%, 94%, 95%, 96%, 97%, 98%, 99%, or 100% identical to the sequence set forth in SEQ ID NO: 143.

In certain embodiments, an anti-KLB/anti-FGFR1 bispecific antibody of the present disclosure binds to a fragment of FGFR1c having an amino acid sequence that is at least 90%, 91%, 92%, 93%, 94%, 95%, 96%, 97%, 98%, 99%, or 100% identical to the sequence set forth in SEQ ID NO: 144.

In certain embodiments, an anti-KLB/anti-FGFR1 bispecific antibody is provided that binds to a fragment of KLB having an amino acid sequence that is at least 90%, 91%, 92%, 93%, 94%, 95%, 96%, 97%, 98%, 99%, or 100% identical to the sequence set forth in SEQ ID NO: 142, and binds to a fragment of FGFR1c having an amino acid sequence that is at least 90%, 91%, 92%, 93%, 94%, 95%, 96%, 97%, 98%, 99%, or 100% identical to the sequence set forth in SEQ ID NO: 143 or 144.

In certain embodiments, an anti-KLB/anti-FGFR1 bispecific antibody is provided that binds to a fragment of KLB having the amino acid sequence set forth in SEQ ID NO: 142 and binds to a fragment of FGFR1c having the amino acid sequence set forth in SEQ ID NO: 143 or 144.

1. Antibody Affinity

In certain embodiments, an antibody of the present disclosure can have a dissociation constant ($K_d$) of ≤1 M, ≤100 mM, ≤10 mM, ≤1 mM, ≤100 µM, ≤10 µM, ≤1 µM, ≤100 nM, ≤10 nM, ≤1 nM, ≤0.1 nM, ≤0.01 nM, or ≤0.001 nM. In certain embodiments, an antibody of the present disclosure can have a $K_d$ of about $10^{-3}$ or less, or $10^{-8}$ M or less, e.g., from $10^{-8}$ M to $10^{-13}$ M, e.g., from $10^{-9}$ M to $10^{-13}$ M.

In certain embodiments, an anti-KLB/anti-FGFR1 bispecific antibody can include an anti-FGFR1 arm that has a $K_d$ of about 10 nM to about 10 µM. In certain embodiments, an anti-KLB/anti-FGFR1 bispecific antibody with an FGFR1 arm that has a low affinity can mitigate the risk of the anti-KLB/anti-FGFR1 bispecific antibody from binding to FGFR1 tightly in the absence of KLB and preventing the binding and/or activation of FGFR1 by other FGF ligands such as, but not limited to, FGF1, FGF2, FGF8 and FGF23. In certain embodiments, an FGFR1 arm with a low affinity can permit the presence of higher levels of anti-FGFR1 impurities such as, but not limited to, anti-FGFR1 half-knob antibodies, non-covalent anti-FGFR1 dimers, covalent anti-FGFR1 dimers and high-molecular weight species, without resulting in clinically significant side effects. For example, in certain embodiments, approximately 2% high molecular weight species and 1.5% anti-FGFR1 half-antibody can be present in a preparation of an anti-KLB/anti-FGFR1 bispecific antibody of the present disclosure without resulting in adverse biological effects.

In certain embodiments, $K_d$ can be measured by a radiolabeled antigen binding assay (RIA). In certain embodiments, an RIA can be performed with a Fab version of an antibody of interest and its antigen. For example, and not by way of limitation, a solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

In certain embodiments, $K_d$ can be measured using a BIACORE® surface plasmon resonance assay. For example, and not by way of limitation, an assay using a BIACORE®-2000 or a BIACORE®-3000 (Biacore, Inc., Piscataway, N.J.) is performed at 25° C. with immobilized antigen CM5 chips at ~10 response units (RU). In certain embodiments, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) can be calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody of the present disclosure is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

In certain embodiments, an antibody of the present disclosure can be a diabody. Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

In certain embodiments, an antibody of the present disclosure can be a single-domain antibody. Single-domain antibodies are antibody fragments that comprise all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516B).

Antibody fragments can be made by various techniques including, but not limited to, proteolytic digestion of an intact antibody as well as production by recombinant host cells (e.g., *E. coli* or phage), as described herein.

3. Chimeric and Humanized Antibodies

In certain embodiments, an antibody of the present disclosure is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In certain embodiments, a chimeric antibody of the present disclosure comprises a non-human variable region (e.g., a variable region derived from a mouse, rat, hamster, rabbit, or non-human primate, such as a monkey) and a human constant region. In a further example, a chimeric antibody can be a "class switched" antibody in which the class or subclass has been changed from that of the parent antibody. Chimeric antibodies include antigen-binding fragments thereof.

In certain embodiments, a chimeric antibody of the present disclosure can be a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In certain embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody of the present disclosure can be a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the present disclosure can be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). In certain embodiments, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody of the present disclosure can be a multispecific antibody, e.g., a bispecific antibody. Multispecific antibodies are monoclonal antibodies that have binding specificities for at least two different epitopes. In certain embodiments, one of the binding specificities is for an epitope present on KLB and the other is for any other antigen. In certain embodiments, one of the binding specificities is for an epitope present on FGFR1 and the other is for any other antigen. In certain embodiments, a bispecific antibody of the present disclosure can bind an epitope on KLB and can bind an epitope on FGFR1. In certain embodiments, a bispecific antibody of the present disclosure can bind an epitope on KLB and can bind an epitope on FGFR1c. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A).

7. Antibody Variants

The presently disclosed subject matter further provides amino acid sequence variants of the disclosed antibodies. For example, it may be desirable to improve the binding affinity and/or other biological properties of the antibody. Amino acid sequence variants of an antibody can be prepared by introducing appropriate modifications into the nucleotide sequence encoding the antibody, or by peptide synthesis. Such modifications include, but are not limited to, deletions from, and/or insertions into and/or substitutions of residues within the amino acid sequences of the antibody. Any combination of deletion, insertion, and substitution can be made to arrive at the final construct, provided that the final antibody, i.e., modified, possesses the desired characteristics, e.g., antigen-binding.

a) Substitution. Insertion, and Deletion Variants

In certain embodiments, antibody variants can have one or more amino acid substitutions. Sites of interest for substitutional mutagenesis include the HVRs and FRs. Non-limiting examples of conservative substitutions are shown in Table 1 under the heading of "preferred substitutions." Non-limiting examples of more substantial changes are provided in Table 1 under the heading of "exemplary substitutions," and as further described below in reference to amino acid side chain classes. Amino acid substitutions can be introduced into an antibody of interest and the products screened for a desired activity, e.g., retained/improved antigen binding, decreased immunogenicity or improved complement dependent cytotoxicity (CDC) or antibody-dependent cell-mediated cytotoxicity (ADCC).

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |

TABLE 1-continued

| Original Residue | Exemplary Substitutions | Preferred Substitutions |
| --- | --- | --- |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

In certain embodiments, non-conservative substitutions will entail exchanging a member of one of these classes for another class.

In certain embodiments, a type of substitutional variant involves substituting one or more hypervariable region residues of a parent antibody, e.g., a humanized or human antibody. Generally, the resulting variant(s) selected for further study will have modifications, e.g., improvements, in certain biological properties such as, but not limited to, increased affinity, reduced immunogenicity, relative to the parent antibody and/or will have substantially retained certain biological properties of the parent antibody. A non-limiting example of a substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

In certain embodiments, alterations (e.g., substitutions) can be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In certain embodiments of affinity maturation, diversity can be introduced into the variable genes chosen for maturation by any of a variety of methods (e.g., error-prone PCR, chain shuffling, or oligo-nucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding can be specifically identified, e.g., using alanine scanning mutagenesis or modeling. CDR-H3 and CDR-L3 in particular are often targeted.

In certain embodiments, substitutions, insertions, or deletions can occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for Antibody-directed enzyme prodrug therapy (ADEPT)) or a polypeptide which increases the serum half-life of the antibody.

b) Glycosylation variants

In certain embodiments, an antibody of the present disclosure can be altered to increase or decrease the extent to which the antibody is glycosylated. Addition or deletion of glycosylation sites to an antibody may be conveniently accomplished by altering the amino acid sequence such that one or more glycosylation sites is created or removed.

In certain embodiments, where the antibody comprises an Fc region, the carbohydrate attached thereto can be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In certain embodiments, modifications of the oligosaccharide in an antibody of the present disclosure can be made in order to create antibody variants with certain improved properties.

In certain embodiments, antibody variants are provided having a carbohydrate structure that lacks fucose attached (directly or indirectly) to an Fc region. For example, the amount of fucose in such antibody can be from about 1% to about 80%, from about 1% to about 65%, from about 5% to about 65% or from about 20% to about 40% and values in between.

In certain embodiments, the amount of fucose can be determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 can also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004).

Defucosylated antibodies can be produced in any cell line that are deficient in protein fucosylation. Non-limiting examples of cell lines include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Non-limiting examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants can have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications can be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the present disclosure provides an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods can be employed (see, for example, ACTI™ non-radioactive cytotoxicity assay for flow cytometry (Cell Technology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays can also be carried out to confirm that the antibody is unable to bind C1q and hence lacks CDC activity. See, e.g., C1q and C3c binding ELISA in WO 2006/029879 and WO 2005/100402. To assess complement activation, a CDC assay can be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)). In certain embodiments, alterations can be made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. See, e.g., U.S. Pat. No. 6,737,056; WO 2004/056312, and Shields et al., *J. Biol. Chem.* 9(2): 6591-6604 (2001).

In certain embodiments, an antibody variant of the present disclosure comprises an Fc region with one or more amino acid substitutions which improve ADCC, e.g., substitutions at positions 298, 333, and/or 334 of the Fc region (EU numbering of residues).

In certain embodiments, alteration made in the Fc region of an antibody, e.g., a bispecific antibody, disclosed herein, can produce a variant antibody with an increased half-life and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein, which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies can be generated as described, e.g., in U.S. Pat. No. 7,521,541.

e) Antibody Derivatives

In certain embodiments, an antibody of the present disclosure can be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In certain embodiments, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). In certain embodiments, the radiation can be of any wavelength, and includes, but is not limited to, wavelengths that do not harm ordinary cells, but which heat the nonproteinaceous moiety to a temperature at which cells proximal to the antibody-nonproteinaceous moiety are killed.

D. Methods of Antibody Production

The antibodies disclosed herein can be produced using any available or known technique in the art. For example, but not by way of limitation, antibodies can be produced using recombinant methods and compositions, e.g., as described in U.S. Pat. No. 4,816,567. Detailed procedures to generate antibodies are described in the Examples below.

The presently disclosed subject matter further provides an isolated nucleic acid encoding an antibody disclosed herein. For example, the isolated nucleic acid can encode an amino acid sequence that includes the VL and/or an amino acid sequence comprising the VH of the antibody, e.g., the light and/or heavy chains of the antibody. In certain embodiments, the isolated nucleic acid can include a nucleotide sequence that encodes a heavy chain variable region amino acid sequence having the sequence set forth in SEQ ID NO: 128, and/or a nucleotide sequence that encodes a light chain variable region amino acid sequence having the sequence set forth in SEQ ID NO: 130.

In certain embodiments, the nucleic acid can be present in one or more vectors, e.g., expression vectors. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the disclosed subject matter is intended to include such other forms of expression vectors, such as viral vectors (e.g., replication defective retroviruses, adenoviruses and adeno-associated viruses) that serve equivalent functions.

In certain embodiments, the nucleic acid encoding an antibody of the present disclosure and/or the one or more vectors including the nucleic acid can be introduced into a host cell. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, a host cell can include, e.g., has been transformed with: (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In certain embodiments, the host cell is eukaryotic, e.g., a Chinese Hamster Ovary (CHO) cell or lymphoid cell (e.g., Y0, NS0, Sp20 cell).

In certain embodiments, the methods of making an anti-KLB antibody or anti-FGFR1c can include culturing a host cell, in which a nucleic acid encoding the antibody has been introduced, under conditions suitable for expression of the antibody, and optionally recovering the antibody from the host cell and/or host cell culture medium. In certain embodiments, the antibody is recovered from the host cell through chromatography techniques.

For recombinant production of an antibody of the present disclosure, a nucleic acid encoding an antibody, e.g., as described above, can be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies can be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006). Suitable host cells for the expression of glycosylated antibody can also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

In certain embodiments, plant cell cultures can be utilized as host cells. See, e.g., U.S. Pat. Nos. 5,959,177, 6,040,498, 6,420,548, 7,125,978, and 6,417,429 (describing PLANTIBODIES™ technology for producing antibodies in transgenic plants).

In certain embodiments, vertebrate cells can also be used as hosts. For example, and not by way of limitation, mammalian cell lines that are adapted to grow in suspension can be useful. Non-limiting examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

In certain embodiments, techniques for making bispecific and/or multispecific antibodies include, but are not limited to, recombinant co-expression of two immunoglobulin heavy chain-light chain pairs having different specificities (see Milstein and Cuello, *Nature* 305: 537 (1983)), PCT Patent Application No. WO 93/08829, and Traunecker et al., *EMBO J.* 10: 3655 (1991)), and "knob-in-hole" engineering (see, e.g., U.S. Pat. No. 5,731,168). Bispecific antibodies can also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bispecific antibodies (see, e.g., Kostelny et al., *J. Immunol.*, 148(5): 1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Bispecific and multispecific molecules of the present disclosure can also be made using chemical techniques (see, e.g., Kranz (1981) *Proc. Natl. Acad. Sci. USA* 78:5807), "polydoma" techniques (see, e.g., U.S. Pat. No. 4,474,893), or recombinant DNA techniques. Bispecific and multispecific molecules of the presently disclosed subject matter can also be prepared by conjugating the constituent binding specificities, e.g., a first epitope and a second epitope binding specificities, using methods known in the art and as described herein. For example, and not by way of limitation, each binding specificity of the bispecific and multispecific molecule can be generated separately and then conjugated to one another. When the binding specificities are proteins or peptides, a variety of coupling or cross-linking agents can be used for covalent conjugation. Non-limiting examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfoSMCC) (see, e.g., Karpovsky (1984) *J. Exp. Med.* 160:1686; Liu (1985) *Proc. Natl. Acad. Sci. USA* 82:8648). Other methods include those described by Paulus (*Behring Ins. Mitt.* (1985) No. 78, 118-132; Brennan (1985) *Science* 229:81-83), Glennie (1987) *J. Immunol.* 139: 2367-2375). When the binding specificities are antibodies (e.g., two humanized antibodies), they can be conjugated via sulfhydryl bonding of the C-terminus hinge regions of the two heavy chains. In certain embodiments, the hinge region can be modified to contain an odd number of sulfhydryl residues, e.g., one, prior to conjugation.

In certain embodiments, both binding specificities of a bispecific antibody can be encoded in the same vector and expressed and assembled in the same host cell. This method is particularly useful where the bispecific and multispecific molecule is a MAb×MAb, MAb×Fab, Fab×F(ab')$_2$ or ligand x Fab fusion protein. In certain embodiments, a bispecific antibody of the present disclosure can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or can comprise at least two single chain molecules. Methods for preparing bi- and multispecific molecules are described, for example, in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858. Engineered antibodies with three or more functional antigen binding sites (e.g., epitope binding sites) including "Octopus antibodies," are also included herein (see, e.g., US 2006/0025576A1).

The present disclosure further provides tri-specific, e.g., tri-functional, antibodies. For example, and not by way of limitation, a tri-specific antibody of the present disclosure can bind to and/or interact with an epitope present on KLB, an epitope present on FGFR1, and an epitope or antigen present on a third protein such as, but not limited to, PCSK9, GCGR, AdipoR, ZnT8, ApoL1, MSTN, InsR or FABP4.

In certain embodiments, an animal system can be used to produce an antibody of the present disclosure. One animal system for preparing hybridomas is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known (see, e.g., Harlow and Lane (1988), Antibodies, A Laboratory Manual, Cold Spring Harbor Laboratory Press, Cold Spring Harbor New York).

E. Assays

The antibodies of the present disclosure provided herein can be identified, screened for, or characterized for their physical/chemical properties and/or biological activities by various assays known in the art and provided herein.

1. Binding Assays and Other Assays

In certain embodiments, an antibody of the present disclosure can tested for its antigen binding activity by known methods, such as enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. For example, the KLB-antibody complexes can be detected using, e.g., an enzyme-linked antibody or antibody fragment which recognizes and specifically binds to the antibody-KLB complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a Geiger counter or a scintillation counter or by autoradiography.

In certain embodiments, competition assays can be used to identify an antibody that competes with an anti-KLB antibody of the present disclosure, e.g., 12A11 or 8C5, for binding to KLB. In certain embodiments, such a competing antibody binds to the same epitope (e.g., a linear or a conformational epitope) that is bound by 12A11 or 8C5.

Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In a non-limiting example of a competition assay, immobilized KLB can be incubated in a solution comprising a first labeled antibody that binds to KLB (e.g., 12A11 or 8C5) and a second unlabeled antibody that is being tested for its ability to compete with the first antibody for binding to KLB. The second antibody may be present in a hybridoma supernatant. As a control, immobilized KLB is incubated in a solution comprising the first labeled antibody but not the second unlabeled antibody. After incubation under conditions permissive for binding of the first antibody to KLB, excess unbound antibody is removed, and the amount of label associated with immobilized KLB is measured. If the amount of label associated with immobilized KLB is substantially reduced in the test sample relative to the control sample, then that indicates that the second antibody is competing with the first antibody for binding to KLB. See Harlow and Lane (1988) *Antibodies: A Laboratory Manual* ch.14 (Cold Spring Harbor Laboratory, Cold Spring Harbor, N.Y.).

2. Activity Assays

The present disclosure provides assays for identifying anti-KLB antibodies thereof having biological activity. Biological activity may include, e.g., activating a KLB/FGFR1c receptor complex. Antibodies having such biological activity in vivo and/or in vitro are also provided. In certain embodiments, the assays can include binding antibodies of the present disclosure to cells, e.g., 293T cells expressing KLB, and analyzing the activity and/or phosphorylation states of one or more downstream targets of the KLB-FGFR1c receptor complex, e.g., ERK. In certain embodiments, the assay can include the administering of an antibody of the present disclosure to a subject, e.g., a non-human animal, and analyzing the effect the antibody has on the glucose level in the subject.

F. Immunoconjugates

The presently disclosed subject matter further provides immunoconjugates comprising an antibody, disclosed herein, conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes. For example, an antibody or antigen-binding portion of the disclosed subject matter can be functionally linked (e.g., by chemical coupling, genetic fusion, noncovalent association or otherwise) to one or more other binding molecules, such as another antibody, antibody fragment, peptide or binding mimetic.

In certain embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In certain embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In certain embodiments, an immunoconjugate comprises an antibody as described herein conjugated to a radioactive atom to form a radioconjugate. A variety of radioactive isotopes are available for the production of radioconjugates. Non-limiting examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it can include a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent can be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) can be used.

The immunuoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

III. Methods of Use

The presently disclosed subject matter further provides methods for using the disclosed antibodies, e.g., an anti- KLB/anti-FGFR1c bispecific antibody. In certain embodiments, the methods are directed to therapeutic uses of the presently disclosed antibodies. In certain embodiments, the methods are directed to the use of the disclosed antibodies in diagnostic methods.

A. Diagnostic and Detection Methods

In certain embodiments, any antibody disclosed herein that has specificity for KLB, e.g., an anti-KLB antibody and/or an anti-KLB/anti-FGFR1 bispecific antibody, disclosed above, can be useful for detecting the presence of KLB in a biological sample. In a further aspect, the presently disclosed subject matter provides methods for diagnosing and/or detecting a disease using an anti-KLB antibody or an anti-KLB/anti-FGFR1 bispecific antibody, disclosed herein. The term "detecting," as used herein, encompasses quantitative and/or qualitative detection.

In certain non-limiting embodiments, a biological sample includes, but is not limited to, a clinical sample, one or more cells, cells in culture, cell supernatants, cell lysates and tissue samples. The source of the sample may be solid tissue (e.g., from a fresh, frozen, and/or preserved organ, tissue sample, biopsy, or aspirate) or cells from the individual. In certain embodiments, a biological sample can include one or more cells and/or tissue from a liver, e.g., from a liver of a subject.

In certain embodiments, an anti-KLB antibody for use in a method of diagnosis or detection is provided. In a further aspect, a method of detecting the presence of KLB in a biological sample is provided. In certain embodiments, the method of diagnosis or detection includes contacting a biological sample with an antibody that binds an epitope present on KLB, as described herein, under conditions permissive for binding of the antibody to KLB, and detecting whether a complex is formed between the antibody and KLB. Such method may be an in vitro or in vivo method, e.g., immunofluorescence or western blot. In certain embodiments, an anti-KLB antibody is used to select subjects eligible for therapy with an anti-KLB antibody, e.g., where KLB is a biomarker for selection of patients.

In certain embodiments, an antibody of the present disclosure, e.g., an anti-KLB/anti-FGFR1 bispecific antibody, for use in the disclosed methods does not have a significant impact on the liver, e.g., liver function. In certain embodiments, an antibody of the present disclosure does not modulate the activity of an FGFR/KLB receptor complex in the liver as compared to the modulation of an FGFR/KLB receptor complex in the liver by an FGF21 protein. In certain embodiments, an antibody of the present disclosure does not result in the inhibition of the FGFR4/KLB complex and/or does not result in the elevation of liver enzymes such as, but not limited to, ALT, AST, ALP and GLDH. In certain embodiments, an antibody of the present disclosure does not function as an agonist of the FGFR2c/KLB complex and/or the FGFR3c/KLB complex in the liver, which can lead to activated MAPK signaling and/or altered expression of Spry4 and Dusp6 in the liver. In certain embodiments, an antibody of the present disclosure does not result in the activation of MAPK signaling in the liver as compared to the activation of MAPK signaling by an FGF21 protein. In certain embodiments, an antibody of the present disclosure does not function as an agonist of the FGFR4/KLB complex in the liver.

In certain embodiments, an antibody of the present disclosure, e.g., an anti-KLB/anti-FGFR1 bispecific antibody, for use in the disclosed methods include antibodies that do not block binding and/or interaction of the FGF ligands, e.g., FGF19 and FGF21, to the KLB/FGFR1c complex. In certain embodiments, an anti-KLB/anti-FGFR1 bispecific antibody disclosed herein refers to an antibody that modulates KLB/FGFR1c complex activity and does not block the interaction and/or binding of the native FGF ligands, e.g., FGF19 and FGF21, to the KLB/FGFR1c complex. In certain embodiments, an anti-KLB/anti-FGFR1 bispecific antibody disclosed herein refers to an antibody that does not block the binding and/or activity of native FGF ligands to an FGF receptor in the absence of KLB. For example, and not by way of limitation, an anti-KLB/anti-FGFR1 bispecific antibody of the present disclosure does not block the interaction of native FGF ligands with the FGFR1/KLA complex or FGFR1 alone. In certain embodiments, an anti-KLB/anti-FGFR1 bispecific antibody disclosed herein refers to an antibody that does not block the binding and/or activity of native FGF ligands to KLB in the absence of FGFR1. For example, and not by way of limitation, an anti-KLB/anti-FGFR1 bispecific antibody of the present disclosure does not block the interaction of native FGF ligands with the FGFR4/KLB complex, the FGFR2c/KLB complex and/or the FGFR3c/KLB complex.

In certain embodiments, anti-KLB antibodies, anti-FGFR1c and/or anti-KLB/anti-FGFR1, e.g., anti-KLB/anti-FGFR1c, bispecific antibodies for use in the disclosed methods can be labeled. Labels include, but are not limited to, labels or moieties that are detected directly, such as fluorescent, chromophoric, electron-dense, chemiluminescent, and radioactive labels, as well as moieties, such as enzymes or ligands, that are detected indirectly, e.g., through an enzymatic reaction or molecular interaction. Non-limiting examples of labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (see U.S. Pat. No. 4,737,456), luciferin, 2,3-dihydrophthalazinediones, horseradish peroxidase (HRP), alkaline phosphatase, (i-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

B. Therapeutic Methods

In certain embodiments, one or more antibodies of the presently disclosed subject matter can be used for treating a disease and/or disorder in a subject. For example, but not by way of limitation, the disease can be a metabolic disorder. Non-limiting examples of metabolic disorders include polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD) and maturity onset diabetes of the young (MODY). In certain embodiments, the metabolic disorder is type 2 diabetes. In certain embodiments, the metabolic disorder is obesity.

In certain embodiments, one or more antibodies of the presently disclosed subject matter can be used to treat Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Börjeson-Forssman-Lehman syndrome. In certain embodiments, one or more antibodies of the presently disclosed subject matter can be used to treat aging and related diseases such as Alzheimer's disease, Parkinson's disease and ALS.

In certain embodiments, one or more antibodies of the presently disclosed subject matter can be used to treat heart disease, stroke, heart attacks, hyperinsulinemia, high blood pressure, coronary-artery disease, migraines or headaches directly related to obesity or cranial hypertension, congestive heart failure, neoplasia, dyslipidemia, anemia, gallbladder disease, osteoarthritis, degenerative arthritis, degenerative disc, degenerative joint disease, joint replacement, accelerated degenerative joint disease, asthma, repeated pneumonia, repeated pleurisy, repeated bronchitis, lung restriction, gastroesophageal reflex (gerd), excess facial and body hair (hirsutism), rashes, chronic skin infections, excess sweating, frequent yeast infections, urinary stress incontinence, menstrual irregularity, hormonal abnormalities, polycystic ovaries, infertility, carcinoma (e.g., breast, colon and uterine cancer), sleep apnea, pseudotumor cerebri, depression, psychological/sexual dysfunction, social discrimination and premature death.

In certain embodiments, the present disclosure provides an antibody for use in a method of treatment. For example, and not by way of limitation, the present disclosure provides an antibody, e.g., an anti-KLB/anti-FGFR1 bispecific antibody, for use in a method of treating a subject having a metabolic disorder, e.g., PCOS, MetS, obesity, NASH, NAFLD, hyperlipidemia, hypertension, type 2 diabetes, non-type 2 diabetes, type 1 diabetes, LAD, MODY, and aging and related diseases such as Alzheimer's disease, Parkinson's disease and ALS, that includes administering to the individual an effective amount of an antibody, disclosed herein. In certain embodiments, the present disclosure provides an antibody, e.g., an anti-KLB/FGFR1 bispecific antibody, for use in a method of treating a subject having a disease or disorder described above, which includes administering to the individual an effective amount of the antibody.

In certain embodiments, the method can further include administering to the subject an effective amount of at least one additional therapeutic agent. Non-limiting examples of additional therapeutic agents, e.g., a second therapeutic agent, are described below.

In certain embodiments, the present disclosure further provides a method for inducing weight loss comprising administering to an individual an effective amount of one or more antibodies of the present disclosure, e.g., an anti-KLB/FGFR1 bispecific antibody.

An "individual," "patient" or "subject," as used interchangeably herein, refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The presently disclosed subject matter further provides an antibody, e.g., an anti-KLB/anti-FGFR1 bispecific antibody, for use in activating a KLB/FGFR1c coreceptor complex, e.g., in a subject. For example, and not by way of limitation, the anti-KLB/anti-FGFR1 bispecific antibody can be an anti-KLB/anti-FGFR1c bispecific antibody. In certain embodiments, the present disclosure provides an antibody, e.g., an anti-KLB/anti-FGFR1 bispecific antibody, for use in a method of activating a KLB/FGFR1c coreceptor complex in a subject. In certain embodiments, the method includes administering to the subject an effective of the antibody to activate a KLB/FGFR1c receptor complex.

Antibodies of the present disclosure can be used either alone or in combination with other agents in a therapy. For example, and not by way of limitation, an antibody of the present disclosure can be co-administered with at least one additional therapeutic agent. In certain embodiments, the second/additional therapeutic agent can include an anti-diabetic agent, an anti-obese agent or a medication for metabolic conditions such as, but not limited to, anti-hypertensive medications and statins. Non-limiting examples of a second/additional therapeutic agent include metformin, pioglitazone, DPP4i, GLP1-analogs, sulfonylurea, insulin, Leptin-analogs and lorcaserin (e.g., BELVIQ®).

The present disclosure further provides for the use of an antibody, e.g., an anti-KLB/anti-FGFR1 bispecific antibody, in the manufacture or preparation of a medicament. In certain embodiments, the medicament is for treatment of a metabolic disorder, as disclosed above. In certain embodiments, the present disclosure provides the use of an antibody in the manufacture of a medicament for treatment of obesity. In certain embodiments, the present disclosure provides the use of an antibody in the manufacture of a medicament for treatment of type 2 diabetes. In certain embodiments, the method further comprises administering to the individual an effective amount of at least one additional therapeutic agent, e.g., as described herein. In certain embodiments, the medicament is for activating a KLB/FGFR1c coreceptor complex. In certain embodiments, the medicament can be used in a method of activating a KLB/FGFR1c coreceptor complex in an individual comprising administering to the individual an amount of the medicament effective to activate a KLB/FGFR1c receptor complex.

In certain embodiments, an antibody for use in the disclosed therapeutic methods can be present in a pharmaceutical composition. In certain embodiments, the pharmaceutical composition can include a pharmaceutically acceptable carrier. In certain embodiments, the pharmaceutical composition can include one or more of the antibodies of the present disclosure.

Additionally or alternatively, the pharmaceutical composition can include a second therapeutic agent. When one or more of the disclosed antibodies are administered with another therapeutic agent, the one or more antibodies and the other therapeutic agent can be administered in either order or simultaneously. Such combination therapies noted above encompass combined administration (where two or more therapeutic agents are included in the same or separate formulations), and separate administration, in which case, administration of the antibody of the present disclosure can occur prior to, simultaneously, and/or following, administration of the additional therapeutic agent or agents. In one embodiment, administration of an antibody of the present disclosure and administration of an additional therapeutic agent occur within about one month, or within about one, two or three weeks, or within about one, two, three, four, five, or six days, of each other.

An antibody of the present disclosure (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the present disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. In certain embodiments, an antibody of the present disclosure can be administered on an as needed basis. In certain embodiments, the antibody can be administered to the patient one time or over a series of treatments. For example, but not by way of limitation, the antibody and/or pharmaceutical formulation contains an antibody, as disclosed herein, can be administered to a subject twice every day, once every day, once every two days, once every three days, once every four days, once every five days, once every six days, once a week, once every two weeks, once every three weeks, once every month, once every two months, once every three months, once every six months or once every year.

In certain embodiments, depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. In certain embodiments, the daily dosage can be greater than about 100 mg/kg. In certain embodiments, dosage can be adjusted to achieve a plasma antibody concentration of 1-1000 µg/ml and in some methods 25-300 µg/ml.

For repeated administrations over several days or longer, depending on the condition, the treatment could generally be sustained until a desired suppression of disease symptoms occurs. One exemplary dosage of the antibody would be in the range from about 0.05 mg/kg to about 10 mg/kg. In certain embodiments, one or more doses of about 0.5 mg/kg, 2.0 mg/kg, 4.0 mg/kg or 10 mg/kg (or any combination thereof) can be administered to the patient. Alternatively, antibody can be administered as a sustained release formulation, in which case less frequent administration is required. Dosage and frequency can vary based on the half-life of the antibody in the patient. In certain embodiments, such doses may be administered intermittently, e.g., every week or every three weeks (e.g., such that the patient receives from about two to about twenty, or, e.g., about six doses of the antibody). An initial higher loading dose, followed by one or more lower doses may be administered.

In certain embodiments, the method can further include monitoring the subject and determining the effectiveness of the treatment. For example, the progress of this therapy can be easily monitored by conventional techniques and assays.

IV. Pharmaceutical Formulations

The presently disclosed subject matter further provides pharmaceutical formulations containing one or more antibodies, as described herein, with a pharmaceutically acceptable carrier. In certain embodiments, the pharmaceutical compositions can include a combination of multiple (e.g., two or more) antibodies and/or antigen-binding portions thereof of the presently disclosed subject matter. In certain embodiments, a pharmaceutical composition of the present disclosure can include one or more anti-KLB/anti-FGFR1 bispecific antibodies.

In certain embodiments, the disclosed pharmaceutical formulations can be prepared by combining an antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. For example, but not by way of limitation, lyophilized antibody formulations are described in U.S. Pat. No. 6,267,958. In certain embodiments, aqueous antibody formulations can include those described in U.S. Pat. No. 6,171,586 and WO2006/044908, the latter formulations including a histidine-acetate buffer. In certain embodiments, the antibody can be of a purity greater than about 80%, greater than about 90%, greater than about 91%, greater than about 92%, greater than about 93%, greater than about 94%, greater than about 95%, greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8% or greater than about 99.9%.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The carrier can be suitable for intravenous, intramuscular, subcutaneous, parenteral, spinal or epidermal administration (e.g., by injection or infusion). Depending on the route of administration, the active compound, i.e., an anti-KLB/anti-FGFR1 bispecific antibody, can be coated in a material to protect the compound from the action of acids and other natural conditions that may inactivate the compound.

Pharmaceutical compositions of the present disclosure also can be administered in combination therapy, i.e., combined with other agents. In certain embodiments, pharmaceutical compositions disclosed herein can also contain more than one active ingredients as necessary for the particular indication being treated, for example, those with complementary activities that do not adversely affect each other. In certain embodiments, the pharmaceutical formulation can include a second active ingredient for treating the same disease treated by the first therapeutic. Such active ingredients are suitably present in combination in amounts that are effective for the purpose intended. For example, and not by way of limitation, the formulation of the present disclosure can also contain more than one active ingredients as necessary for the particular indication being treated, preferably those with complementary activities that do not adversely affect each other. For example, it may be desirable to further provide a second therapeutic useful for treatment of the same disease. Such active ingredients are suitably present in combination in amounts that are effective for the purpose intended.

A composition of the present disclosure can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, 1978. In certain embodiments, the pharmaceutical compositions are manufactured under Good Manufacturing Practice (GMP) conditions of the U.S. Food and Drug Administration.

Sustained-release preparations containing a disclosed antibody can also be prepared. Suitable examples of sustained-release preparations include semipermeable matrices of solid hydrophobic polymers containing the antibody, which matrices are in the form of shaped articles, e.g. films, or microcapsules. In certain embodiments, active ingredients can be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

To administer an antibody of the present disclosure by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present disclosure is contemplated. Supplementary active compounds can also be incorporated into the compositions.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating one or more disclosed antibodies in the required amount in an appropriate solvent with one or a combination of ingredients enumerated above, as required, followed by sterilization microfiltration, e.g., by filtration through sterile filtration membranes. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Therapeutic compositions can also be administered with medical devices known in the art. For example, a therapeutic composition of the present disclosure can be administered with a needleless hypodermic injection device, such as the devices disclosed in, e.g., U.S. Pat. Nos. 5,399,163, 5,383, 851, 5,312,335, 5,064,413, 4,941,880, 4,790,824, or 4,596, 556. Examples of implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multichamber compartments; and U.S. Pat. No. 4,475,196, which discloses an osmotic drug delivery system. Many other such implants, delivery systems, and modules are known.

For the therapeutic compositions, formulations of the present disclosure include those suitable for oral, nasal, topical (including buccal and sublingual), rectal, vaginal and/or parenteral administration. The formulations can conveniently be presented in unit dosage form and may be prepared by any methods known in the art of pharmacy. The amount of antibody, which can be combined with a carrier material to produce a single dosage form, vary depending upon the subject being treated, and the particular mode of administration. The amount of the antibody which can be combined with a carrier material to produce a single dosage form generally be that amount of the composition which produces a therapeutic effect. Generally, out of one hundred percent, this amount range from about 0.01 percent to about ninety-nine percent of active ingredient, from about 0.1 percent to about 70 percent, or from about 1 percent to about 30 percent.

Dosage forms for the topical or transdermal administration of compositions of the present disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These pharmaceutical compositions can also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In certain embodiments, when the antibodies of the present disclosure are administered as pharmaceuticals, to humans and animals, they can be given alone or as a pharmaceutical composition containing, for example, from about 0.01% to about 99.5% (or about 0.1 to about 90%) of an antibody, described herein, in combination with a pharmaceutically acceptable carrier.

V. Articles of Manufacture

The presently disclosed subject matter further relates articles of manufacture containing materials useful for the treatment, prevention and/or diagnosis of the disorders described above.

In certain embodiments, the article of manufacture includes a container and a label or package insert on or associated with the container. Non-limiting examples of suitable containers include bottles, vials, syringes, IV solution bags, etc. The containers can be formed from a variety of materials such as glass or plastic. The container can hold a composition which is by itself or combined with another composition effective for treating, preventing and/or diagnosing the condition and may have a sterile access port (for example, the container may be an intravenous solution bag or a vial having a stopper pierceable by a hypodermic injection needle).

In certain embodiments, at least one active agent in the composition is an antibody of the presently disclosed subject matter. The label or package insert can indicate that the composition is used for treating the condition of choice.

In certain embodiments, the article of manufacture can comprise (a) a first container with a composition contained therein, wherein the composition comprises an antibody of the present disclosure; and (b) a second container with a composition contained therein, wherein the composition comprises a further cytotoxic or otherwise therapeutic agent. In certain embodiments, the article of manufacture can further comprise a package insert indicating that the compositions can be used to treat a particular condition.

Alternatively, or additionally, the article of manufacture can further an additional container, e.g., a second or third container, including a pharmaceutically-acceptable buffer, such as, but not limited to, bacteriostatic water for injection (BWFI), phosphate-buffered saline, Ringer's solution and dextrose solution. The article of manufacture can include other materials desirable from a commercial and user standpoint, including other buffers, diluents, filters, needles, and syringes.

The following examples are merely illustrative of the presently disclosed subject matter and should not be considered as limitations in any way.

EXAMPLES

Example 1: Characterization of Anti-FGFR1 Agonist Antibodies

Three phage-derived anti-FGFR1 antibodies, YW182.2 (also referred to herein as "R1MAb1"), YW182.3 (also referred to herein as "R1MAb2"), and YW182.5 (also referred to herein as "R1MAb3") were previously described (WO 2012/158704, incorporated by reference herein)). Each of the three antibodies acts as a potent FGFR1-selective agonist and exhibited insulin-sensitizing properties in mice.

To further understand this agonistic activity, the ability of Fab fragments of these antibodies to agonize FGFR1c was tested. HEK293 cells were cultured in Dulbecco's Modified Eagle Medium (DMEM)+10%/o fetal bovine serum (FBS), and transiently-transfected with expression vectors encoding Renilla luciferase (pRL-SV40, Promega), FGFR1c, a transcriptional activator (pFA2-Elk1 or pFA2-CREB, Stratagene), and a firefly luciferase reporter driven by GAL4 binding sites (pFR-luc, Stratagene), using FUGENE® HD Transfection Reagent (Roche). On the next day, the transfected cells were cultured for an additional 6-8 h in serum free media and YW182.5 IgG and each of YW182.2, YW182.3 and YW182.5 were tested at increasing concentrations. The cellular luciferase activity was determined using DUAL-GLO® Luciferase Assay System (Promega) and ENVISION® Multilabel Reader (PerkinElmer). Firefly luciferase activity was normalized to the co-expressed Renilla luciferase activity. Surprisingly, YW182.2 Fab, but not YW182.3 Fab or YW182.5 Fab, exhibited agonistic activity (FIG. 1A).

FIG. 1B depicts the binding competition experiments that were performed to explore the basis for the difference in FGFR1 activation by an YW182.2 Fab and an YW182.3

Fab. YW182.2 was further characterized in comparison to YW182.3, which has high affinity, and in comparison to the lower affinity anti-FGFR1 antibody, YW182.5. Both YW182.2 and YW182.3 competed with YW182.5 for the binding to the FGFR1 extracellular domain (ECD), indicating that all 3 antibodies recognize an overlapping region of FGFR1. However, as shown in FIG. 1B, the relative affinity of YW182.5 was significantly weaker ($IC_{50}$>30 fold) than that of YW182.2 and YW182.3.

FIG. 2A depicts the binding affinities of the anti-FGFR1 antibodies, YW182.2 and YW182.3, for FGFR1b and FGFR1c. The affinity of the anti-FGFR1 antibodies was determined to assess whether differences in affinity of the anti-FGFR1 antibodies explain the differences observed in agonistic activity. The binding affinities of the Fabs to FGFR1b or FGFR1c using a BIACORE® T100 instrument was performed as described in Liang et al. *J. Mol. Biol.* 366(3): 815-29 (2007), with the following modifications. Mouse anti-human Fc antibody was first coated on a BIAcore carboxymethylated dextran CM5 chip using direct coupling to free amino groups following a procedure described by the manufacturer. YW182.2 or YW182.3 was then captured on CM5 biosensor chips to achieve approximately 200 response units (RU). Binding measurements were performed using a running buffer composed of 10 mM HEPES pH 7.4, 150 mM NaCl, 0.005% surfactant P20 (HBS-P buffer). A 2 fold dilution series of FGFR1c ECD-His protein was injected in a range of 1.5-50 nM in HBS P buffer at a flow rate of 30 μL/minute at 25° C. Association rates ($K_{on}$, per mol/s) and dissociation rates ($K_{off}$, per s) were calculated using a simple one-one Langmuir binding model (Biacore Evaluation Software version 3.2). The equilibrium dissociation constant ($K_d$, per mol) was calculated as the ratio of $K_{off}/K_{on}$. As shown in FIG. 2A, the affinities of YW182.2 and YW182.3 were observed to be very similar, indicating that the affinity could not explain the difference between the agonistic activities of the two antibodies.

FIG. 2B shows the ability of YW182.5 (R1MAb3) to specifically interact with FGFR1. Like YW182.2 and YW182.3, YW182.5 showed specific binding to FGFR1 by ELISA (FIG. 2B).

FIG. 2C depicts the agonistic activity of YW182.5 for various FGFRs in L6 cells using a GAL-ELK1 (ETS-like transcription factor 1) based luciferase assay. For the luciferase assay, HEK293T or rat L6 cells were transiently transfected with expression vectors encoding appropriate receptors under the CMV-promoter, Renilla luciferase (pRL-SV40, Promega), GAL-ELK1 transcriptional activator fusion (pFA2-ELK1, Agilent), and a firefly luciferase reporter driven by GAL4 binding sites (pFR-luc, Agilent), using FuGENE HD Transfection Reagent (Promega). On the next day, the transfected cells were cultured for an additional 6-8 hours in serum free DMEM-based media containing appropriate protein ligands at various concentrations. The cellular luciferase activity was determined using Dual-Glo Luciferase Assay System (Promega) and EnVision Multilabel Reader (PerkinElmer). Firefly luciferase activity was normalized to the co-expressed Renilla luciferase activity, and shown as means±SEM. Similar to YW182.2 and YW182.3, YW182.5 acted as a specific agonist for FGFR1 in L6 cells (FIG. 2C).

The agonistic activity of YW182.5 was further tested in HEK293 cells using the GAL-ELK1-based luciferase assay described above. As shown in FIG. 2D, YW182.5 also acted as a specific agonist for FGFR1c in the GAL-ELK1 based luciferase assay in HEK293 cells.

FIG. 2E shows the effect of YW182.5 on blood glucose levels in a diabetic mouse model. To determine blood glucose levels, mice were purchased from Jackson Laboratory and maintained in a pathogen-free animal facility at 21° C. under standard 12 h light/12 h dark cycle with access to chow (LABDIET® 5010) and water ad libitum. db/db mice in C57BLKS/J background were females and other mice were all males. For high-fat diet feeding, a high fat, high carbohydrate diet (Harlan Teklad TD.03584, 58.4% calories from fat) was used. Serum inorganic phosphate and calcium levels were determined by COBAS INTEGRA® 400 Chemistry Analyzer (Roche). Serum FGF23 levels were determined by ELISA (Immutopics). Blood glucose levels were determined by CONTOUR® glucose meter (Bayer). For hepatic lipid analysis, triglyceride quantification kit (MBL International) was used. Serum total cholesterol, triglycerides, β-hydroxybutyrate (Thermo DMA) and free fatty acid (Roche) were determined by colorimetric assays. ELISA was used to determine serum insulin levels (Crystal Chem), serum FGF23 (Immutopics), serum mouse HMW adiponectin (Alpco) and serum monkey HMW adiponectin (R&D systems). Corticosterone was measured by radioimmunoassay (Vanderbilt Hormone Assay & Analytical Services Core). All the mice used for injection were around 2-4 months old, except klb-deficient mice, which were used in certain experiments at 7-8 months old. In a similar manner to YW182.2 and YW182.3, YW182.5 normalized blood glucose levels when injected into diabetic ob/ob mice (FIG. 2E).

Example 2: Epitope Mapping of Anti-FGFR1 Antibodies

The FGFR1 ECD consists of three Ig-like domains called D1 to D3. As shown in FIG. 1C, two non-overlapping peptides (P26: KLHAVPAAKTVKFKCP (SEQ ID NO: 143) and P28: FKPDHRIGGYKVRY (SEQ ID NO: 144) are present within the D2 domain of FGFR1 and were previously identified to bind to both YW182.2 and YW182.3 (WO 2012/158704, incorporated by reference herein).

To identify which residues in these peptides are most responsible for antibody binding, full-length FGFR1 proteins with various alanine substitutions within the identified epitope regions were expressed in HEK293 cells and tested for antibody binding by western blot. As shown in FIG. 1D, alanine substitution in K175, K177, Y205, R208, eliminated binding of YW182.2 and YW182.5, without affecting expression as probed by anti-FGFR1 against D1 domain (anti-D1). Binding of YW182.3 was abolished by R208A, but not by the K175, K177, or Y205 substitutions.

Figure 1F:
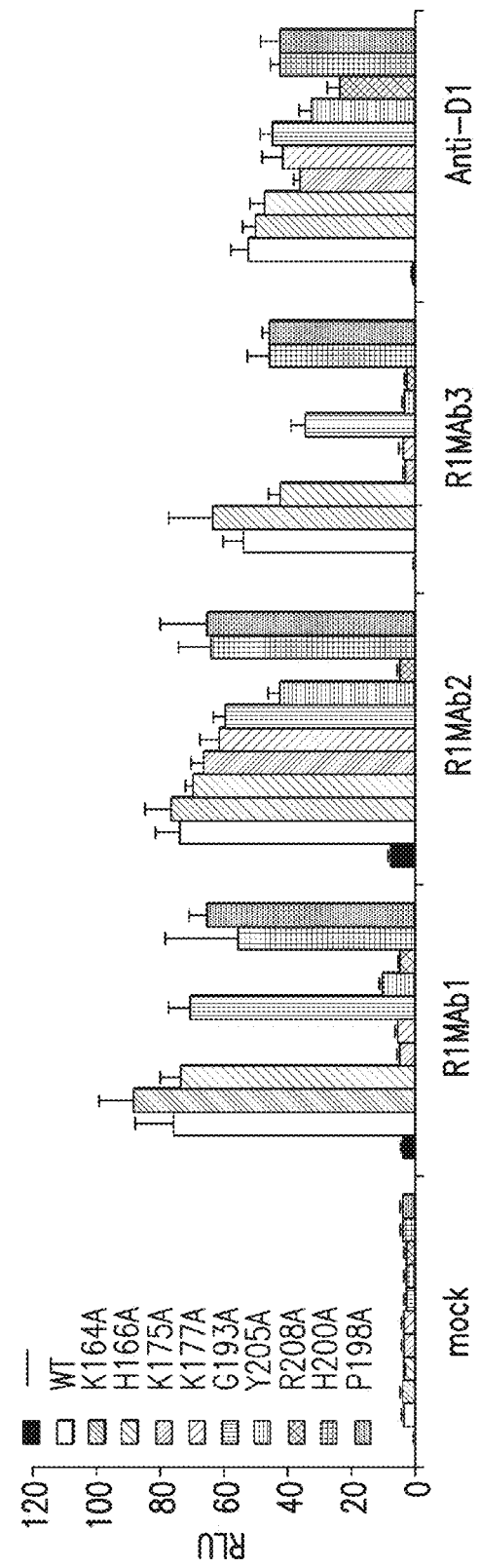
FIG. 1F depicts residues important for binding on a space-filling model of FGFR1.
Figure 1E:
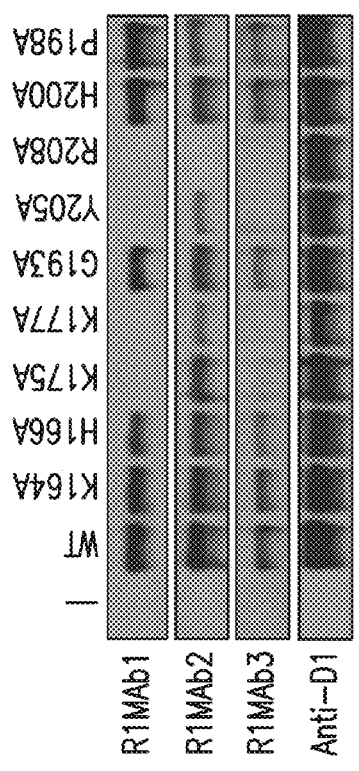
FIG. 1E depicts the results of site-specific mutagenesis to determine amino acid residues important for binding by anti-FGFR1 antibodies of the presently disclosed subject matter.

The ability of the antibodies to activate the alanine substitution mutants of FGFR1 in vivo was tested using the GAL-ELK1 assay described above. It was found that activation correlated well with the binding properties of these mutants to each anti-FGFR1 antibody (FIG. 1E). These results suggest that a similar set of amino acids within the D2 domain are required for YW182.2 and YW182.5 binding with albeit different affinity, whereas a distinct set of amino acids in the same region is important for YW182.3 binding.

Crystal structures of 2:2 FGFR ECD/FGF complex have previously been described (Plotnikov et al. *Cell* 98(5): 641-50 (1999)). In the 2:2 homodimeric FGFR1c ECD/FGF2 structures, one D2 domain interacts with another D2 domain, with each FGF2 binds to both D2 domains from two sides to stabilize the D2 dimer (FIG. 1F). In these structures, the alanine substitutions important for YW182.2 and YW182.5 binding (K175, K177, Y205, and R208) are situated inside of the D2 dimer. Since YW182.2 Fab acts as an agonist, this suggested that YW182.2 Fab may bind to two D2 domains simultaneously from the side to stabilize the D2 dimer, essentially acting as a molecular mimetic of FGF ligands. Based on the alanine substitution analysis, YW182.5 Fab might bind similarly except that the affinity is much lower than YW182.2 Fab.

Example 3: Isolation and Characterization of Anti-KLB Antibodies

Balb/c mice were immunized with HEK293 cells stably expressing hFGFR1c and hKLB protein. Spleens were harvested after 12 weeks and hybridomas were generated. Anti-hKLB antibody producing hybridomas were identified by FACS analysis using the HEK293 cells used for immunization. Briefly, 293 cells expressing hKLB alone, hFGFR1 alone, or both, were stained with diluted hybridoma supernatant and PE-conjugated goat anti-mouse IgG antibody (Jackson Labs) is FACS buffer (0.5% BSA in PBS). The same FACS buffer was used to wash the stained cells. Stained cells were analyzed by FACScan (Becton Dickinson) and FlowJo FACS analysis software (Tree Star). cDNA encoding the IgG heavy chain and light chain were cloned into expression vectors. All the recombinant monoclonal antibody molecules were produced in transiently transfected Chinese hamster ovary (CHO) cells and purified using conventional column chromatography.

Approximately 20 different hybidomas producing anti-KLB antibodies were identified. The CDR light chain and heavy chain sequences for 16 of these anti-KLB antibodies are shown in Tables 2 and 3. The light chain sequences of 16 of these anti-KLB antibodies along with 8C5 are shown in FIG. 3A (11F1, 6D12, 11D4, 8E1, 46C3, 8H7, 21H3, 25F7, 14E6, 14C6, 24A1, 5F8, 6C1, 12A1, 12B8, 14C10 and 8C5; SEQ ID NOs: 111-127, respectively).

The heavy chain sequences of 16 of these anti-KLB antibodies along with 8C5 are shown in FIG. 3B (11F1, 6D12, 11D4, 8E1, 46C3, 8H7, 21H3, 25F7, 14E6, 14C6, 24A1, 5F8, 6C1, 12A1, 12B8, 14C10 and 8C5; SEQ ID NOs: 94-110, respectively).

TABLE 2

CDR H sequences for murine anti-KLB monoclonal antibodies.

| Antibody | CDR H1 | CDR H2 | CDR H3 |
|---|---|---|---|
| 11F1 | SYGIS (SEQ ID NO: 1) | TVSSGGRYTYYPDSVKG (SEQ ID NO: 16) | GGDGYALDY (SEQ ID NO: 32) |
| 6D12 | DYYMN (SEQ ID NO: 2) | WIDPENDDTIYDPKFQG (SEQ ID NO: 17) | FTTVFAY (SEQ ID NO: 33) |
| 11D4 | NYGVS (SEQ ID NO: 3) | VIWGDGSINYHSALIS (SEQ ID NO: 18) | THDWFDY (SEQ ID NO: 34) |
| 8E1 | DTYMN (SEQ ID NO: 4) | RIDPSNGNAKYDPKFQG (SEQ ID NO: 19) | RALGNGYALGY (SEQ ID NO: 35) |
| 46C3 | DTYIH (SEQ ID NO: 5) | RIDPANGNTKYDPKFQD (SEQ ID NO: 20) | GTSYSWFAY (SEQ ID NO: 36) |
| 8H7 | SYWIH (SEQ ID NO: 6) | EIDPSVSNSNYNQKFKG (SEQ ID NO: 21) | LGVMVYGSSPFWFAY (SEQ ID NO: 37) |
| 21H3 | SYWIH (SEQ ID NO: 6) | EIDPSVSNSNYNQKFKG (SEQ ID NO: 21) | LGVMVYGSSPFWFAY (SEQ ID NO: 37) |
| 25F7 | DTFTH (SEQ ID NO: 7) | RIDPSNGNTKYDPKFQG (SEQ ID NO: 22) | RALGNGYAMDY (SEQ ID NO: 38) |
| 14E6 | EYTMN (SEQ ID NO: 8) | GINPNNGETSYNQKFKG (SEQ ID NO: 23) | KTTNY (SEQ ID NO: 39) |
| 14C6 | SYWIE (SEQ ID NO: 9) | EIFPGGGSTIYNENFRD (SEQ ID NO: 24) | RGYYDAAWFDY (SEQ ID NO: 40) |
| 24A1 | DYEMH (SEQ ID NO: 10) | AIWPENADSVYNQKFKG (SEQ ID NO: 25) | EGGNY (SEQ ID NO: 41) |
| 5F8 | DTYIH (SEQ ID NO: 11) | RIDPANGNTKYDPKFQG (SEQ ID NO: 26) | SGNYGAMDY (SEQ ID NO: 42) |
| 6C1 | SYWIE (SEQ ID NO: 9) | EILPGSDSTKYVEKFKV (SEQ ID NO: 27) | GGYHYPGWLVY (SEQ ID NO: 43) |
| 12A11 | RYWMS (SEQ ID NO: 12) | EISPDSSTINYTPSLKD (SEQ ID NO: 28) | PSPALDY (SEQ ID NO: 44) |
| 12B8 | NYGMN (SEQ ID NO: 13) | WIDTDTGEATYTDDFKG (SEQ ID NO: 29) | EEYGLFGFPY (SEQ ID NO: 45) |
| 14C10 | TSAMGIG (SEQ ID NO: 14) | HIWWDDDKRYNPALKS (SEQ ID NO: 30) | IDGIYDGSFYAMDY (SEQ ID NO: 46) |
| 8C5 | TYGVH (SEQ ID NO: 15) | VIWSGGSTDYNAAFIS (SEQ ID NO: 31) | DYGSTYVDAIDY (SEQ ID NO: 47) |

TABLE 3

CDR L sequences for murine anti-KLB monoclonal antibodies.

| Antibody | CDR L1 | CDR L2 | CDR L3 |
|---|---|---|---|
| 11F1 | SASQVISNYLN (SEQ ID NO: 48) | FTSSLRS (SEQ ID NO: 63) | QQYSKLPWT (SEQ ID NO: 79) |
| 6D12 | SASSSGRYTF (SEQ ID NO: 49) | DTSKLAS (SEQ ID NO: 64) | FQGTGYPLT (SEQ ID NO: 80) |
| 11D4 | RASQDISNYFN (SEQ ID NO: 50) | YTSRLQS (SEQ ID NO: 65) | HQVRTLPWT (SEQ ID NO: 81) |
| 8E1 | KASDHINNWLA (SEQ ID NO: 51) | GTTNLET (SEQ ID NO: 66) | QQYWNTPFT (SEQ ID NO: 82) |
| 46C3 | RSSQNIVHSDGNTYLE (SEQ ID NO: 52) | KVSNRFS (SEQ ID NO: 67) | FQGSHVLT (SEQ ID NO: 83) |
| 8H7 | KASQFVSDAVA (SEQ ID NO: 53) | SASYRYT (SEQ ID NO: 68) | QQHYIVPYT (SEQ ID NO: 84) |
| 21H3 | KASQFVSDAVA (SEQ ID NO: 53) | SASYRYT (SEQ ID NO: 68) | QQHYIVPYT (SEQ ID NO: 84) |
| 25F7 | KASDHINNWLA (SEQ ID NO: 51) | GASNLET (SEQ ID NO: 69) | QQYWNTPFT (SEQ ID NO: 82) |
| 14E6 | RASQEISGYLS (SEQ ID NO: 54) | AASTLDS (SEQ ID NO: 70) | LQYGSYPWT (SEQ ID NO: 85) |
| 14C6 | SASSSLSSSYLY (SEQ ID NO: 55) | GASNLAS (SEQ ID NO: 71) | HQWSSYPLT (SEQ ID NO: 86) |
| 24A1 | KSSQSLLNSGNQKNSLA (SEQ ID NO: 56) | LASTRES (SEQ ID NO: 72) | QQHHSTPYT (SEQ ID NO: 87) |
| 5F8 | RASSSVNHMY (SEQ ID NO: 57) | YTSTLAP (SEQ ID NO: 73) | QQFTISPSMYT (SEQ ID NO: 88) |
| 6C1 | KASQNVDSYVA (SEQ ID NO: 58) | SASYRFS (SEQ ID NO: 74) | QQYNISPYT (SEQ ID NO: 89) |
| 12A11 | RASQSISDYVY (SEQ ID NO: 59) | YASQSIS (SEQ ID NO: 75) | QNGHNFPYT (SEQ ID NO: 90) |
| 12B8 | KASEDIYNRLA (SEQ ID NO: 60) | AATSLET (SEQ ID NO: 76) | QQYWSNPLT (SEQ ID NO: 91) |
| 14C10 | RASESVDSYGNSFMH (SEQ ID NO: 61) | RASNLES (SEQ ID NO: 77) | QQSNEDYT (SEQ ID NO: 92) |
| 8C5 | RASESVESYGNRYMT (SEQ ID NO: 62) | RAANLQS (SEQ ID NO: 78) | QQSNEDPWT (SEQ ID NO: 93) |

Figure 4:
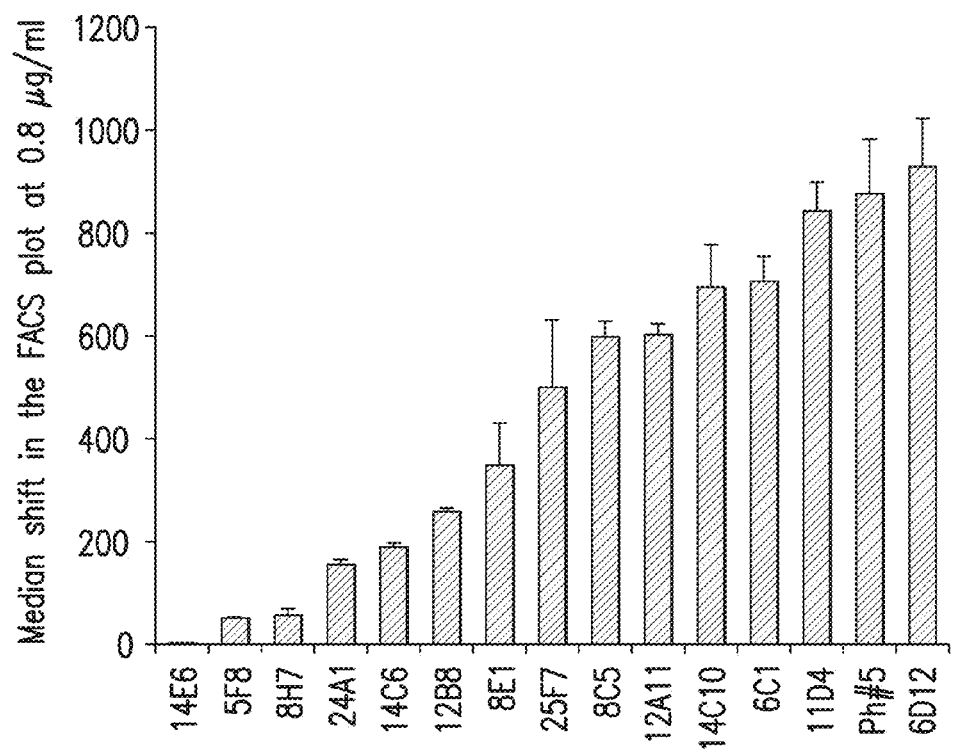
FIG. 4 depicts the median shift observed in the FACS plot at 0.8 µg/ml measuring binding of various anti-KLB antibodies to 293 cells expressing hKLB.

Most of the hybridoma-derived anti-KLB antibodies along with one phage-derived antibody (designate Ph#5, which was obtained by phage panning using recombinant hKLB-ECD-HIS protein (R&D Systems)) were ranked based on the median shift observed in the FACS plot at 0.8 μg/ml measuring binding of the antibodies to 293 cells expressing hKLB (FIG. 4).

Figure 5:
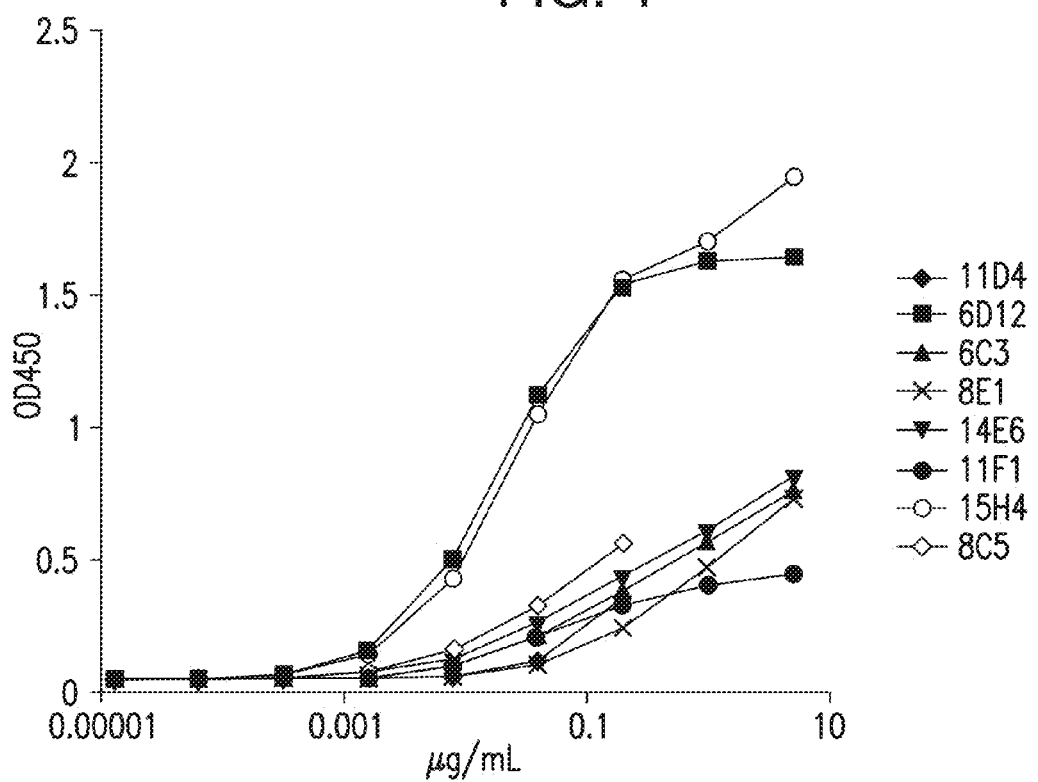
FIG. 5 depicts the relative binding of various anti-KLB antibodies to hKLB-ECD-HIS protein.

In addition, some of the antibodies were ranked by ELISA. For these experiments, anti-KLB antibodies that were chimeric recombinant IgG with murine variable regions and hIgG1 constant regions were used to measure binding to hKLB-ECD-HIS protein. The relative binding of the antibodies tested were similar except for 14E6, which appeared to bind better under the ELISA conditions than in the FACS analysis (FIG. 5).

Example 4: KLB Binding of Anti-KLB Antibodies

To test competition between various anti-KLB antibodies, ELISA was used. In some experiments, IgG antibodies purified from hybridoma supernatants corresponding to 6D12, 8C5, and 11F1 were biotinylated using EZ-link NHS-PEO Solid Phase Biotinylation Kit (Pierce). Binding to KLB-ECD-HIS protein was tested using HRP-conjugated streptavidin in the presence of various concentrations of hybridoma-derived anti-KLB. In some experiments, binding of recombinant human IgG to KLB-ECD-HIS protein was tested using HRP-conjugated anti-human IgG (Jackson ImmunoResearch Inc.) in the presence of various concentrations of hybridoma-derived anti-KLB. It was observed that none of 11F1, 11D4, 8E1 and 46C3 compete with 6D12 for binding (others were not tested against 6D12). Anti-KLB antibodies 14E6 and 12A11 compete for binding with 8C5, but 11D4 and 14C10 do not (others were not tested against 8C5), and 11D4 competes for binding with 11F1, but 6D12, 8E1, and 46C3 (others were not tested against 11F1).

Example 5: Cross-Species Crossreactivity of Anti-KLB Antibodies

Species cross reactivity of the disclosed anti-KLB antibodies were analyzed by FACS analysis using KLB cDNA from mouse, rat, rabbit, cynomolgus monkey and rhesus monkey cloned into pRK mammalian expression vectors transiently transfected into HEK293T cells. The KLB extracellular domain polypeptide sequences that were expressed are as follows:

```
Mouse:
                              (SEQ ID NO: 158)
FSGDGKAIWDKKQYVSPVNPSQLFLYDTFPKNFSWGVGTGAFQVEGSWKT
DGRGPSIWDRYVYSHLRGVNGTDRSTDSYIFLEKDLLALDFLGVSFYQFS
ISWPRLFPNGTVAAVNAQGLRYYRALLDSLVLRNIEPIVTLYHWDLPLTL
QEEYGGWKNATMIDLFNDYATYCFQTFGDRVKYWITIHNPYLVAWHGFGT
GMHAPGEKGNLTAVYTVGHNLIKAHSKVWHNYDKNFRPHQKGWLSITLGS
HWIEPNRTDNMEDVINCQHSMSSVLGWFANPIHGDGDYPEFMKTGAMIPE
FSEAEKEEVRGTADFFAFSFGPNNFRPSNTVVKMGQNVSLNLRQVLNWIK
LEYDDPQILISENGWFTDSYIKTEDTTAIYMMKNFLNQVLQAIKFDEIRV
FGYTAWTLLDGFEWQDAYTTRRGLFYVDFNSEQKERKPKSSAHYYKQIIQ
DNGFPLKESTPDMKGRFPCDFSWGVTESVLKPEFTVSSPQFTDPHLYVWN
VTGNRLLYRVEGVRLKTRPSQCTDYVSIKKRVEMLAKMKVTHYQFALDWT
SILPTGNLSKVNRQVLRYYRCVVSEGLKLGVFPMVTLYHPTHSHLGLPLP
LLSSGGWLNMNTAKAFQDYAELCFRELGDLVKLWITINEPNRLSDMYNRT
SNDTYRAAHNLMIAHAQVWHLYDRQYRPVQHGAVSLSLHCDWAEPANPFV
DSHWKAAERFLQFEIAWFADPLFKTGDYPSVMKEYIASKNQRGLSSSVLP
RFTAKESRLVKGTVDFYALNHFTTRFVIHKQLNTNRSVADRDVQFLQDIT
RLSSPSRLAVTPWGVRKLLAWIRRNYRDRDIYITANGIDDLALEDDQIRK
YYLEKYVQEALKAYLIDKVKIKGYYAFKLTEEKSKPRFGFFTSDFRAKSS
VQFYSKLISSSGLPAENRSPACGQPAEDTDCTICSFLV.

Rat (+N-ter FLAG):
                              (SEQ ID NO: 147)
DYKDDDDKLEFSGDGKAIWDKKQYVSPVNPGQLFLYDTFPKNFSWGVGTG
AFQVEGSWKADGRGPSIWDRYVDSHLRGVNSTDRSTDSYVFLEKDLLALD
FLGVSFYQFSISWPRLFPNGTVAAVNAKGLQYYRALLDSLVLRNIEPIVT
LYHWDLPLTLQEEYGGWKNATMIDLFNDYATYCFQTFGDRVKYWITIHNP
YLVAWHGFGTGMHAPGEKGNLTAVYTVGHNLIKAHSKVWHNYDKNFRPHQ
KGWLSITLGSHWIEPNRTENMEDVINCQHSMSSVLGWFANPIHGDGDYPE
FMKTSSVIPEFSEAEKEEVRGTADFFAFSFGPNNFRPSNTVVKMGQNVSL
NLRQVLNWIKLEYDNPRILISENGWFTDSYIKTEDTTAIYMMKNFLNQVL
QAIKFDEIQVFGYTAWTLLDGFEWQDAYTTRRGLFYVDFNSEQKERKPKS
SAHYYKQIIQDNGFPLQESTPDMKGQFPCDFSWGVTESVLKPEFTVSSPQ
```

-continued
```
FTDPHLYVWNVTGNRLLYRVEGVRLKTRPSQCTDYVSIKKRVEMLAKMKV
THYQFALDWTSILPTGNLSKINRQVLRYYRCVVSEGLKLGISPMVTLYHP
THSHLGLPMPLLSSGGWLNTNTAKAFQDYAGLCFKELGDLVKLWITINEP
NRLSDMYNRTSNDTYRAAHNLMIAHAQVWHLYDRQYRPVQHGAVSLSLHS
DWAEPANPYVESHWKAAERFLQFEIAWFADPLFKTGDYPLAMKEYIASKK
QRGLSSSVLPRFTLKESRLVKGTIDFYALNHFTTRFVIHKQLNTNCSVAD
RDVQFLQDITRLSSPSRLAVTPWGMRKLLGWIRRNYRDMDIYVTANGIDD
LALEDDQIRKYYLEKYVQEALKAYLIDKVKIKGYYAFKLTEEKSKPRFGF
FTSDFKAKSSVQFYSKLISSSGFSSENRSPACGQPPEDTECAICSFLT.

Rabbit (+N-ter FLAG):
                              (SEQ ID NO: 148)
DYKDDDDKLDFPGDGRAVWSQNPNLSPVNESQLFLYDTFPKNFFWGVGTG
AFQVEGSWKKDGKGLSVWDHFIATHLNVSSRDGSSDSYIFLEKDLSALDF
LGVSFYQFSISWPRLFPDGTVAVANAKGLQYYNRLLDSLLLANIEPVVTL
YHWDLPWALQEKYGGWKNETLIDLFNDYATYCFQTFGDRVKYWITIHNPY
LVAWHGYGTGLHAPGEKGNVAAVYTVGHNLLKAHSKVWHNYNRNFRPHQK
GWLSITLGSHWIEPNRAESIVDILKCQQSMVSVLGWFANPIHGDGDYPEV
MTKKLLSVLPAFSEAEKNEVRGTADFFAFSFGPNNFKPLNTMAKMGQNVS
LNLRQVLNWIKLEYGNPRILIAENGWFTDSYVQTEDTTAIYMMKNFLNQV
LQAIRLDGVRVFGYTAWSLLDGFEWQDAYNTRRGLFYVDFNSEQRERRPK
SSAHYYKQVIGENGFTLREATPDLQGQFPCDFSWGVTESVLKPESVASSP
QFSDPHLYVWNATGNRMLHRVEGVRLKTRPAQCTDFITIKKQLEMLARMK
VTHFRFALDWASVLPTGNLSEVNRQALRYYRCVVTEGLKLNISPMVTLYY
PTHAHLGLPAPLLHSGGWLDPSTAKAFRDYAGLCFRELGDLVKLWITINE
PNRLSDVYNRTSNDTYQAAHNLLIAHAIVWHLYDRQYRPSQRGALSLSLH
SDWAEPANPYVASHWQAAERFLQFEIAWFAEPLFKTGDYPVAMREYIASK
TRRGLSSSVLPRFSDAERRLVKGAADFYALNHFTTRFVMHEQQNGSRYDS
DRDVQFLQDITRLASPSRLAVMPWGEGKLLRWMRNNYGDLDVYITANGID
DQALQNDQLRQYYLEKYVQEALKAYLIDKIKIKGYYAFKLTEEKSKPRFG
FFTSDFKAKSSIQFYNKLITSNGFPSENGGPRCNQTQGNPECTVCLLLL.

Cynomolgus monkey (+N-ter FLAG):
                              (SEQ ID NO: 149)
DYKDDDDKLEFSGDGRAVWSKNPNFTPVNESQLFLYDTFPKNFFWGVGTG
ALQVEGSWKKDGKGPSIWDHFVHTHLKNVSSTNGSSDSYIFLEKDLSALD
FIGVSFYQFSISWPRLFPDGIVTVANAKGLQYYNTLLDSLVLRNIEPIVT
LYHWDLPLALQEKYGGWKNDTIIDIFNDYATYCFQTFGDRVKYWITIHNP
YLVAWHGYGTGMHAPGEKGNLAAVYTVGHNLIKAHSKVWHNYNTHFRPHQ
KGWLSITLGSHWIEPNRSENTMDILKCQQSMVSVLGWFASPIHGDGDYPE
GMKKKLLSILPLFSEAEKNEVRGTADFFAFSFGPNNFKPLNTMAKMGQNV
SLNLREALNWIKLEYNNPRILIAENGWFTDSHVKTEDTTAIYMMKNFLSQ
VLQAIRLDEIRVFGYTAWSLLDGFEWQDAYTIRRGLFYVDFNSKQKERKP
KSSAHYYKQIIRENGFSLKEATPDVQGQFPCDFSWGVTESVLKPESVASS
PQFSDPYLYVWNATGNRLLHRVEGVRLKTRPAQCTDFVNIKKQLEMLARM
```

-continued

KVTHYRFALDWASVLPTGNLSAVNRQALRYYRCVVSEGLKLGISAMVTLY

YPTHAHLGLPEPLLHAGGWLNPSTVEAFQAYAGLCFQELGDLVKLWITIN

EPNRLSDIYNRSGNDTYGAAHNLLVAHALAWRLYDRQFRPSQRGAVSLSL

HADWAEPANPYADSHWRAAERFLQFEIAWFAEPLFKTGDYPAAMREYIAS

KHRRGLSSSALPRLTEAERRLLKGTVDFCALNHFTTRFVMHEQLAGSRYD

SDRDIQFLQDITRLSSPTRLAVIPWGVRKLLRWVRRNYGDMDIYITASGI

DDQALEDDRLRKYYLEKYLQEVLKAYLIDKVRIKGYYAFKLAEEKSKPRF

GFFTSDFKAKSSIQFYNKMISSSGFPSENSSSRCSQTQKNTECTVCLFL

A.

Rhesus monkey (+N-ter FLAG):
(SEQ ID NO: 150)
DYKDDDDKLEFSGDGRAVWSKNPNFTPVNESQLFLYDTFPKNFFWGVGTG

ALQVEGSWKKDGKGPSIWDHFVHTHLKNVSSTNGSSDSYIFLEKDLSALD

FIGVSFYQFSISWPRLFPDGIVTVANAKGLQYYNALLDSLVLRNIEPIVT

LYHWDLPLALQEKYGGWKNDTIIDIFNDYATYCFQTFGDRVKYWITIHNP

YLVAWHGYGTGMHAPGEKGNLAAVYTVGHNLIKAHSKVWHNYNTHFRPHQ

KGWLSITLGSHWIEPNRSENTMDILKCQQSMVSVLGWFANPIHGDGDYPE

GMKKKLLSILPLFSEAEKNEVRGTADFFAFSFGPNNFKPLNTMAKMGQNV

SLNLREALNWIKLEYNNPQILIAENGWFTDSHVKTEDTTAIYMMKNFLSQ

VLQAIRLDEIRVFGYTAWSLLDGFEWQDAYTIRRGLFYVDFNSKQKERKP

KSSAHYYKQIIRENGFSLKEATPDVQGQFPCDFSWGVTESVLKPESVASS

PQFSDPYLYVWNATGNRLLHRVEGVRLKTRPAQCTDFVNIKKQLEMLARM

KVTHYRFALDWASVLPTGNLSAVNRQALRYYRCVVSEGLKLGISAMVTLY

YPTHAHLGLPEPLLHAGGWLNPSTVEAFQAYAGLCFQELGDLVKLWITIN

EPNRLSDIYNRSGNDTYGAAHNLLVAHALAWRLYDRQFRPSQRGAVSLSL

HADWAEPANPYADSHWRAAERFLQFEIAWFAEPLFKTGDYPAAMREYIAS

KHRRGLSSSALPRLTEAERRLLKGTVDFCALNHFTTRFVMHEQLAGSRYD

SDRDIQFLQDITRLSSPTRLAVIPWGVRKLLRWVRRNYGDMDIYITASGI

DDQALEDDRLRKYYLEKYLQEVLKAYLIDKVRIKGYYAFKLAEEKSKPRF

GFFTSDFKAKSSIQFYNKMISSSGFPSENSSSRCSQTQKNTECTVCLFL

V.

As shown in Table 4, most antibodies, e.g., 6D12, 11D4 and 8E1, were found to bind to KLB from rabbit, cynomolgus monkey and rhesus monkey and about half of the anti-KLB antibodies, e.g., 8C5, 14E6 and 14C6, were found to bind to mouse and rat KLB.

TABLE 4

Binding of murine anti-KLB antibodies to KLB from different species.

| Anti-KLB Antibody | Mouse | Rat | Rabbit | Cynomolgus Monkey | Rhesus Monkey |
|---|---|---|---|---|---|
| 11F1 | no | no | no | YES | YES |
| 6D12 | no | no | YES | YES | YES |
| 11D4 | no | no | YES | YES | YES |
| 8E1 | no | no | YES | YES | YES |
| 46C3 | no | no | YES | no | no |
| 8H7 | Weak | no | YES | YES | YES |
| 21H3 | Weak | no | YES | YES | YES |
| 25F7 | no | no | Weak | YES | YES |
| 8C5 | YES | YES | no | YES | YES |
| 14E6 | YES | YES | YES | YES | YES |
| 14C6 | YES | YES | YES | YES | YES |
| 24A1 | YES | YES | YES | YES | YES |
| 5F8 | no | no | YES | YES | YES |
| 6C1 | no | no | YES | YES | YES |
| 12A11 | Weak | no | YES | YES | YES |
| 12B8 | no | no | YES | YES | YES |
| 14C10 | no | no | YES | YES | YES |

Example 6: Epitope Mapping of Anti-KLB Antibodies

To determine whether the anti-KLB antibodies do not bind the extracellular domain (ECD) of human alpha-Klotho (hKLA), a construct having the following sequence was used:

Predicted polypeptide sequence expressed
(with C-t erminal (intracellular) FLAG):
(SEQ ID NO: 151)
EPGDGAQTWARFSRPPAPEAAGLFQGTFPDGFLWAVGSAAYQTEGGWQQH

GKGASIWDTFTHHPLAPPGDSRNASLPLGAPSPLQPATGDVASDSYNNVF

RDTEALRELGVTHYRFSISWARVLPNGSAGVPNREGLRYYRRLLERLREL

GVQPVVTLYHWDLPQRLQDAYGGWANRALADHFRDYAELCFRHFGGQVKY

WITIDNPYVVAWHGYATGRLAPGIRGSPRLGYLVAHNLLLAHAKVWHLYN

TSFRPTQGGQVSIALSSHWINPRRMTDHSIKECQKSLDFVLGWFAKPVFI

DGDYPESMKNNLSSILPDFTESEKKHKGTADFFALCFGPTLSFQLLDPHM

KFRQLESPNLRQLLSWIDLEFNHPQIFIVENGWFVSGTTKRDDAKYMYYL

KKFIMETLKAIKLDGVDVIGYTAWSLMDGFEWHRGYSIRRGLFYVDFLSQ

DKMLLPKSSALFYQKLIEKNGFPPLPENQPLEGTFPCDFAWGVVDNYIQV

DTTLSQFTDLNVYLWDVHHSKRLIKVDGVVTKKRKSYCVDFAAIQPQIAL

LQEMHVTHFRFSLDWALILPLGNQSQVNHTILQYYRCMASELVRVNITPV

VALWQPMAPNQGLPRLLARQGAWENPYTALAFAEYARLCFQELGHHVKLW

ITMNEPYTRNMTYSAGHNLLKAHALAWHVYNEKFRHAQNGKISIALQADW

IEPACPFSQKDKEVAERVLEFDIGWLAEPIFGSGDYPWVMRDWLNQRNNF

LLPYFTEDEKKLIQGTFDFLALSHYTTILVDSEKEDPIKYNDYLEVQEMT

DITWLNSPSQVAVVPWGLRKVLNWLKFKYGDLPMYIISNGIDDGLHAEDD

QLRVYYMQNYINEALKAHILDGINLCGYFAYSFNDRTAPRFGLYRYAADQ

FEPKASMKHYRKIIDSNGFPGPETLERFCPEEFTVCTECSFFHTRKSLLA

FIAFLFFASIISLSLIFYYSKKGRRSYKLEDYKDDDDK.

Both KLA and KLB have two glycosidase-like domains, one N-terminal and one C-terminal. To identify the region of KLB recognized by the anti-KLB antibodies, hKLB, hKLA and a chimeric construct comprising the hKLA N-terminal glycosidase-like domain and the hKLB c-terminal glycosidase-like domain were cloned into a pCMV-Tag4A mammalian expression vector (Agilent). The N- and C-terminal domains of hKLA and hKLB correspond to sequences from SEQ ID NO: 151 and SEQ ID NO: 145, respectively, as shown in the Table 5. The N-terminal domains of hKLA and hKLB were divided into 5 segments and the C-terminal domains were divided into 5 segments based on sequence homology between the two proteins.

TABLE 5

Subsequence of KLA and KLB.

| Polypeptide Segment | Amino acid sequence |
|---|---|
| N-terminal glycosidase-like domain of KLA | 28-469 of SEQ ID NO: 151 |
| C-terminal glycosidase-like domain of KLA | 486-928 of SEQ ID NO: 151 |
| N-terminal glycosidase-like domain of KLB | 29-452 of SEQ ID NO: 145 |
| C-terminal glycosidase-like domain of KLB | 469-923 of SEQ ID NO: 145 |
| Segment 1 of KLA ECD | 1-94 of SEQ ID NO: 151 |
| Segment 2 of KLA ECD | 95-201 of SEQ ID NO: 151 |
| Segment 3 of KLA ECD | 202-329 of SEQ ID NO: 151 |
| Segment 4 of KLA ECD | 330-442 of SEQ ID NO: 151 |
| Segment 5 of KLA ECD | 443-472 of SEQ ID NO: 151 |
| Segment 6 of KLA ECD | 473-529 of SEQ ID NO: 151 |
| Segment 7 of KLA ECD | 530-613 of SEQ ID NO: 151 |
| Segment 8 of KLA ECD | 614-729 of SEQ ID NO: 151 |
| Segment 9 of KLA ECD | 730-831 of SEQ ID NO: 151 |
| Segment 10 of KLA ECD | 832-944 of SEQ ID NO: 151 |
| Segment 1 of KLB ECD | 1-77 of SEQ ID NO: 145 |
| Segment 2 of KLB ECD | 78-184 of SEQ ID NO: 145 |
| Segment 3 of KLB ECD | 185-313 of SEQ ID NO: 145 |
| Segment 4 of KLB ECD | 314-425 of SEQ ID NO: 145 |
| Segment 5 of KLB ECD | 426-455 of SEQ ID NO: 145 |
| Segment 6 of KLB ECD | 456-514 of SEQ ID NO: 145 |
| Segment 7 of KLB ECD | 515-598 of SEQ ID NO: 145 |
| Segment 8 of KLB ECD | 599-722 of SEQ ID NO: 145 |
| Segment 9 of KLB ECD | 723-829 of SEQ ID NO: 145 |
| Segment 10 of KLB ECD | 830-992 of SEQ ID NO: 145 |

A FACS analysis was performed with the antibodies of the present disclosure and about half of the antibodies were observed to recognize the N-terminal glycosidase-like domain of hKLB, whereas others recognize the C-terminal glycosidase-like domain (Table 6). As shown in Table 6, two of the antibodies that recognized the N-terminal domain of hKLB bound to a portion of the domain comprising segment 1, whereas the others required only segments 2-5 for binding.

TABLE 6

Mapping of binding of murine anti-KLB antibodies.

| Anti-KLB Antibody | N- or C-terminal domain | Segment (1-10) |
|---|---|---|
| 11F1 | N-terminal | 1-5 |
| 6D12 | N-terminal | 1-5 |
| 11D4 | N-terminal | 2-5 |
| 8E1 | N-terminal | 2-5 |
| 46C3 | N-terminal | 2-5 |
| 8H7 | N-terminal | 2-5 |
| 21H3 | N-terminal | 2-5 |
| 25F7 | N-terminal | 2-5 |
| 8C5 | C-terminal | 5-10 |
| 14E6 | C-terminal | 5-10 |
| 14C6 | C-terminal | 5-10 |
| 24A1 | C-terminal | 5-10 |
| 5F8 | C-terminal | 5-10 |
| 6C1 | C-terminal | 5-10 |
| 12A11 | C-terminal | 5-10 |
| 12B8 | C-terminal | 5-10 |
| 14C10 | C-terminal | 5-10 |

Example 7: Identification of Bispecific Antibodies that Specifically Activate the FGFR1c/KLB Complex Based on the ability of the R1MAbs to activate FGFR1 as a Fab, a molecule that incorporates tethering of a lower affinity R1MAb to a higher affinity anti-KLB antibody was produced to generate an anti-KLB/anti-FGFR1 bispecific antibody (FIG. 6A; WO2012/158704).

Without being bound to a particular theory, FGF21-mediated activation is proposed to work through the recruitment of FGF21 to the FGFR1c/KLB complex through the C-terminal KLB-binding tail, while the determinants for FGFR-specificity reside in the N-terminal region, which likely binds to FGFR via low affinity interaction (See FIG. 6B) (Yie et al. *FEBS Lett.* 583(1): 19-24 (2009)). Therefore, the tethering of an affinity-lowered R1MAb1 to a high affinity anti-KLB antibody as a bispecific antibody could yield a KLB-dependent FGFR1 agonist. Without being bound to a particular theory, an anti-KLB/anti-FGFR1 bispecific antibody that includes a FGFR1 arm having a low affinity can mitigate the risk of the anti-KLB/anti-FGFR1 bispecific antibody from binding to FGFR1 tightly in the absence of KLB and preventing the binding and/or activation of FGFR1 by other FGF ligands (e.g., FGF1, FGF2, FGF8 and FGF23). In addition, an FGFR1 arm with a low affinity can permit the presence of higher levels of anti-FGFR1 impurities such as, but not limited to, anti-FGFR1 half-knob antibodies, non-covalent anti-FGFR1 dimers, covalent anti-FGFR1 dimers and high-molecular weight species, without resulting in clinically significant side effects.

As used herein, bFKB1, in general, refers to any of the several anti-KLB/anti-FGFR1 bispecific antibodies disclosed herein. Details regarding the specific anti-KLB/anti-FGFR1 bispecific antibodies disclosed in the Figures are described below. HEK293 cells were co-transfected with a mixture of four expression vectors encoding the heavy and light chains of anti-FGFR1 (YW182.2 (R1MAb1) and YW182.3 (R1MAb2)) and the anti-KLB antibodies described above. The heavy chain of anti-FGFR1 and anti-KLB were respectively tagged with the Flag peptide and Oct-Histidine so that heterodimeric IgG could be purified by sequential affinity purification from conditioned medium. Partially purified heterodimeric IgG were then analyzed in a GAL-ELK1 based luciferase assay to identify KLB-dependent agonists. To minimize mispairing of heavy and light chains, anti-FGFR1 was expressed with human Fab constant region, and anti-KLB was expressed with mouse Fab constant region. The tagged-bispecific IgGs were initially tested in a crude form using 28 combinations of 3 anti-R1MAbs and 18 anti-KLB Abs (Table 7).

FIG. 7A shows induction data for certain bispecific combinations of YW182.2 (R1MAb1), YW182.3 (R1MAb2) and YW182.5 (R1MAb3) with 18C5, 12A11 and 14E6 in a GAL-ELK1 luciferase assay. In most cases, it was observed that the bispecific antibodies activated signaling significantly better in cells that coexpressed FGFR1c and KLB compared with cells that expressed only FGFR1c, but not KLB.

Figure 8A:
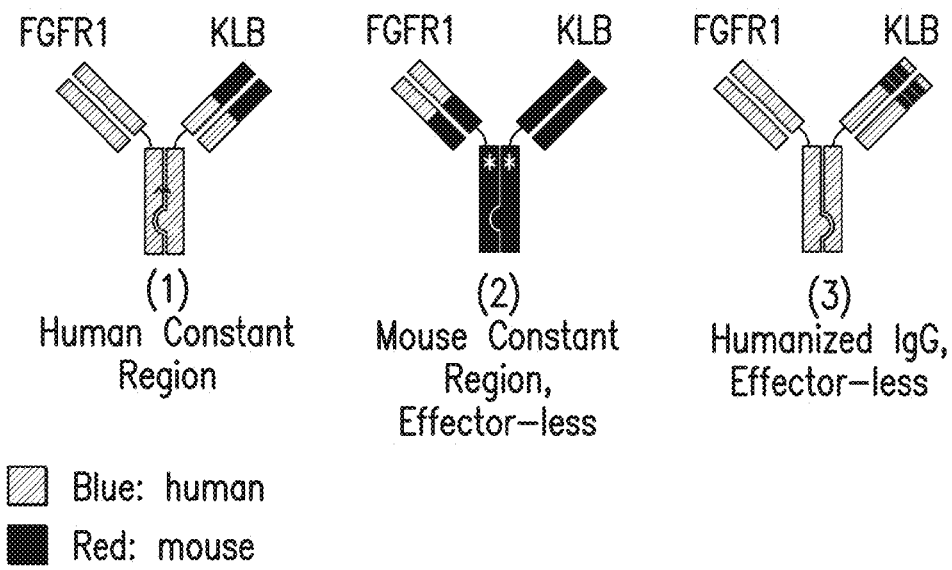
FIG. 8A is a schematic representation of three variants of anti-KLB/anti-FGFR1c bispecific antibodies. Blue: human, and Red: mouse. Approximate position of the oligosaccharide chain at N297 in (1) is indicated by ˆ. The effector-less versions ((2) and (3)) lack the oligosaccharide chains due to the N297G mutation. Asterisks in (2) indicate approximate position of the D265A mutation. The orientation of knob vs hole is also shown. (1) represents BsAb10; (2) represents BsAb20; and (3) represents BsAb17.

Based on the activity of these antibodies in these initial experiments, 8 representative anti-KLB Abs (Ph#5, 8C5, 12A11, 14C10, 6D12, 11D4, 6C1 and, as a negative control, 14E6) were used to produce un-tagged bispecific antibodies with YW182.5 (by using a previously described knob-hole technology for further characterization (supra, and, e.g., Atwell, et al. *FEBS Lett.* 583(1): 19-24 (2009)). As shown in FIG. 8A, bispecific antibodies were produced with human IgG1 constant region (wild-type, with effector function (1)) and with human IgG1 constant region with N297G mutation to eliminate the effector function (3), or mouse constant region with dual [D265G/N297G] mutations (DANG) to eliminate effector function (2).

Table 7 below lists various bispecific antibodies that were made using the knob-in-hole technology.

iodinated FGF21 from Phoenix Pharmaceuticals and in-house produced unlabeled FGF21. Each of the bispecific combinations (except for the negative control) showed signaling dependent on both FGFR1c and KLB. The data for certain combinations are shown in FIG. 7B. In addition, the combination of the anti-KLB arms with the YW182.5 (R1MAb3) arm showed lower background signaling in cells that expressed FGFR1c, but not KLB.

TABLE 7

Bispecific anti-KLB/anti-FGFR1 antibodies.

| BsAb ID# | Anti-FGFR1 Arm | Anti-FGFR1 Platform | Anti-KLB Arm | Anti-KLB Platform |
| --- | --- | --- | --- | --- |
| 1 | YW182.3 | Human IgG1 | Ph#5 | Human IgG1 |
| 2 | YW182.2 | Human IgG1 | Ph#5 | Human IgG1 |
| 3 | YW182.3 | Human IgG1 | 14E6 | Murine VH/VL-Human IgG1 chimera |
| 4 | YW182.3 | Human IgG1 | 8C5 (KLBmAb1) | Murine VH/VL-Human IgG1 chimera |
| 5 | YW182.5 | Human IgG1 | 11D4 (KLBmAb5) | Murine VH/VL-Human IgG1 chimera |
| 6 | YW182.5 | Human IgG1 | 14C10 (KLBmAb3) | Murine VH/VL-Human IgG1 chimera |
| 7 | YW182.5 | Human IgG1 | 6C1 (KLBmAb4) | Murine VH/VL-Human IgG1 chimera |
| 8 | YW182.5 | Human IgG1 | 6D12 (KLBmAb6) | Murine VH/VL-Human IgG1 chimera |
| 9 | YW182.5 | Human IgG1 | 12A11 (KLBmAb2) | Murine VH/VL-Human IgG1 chimera |
| 10 | YW182.5 | Human IgG1 | 8C5 (KLBmAb1) | Murine VH/VL-Human IgG1 chimera |
| 11 | YW182.5 | Human IgG1 N297G | 8C5.K4H3.RNL | Human IgG1 N297G |
| 12 | YW182.5 | Human IgG1 N297G | 8C5.K4H3.KNV | Human IgG1 N297G |
| 13 | YW182.5 | Human IgG1 N297G | 8C5.K4H3.M4L.KNV | Human IgG1 |
| 14 | YW182.5 | Human IgG1 N297G | 8C5.K4H3.M4L.KNV | Human IgG1 N297G |
| 15 | YW182.5_W33Y | Human IgG1 N297G | 8C5.K4H3.M4L.KNV | Human IgG1 N297G |
| 16 | YW182.2_W33Y | Human IgG1 N297G | 8C5.K4H3.M4L.KNV | Human IgG1 N297G |
| 17 | YW182.5_YGDY | Human IgG1 N297G | 8C5.K4H3.M4L.KNV | Human IgG1 N297G |
| 18 | YW182.2_YA | Human IgG1 N297G | 8C5.K4H3.M4L.KNV | Human IgG1 N297G |
| 19 | YW182.5 | Human IgG1 N297G | 8C5_W52Y.K4H3.M4L.KNV | Human IgG1 N297G |
| 20 | YW182.5 | Human VH/VL-Murine IgG2a chimera DANG | Murine 8C5 | Murine IgG2a DANG |

Figure 6C:
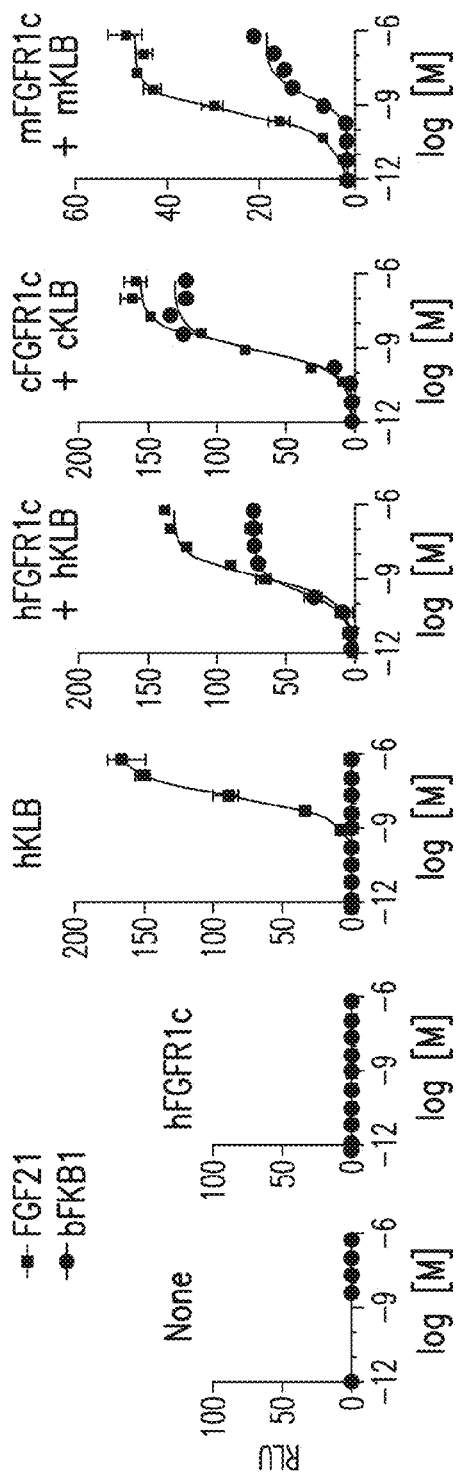
FIG. 6C depicts a GAL-ELK1 luciferase assay of FGF21 and bispecific antibody (BsAb) 17 activity using FGFR1-deficient HEK293 cells. Cells were transfected to express indicated receptors.

The isotype control IgG used was either anti-ragweed (murine IgG2a) or the anti-human Her2 trastuzumab (human IgG1). Fab fragments were expressed in *E. coli* and purified using conventional column chromatography. Recombinant FGF21 was from R&D systems (2539-FG/CF) except for radioligand cell binding assay, which was performed with As shown in FIG. 6C, the activity of an anti-KLB/anti-FGFR1c antibody (BsAb17) was tested in FGFR1-deficient HEK293 cells expressing various receptors. FGFR1-deficient HEK293T cells were generated using the CRISPR-cas9 method using guide RNAs. The anti-KLB/antiFGFR1c antibody was observed to induce luciferase activity - in cells coexpressing recombinant hFGFR1c and hKLB (FIG. 6C).

Figure 7C:
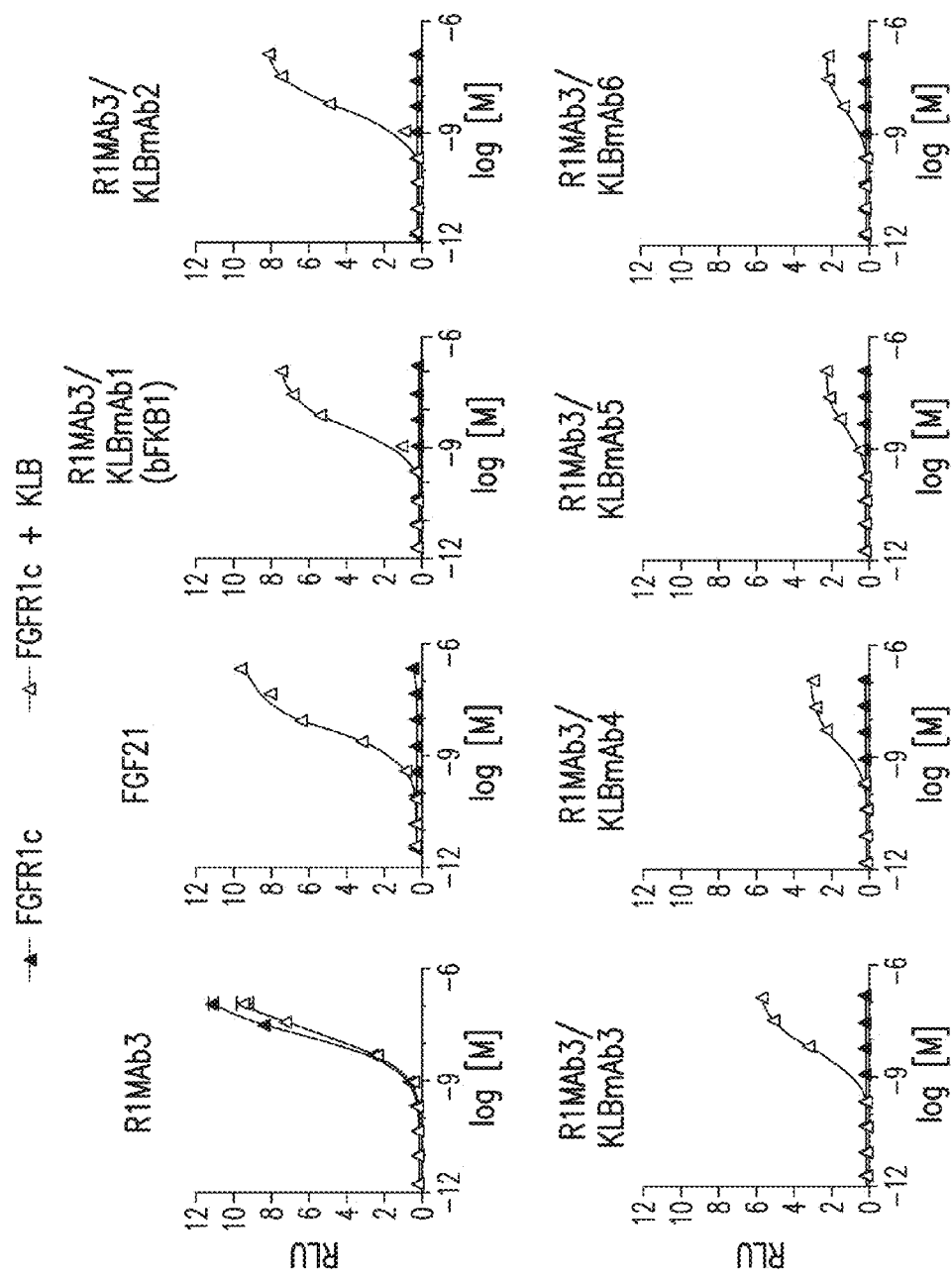
FIG. 7C depicts a bispecific antibody with anti-FGFR1 and anti-KLB arms that induced luciferase activity in a dose-dependent manner in cells expressing recombinant hFGFR1c and hKLB, but not in cells without KLB expression.

Similar results were observed for other anti-KLB/anti-FGFR1c antibodies. As shown in FIG. 7C, when tested in a GAL-ELK1-based luciferase assay in HEK293 cells expressing FGFR1c with or without KLB, multiple bispecific antibody combinations of anti-FGFR1 and anti-KLB arms, e.g., BsAb5, 6, 7, 8, 9, 10, induced luciferase activity in a dose-dependent manner in cells expressing recombinant hFGFR1c and hKLB, but not in cells without KLB expression. These results indicate that these bispecific antibodies act as KLB-dependent FGFR agonists, just like FGF21.

Synergy of an anti-KLB/anti-FGFR1c antibody (BsAb17) with FGF21 was also tested. As shown in FIG. 9B, no synergy between BsAb17 and FGF21 was observed when the concentration of FGF21 was increased incrementally and the concentration of BsAb17 remained unchanged.

In addition, as the concentration of the anti-KLB/anti-FGFR1c antibody (BsAb17) was increased incrementally and the concentration of FGF21 remained unchanged no synergy between BsAb17 and FGF21 was observed (FIG. 9C).

The solution binding affinity ($K_d$) of two of the bispecific antibodies, BsAb10 and BsAb9, (along with hFGF21) to HEK293 cells expressing KLB from human, cynomolgous monkey and mice, human FGFR1c, or both hFGFR1c and hKLB was measured by a radiolabeled ligand binding assay. For the radioligand cell binding assay, HEK293 cells that stably co-expressing KLB and/or FGFR1c were placed into 96-well plate at a density of 100,000 to 200,000 cells per 0.2 mL in binding buffer (DMEM with 1% bovine serum albumin (BSA), 50 mM HEPES, pH 7.2, 0.1% sodium azide and 350 mM human IgG). Competition reaction mixtures of 50 µL containing a fixed concentration of iodinated FGF21 (Phoenix Pharmaceuticals) or iodinated BsAb, and serially diluted concentrations of unlabeled FGF21 (Genentech) or unlabeled BsAb were added to the cells. Competition reactions with cells were incubated for 2 h at room temperature. After the 2 h incubation, the competition reactions were transferred to a Millipore Multiscreen filter plate and washed four times with binding buffer to separate the free from bound iodinated FGF21 or antibody. The filters were counted on a Wallac Wizard 1470 gamma counter (PerkinElmer Life and Analytical Sciences). The binding data were evaluated using New Ligand software (Genentech), which uses the fitting algorithm of Munson and Rodbard (Munson and Rodbard *Anal. Biochem.* 107, 220-239 (1980)) to determine the binding affinity.

As shown in Table 8, both antibodies exhibited some good reactivity to cells expressing only KLB (in a cross-species pattern consistent with that observed previously), but both bound much more weakly to cells expressing only hFGFR1c and more strongly to cells expressing both hKLB and hFGFR1c.

TABLE 8

Binding of bispecific anti-KLB antibodies to KLB/FGFR1 from different species.

| | | | | FGFR1c | |
|---|---|---|---|---|---|
| KLB | (none) Human | (none) Cyno | (none) Mouse | Human Human | Human (none) |
| BsAb10 | 6.6 nM | 15.4 nM | 15.5 nM | 2.3 nM | 300 nM |
| BsAb9 | 9.8 nM | 35 nM | n.d. | 2.2 nM | 300 nM |
| hFGF21 | n.d. | n.d. | n.d. | 5.3 nM | n.d. |

FIG. 9D shows the affinity of BsAb10 and BsAb9 to HEK293 cells stably expressing hKLB, hFGFR1c, or both, as compared to an antibody with two corresponding anti-FGFR1-binding arms (YW182.5) using FACS analysis. Similar results were obtained to those indicated above (FIG. 9D).

Further experiments were conducted with one bispecific antibody, BsAb10, which has YW182.5 as the anti-FGFR1 arm and 8C5 as the anti-KLB arm, and derivatives of BsAb10 (BsAb11-20). As shown in FIG. 6C, murine receptors were expressed in HEK293 cells and showed that BsAb17 induced luciferase activity in these cells as well, confirming the species cross reactivity of this Ab.

Figure 9A:
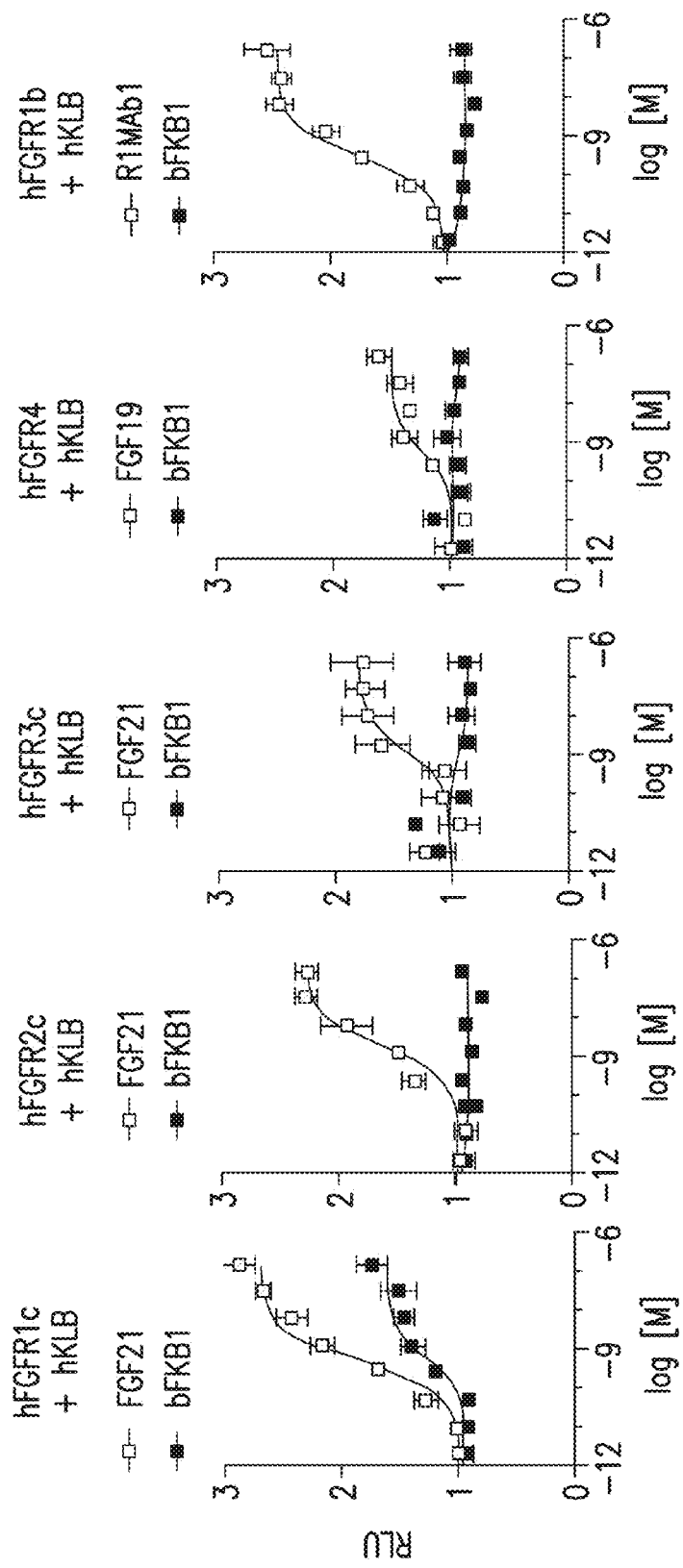
FIG. 9A depicts a GAL-ELK1 luciferase assay in rat L6 myoblast cells. Cells were co-transfected with an expression vector for indicated receptors. Transfected cells were incubated with various concentrations of BsAb10 or a positive control, FGF21, FGF19 or R1MAb1, for 6 h before luciferase assays.

BsAb10 was next tested in rat L6 myoblast cells lacking endogenous KLB and FGFRs, but transfected to express hKLB and each of 5 hFGFR isoforms (FIG. 9A). BsAb10 was found to induce luciferase activity only in cells expressing both FGFR1c and KLB, indicating that BsAb10 acts as a specific agonist for the FGFR1c/KLB complex but not KLB in complex with other FGFRs (FIG. 9A). FGF21 and FGF19 were used as controls to demonstrate that FGF21 induced luciferase activity when cells expressed a combination of KLB and any one of FGFR1c, 2c, or 3c, and FGF19 induced activity in cells that expressed a combination of KLB and FGFR4. Recombinant FGF21 was from R&D systems (2539-FG/CF) except for radioligand cell binding assay, which was performed with iodinated FGF21 from Phoenix Pharmaceuticals and in-house produced unlabeled FGF21. cDNAs encoding the extracellular domain (ECD) of human FGFR1b, 1c, 2b, 2c, 3b, 3c, and 4 were cloned into expression vector containing the cytomegalovirus (CMV) promoter to generate human FGFR-human Fc chimeric proteins or His-tagged FGFR proteins.

However, as described above, the parental anti-FGFR1c antibody, R1MAb3 (YW182.5) of BsAb10 can, surprisingly, binds to FGFR1b, an isoform of FGFR1 that does not interact with KLB. In addition, R1MAb3 (YW182.5) and can activate FGFR1b in the GAL-ELK1 assay in L6 cells, which is in contrast to the activity of BsAb10 (see FIGS. 2C and 2B).

Further, a combination of FGFR1b and KLB did not support activation by BsAb10 (FIG. 9A). Without being bound to a particular theory, these data suggest that the presence of preformed FGFR1/KLB complex is a prerequisite for the KLB-dependent activation of FGFR1 by BsAb10.

Example 8: BsAb10, and its Derivatives, Act as Molecular Mimetics of FGF21

Further characterizations of BsAb10 and its derivatives (BsAb11-20) and FGF21 revealed some similarities and differences. To determine the phosphorylation level of the MAPK signaling intermediates, cells were grown in preadipocyte basal medium-2 containing FBS, L-glutamine and GA-1000. Once confluent, subcutaneous pre-adipocytes (acquired from Lonza) were differentiated in growth media containing dexamethasone, indomethacin, and 3-isobutyl-1-methylxanthine (IBMX). For gene expression analysis, cells were differentiated for 14 days, and then further cultured for additional 48 h with indicated agonists. For MAPK signaling analysis, cells were differentiated for 10 days, grown in serum-free medium for 3 h, and then further cultured for an additional h with indicated agonists.

Figure 6D:
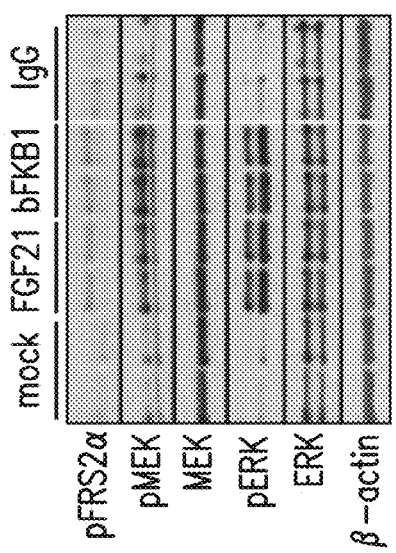
FIG. 6D depicts a western blot analysis of primary human adipocytes treated with the indicated protein (FGF21 (100 nM) or IgG (33 nM)) for 1 hr. Samples were duplicated for each treatment.

As shown in FIG. 6D, BsAb10, BsAb17, BsAb20, and FGF21 showed a comparable activity to induce phosphorylation of the MAPK signaling intermediates such as MEK and ERK in primary human adipocytes, which represent the relevant cell type for the anti-diabetic activity of FGF21, as determined by western blot. Antibodies used for the Western blot analysis were from Cell Signaling Technology: pFRS2a (T196) (#3864), pMEK1/2 (S217/221) (#9154), pERK1/2 (T202/204)(#4370), ERK1/2 (#4695), HSP90 (#4874), 13-Actin (#5125), from abcam: UCP1 (ab10983), or from R&D Systems: KLB (AF2619).

Figure 8B:
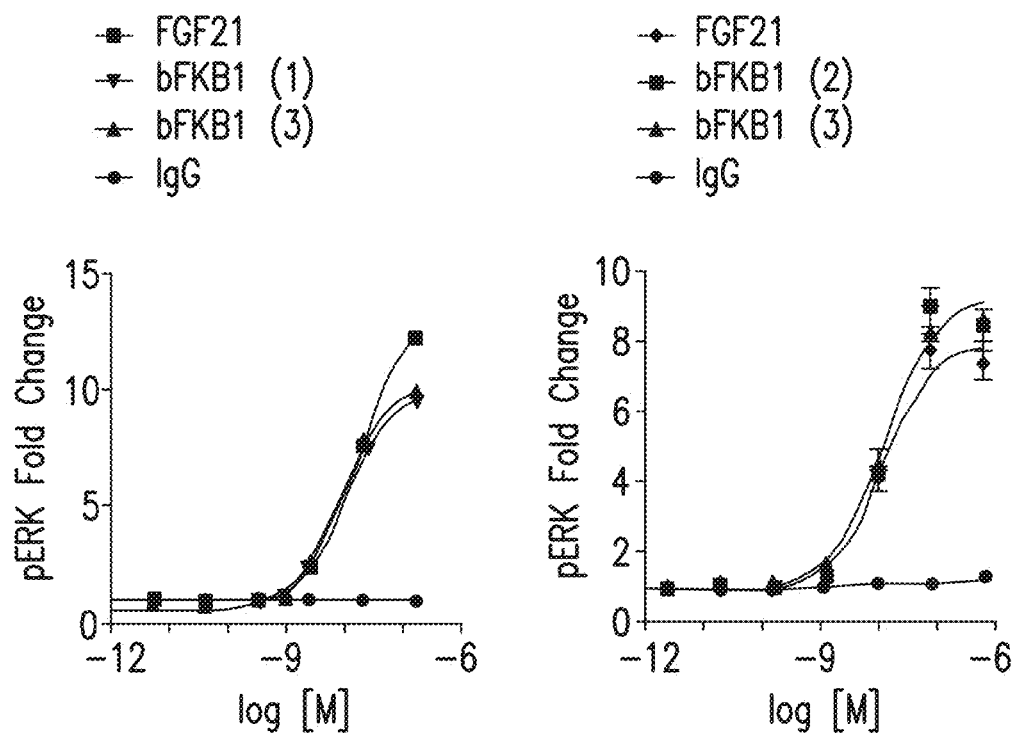
FIG. 8B depicts an MSD pERK assay in primary human adipocytes treated with BsAb10 and its derivatives, control IgG or FGF21 for 10 min. Data represent means±SEM (N=3). bFKB1 (1) represents BsAb10; bFKB1 (2) represents BsAb20; and bFKB1 (3) represents BsAb17.

As shown in FIG. 8B, an increase in the phosphorylation of ERK, represented as a fold change in pERK levels, was observed in primary human adipocytes treated with BsAb10, BsAb17, BsAb20 or FGF21.

Figures 10A, 10B:
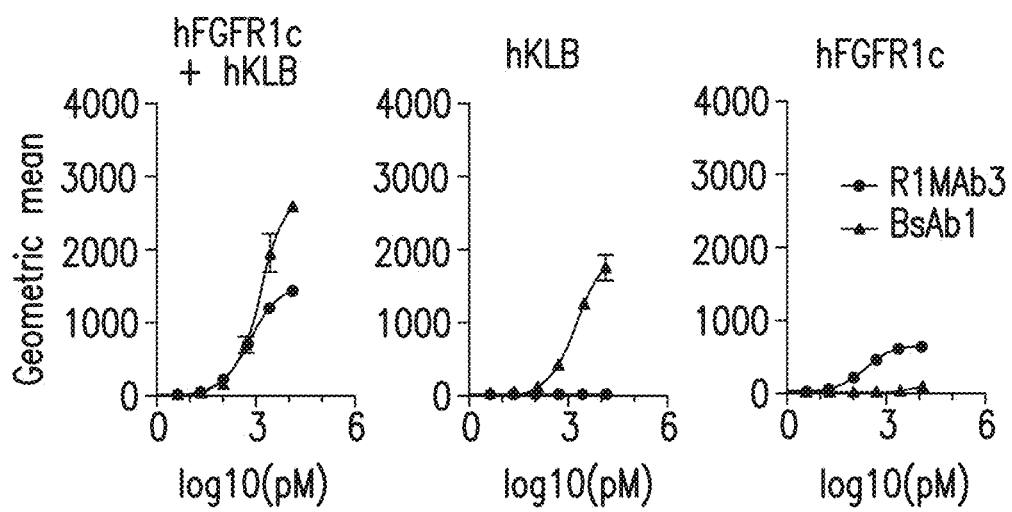
FIG. 10A depicts binding of a bispecific antibody with anti-FGFR1 and anti-KLB arms and an anti-FGFR1 antibody to cells expressing FGFR1c, KLB or both.
FIG. 10B depicts the $K_d$ of BsAb10 for binding to HEK293 cell expressing various combinations of human and murine KLB/FGFR1.

In addition, the affinity profile of BsAb10 resembles that of FGF21. When tested by FACS, BsAb10 showed strong binding to cells expressing hKLB, whether or not FGFR1c was coexpressed (FIG. 10A). Somewhat surprisingly, very little binding of BsAb10 was observed when cells expressed FGFR1c, but not KLB, indicating that monovalent affinity of the YW182.5 arm is extremely low (FIG. 10A).

As shown in FIG. 10B, a radiolabelled-ligand assay indicated that the dissociation constant ($K_d$) of BsAb10 to the cells expressing both FGFR1c and KLB is 2.3 nM, close to 5.3 nM observed for hFGF21 in a similar assay format. These values were close to the observed $EC_{50}$ of these molecules in GAL-ELK1 assay in HEK293 cells (3.2 nM and 4.7 nM, respectively for BsAb10 and FGF21. When cells expressing human KLB alone, or mouse KLB alone, the $K_d$ were 6.6 nM and 15.5 nM, respectively.

Since the affinity to FGFR1 was so low, the radiolabel ligand assay could not reliably determine the $K_d$ of BsAb10 to the cells expressing only FGFR1c, but it was estimated to be >300 nM, as shown in FIG. 3B. Due to a similar reason, binding kinetics of BsAb10 to FGFR1 could not be reliably determined by SPR either.

Further, the interaction between FGFR1c-ECD and KLB-ECD proteins were stabilized by BsAb10 as previously observed for FGF21, consistent with the notion that BsAb10 acts as a FGFR1c-selective FGF-21 mimetic (FIG. 11) (Yie et al., *Chemical Biology; Drug Design* 79, 398-410(2012)). FGFR1/KLB/BsAb100 interaction was studied by surface plasmon resonance (SPR) measurements on a PROTEON™ XPR36 (Bio-Rad Laboratories) instrument at 25° C. FGFR1-HIS protein (20 μg/ml) at pH4.5 was immobilized at surface density (1000 RU) on an activated PROTEON™ GLC sensor chip using standard amine coupling procedures as described by the manufacturer. BsAb10 and/or 1:1 mixtures of BsAb10 and KLB-ECD were injected at 6.25 nM, 12.5 nM, 25 nM, 50 nM, 100 nM, or 200 nM in PBS containing 0.005% v/v TWEEN®-20, 0.3M NaCl (pH7.4) at a flow rate of 80 μl/min and sensorgrams for association and disassociation phases were recorded. Analytes were injected for 300 sec and allowed to disassociate for 600 sec. Data was referenced with interspots, processed, and disassociation constants measured with the PROTEON™ Manager software (version 3.0, Bio-Rad). The activation of FGFR1c/KLB complex by BsAb10 suggested a ternary complex formation by FGFR1c-ECD, KLB-ECD and BsAb10.

Figure 11:
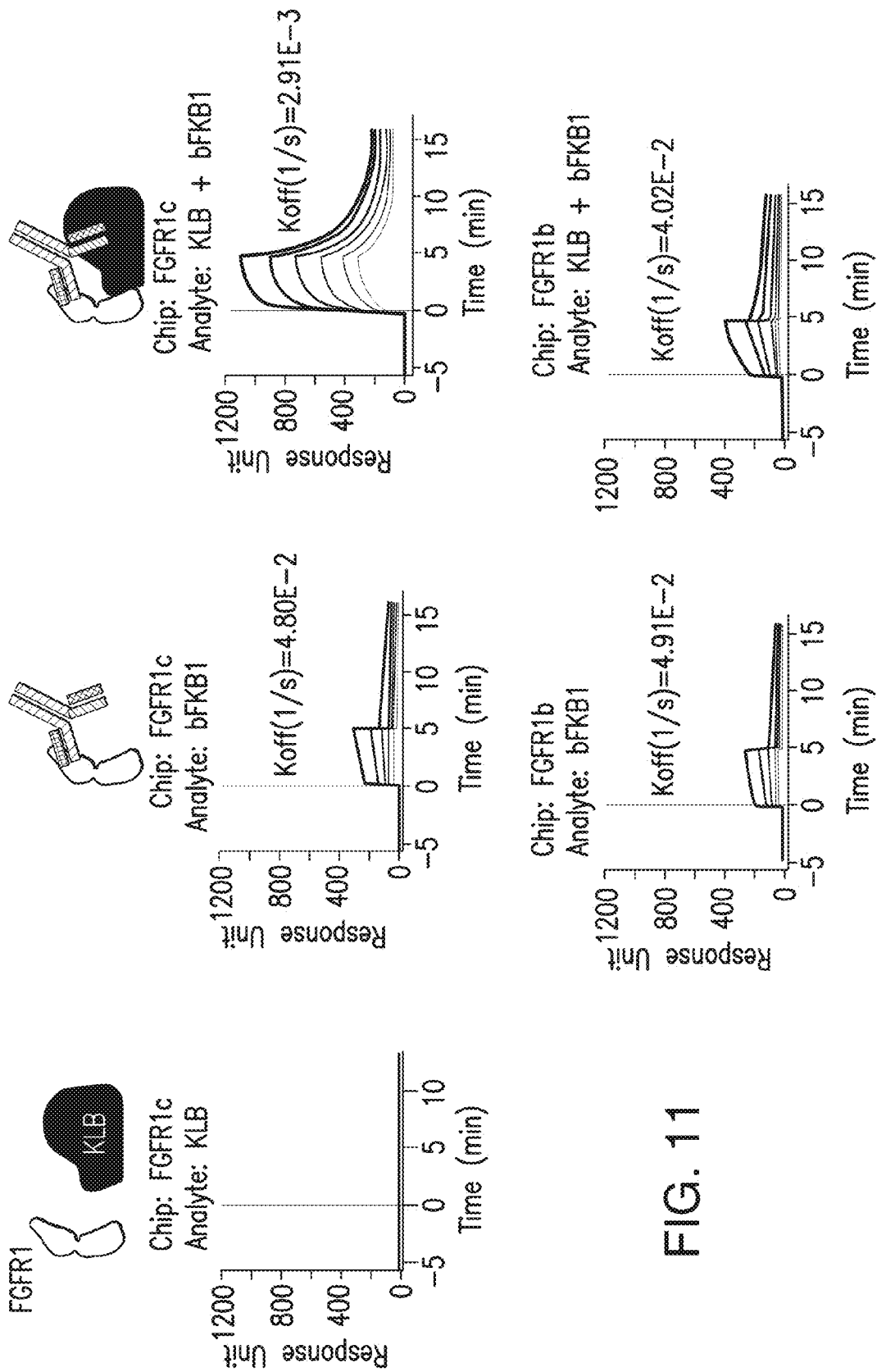
FIG. 11 depicts the binding analysis of BsAb10 or preformed BsAb10/KLB complexes at 200 nM, 100 nM, 50 nM, 25 nM, 12.5 nM, 6.25 nM to FGFR1-ECD-Fc fusion protein that was immobilized on the chip. To generate preformed BsAb10/KLB complexes, BsAb10 and recombinant KLB-ECD protein was preincubated at 1:1 ratio. Note the dissociation rate was slower with BsAb10/KLB complex than with BsAb10 alone, but only when FGFR1c, but not FGFR1b, was captured on the chip, indicating the formation of a ternary complex.

As shown in FIG. 11, it was also observed that BsAb10 formed a ternary complex with recombinant KLB-ECD and FGF21 or FGF19. BsAb10/KLB/FGF interaction was studied by bio-layer interferometry (BLI) measurements on an Octet RED (ForteBio) instrument at 25° C. BsAb10 (20 μg/ml) at pH 4.5 was immobilized on activated amine reactive biosensor tips as described by the manufacturer. KLB-ECD (20 μg/ml) in PBS containing 0.005% v/v TWEEN®-20, 0.3M NaCl (pH 7.4) was captured onto the same biosensor tips and measured with FGF21 (R&D Systems) at 0, 0.2, 0.8, or 2 μM in the same buffer. Qualitative data was processed with the data acquisition software (ForteBio).

Figure 12A:
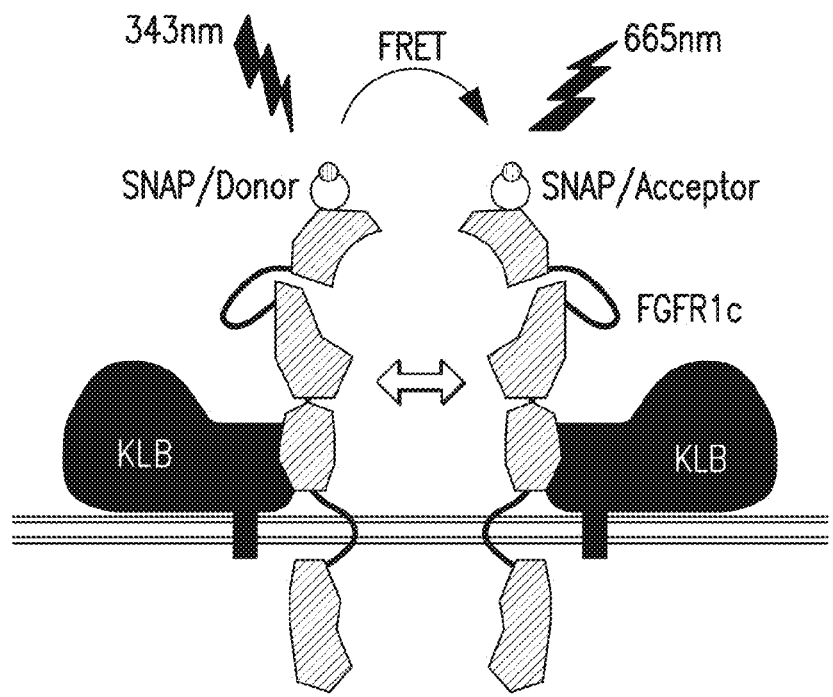
FIG. 12A is a schematic representation of the TR-FRET experiment design.

FIG. 12A shows a schematic of a cell-surface time-resolved fluorescence resonance energy transfer (TR-FRET) experiment that was performed. For TR-FRET, COS7 cells were co-transfected to express SNAP-tagged FGFR1 and untagged KLB and seeded in a white bottom 96-well plate (Costar) at 100,000 cells per well. Transfected cells were labeled 24 h post-transfection with 100 nM of donor-conjugated benzylguanine SNAP-Lumi4-Tb (Cisbio) and 1 μM of acceptor-conjugated benzyl-guanine SNAPAlexa647 (NEB) for 1 h at 37° C., 5% $CO_2$. After three washes, the Lumi4-Tb emission and the TR-FRET signal were recorded at 620 nm and 665 nm, respectively, for 400 μs after a 60 μs delay following laser excitation at 343 nm using a Safire2 plate reader (Tecan) at t=0 and t=15 min after ligand addition. The emission signal of the Alexa647 was detected at 682 nm after excitation at 640 nm using the same plate reader. FRET intensity was then calculated as: (signal at 665 nm from cells labeled with SNAP-donor and SNAP-acceptor)−(signal at 665 nm from the same batch of transfected cells labeled with SNAP-donor and non labeled SNAP).

Figure 12B:
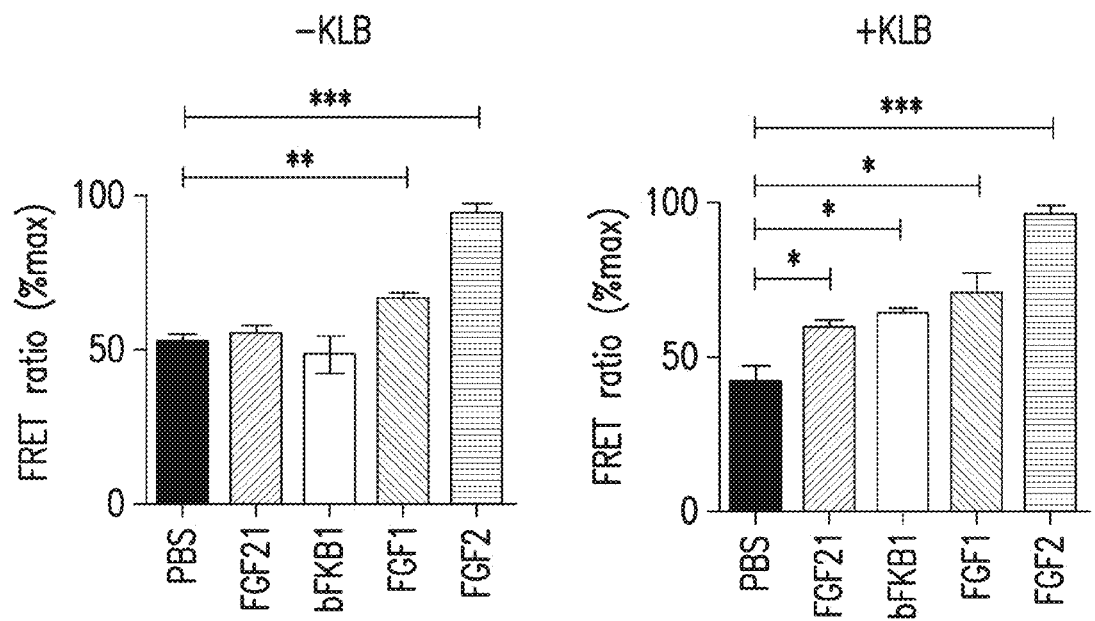
FIG. 12B depicts the TR-FRET intensity on COS7 cells expressing labeled SNAP-tagged FGFR1c protein with or without untagged KLB at 15 minutes after addition of indicated ligands. BsAb17, FGF21, FGF1 and FGF2 were used at 67 nM, 50 nM, 62.5 nM, 12 nM, respectively. The data represents FRET intensity at 665 nm divided by the donor emission at 620 nm (FRET ratio), and means±SEM of three independent experiments (N=3). $p<0.05$ (*), $<0.01$ (), $<0.0001$ (*) vs PBS control.

As shown in FIG. 12B, the TR-FRET experiment suggested that both BsAb17 and FGF21 enhances dimerization of FGFR1c-ECD when KLB is also present in the cell. The results were shown as FRET ratio: FRET intensity divided by the donor emission at 620 nm.

Figure 13A:
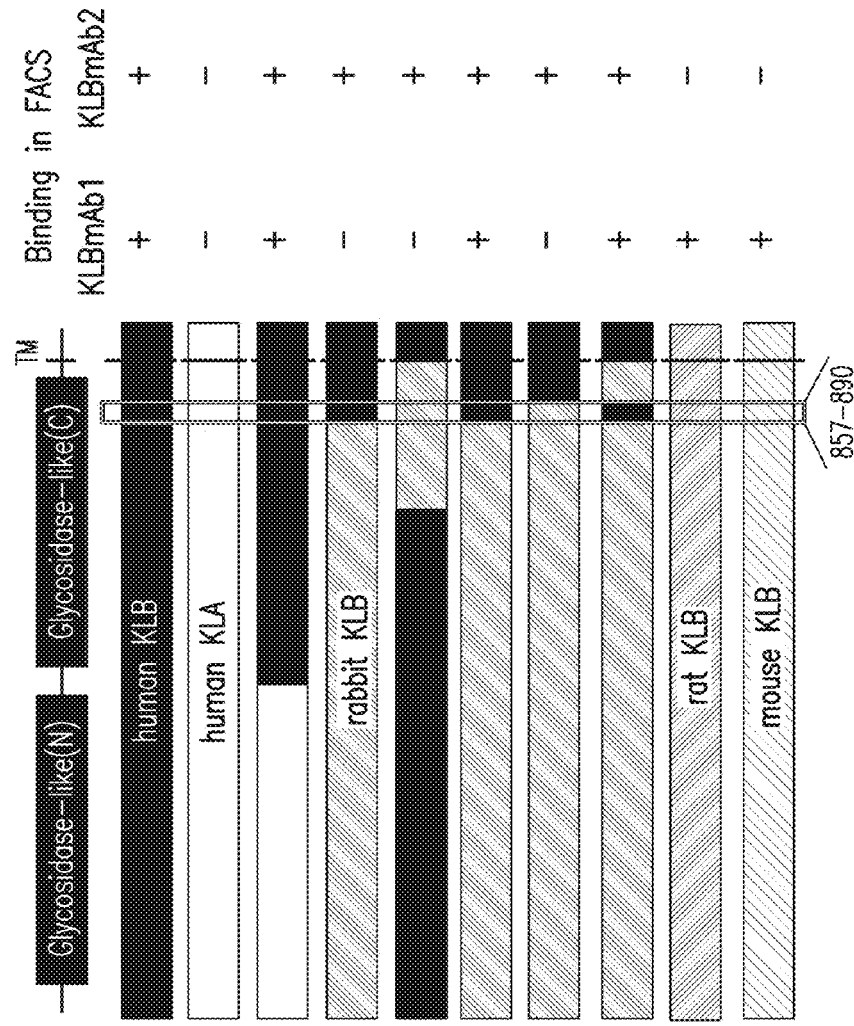
FIG. 13A depicts the results of experiments to determine which part of KLB was important for binding by two anti-KLB antibodies. A schematic representation of KLB protein structure is shown at the top. Each bar represents human KLB, human KLA, rabbit KLB, rat KLB, mouse KLB, or chimeric constructs as color coded. At right, binding of KLBmAb1 and control KLBmAb2 based on FACS with HEK293 cells transiently expressing each construct is shown. Note that KLBmAb1 does not bind to rabbit KLB, but replacement of a 34 amino acid fragment (amino acid 805-838) to the corresponding human sequence confers binding.

In addition, BsAb10 binds to the C-terminal half of KLB-ECD, whereas FGF21 and FGF19 have been thought to bind to the same site on KLB in the N-terminal half (Goetz et al. *Mol. Cell. Biol.* 32(10): 1944-54 (2012); Foltz et al. *Sci. Transl. Med.* 4: 162ra153 (2012)), which suggests that the epitope of BsAb10 on KLB should be distinct from the FGF21 and FGF19 binding site. In order to map the KLB epitope for BsAb10, binding of 8C5 (the KLB-binding arm of BsAb10) to a series of chimeric antigens expressed in HEK293 cells. Each chimera was constructed by fusing human KLB and human Klotho alpha (KLA) protein (50% identity to human KLB proteins) or rabbit KLB (86% identity to human KLB). As summarized in FIG. 13A, 8C5 binds the C-terminal domain of KLB, in particular, in the region containing 34 amino acids in the C-terminal domain of KLB (SSPTRLAVIPWGVRKLLRWVRRNYGDMDI-YITAS; SEQ ID NO: 142).

Figure 13B:
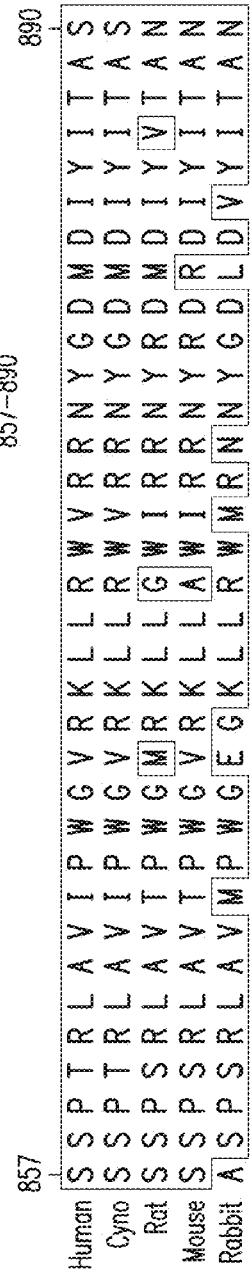
FIG. 13B depicts the amino acid sequence of the position 857-890 segment of a human KLB protein with a signal sequence (which corresponds to the amino acid sequence at positions 805-838 of a KLB protein that does not include a signal sequence) and corresponding sequences in various indicated species.

As shown in FIG. 13B, the amino acid sequence of SEQ ID NO: 142 can correspond to amino acids 857-890 of a KLB protein that includes a signal sequence, e.g., such as a 52 amino acid sequence having the sequence set forth in SEQ ID NO: 157, or can refer to amino acids 805-838 of a KLB protein that does not include a signal sequence.

Figure 14A:
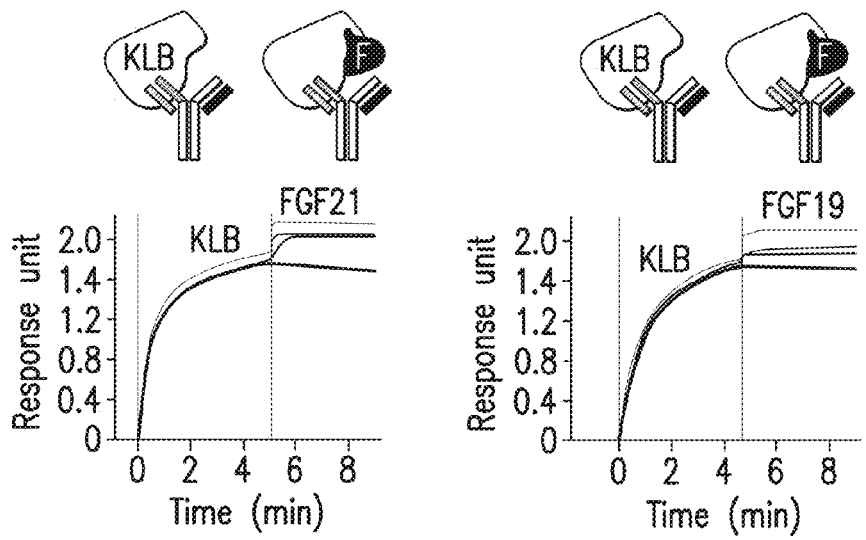
FIG. 14A depicts the binding of FGF21 and FGF19 to BsAb10/KLB complex by SPR. BsAb10 was captured on the chip, and KLB-ECD protein and FGF protein (at 0.2, 0.8, or 2 µM) were sequentially injected.

Despite the similarity between FGF21 and BsAb10 and its derivatives in the downstream action, the epitope of BsAb10 on KLB is distinct from the FGF21 and FGF19 binding site (FIG. 14A).

Figure 14B:
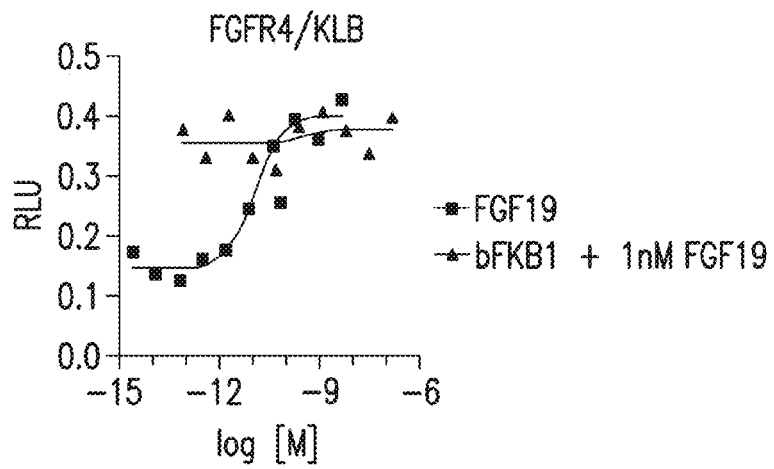
FIG. 14B depicts the results of a GAL-ELK luciferase assay in rat L6 myoblast cells. Cells were co-transfected with an expression vector for both FGFR4 and KLB. Transfected cells were incubated with various concentrations of indicated proteins for 6 h before luciferase assays.

FIG. 14B shows the results of a GAL-ELK1 luciferase assay performed in rat L6 myoblast cells co-transfected with FGFR4 and KLB and treated with FGF19 alone or in combination with an anti-KLB/anti-FGFR1c antibody (BsAb17). As shown in FIG. 14B, BsAb17 pretreatment also did not block FGF19-activity in L6 cells expressing FGFR4/KLB complex.

Figure 14C:
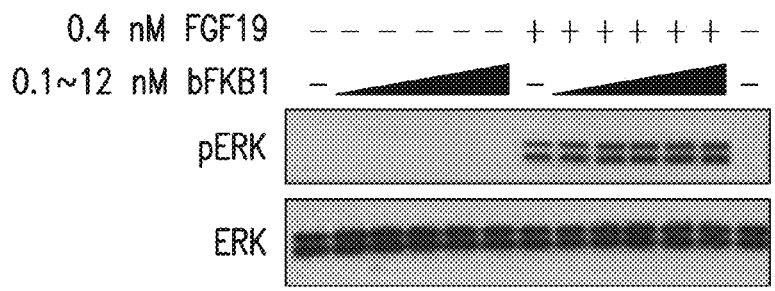
FIG. 14C depicts a Western blot that was performed to monitor ERK phosphorylation in H4IIE hepatoma cells. Note that BsAb17 did not block the ability of FGF19 to activate FGFR4/KLB complex (FIG. 14B), or to induce ERK phosphorylation in H4IIE hepatoma cells (FIG. 14C).

Additionally, and as shown in FIG. 14C, BsAb17 pretreatment did not block FGF19-activity in H4IIE hepatoma cells expressing FGFR4 and KLB. In the presence of BsAb17, FGF19 was still able to activate the FGFR4/KLB complex to induce phosphorylation of ERK (FIG. 14C).

These data indicate that the disclosed anti-KLB/anti-FGFR1 bispecific antibody, e.g., an anti-KLB/anti-FGFR1c bispecific antibody, does not interfere with the interaction of FGF19 or FGF21 with the KLB/FGFR1c complex.

Example 9: BsAb10, and its Derivatives, Act as a Long Acting FGF21 Mimetic In Vivo The cross-reactivity of BsAb10 and its derivatives with murine receptor complex as described above (see, e.g., FIGS. 6C and 10B) allowed the testing of its in vivo activity in mouse models. To avoid potential toxicity from the IgG effector function, a dual mutation [D265A/N297G] was introduced to BsAb20 in the Fc region that abolishes binding to FcgRs and recruitment of immune effector cells. In addition, to avoid potential toxicity from the IgG effector function, N297G was introduced to BsAb17 in the Fc region that abolishes binding to FcgRs and recruitment of immune effector cells.

As shown in FIG. 15A, when i.p. injected into diabetic db/db mice at 5 mg/kg, BsAb17 reduced blood glucose levels to a similar extent without affecting food intake or body weight. Lean C57BL/6 mice treated with BsAb17 showed reduced blood glucose, but did not achieve toxic hypoglycemia (FIG. 15A).

In addition, when high fat diet-fed C57BL/6 mice (Diet Induced Obesity, DIO) were injected with BsAb17 at 3 mg/kg on day 0 and 6, significant reductions in weight loss and blood glucose were observed (FIG. 15B). For high-fat diet feeding, a high fat, high carbohydrate diet (Harlan Teklad TD.03584, 58.4% calories from fat) was used.

As shown in FIG. 15C, an improvement in glucose tolerance was observed in high fat diet-fed C57BL/6 mice (Diet Induced Obesity, DIO) that were injected with BsAb17 at 3 mg/kg.

Reductions in hepatic triglyceride, serum insulin, free fatty acid, triglyceride and total cholesterol were also observed in high fat diet-fed C57BL/6 mice (Diet Induced Obesity, DIO) that were injected with BsAb17 at 3 mg/kg (FIG. 15D). Similar results were previously observed with FGF21 injections.

A separate experiment was performed in klb heterozygous mice and homozygous klb deficient mice to determine if the improvement in glucose tolerance observed upon treatment with an anti-KLB/anti-FGFR1c bispecific antibody requires functional KLB. To generate klb-deficient (KO) mice, a Klb-specific Zinc Finger Nuclease (ZFN) pair was obtained from Sigma-Aldrich and used for pronuclear microinjection according to established methods. The ZFN pair targets the following Klb sequence in the mouse genome (cut site in small letters), and the KO mice lack one bp deletion (g in bold) causing a frameshift: GTTACCGGCTTCtccggaGACGGGAAAGCAATATGG (SEQ ID NO: 156). FIG. 16A shows the N-terminal amino acid sequence of mouse KLB protein and the corresponding amino acid sequence encoded by the klb allele in the k/b deficient mice.

FIG. 16B shows the results of a western blot that was performed to confirm the lack of KLB protein expression in klb deficient mice.

As shown in FIG. 16C, BsAb20 improved the glucose tolerance in klb heterozygous mice as measured by the glucose tolerance test (GTT), but not homozygous klb deficient mice, indicating that the improvements in glucose tolerance require functional KLB. For the glucose tolerance test (GTT), mice were fasted overnight and i.p. injected with 2 g/kg glucose solution.

In addition, unlike anti-FGFR1 R1MAb1, which alters the levels of serum FGF23 and phosphorus (Wu et al., *Sci Transl Med* 3, 113ra126 (2011) and Wu et al., *PLoS One* 8, e57322 (2013)), the anti-KLB/anti-FGFR1 bispecific antibody did not affect these serum parameters, indicating the absence of KLB-independent FGFR1 agonistic activity (FIG. 16D).

Figure 17:
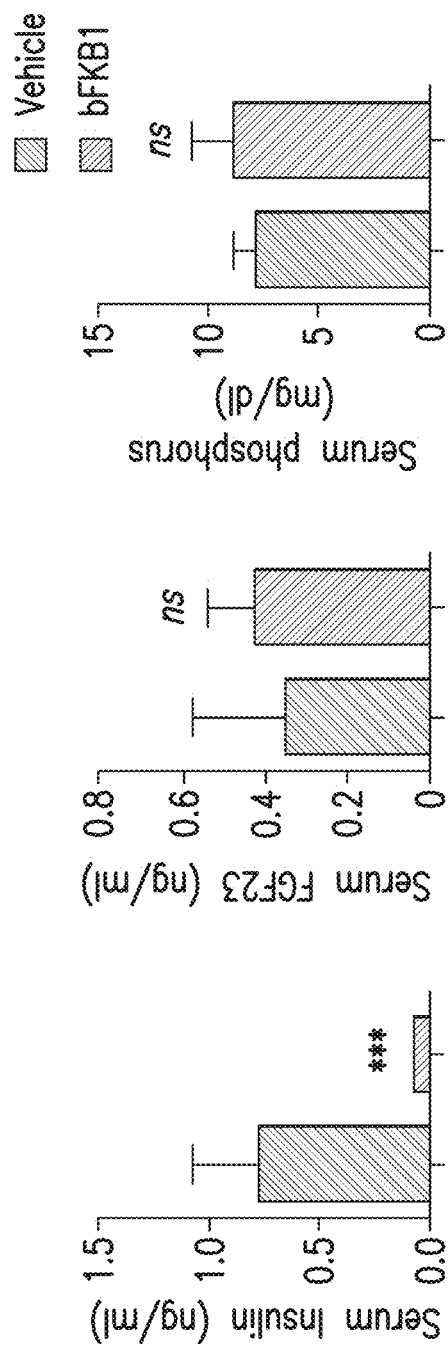
FIG. 17 depicts the amount of FGF23 and inorganic phosphorous in the serum of DIO mice on day 7 after i.p. injection of BsAb17 at 50 mg/kg. N=6. ***$p<0.0005$.

As shown in FIG. 17, BsAb17 did not alter serum FGF23 or phosphorous levels, which are sensitive markers of KLB-independent FGFR1. Insulin action in BsAb17 treated mice was measured by hyperinsulinemic-euglycemic clamp. In brief, mice were anesthetized with isoflurane and the left common carotid artery and right jugular vein were catheterized for sampling and infusing, respectively. The free ends of the catheters were tunneled under the skin to the back of the neck where the loose ends of the catheters were attached to tubing made of MICRO-RENATHANE® (0.033 in OD). Animals were individually housed after surgery and body weight was recorded daily. All metabolic experiments were performed following a 5-day postoperative recovery period and have been previously described. Conscious, unrestrained mice were placed in a 1-L plastic container lined with bedding and fasted at 7:00 am (t=−300 min). The mice were immediately connected to a Dual Channel Stainless Steel Swivel (Instech Laboratories) to allow simultaneous jugular vein infusion and sampling of arterial blood. Mice were not handled and were allowed to move freely to eliminate stress. 2 h prior to initiation of the clamp a 5 μCi bolus of [3-3H]-D-glucose was given into the jugular vein (t=−120 min) this followed by a constant infusion at a rate at 0.05 μCi/min. Following a 2 h equilibrium period at t=0 min (i.e., a 5 h fast) a baseline arterial blood sample was drawn for measurement of blood glucose, [3-3H]-D-glucose, hematocrit and plasma insulin. A 145 min hyperinsulinemic-euglycemic (4 mU/kg/min) clamp was then initiated. [3-3H]-D-glucose was added to the variable glucose infusion that was used to maintain euglycemia and the constant infusion of [3-3H]-D-glucose was discontinued so as to clamp arterial glucose specific activity at a constant level. Red blood cells from a donor mouse on a C57Bl/6J background were washed with and reconstituted in an equal volume of 0.9% heparinized saline (hematocrit ~50%) and infused at a rate of 4 μl/min for the duration of the study to replace blood removed during study. Arterial blood samples were taken every ten minutes to determine blood glucose levels. At t=80, 90, 100 and 120 min, blood samples were taken to determine [3-3H]-D-glucose. At t=120 min, a 13 μCi bolus of 2-deoxy [14C]glucose ([2-14C]DG) was administered into the jugular vein catheter. At t=122, 125, 130, 135, and 145 min arterial blood was sampled to determine blood glucose, plasma [3-3H]-D-glucose and [2-14C]DG. Arterial insulin concentration was measured at 100 and 120 min. At t=145 min mice were then anesthetized. The soleus, gastrocnemius, white superficial vastus lateralis (Quad), liver, heart, epididymal and subcutaneous white adipose tissue, brown adipose tissue and brain were excised, immediately frozen in liquid nitrogen, and stored at −70° C. until future tissue analysis. Immunoreactive insulin was assayed using a Linco Rat Radioimmunoassay kit (LincoResearch).

To measure [3-$^3$H]-D-glucose, plasma samples were deproteinized with barium hydroxide (Ba(OH)$_2$) and zinc sulfate (ZnSO$_4$), dried, and radioactivity was determined using liquid scintillation counting. Excised tissues were deproteinized with perchloric acid and then neutralized to a pH of ~7.5. A portion of the sample was counted ([2-$^{14}$C]DG and [2-$^{14}$C]DG-Gphosphate ([2-$^{14}$C]DGP) and a portion was treated with Ba(OH)$_2$ and ZnSO$_4$ and the supernatant was counted ([2-$^{14}$C]DG). Both [2-$^{14}$C]DG and [2-$^{14}$C]DG-phosphate ([2-$^{14}$C]DGP) radioactivity levels were determined using liquid scintillation counting. Glucose flux rates were assessed using non-steady state equations assuming a volume of distribution (130 ml/kg). Tissue-specific clearance ($K_g$) of [2-$^{14}$C]DG and an index of glucose uptake ($R_g$) was calculated as previously described (Kraegen, E. W. et al., *Am. J. Physiol.* 248, E353-362 (1985)): $K_g$=[2-$^{14}$C]DGP$_{tissue}$/AUC [2-$^{14}$C]DG$_{plasma}$, $R_g$=$K_g$×[glucose]$_{plasma}$, where [2-$^{14}$C]DGP$_{tissue}$ is the [2-$^{14}$C]DGP radioactivity (dpm/g) in the tissue, AUC [2-$^{14}$C]DG$_{plasma}$ is the area under the plasma [2-$^{14}$C]DG disappearance curve (dpm/mL/min), and [glucose]$_{plasma}$ is the average blood glucose (μg/μl) during the experimental period (t=102-125 min). Data are presented as mean±SEM.

As shown in FIG. 15E, which depicts whole body glucose utilization measured following a single injection of BsAb17 at 10 mg/kg, BsAb17 improved the rates of insulin stimulated whole body glucose utilization.

In addition, and as shown in FIG. 15F, BsAb17 improved insulin suppression of endogenous glucose production rates following a single injection of BsAb17 at 10 mg/kg. These results indicate that a single injection of 10 mg/kg of BsAb17 in DIO mice 5 days prior to the clamp markedly lowered fasted glucose and insulin concentrations.

Tissue glucose uptake ($R_g$) at the end of the insulin-stimulated period was enhanced in heart, skeletal muscle, white adipose tissues (WAT) and interscapular BAT tissue (iBAT), indicating whole body insulin sensitization by BsAb17 (FIG. 15G).

Figure 18A:
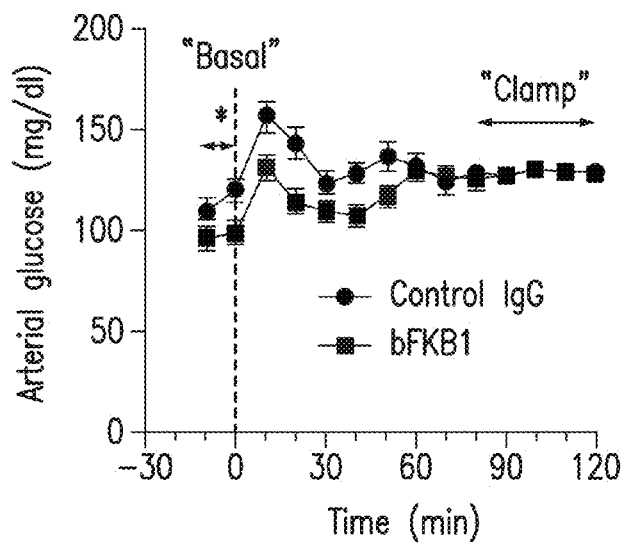
FIG. 18A depicts the amount of arterial blood glucose excursion during the clamp experiment. DIO mice received BsAb17 or control IgG at 10 mg/kg on 5 days before the clamp experiment.

The amount of arterial blood glucose excursion was determined during the clamp experiment. As shown in FIG. 18A, the amount of arterial blood glucose excursion was different between mice injected with BsAb17 versus mice injected with control IgG during the hyperinsulinemic-euglycemic clamp experiment.

Figure 18B:
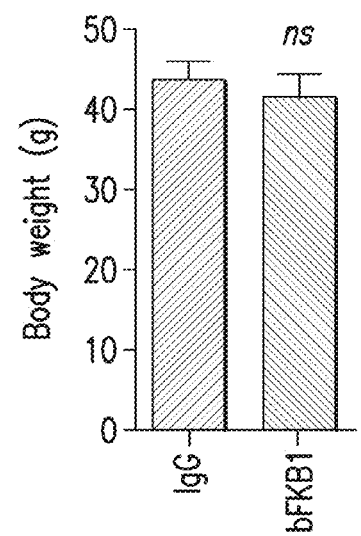
FIG. 18B depicts the body weight on the day of the clamp experiment.

The difference in weight between mice injected with BsAb17 versus mice injected with control IgG was also determined. As shown in FIG. 18B, the changes observed in glucose and insulin concentrations were without an apparent loss in weight.

Figure 18C:
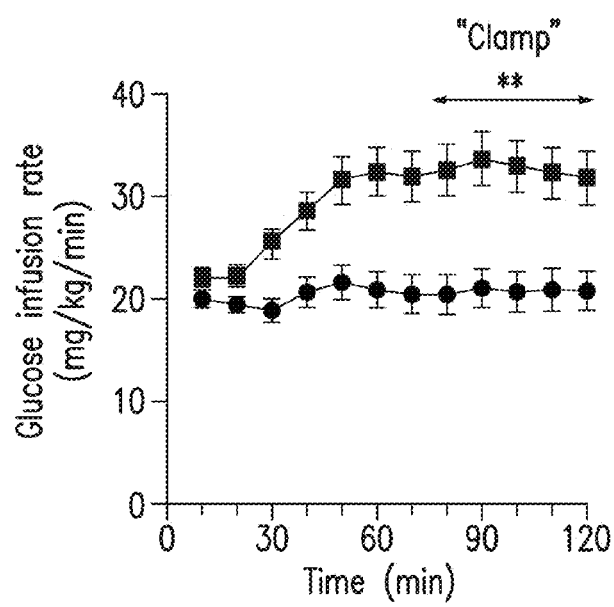
FIG. 18C depicts the glucose infusion rate during the clamp experiment. $p<0.05$ (*), $<0.001$ (**) vs control.

The steady state glucose infusion rate was also analyzed following an injection with BsAb17. As shown in FIG. 18C, the steady state glucose infusion rate was increased by 64% following a BsAb17 injection. These results demonstrate that BsAb17 improved whole body insulin sensitivity in DIO mice even before weight loss becomes apparent.

Previous studies with pharmacological doses of FGF19 or FGF21 have shown increased energy expenditure (EE) (Fu et al., *Endocrinology* 145, 2594-2603 (2004); Coskun et al., *Endocrinology* 149, 6018-6027 (2008); Wu et al., *PLoS One* 8, e57322 (2013); Lin et al., *Cell Metab* 17, 779-789 (2013)), thus it was reasoned that a similar effect would be observed. The following equations were used to calculate EE and Respiratory quotient (RQ). EE=VO$_2$×(3.815+1.232×RQ), where (RQ=VCO$_2$/VO$_2$). Indeed, single BsAb17 injection into DIO or lean mice at normal room temperature (21° C.) led to significant increase in O$_2$ consumption (VO$_2$), CO$_2$ production (VCO$_2$), and EE per injected animal without significant change in activity count (FIG. 19A). Unexpectedly, the observed 15-46% increase in EE did not accompany significant changes in respiratory quotients (RQ=VCO$_2$/VO$_2$) (FIG. 19A).

Figure 21A:
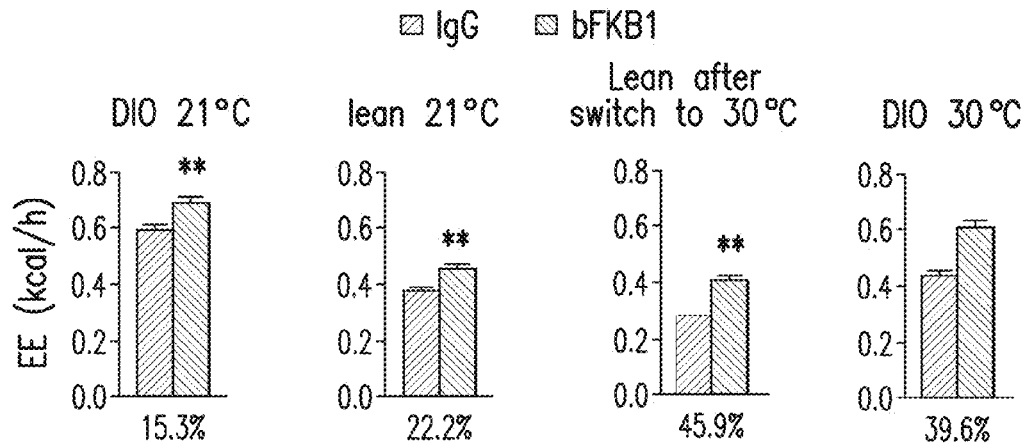
FIG. 21A depicts the average EE value in indirect calorimetry. The magnitude in average increase is shown under the graphs. DIO 21° C.: Average value of EE during D3-D6 post IgG injection in the experiment shown in FIG. 19A. Lean 21° C.: Average value of EE during D3-D6 post IgG injection in the experiment shown in FIG. 19B. Lean after switch to 30° C.: Average values of EE during D6-D9 post IgG injection (i.e., 3 days after temperature switch) in the experiment shown in FIG. 19B. DIO 30° C.: Average value of EE during D3-D6 post IgG injection in DIO mice acclimated at thermoneutrality.
Figure 21B:
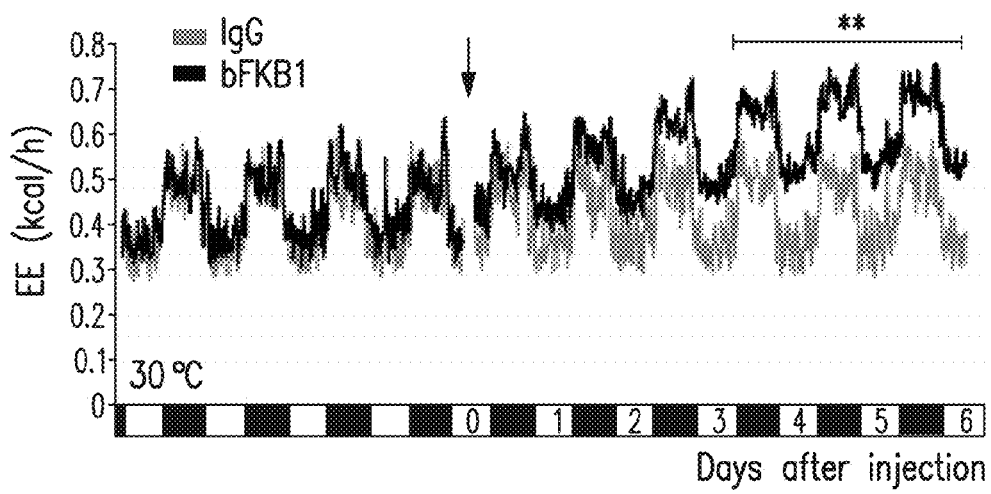
FIG. 21B depicts the changes in EE in DIO mice at thermoneutrality. DIO mice were acclimated to thermoneutrality for 2 weeks prior to single i.p. injection (arrow) of BsAb17 or control IgG at 10 mg/kg. N=3~4.
Figure 21C:
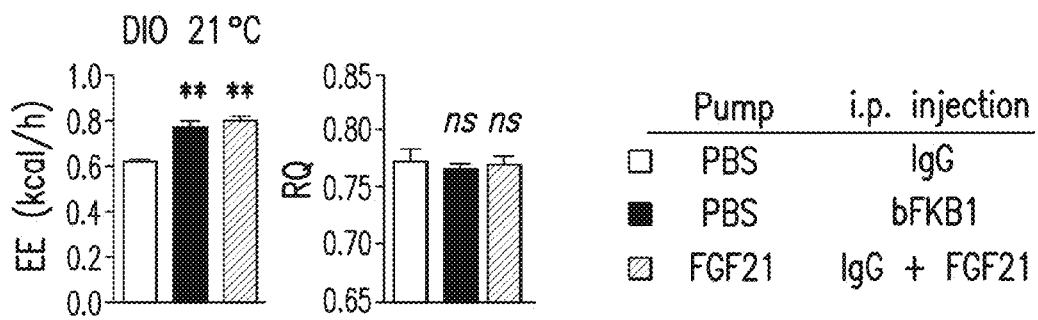
FIG. 21C depicts the average EE and RQ in DIO mice at normal lab temperature (21° C.) during D3-5 after surgical implantation of an osmotic pump and drug injection. On D0, mice received i.p. injection of BsAb17 or control IgG at 10 mg/kg. The FGF21 group also received bolus 2 mg/kg FGF21 i.p. injection on D0. Each mouse was also subcutaneously implanted with an osmotic pump to infuse FGF21 at 60 μg/day or PBS control on D0. N=8~9. **p<0.005.

A similar increase in EE without change in RQ was elicited by continuously infusing FGF21 into DIO mice (FIG. 21C).

Figure 20A:
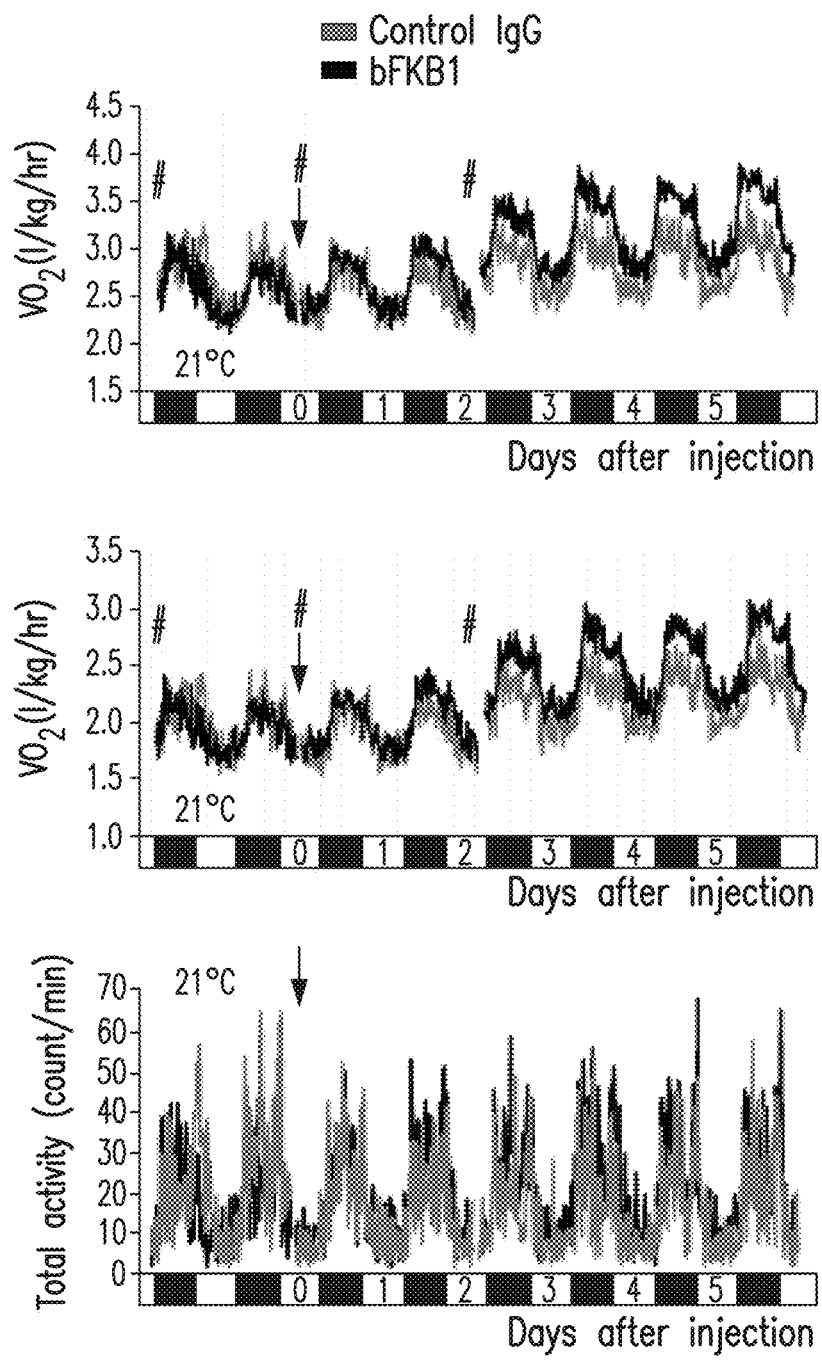
FIG. 20A depicts the amount of $VO_2$ (top), $VCO_2$ (middle) and total activity counts of DIO mice described in FIG. 19A. $VO_2$ and $VCO_2$ values are normalized by body weight values measured at times indicated by #. DIO mice received 10 mg/kg of BsAb17 or control IgG.

FIG. 20A shows the amount of VO$_2$, VCO$_2$ and total activity counts of DIO mice treated with a single BsAb17 injection at normal room temperature.

Figure 19B:
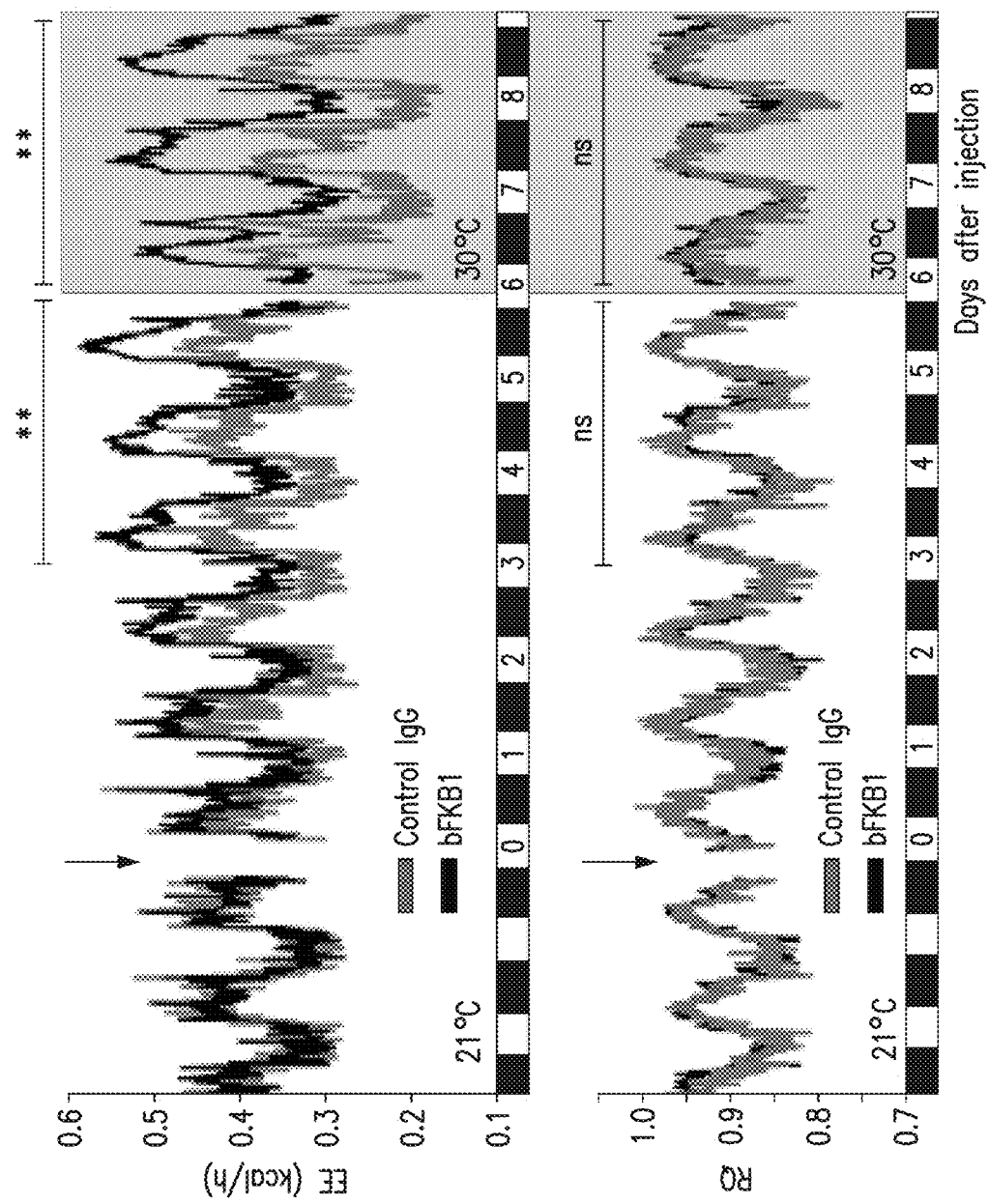
FIG. 19B depicts the EE (top) and RQ (bottom) of lean mice that received a single i.p. injection of 10 mg/kg IgG at the indicated time. Mice were maintained at 21-22° C., then cage temperature was shifted to thermoneutrality (29-30° C.) on 6 days post IgG injection. N=6~7.

As shown in FIG. 19B, the increase in EE was sustained when the cage temperature was elevated to thermoneutrality (29-30° C.), suggesting that BsAb17-induction of brown fat activation does not rely on adaptive thermogenic input from the sympathetic nervous system.

Figure 20B:
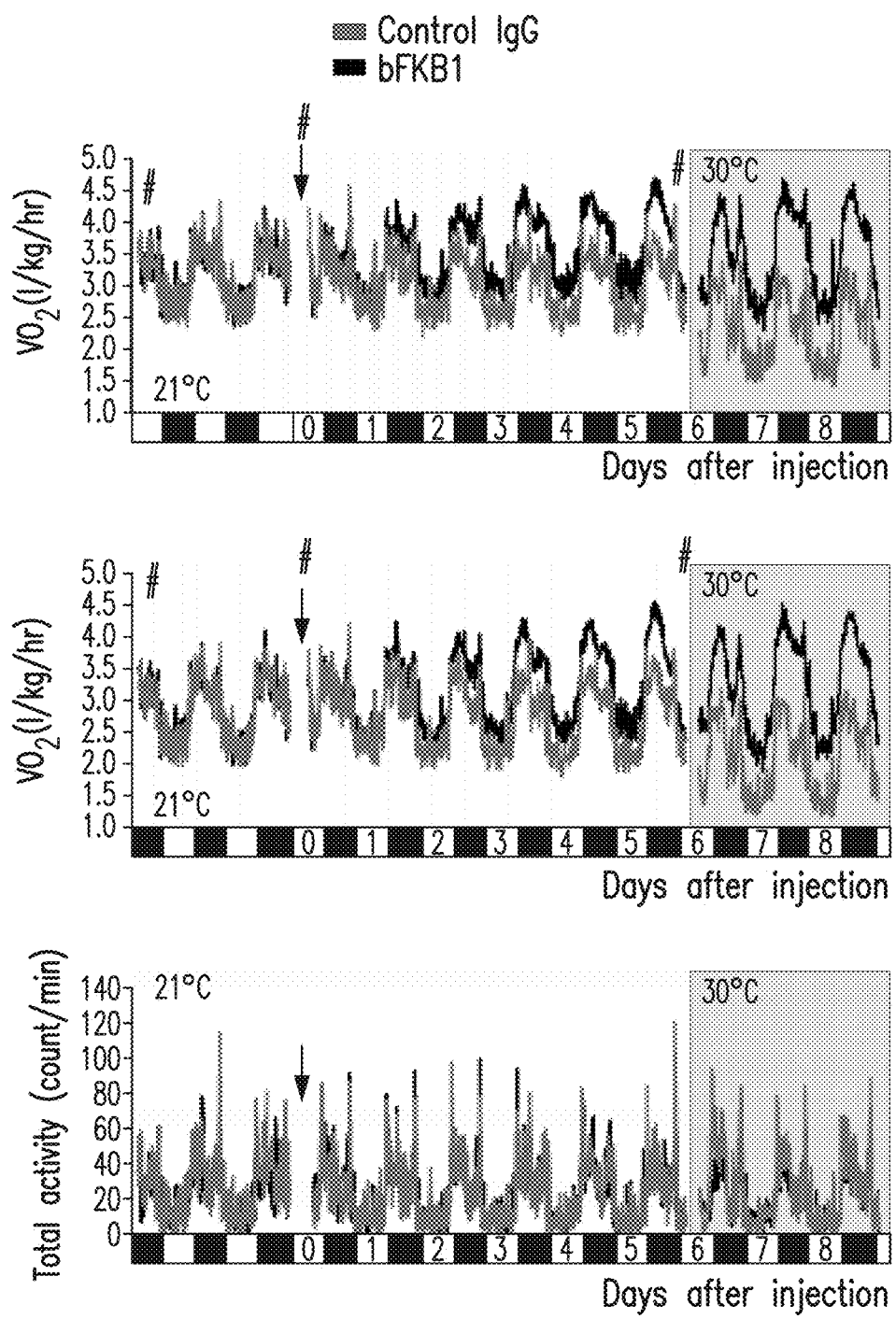
FIG. 20B depicts the amount of $VO_2$ (top), $VCO_2$ (middle) and total activity counts of DIO mice described in FIG. 19B. $VO_2$ and $VCO_2$ values are normalized by body weight values measured at times indicated by #. DIO mice received 10 mg/kg of BsAb17 or control IgG.

FIG. 20B shows the amount of VO$_2$, VCO$_2$ and total activity counts of DIO mice treated with a single BsAb17 injection at normal room temperature followed by a shift in temperature to thermoneutrality.

An increase in EE was also evident when DIO mice acclimated at thermoneutral room temperature (29-30° C.) were tested for two weeks (FIG. 21B).

As summarized in FIG. 21A, which shows the average EE values, changes in EE were observed in lean and DIO mice at normal room temperature and in lean and DIO mice acclimated at thermoneutral room temperature.

Figure 19G:
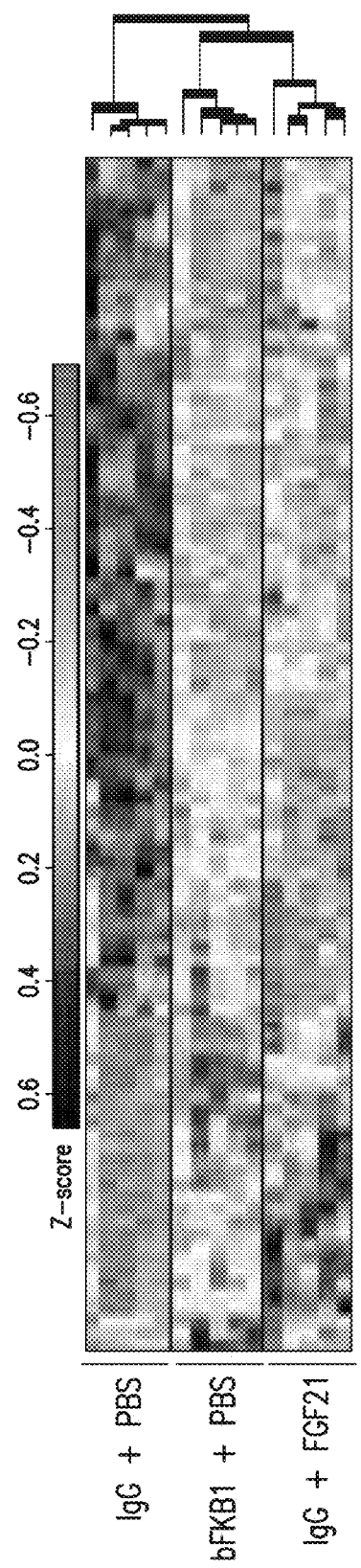
FIG. 19G depicts the gene expression profile in iBAT of DIO mice received single 10 mg/kg of IgG and FGF21 b.i.d. at 2 mg/kg/day or control PBS for 5 days. All the genes that were significantly different between BsAb17 and control, or between FGF21 and control were listed.
Figure 19H:
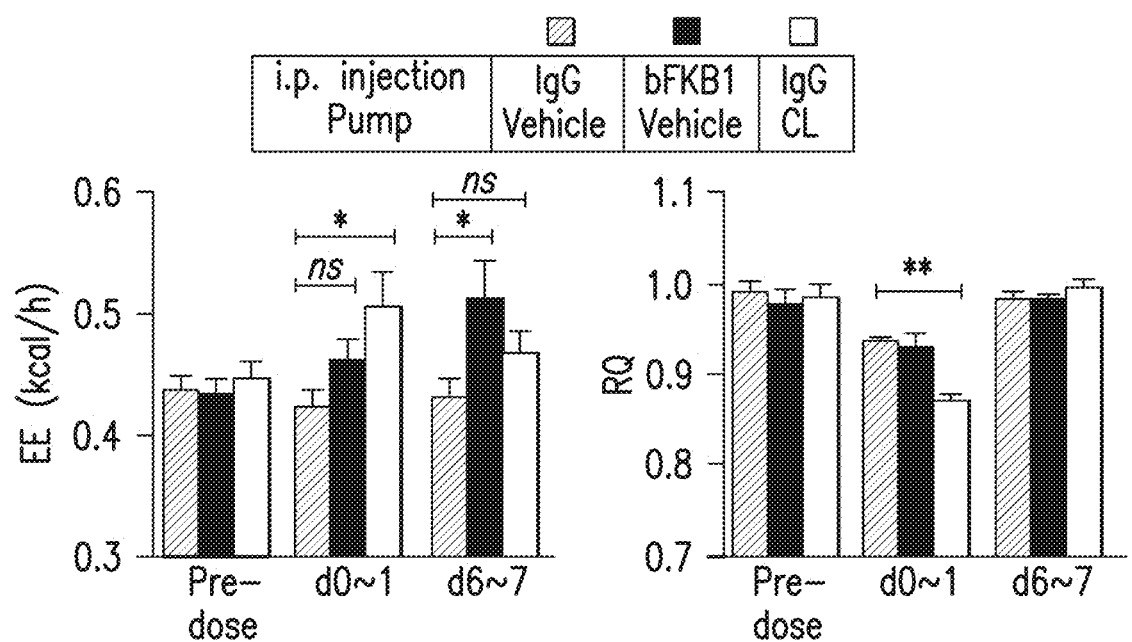
FIG. 19H depicts the EE (left) and RQ (right) of lean mice that received a single i.p. injection of an anti-KLB/anti-FGFR1 bispecific antibody or control IgG at 10 mg/kg and surgical implantation of an osmotic pump (CL-316,243 at 0.5 nmol/h or vehicle) on day 0. The mean values during the indicated 24 h period are shown.

In contrast, a continuous infusion with β3-specific adrenoceptor agonist CL-316,243 induced an acute increase in EE and reduction in RQ as anticipated (FIG. 19H). Continuous infusion of FGF21 or CL-316,243 was performed using an osmotic mini-pump (Alzet 2001) that was subcutaneously implanted. Thus, the BsAb17- and FGF21-induced EE is robust, but appears more selective than other previously described BAT activation mechanisms, such as administration of sympathomimetics (norepinephrine or β3-specific adrenoceptor agonist CL-316,243), cardiac natriuretic peptides, or Interleukin-4, that accompany promotion of lipid oxidation and reduction in RQ (Gerhart-Hines et al., Mol. Cell 44, 851-863 (2011); Mattsson et al., *American journal of physiology. Endocrinology and metabolism* 299, E374-383 (2010); Nguyen et al., Nature 480, 104-108 (2011); Birkenfeld et al. Diabetes 57, 3199-3204 (2008); Bordicchia et al., J. Clin. Invest. 122, 1022-1036 (2012); and de Souza et al., Diabetes 46, 1257-1263 (1997)).

Without being bound to a particular theory, several lines of evidence suggested the dominant role of BAT activation in the metabolic action of BsAb17. First, as shown in FIG. 19C, BsAb17 injection increased uptake of 18F-Fludeoxyglucose (FDG) specifically into iBAT.

Second, a single BsAb17 injection induced UCP1 protein expression in inguinal WAT (ingWAT), which is indicative of adipose tissue browning (FIG. 19D).

As shown in FIG. 19E, induction of UCP1 expression was also observed in cultured primary adipocytes treated with FGF21 or BsAb17, indicating direct action on mature adipocytes. To determine UCP1 expression, total RNA was used to synthesize cDNA using SUPERSCRIPT® VILO cDNA Synthesis Kit (ABI). For qPCR, samples were run in triplicate in the ViiA 7 Real-Time PCR instrument (Applied Biosystems). The Applied Biosystems predesigned TAQ-MAN® Gene Expression Assay probe used was UCP1 (Hs01027785_m1). For each sample, mRNA abundance was normalized to the amount of TBP (Hs00427620_m1) and SDHA (Hs00188166_m1) transcripts.

Third, using telemetry system, an increase in resting core body temperature was observed after single BsAb17 injection that lasted for ≥26 days before gradually returning to baseline (FIG. 19F).

Figure 22:
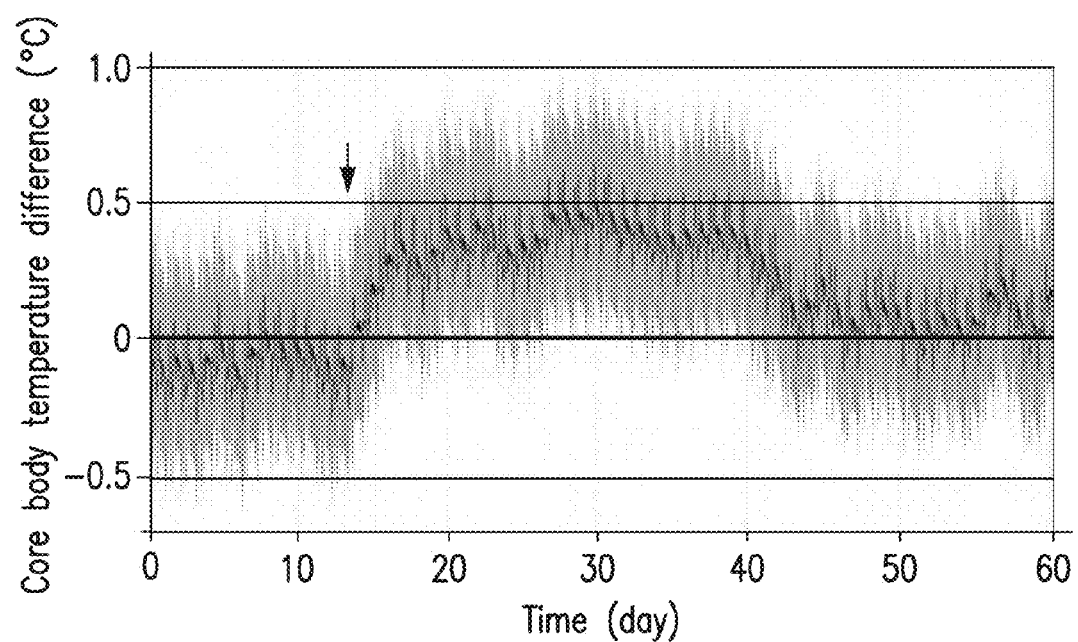
FIG. 22 depicts the data shown in FIG. 19F replotted to show the fitted difference in core body temperature over the course of the study between DIO mice received 10 mg/kg of BsAb17 or control IgG. The black line is the estimated difference and the blue lines are the 95% pointwise confidence intervals of the difference. IgG was administered at day 13 (arrow). N=7~8.

FIG. 22 shows the differences in the core body temperature that was observed in mice after a single BsAb17 injection compared to mice treated with control IgG. Core body temperatures were monitored using a TA-F10 transmitter (Data Sciences International, DSI) that was surgically implanted into peritoneal cavity. After recovery from the surgery, mice were randomized into groups based on body weight and core body temperature. Core body temperature and activity were monitored using DSI Implantable Telemetry System.

Gene expression profiles were analyzed in iBAT of DIO mice that received a single injection of BsAb17, FGF21 or control IgG. As shown in FIG. 19G, single BsAb17 injection induced gene expression changes in iBAT that resembles twice-daily injections with FGF21.

Figure 23:
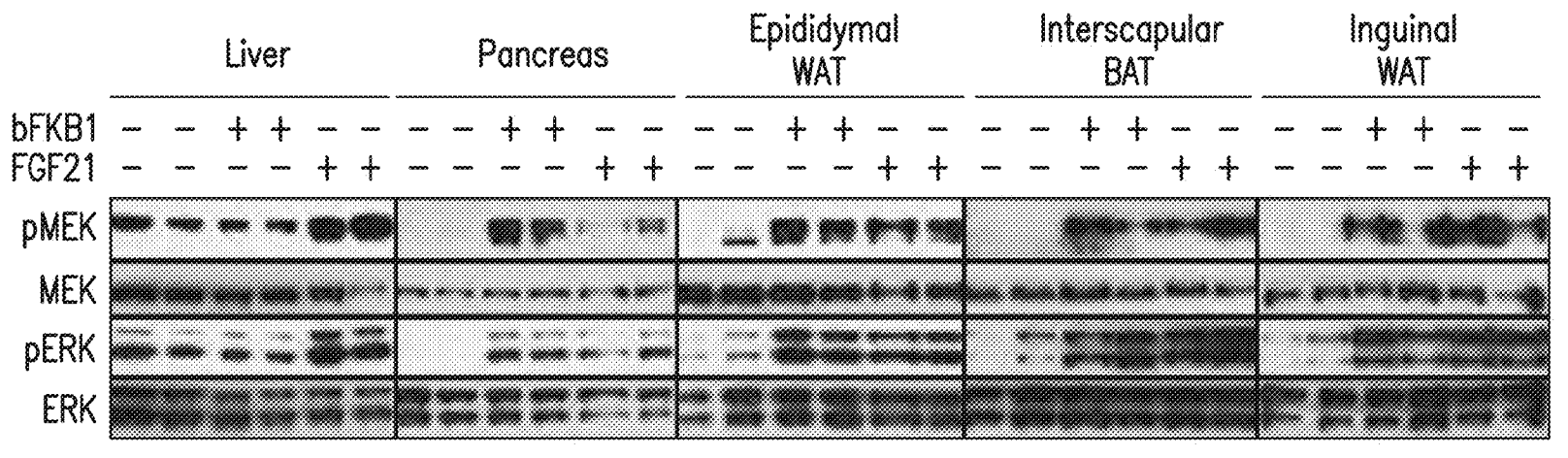

Finally, when injected into C57BL/6 mice, both FGF21 and BsAb20 induced ERK and MEK phosphorylation in various adipose tissues, including iBAT and ingWAT (FIG. 23).

In previous studies, adiponectin was suggested to contribute to the full action of FGF21 (Lin et al., Cell Metab 17, 779-789 (2013); Holland et al., Cell Metab 17, 790-797 (2013)). Indeed, single injection of BsAb17 into DIO mice led to an increase in serum high molecular weight (HMW) adiponectin levels, with associated weight loss (FIG. 24A).

Similarly, a single injection of BsAb17 into lean cynomolgus monkeys (FIG. 24B) led to an increase in serum high molecular weight (HMW) adiponectin levels, with associated weight loss.

As shown in FIG. 24C, upon single injection of BsAb17, adiponectin (Adipoq) KO mice on HFD exhibited a robust response in elevating EE (25.3% increase vs 20.9% increase in wt mice).

Figure 24D:
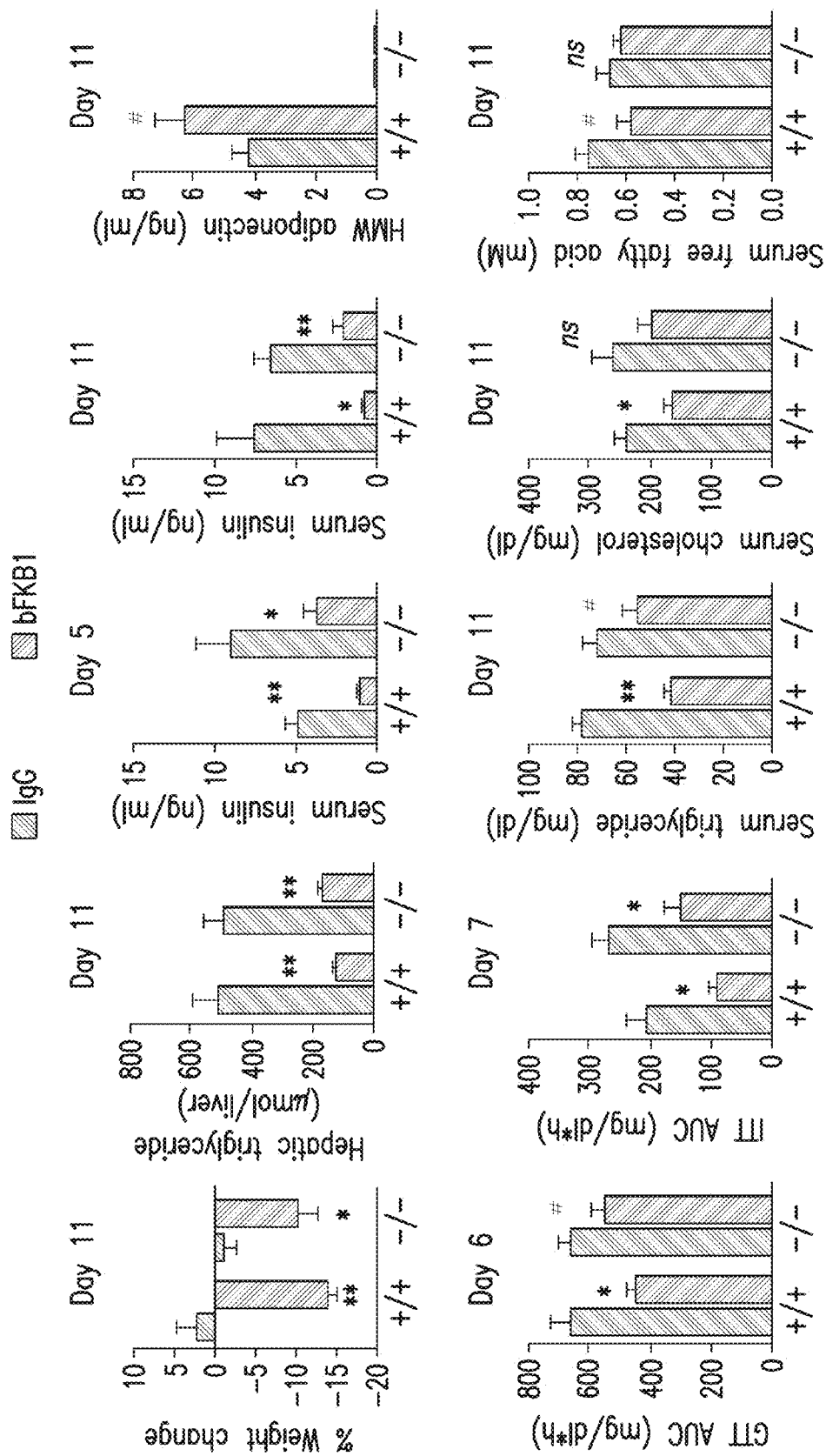
FIG. 24D depicts the various metabolic parameters in wt (+/+) and adipoq KO (-/-) DIO mice, which received single i.p. injection of indicated IgG (BsAb17) at 10 mg/kg. N=6. AUC: Area under the curve in GTT or ITT (T=0~2 h). $p<0.1$ (#), <0.05 (*), <0.005 (**) vs control.

In addition, upon single injection of BsAb17, adiponectin (Adipoq) KO mice on HFD exhibited reduced body weight and hepatic triglyceride levels (FIG. 24D). However, the response in glucose tolerance, insulin tolerance, changes in serum insulin and various lipids were all somewhat blunted in the KO mice (FIG. 24D), consistent with the idea that BsAb17 acts as a FGF21 mimetic in regulating whole body nutrient metabolism in part via adiponectin function. For determining insulin tolerance, mice were fasted for 4 h, and i.p. injected with 1 U/kg human insulin solution (Humulin R, Eli Lilly and Company).

Figure 25:
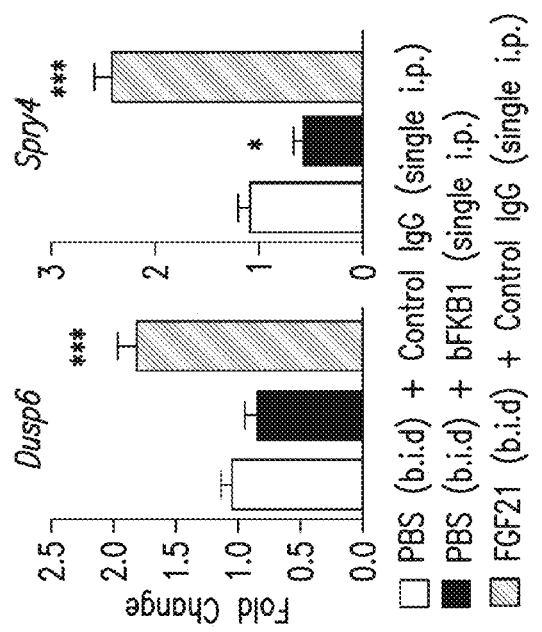
FIG. 25 depicts the total RNA that was prepared from the mice described in FIG. 19G using qPCR.

The heightened receptor selectivity of BsAb10 (see FIG. 9A) and previously described low brain penetrance of IgG molecules (Yu et al., *Sci Transl Med* 3, 84ra44 (2011)) predict an altered safety profile of BsAb10 and its derivatives compared with FGF21/19. Consistent with the low expression level of FGFR1 in the liver, FGF21, but not BsAb17, induced mRNA expression of classical FGFR target genes Spry4 and Dusp6 in the liver (FIG. 25).

BsAb17 or BsAb20 also resulted in an increased phospho-ERK signal in various adipose tissues and pancreatic acinar cells, but not in the liver (FIG. 23).

Figure 26:
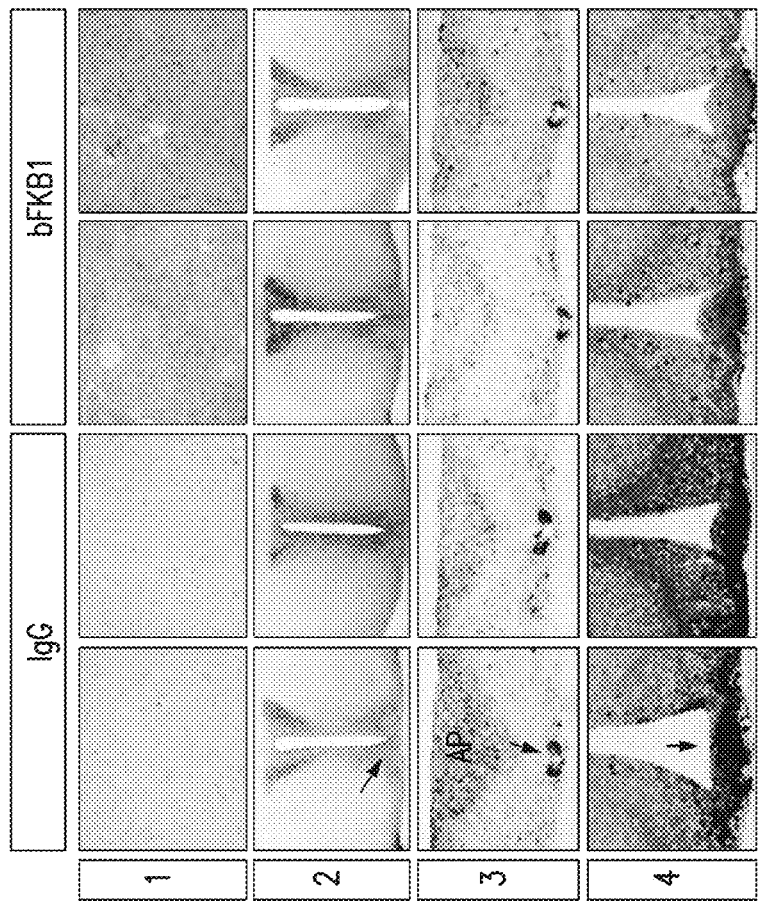
FIG. 26 depicts the level of ERK phosphorylation by BsAb17 in mouse tissues. Tissues were harvested at 1 h after i.p. injection of lean C57BL/6 mice at 10 mg/kg BsAb17 or control IgG, and subjected to immunohistochemistry using an antibody specific to phosphorylated ERK. Representative images from 2 animals are shown for each group. (1) Pancreas, (2) coronal brain section containing suprachiasmatic nuclei (arrow), (3) coronal brain section containing area postrema (triangular collection of stained cells) and the central canal (arrow), and (4) coronal brain section containing median eminence (arrow). Note that BsAb17-induced signal was apparent in the pancreatic acinar cells, but not in any of the brain sections examined.

FIG. 26 shows that BsAb17 also does not increase the phosphorylation of ERK in various brain sections including circumventricular organs, as determined by immunohistochemistry.

Figure 27:
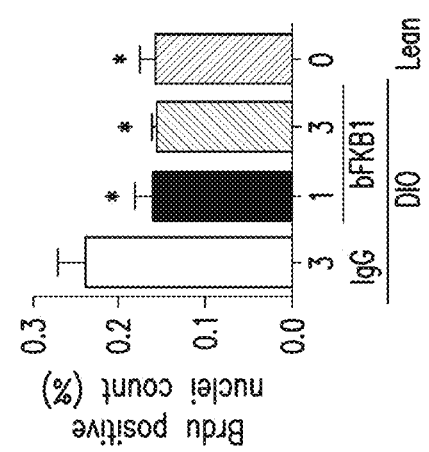
FIG. 27 depicts the normalization of HFD-induced hepatocyte proliferation by BsAb20. Hepatic BrdU incorporation in DIO mice treated with BsAb20 (1 or 3 mg/kg/week) or control IgG (3 mg/kg/week) for 8 weeks or control lean C57BL/6 mice. *p<0.05 vs IgG-treated DIO mice (N=5~8).

In addition, chronic BsAb20 treatment of DIO mice for 8 weeks reduced the number of BrdU+ cells in the liver to the level of lean C57BL/6 mice, the opposite of what was expected for FGF19-like activity (FIG. 27). For hepatic BrdU incorporation, mice were intraperitoneally injected with 100 mg/kg BrdU (BD Biosciences) at 2 h prior to euthanasia. Anti-BrdU staining was carried out as described (Nicholes, K., et al. *Am. J. Pathol.* 160, 2295-2307 (2002)) and BrdU positive hepatocytes were counted by using the Ariol automated image analysis system.

Bone analysis of mice that were treated with an anti-KLB/ anti-FGFR1c antibody was performed. FIG. 28A shows a schematic representation of the analysis. To perform the bone analysis, femur samples were imaged by a SCANCO Medical (Bassersdorf, Switzerland) μCT40 micro-imaging system operating with x-ray tube energy level a 70 keV and a current of 114 microamperes. Contiguous axial image slices were obtained with an isotropic voxel size of 12 μm. Morphometric analysis of the trabecular bone within the femur was performed with the SCANCO Medical (Bassersdorf, Switzerland) μCT40 evaluation software. Semi-automated contouring was used to define a volume of interest (VOI), comprising secondary trabecular bone dorsal to the proximal femur growth plate and extending 1.5 mm distal to primary trabecular bone. The cortical bone was excluded by placement of the VOI boundaries within the inner boundary of the cortical bone. Prior to image segmentation, a constrained three-dimensional (3D) Gaussian low-pass filter was applied to the image data for noise suppression (filter sigma=0.5, filter support=1). A global threshold (0.36 gHA/cm3) was applied to extract a "binarized" trabecular structure from the VOI. The trabecular segmentation threshold was chosen by visual inspection of the segmentation results from a representative subset of the samples. The trabecular structural characteristics were quantified by direct 3D morphometric analysis. Previous studies have shown that morphometric analysis of trabecular bone by microcomputed tomography is well correlated with similar estimates made by histomorphometry.

As shown in FIG. 28B, chronic BsAb20 treatment of DIO mice for 6 weeks resulted in the expected changes in metabolic parameters without any negative signal in various bone parameters in tibial trabecular and femoral cortical bones based on micro-computed tomography.

Figure 29:
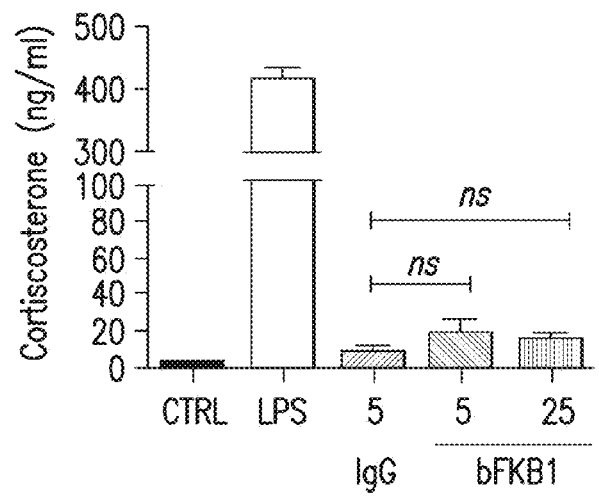
FIG. 29 depicts the corticosterone levels in mice after BsAb17 treatment. Serum corticosterone levels were measured at Zeitgeber time (ZT)=3 after euthanasia by decapitation. Control (CTRL) lean mice received no treatment. Lipopolysaccharide (LPS) was i.p. injected into lean mice at 1 mg/kg at 3 hr prior to euthanasia (ZT=0) as a positive control (12). IgG was i.p. injected into DIO mice at 5 or 25 mg/kg on 5 days prior to euthanasia as indicated. Indicated statistical analysis was conducted without LPS group. N=12.

As shown in FIG. 29, injection of BsAb17 into DIO mice did not increase serum corticosterone levels above control. Chronic positive energy balance common in the modern society has been driving the obesity pandemic and the associated metabolic derangements characterized by insulin resistance, hyperinsulinemia, glucose intolerance, hyperlipidemia, and hepatosteatosis, which often lead to severe illnesses such as type 2 diabetes, cirrhosis, stroke and heart disease. In 2009, the presence of UCP1-positive BAT in adult humans and their functional significance in driving EE via heat dissipation were reported, igniting an immense interest in therapeutic induction and activation of BAT for the treatment of obesity and related metabolic disease (Yoneshiro and Saito, Ann. Med., 1-9 (2014)).

However, most known BAT-activating mechanisms also induce white adipose tissue lipolysis, which may have a negative impact on cardiovascular outcome (Dong et al., *Cell Metab.* 18, 118-129 (2013)). Of note, BAT transplant increases EE and induces weight loss without change in RQ (Stanford et al., J. Clin. Invest. 123, 215-223 (2013)). In this regard, FGF21 and anti-FGFR1/KLB agonist antibody described herein present a unique approach to selectively induce thermogenic response in BAT without changing RQ, thus mimicking BAT transplant, rather than non-specific sympathoactivation. In addition, based on what was observed in mice, it is envisioned that antibody-mediated activation of FGFR1c/KLB complex may provide a safer and more efficient mean for anti-obese and anti-diabetic therapy, as opposed to the broader FGFR/KLB complex activation by FGF21 or FGF19 analogs.

Example 10: Humanization of Anti-KLB Antibody 845

The murine light chain CDRs of 8C5 were grafted into the human Kappa2 and Kappa4 light chain frameworks. In addition to the primary graft, point mutations were also generated in each such that position 4 of the light chain was converted to a leucine (designated "M4L"). Analysis was performed to identify those that expressed the best and did not show significant aggregation. Similarly, the heavy chain CDRs were grafted into the human H1, H2, H3 and H4 IgG1 heavy chain frameworks. Various residues in the heavy chain backbones were mutated as follows: for H1 the following changes were introduced: K71R, N73T and V78A (parent designated as "KNV" and construct designated "RTA"); for H2 the following change was introduced: N73T (parent designated as "KNV" and construct designated "KTV"); for H3 the following changes were introduced: K71R and V78L (parent designated as "KNV" and construct designated "RNL"; and for H4 the following changes were introduced: K71 V, N73T, and V78F (parent designated as "KNV" and construct designated "VTF").

Antibodies based on all pairwise combinations of the 4 light chains and 8 heavy chains (for a total of 32 antibodies) were produced and expression levels and affinity were tested. Based on these experiments, the 8C5 derived light chain K4.M4L and the heavy chain H3.KNV exhibited the best combination of expression level and desired affinity.

The sequences of the 8C5.K4.M4L.H3.KNV variable regions and full-length antibody are as follows:

```
8C5.K4.M4L.H3.KNV Heavy Chain Variable Region
                                    (SEQ ID NO: 128)
EVQLVESGGGLVQPGGSLRLSCAASDFSLTTYGVHWVRQAPGKGLEWLGV

IWSGGSTDYNAAFISRLTISKDNSKNTVYLQMNSLRAEDTAVYYCARDYG

STYVDAIDYWGQGTLVTVSS

8C5.K4.M4L.H3.KNV Full Heavy Chain
                                    (SEQ ID NO: 129)
EVQLVESGGGLVQPGGSLRLSCAASDFSLTTYGVHWVRQAPGKGLEWLGV

IWSGGSTDYNAAFISRLTISKDNSKNTVYLQMNSLRAEDTAVYYCARDYG

STYVDAIDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYG

STYRVVSVLTVLHQDWLNGKEYKCKVSNKALPAPIEKTISKAKGQPREPQ

VYTLPPSREEMTKNQVSLSCAVKGFYPSDIAVEWESNGQPENNYKTTPPV

LDSDGSFFLVSKLTVDKSRWQQGNVFSCSVMHEALHNHYTQKSLSLSPGK

8C5.K4.M4L.H3.KNV Light Chain Variable Region
                                    (SEQ ID NO: 130)
DIVLTQSPDSLAVSLGERATINCRASESVESYGNRYMTWYQQKPGQPPKL

LIYRAANLQSGVPDRFSGSGSGTDFTLTISSLQAEDVAVYYCQQSNEDPW

TFGQGTKVEIK

8C5.K4.M4L.H3.KNV Full Light Chain
                                    (SEQ ID NO: 131)
DIVLTQSPDSLAVSLGERATINCRASESVESYGNRYMTWYQQKPGQPPKL

LIYRAANLQSGVPDRFSGSGSGTDFTLTISSLQAEDVAVYYCQQSNEDPW

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC
```

Example 11: Generation of an Anti-FGFR1 Antibody Hybrid Between YW182.3 and YW182.5

Figure 31:
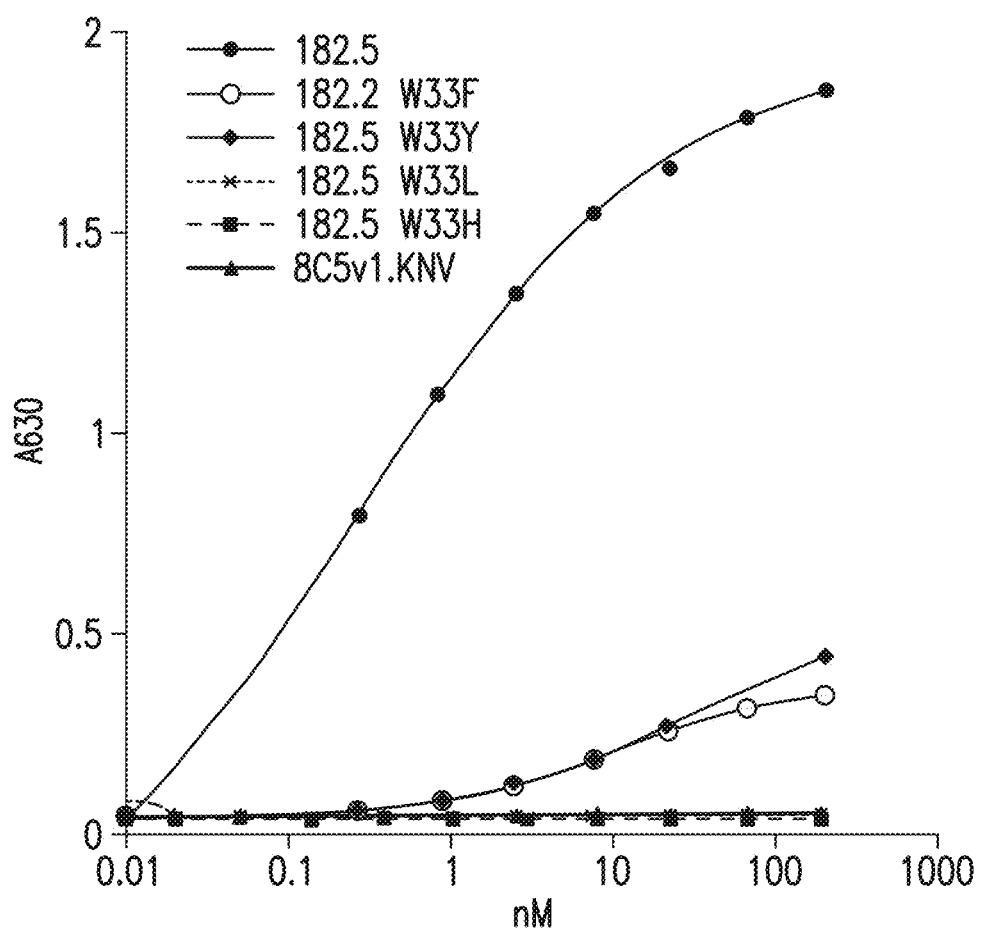
FIG. 31 depicts binding of YW182.5 and YW182.5 derivatives to FGFR1 proteins by ELISA.

YW182.5, which was the anti-FGFR1 arm that did not activate the KLB/FGFR1c complex in the absence of an anti-FGFR1 arm, was discovered to give good results when combined with 8C5, and has a tryptophan as position 33 of the heavy chain which is susceptible to oxidation. YW182.2, which appears to bind the same epitope as YW182.5, also has such a tryptophan at position 33 of the heavy chain. Several mutations were introduced at this position to obviate this problem: for YW182.5 W33Y, W33H, W33F and W33L were introduced and for YW182.2 W33Y and W33F were introduced. Surprisingly, the introduced mutations had different effects in the two antibodies. In the case of YW182.2, it was observed that the mutations did not appreciably affect the affinity or agonistic activity for FGFR1, whereas for YW182.5 the mutations greatly decreased the affinity and agonistic activity for FGFR1 (see, for example, FIG. 31). Therefore, experiments were performed to identify an antibody with the W33Y mutations, but with an affinity closer to that of the YW182.5 antibody using two approaches.

In one approach, for the YW182.2 W33Y heavy chain sequence alanine scanning across CDR3 was performed, mutating positions 95, 96, 97, 98, 99, 100, 100a and 100b to alanine. The affinity of the resulting antibodies were analyzed and those that retained the very high affinity of the YW182.2 W33Y parent were identified (Table 9).

TABLE 9

| Affinity of YW182.2 derivatives. | |
| --- | --- |
| Antibody | $EC_{50}$ (nM) |
| YW182.2_W33Y_96A | 2.4 |
| YW182.2_W33Y_97A | 5.3 |
| YW182.2_W33Y_100A | 5.8 |
| YW182.2_W33Y_98A | 8.8 |
| YW182.2_W33Y_GDY | 11.1 |
| YW182.5 | 34.6 |
| YW182.2_W33Y_100aA | 55.1 |
| YW182.2_W33Y_95A | 221.1 |
| YW182.2_W33Y_99A | 316.2 |
| YW182.2_W33Y_100bA | None detected |

In a second approach, CDRs from the YW182.2 W33Y antibody (with very high affinity) and the YW182.5 W33Y antibody (with almost no binding) were mix-and-matched. The YW182.2 W33Y and YW182.5 W33Y antibodies have identical CDR sequences in the light chain (CDR-L1, RASQDVSTAVA (SEQ ID NO: 139); CDR-L2, SASFLYS (SEQ ID NO: 140); and CDR-L3 QQSYTTPPT (SEQ ID NO: 141) a single amino acid difference in CDR-H1 (YW182.2 W33Y CDR-H1, STYIS (SEQ ID NO: 152) and YW182.5 W33Y CDR-H1, SNYIS (SEQ ID NO: 136)); three amino acid differences in or adjacent to CDR-H2 (YW182.2 W33Y CDR-H2, EIDPYDGDTYYADSVKG (SEQ ID NO: 137 and YW182.5 W33Y, EIDPYDGATDY-ADSVKG (SEQ ID NO: 153)); and very difference CDR-H3 sequences (YW182.2 W33Y, EHFDAWVHYYVMDY (SEQ ID NO: 154) and YW182.5 W33Y GTDVMDY (SEQ ID NO: 138). Antibodies with heavy chains based on all possible combinations of heavy chain CDRs from YW182.5 W33Y and YW182.2 W33Y (eight including the two parental antibodies) were constructed and tested. Most of the antibodies had affinity similar to one or the other, but, surprisingly, one combination demonstrated binding that was nearly identical to the parent YW182.5 antibody. This antibody has the CDR-H1 and CDR-H3 from YW182.5 W33Y, but the CDR-H2 from YW182.2 W33Y. This antibody was designated as "YW182.5 YGDY" to represent the following changes in the YW182.5 sequence: W33Y, A49G, A56D, and D58Y.

The sequences of the YW182.5 YGDY antibody are as follows:

YW182.5_YGDY Heavy Chain Variable Region
(SEQ ID NO: 132)
EVQLVESGGGLVQPGGSLRLSCAASGFTFTSNYISWVRQAPGKGLEWVGE

IDPYDGDTYYADSVKGRFTISADTSKNTAYLQMNSLRAEDTAVYYCATGT

DVMDYWGQGTLVTVSS.

YW182.5_YGDY Full Heavy Chain
(SEQ ID NO: 133)
EVQLVESGGGLVQPGGSLRLSCAASGFTFTSNYISWVRQAPGKGLEWVGE

IDPYDGDTYYADSVKGRFTISADTSKNTAYLQMNSLRAEDTAVYYCATGT

DVMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYGSTYR

VVSVLTVLHQDWLNGKEYKCKVSNKALPAPIEKTISKAKGQPREPQVYTL

PPSREEMTKNQVSLWCLVKGFYPSDIAVEWESNGQPENNYKTTPPVLDSD

GSFFLYSKLTVDKSRWQQGNVFSCSVMHEALHNHYTQKSLSLSPGK.

YW182.5_YGDY Light Chain Variable Region
(SEQ ID NO: 134)
DIQMTQSPSSLSASVGDRVTITCRASQDVSTAVAWYQQKPGKAPKLLIYS

ASFLYSGVPSRFSGSGSGTDFTLTISSLQPEDFATYYCQQSYTTPPTFGQ

GTKVEIK.

YW182.5_YGDY Full Light Chain
(SEQ ID NO: 135)
DIQMTQSPSSLSASVGDRVTITCRASQDVSTAVAWYQQKPGKAPKLLIYS

ASFLYSGVPSRFSGSGSGTDFTLTISSLQPEDFATYYCQQSYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Figure 30:
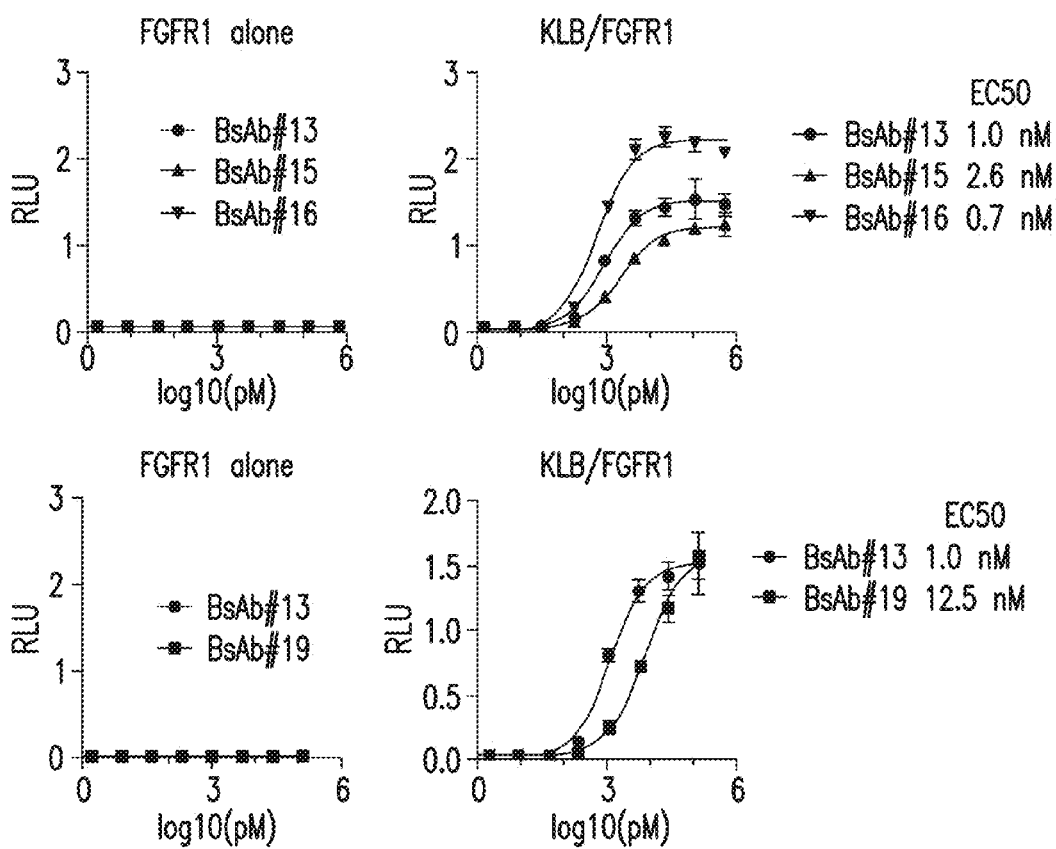
FIG. 30 shows the binding of various different bispecific antibodies with anti-FGFR1 and anti-KLB arms to cells expressing FGFR1c or FGFR1c and KLB.

Example 12: Testing of Bispecific Antibodies with Humanized 8C5 and Anti-FGFR1 Variants Various bispecific antibody combinations of 8C5.K4H3.M4L.KNV and different anti-FGFR1 arms were tested in the GAL-ELK1-based luciferase assay in HEK293 cells expressing FGFR1c with or without KLB. As previously observed, each bispecific antibody combination induced luciferase activity in a dose-dependent manner in cells expressing recombinant hFGFR1c and hKLB, but not in cells without KLB expression (FIG. 30). These data confirm that these modified variants retain the advantages of the parent antibodies, e.g., BsAb13. The binding affinity of an anti-KLB/anti-FGFR1 antibody that has a humanized 8C5 arm (8C5.K4.M4L.H3.KNV) and a YW182.5_YGDY arm to human, cynomolgus monkey and mouse KLB/FGFR1c complexes on the surface of HEK293 cells are shown in Table 10.

TABLE 10

| | Binding affinities. | | |
|---|---|---|---|
| Cell Line | anti-KLB/anti-FGFR1c antibody $K_d$ (nM) | Average $K_d$ (nM) | Standard deviation |
| 293huKLB/huR1c | 1.87<br>1.95<br>1.83 | 1.88 | 0.06 |
| 293cynoKLB/cynoR1c | 2.54<br>2.80<br>2.31 | 2.55 | 0.25 |
| 293msKLB/msR1c | 4.12<br>3.85<br>3.80 | 3.92 | 0.17 |

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

What is claimed is:

1. A method of reducing blood glucose or hepatic triglyceride levels in an individual having a disease selected from the group consisting of obesity, non-alcoholic steatohepatitis (NASH), non-alcoholic fatty liver disease (NAFLD), type 2 diabetes, non-type 2 diabetes, type 1 diabetes, latent autoimmune diabetes (LAD), and maturity onset diabetes of the young (MODY), comprising administering to the individual an effective amount of a bispecific antibody, or an antigen-binding portion thereof, that binds to beta-Klotho (KLB) and Fibroblast Growth Factor Receptor 1c (FGFR1c), wherein the bispecific antibody, or antigen-binding portion thereof, comprises:
(a) a first arm comprising: (i) a heavy chain variable region CDR1 domain comprising the amino acid sequence of SEQ ID NO: 136; (ii) a heavy chain variable region CDR2 domain comprising the amino acid sequence of SEQ ID NO: 137; (iii) a heavy chain variable region CDR3 domain comprising the amino acid sequence of SEQ ID NO: 138; (iv) a light chain variable region CDR1 domain comprising the amino acid sequence of SEQ ID NO: 139; (v) a light chain variable region CDR2 domain comprising the amino acid sequence of SEQ ID NO: 140; and (vi) a light chain variable region CDR3 domain comprising the amino acid sequence of SEQ ID NO: 141; and
(b) a second arm comprising: (i) a heavy chain variable region CDR1 domain comprising the amino acid sequence of SEQ ID NO: 15; (ii) a heavy chain variable region CDR2 domain comprising the amino acid sequence of SEQ ID NO: 31; (iii) a heavy chain variable region CDR3 domain comprising the amino acid sequence of SEQ ID NO: 47; (iv) a light chain variable region CDR1 domain comprising the amino acid sequence of SEQ ID NO: 62; (v) a light chain variable region CDR2 domain comprising the amino acid sequence of SEQ ID NO: 78; and (vi) a light chain variable region CDR3 domain comprising the amino acid sequence of SEQ ID NO: 93.

2. The method of claim 1, wherein the bispecific antibody, or antigen-binding portion thereof, is a human, humanized or chimeric antibody.

3. The method of claim 1, wherein the disease is obesity.

4. The method of claim 1, wherein the disease is non-alcoholic steatohepatitis (NASH).

5. The method of claim 1, wherein the disease is diabetes.

6. The method of claim 5, wherein the disease is type 2 diabetes.

7. A method of reducing blood glucose or hepatic triglyceride levels in an individual having a disease selected from the group consisting of obesity, non-alcoholic steatohepatitis (NASH), non-alcoholic fatty liver disease (NAFLD), type 2 diabetes, non-type 2 diabetes, type 1 diabetes, latent autoimmune diabetes (LAD), and maturity onset diabetes of the young (MODY), comprising administering to the individual an effective amount of a bispecific antibody, or an antigen-binding portion thereof, that binds to beta-Klotho (KLB) and Fibroblast Growth Factor Receptor 1c (FGFR1c), wherein the bispecific antibody, or antigen-binding portion thereof, comprises:
(a) a first arm comprising a heavy chain variable region and a light chain variable region, wherein the heavy chain variable region comprises the amino acid sequence of SEQ ID NO: 132, and the light chain variable region comprises the amino acid sequence of SEQ ID NO: 134; and
(b) a second arm comprising a heavy chain variable region and a light chain variable region, wherein the heavy chain variable region comprises the amino acid sequence of SEQ ID NO: 128, and the light chain variable region comprises the amino acid sequence of SEQ ID NO: 130.

8. The method of claim 7, wherein the disease is obesity.

9. The method of claim 7, wherein the disease is non-alcoholic steatohepatitis (NASH).

10. The method of claim 7, wherein the disease is diabetes.

11. The method of claim 10, wherein the disease is type 2 diabetes.

12. A method of reducing blood glucose or hepatic triglyceride levels in an individual having a disease selected from the group consisting of obesity, non-alcoholic steatohepatitis (NASH), non-alcoholic fatty liver disease (NAFLD), type 2 diabetes, non-type 2 diabetes, type 1 diabetes, latent autoimmune diabetes (LAD), and maturity onset diabetes of the young (MODY), comprising administering to the individual an effective amount of a bispecific antibody, or an antigen-binding portion thereof, that binds to beta-Klotho (KLB) and Fibroblast Growth Factor Receptor 1c (FGFR1c), wherein the bispecific antibody, or antigen-binding portion thereof, comprises:
(a) a first arm comprising a heavy chain region and a light chain region, wherein the heavy chain region comprises the amino acid sequence of SEQ ID NO: 133, and the light chain region comprises the amino acid sequence of SEQ ID NO: 135; and
(b) a second arm comprising a heavy chain region and a light chain region, wherein the heavy chain region comprises the amino acid sequence of SEQ ID NO: 129, and the light chain region comprises the amino acid sequence of SEQ ID NO: 131.

13. The method of claim 12, wherein the disease is obesity.

14. The method of claim 12, wherein the disease is non-alcoholic steatohepatitis (NASH).

15. The method of claim 12, wherein the disease is diabetes.

16. The method of claim 15, wherein the disease is type 2 diabetes.

* * * * *

SEQUENCE LISTING

```
<160> NUMBER OF SEQ ID NOS: 166

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Ser Tyr Gly Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Tyr Tyr Met Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Gly Val Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Thr Tyr Met Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Thr Tyr Ile His
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Tyr Trp Ile His
1               5

<210> SEQ ID NO 7
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 7

Asp Thr Phe Thr His
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Tyr Thr Met Asn
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Tyr Trp Ile Glu
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Glu Met His
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Thr Tyr Ile His
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Tyr Trp Met Ser
1               5

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Tyr Gly Met Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Ala Met Gly Ile Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Tyr Gly Val His
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Val Ser Ser Gly Gly Arg Tyr Thr Tyr Tyr Pro Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ile Asp Pro Glu Asn Asp Asp Thr Ile Tyr Asp Pro Lys Phe Gln
1               5                   10                  15

Gly

<210> SEQ ID NO 18
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 18

Val Ile Trp Gly Asp Gly Ser Ile Asn Tyr His Ser Ala Leu Ile Ser
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ile Asp Pro Ser Asn Gly Asn Ala Lys Tyr Asp Pro Lys Phe Gln
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ile Asp Pro Ala Asn Gly Asn Thr Lys Tyr Asp Pro Lys Phe Gln
1               5                   10                  15

Asp

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Ile Asp Pro Ser Val Ser Asn Ser Asn Tyr Asn Gln Lys Phe Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ile Asp Pro Ser Asn Gly Asn Thr Lys Tyr Asp Pro Lys Phe Gln
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 23

Gly Ile Asn Pro Asn Asn Gly Glu Thr Ser Tyr Asn Gln Lys Phe Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ile Phe Pro Gly Gly Gly Ser Thr Ile Tyr Asn Glu Asn Phe Arg
1               5                   10                  15

Asp

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ile Trp Pro Glu Asn Ala Asp Ser Val Tyr Asn Gln Lys Phe Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ile Asp Pro Ala Asn Gly Asn Thr Lys Tyr Asp Pro Lys Phe Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ile Leu Pro Gly Ser Asp Ser Thr Lys Tyr Val Glu Lys Phe Lys
1               5                   10                  15

Val

<210> SEQ ID NO 28
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 28

Glu Ile Ser Pro Asp Ser Ser Thr Ile Asn Tyr Thr Pro Ser Leu Lys
1               5                   10                  15

Asp

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Ile Asp Thr Asp Thr Gly Glu Ala Thr Tyr Thr Asp Asp Phe Lys
1               5                   10                  15

Gly

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Ile Trp Trp Asp Asp Asp Lys Arg Tyr Asn Pro Ala Leu Lys Ser
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Ile Trp Ser Gly Gly Ser Thr Asp Tyr Asn Ala Ala Phe Ile Ser
1               5                   10                  15

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Asp Gly Tyr Ala Leu Asp Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Phe Thr Thr Val Phe Ala Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr His Asp Trp Phe Asp Tyr
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Leu Gly Asn Gly Tyr Ala Leu Gly Tyr
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Thr Ser Tyr Ser Trp Phe Ala Tyr
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Gly Val Met Val Tyr Gly Ser Ser Pro Phe Trp Phe Ala Tyr
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ala Leu Gly Asn Gly Tyr Ala Met Asp Tyr
1               5                   10

<210> SEQ ID NO 39
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 39

Lys Thr Thr Asn Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Gly Tyr Tyr Asp Ala Ala Trp Phe Asp Tyr
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Gly Gly Asn Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Gly Asn Tyr Gly Ala Met Asp Tyr
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Tyr His Tyr Pro Gly Trp Leu Val Tyr
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Ser Pro Ala Leu Asp Tyr
1               5

```
<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Glu Tyr Gly Leu Phe Gly Phe Pro Tyr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Asp Gly Ile Tyr Asp Gly Ser Phe Tyr Ala Met Asp Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Tyr Gly Ser Thr Tyr Val Asp Ala Ile Asp Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Ala Ser Gln Val Ile Ser Asn Tyr Leu Asn
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Ala Ser Ser Ser Gly Arg Tyr Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

```
Arg Ala Ser Gln Asp Ile Ser Asn Tyr Phe Asn
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Ala Ser Asp His Ile Asn Asn Trp Leu Ala
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ser Gln Asn Ile Val His Ser Asp Gly Asn Thr Tyr Leu Glu
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Ala Ser Gln Phe Val Ser Asp Ala Val Ala
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Glu Ile Ser Gly Tyr Leu Ser
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Ser Ser Ser Leu Ser Ser Ser Tyr Leu Tyr
1               5                   10

<210> SEQ ID NO 56
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 56

Lys Ser Ser Gln Ser Leu Leu Asn Ser Gly Asn Gln Lys Asn Ser Leu
1               5                   10                  15

Ala

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Ser Ser Val Asn His Met Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Ala Ser Gln Asn Val Asp Ser Tyr Val Ala
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ala Ser Gln Ser Ile Ser Asp Tyr Val Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Ala Ser Glu Asp Ile Tyr Asn Arg Leu Ala
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Glu Ser Val Asp Ser Tyr Gly Asn Ser Phe Met His
```

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ala Ser Glu Ser Val Glu Ser Tyr Gly Asn Arg Tyr Met Thr
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Thr Ser Ser Leu Arg Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Thr Ser Lys Leu Ala Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Thr Ser Arg Leu Gln Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Thr Thr Asn Leu Glu Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 67

Lys Val Ser Asn Arg Phe Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Ala Ser Tyr Arg Tyr Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ala Ser Asn Leu Glu Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ala Ser Thr Leu Asp Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ala Ser Asn Leu Ala Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ala Ser Thr Arg Glu Ser
1               5

<210> SEQ ID NO 73
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Thr Ser Thr Leu Ala Pro
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Ala Ser Tyr Arg Phe Ser
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Ala Ser Gln Ser Ile Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Ala Thr Ser Leu Glu Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Ser Asn Leu Glu Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

Arg Ala Ala Asn Leu Gln Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Gln Tyr Ser Lys Leu Pro Trp Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Gln Gly Thr Gly Tyr Pro Leu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Gln Val Arg Thr Leu Pro Trp Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Tyr Trp Asn Thr Pro Phe Thr
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Gln Gly Ser His Val Leu Thr
1               5

<210> SEQ ID NO 84
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 84

Gln Gln His Tyr Ile Val Pro Tyr Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Gln Tyr Gly Ser Tyr Pro Trp Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

His Gln Trp Ser Ser Tyr Pro Leu Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln His His Ser Thr Pro Tyr Thr
1               5

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Phe Thr Ile Ser Pro Ser Met Tyr Thr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Tyr Asn Ile Ser Pro Tyr Thr
1               5
```

```
<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Asn Gly His Asn Phe Pro Tyr Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gln Tyr Trp Ser Asn Pro Leu Thr
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Ser Asn Glu Asp Tyr Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Ser Asn Glu Asp Pro Trp Thr
1               5

<210> SEQ ID NO 94
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Lys Pro Gly Gly
1               5                   10                  15

Ser Leu Lys Leu Ser Cys Ala Pro Ser Gly Phe Thr Phe Ser Ser Tyr
            20                  25                  30

Gly Ile Ser Trp Val Arg Gln Thr Pro Glu Lys Arg Leu Glu Trp Val
        35                  40                  45

Ala Thr Val Ser Ser Gly Gly Arg Tyr Thr Tyr Tyr Pro Asp Ser Val
    50                  55                  60

Lys Gly Arg Phe Thr Ile Ser Arg Asp Asn Ala Glu Asn Thr Leu Tyr
```

```
                65                  70                  75                  80
Leu Gln Met Ser Ser Leu Arg Ser Glu Asp Thr Ala Met Tyr Tyr Cys
            85                  90                  95

Thr Arg Gly Gly Asp Gly Tyr Ala Leu Asp Tyr Trp Gly Gln Gly Thr
            100                 105                 110

Ser Val Thr Val Ser Ser
        115

<210> SEQ ID NO 95
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Gln Gln Ser Gly Ala Glu Leu Val Arg Pro Gly Ala
1               5                   10                  15

Leu Val Asn Leu Ser Cys Lys Ala Ser Gly Phe Asn Ile Lys Asp Tyr
            20                  25                  30

Tyr Met Asn Trp Val Lys Gln Arg Pro Glu Gln Gly Leu Glu Trp Thr
        35                  40                  45

Gly Trp Ile Asp Pro Glu Asn Asp Asp Thr Ile Tyr Asp Pro Lys Phe
    50                  55                  60

Gln Gly Lys Ala Thr Ile Thr Ala Asp Thr Ser Ser Asn Thr Val Tyr
65                  70                  75                  80

Leu Gln Leu Thr Ser Leu Thr Ser Glu Asp Thr Ala Val Tyr Tyr Cys
            85                  90                  95

Ala Ala Phe Thr Thr Val Phe Ala Tyr Trp Gly His Gln Thr Met Val
            100                 105                 110

Thr Val Ser Ala
        115

<210> SEQ ID NO 96
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Ile Arg Gln Pro Pro Gly Lys Gly Leu Glu Trp Leu
        35                  40                  45

Gly Val Ile Trp Gly Asp Gly Ser Ile Asn Tyr His Ser Ala Leu Ile
    50                  55                  60

Ser Arg Leu Thr Ile Thr Lys Asp Asn Ser Lys Ser Gln Val Phe Leu
65                  70                  75                  80

Lys Leu Asn Ser Leu Glu Ala Asp Asp Thr Ala Thr Tyr Tyr Cys Ala
            85                  90                  95

Lys Thr His Asp Trp Phe Asp Tyr Trp Gly Gln Gly Thr Leu Val Thr
            100                 105                 110

Val Ser Ala
```

-continued

115

<210> SEQ ID NO 97
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Gln Gln Ser Gly Ala Glu Leu Val Lys Pro Gly Ala
1               5                   10                  15

Ser Val Lys Leu Ser Cys Thr Ala Ala Asp Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ser Asn Gly Asn Ala Lys Tyr Asp Pro Lys Phe
    50                  55                  60

Gln Gly Lys Ala Ser Ile Thr Ala Asp Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Ser Arg Ala Leu Gly Asn Gly Tyr Ala Leu Gly Tyr Trp Gly Gln
            100                 105                 110

Gly Thr Ser Val Thr Val Ser Ser
            115                 120

<210> SEQ ID NO 98
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Ile Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Asp Lys Ala Ala Leu Thr Ser Asp Thr Asp Ser Asn Thr Ala Tyr
65                  70                  75                  80

Leu Leu Phe Asn Ser Leu Thr Ser Glu Asp Thr Ala Val Tyr Tyr Cys
                85                  90                  95

Ala Arg Gly Thr Ser Tyr Ser Trp Phe Ala Tyr Trp Gly Gln Gly Thr
            100                 105                 110

Leu Val Ser Val Ser Ala
        115

<210> SEQ ID NO 99
<211> LENGTH: 124
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 99

Gln Val Gln Leu Gln Gln Pro Gly Ala Glu Ile Val Lys Pro Gly Ala
1               5                   10                  15

Ser Val Arg Leu Ser Cys Lys Ala Ser Gly Tyr Ser Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Val Ser Asn Ser Asn Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Phe Cys
                85                  90                  95

Val Arg Leu Gly Val Met Val Tyr Gly Ser Ser Pro Phe Trp Phe Ala
            100                 105                 110

Tyr Trp Gly Gln Gly Thr Leu Val Thr Val Ser Ala
        115                 120

<210> SEQ ID NO 100
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Gln Pro Gly Ala Glu Ile Val Lys Pro Gly Ala
1               5                   10                  15

Ser Val Arg Leu Ser Cys Lys Ala Ser Gly Tyr Ser Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Val Ser Asn Ser Asn Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Phe Cys
                85                  90                  95

Val Arg Leu Gly Val Met Val Tyr Gly Ser Ser Pro Phe Trp Phe Ala
            100                 105                 110

Tyr Trp Gly Gln Gly Thr Leu Val Thr Val Ser Ala
        115                 120

<210> SEQ ID NO 101
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Gln Gln Ser Gly Ala Glu Leu Leu Lys Pro Gly Ala
1               5                   10                  15

Ser Val Arg Leu Ser Cys Thr Ala Ser Gly Phe Asn Ile Gln Asp Thr
            20                  25                  30
```

```
Phe Thr His Trp Val Arg Gln Arg Pro Glu Gln Gly Leu Glu Trp Ile
            35                  40                  45

Gly Arg Ile Asp Pro Ser Asn Gly Asn Thr Lys Tyr Asp Pro Lys Phe
    50                  55                  60

Gln Gly Lys Ala Lys Ile Leu Ala Asp Thr Ser Ser Asn Thr Ala Tyr
65                  70                  75                  80

Leu Gln Leu Ile Gly Leu Thr Ser Glu Asp Thr Ala Val Tyr Tyr Cys
                85                  90                  95

Ala Ser Arg Ala Leu Gly Asn Gly Tyr Ala Met Asp Tyr Trp Gly Gln
            100                 105                 110

Gly Thr Ser Val Thr Val Ser Ser
            115                 120
```

<210> SEQ ID NO 102
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 102

```
Glu Val Pro Leu Gln Gln Ser Gly Pro Glu Leu Val Lys Pro Gly Ala
1               5                   10                  15

Thr Val Lys Ile Ser Cys Lys Pro Ser Gly Asp Thr Phe Thr Glu Tyr
            20                  25                  30

Thr Met Asn Trp Val Arg Gln Ser His Gly Lys Ser Leu Glu Trp Ile
            35                  40                  45

Gly Gly Ile Asn Pro Asn Asn Gly Glu Thr Ser Tyr Asn Gln Lys Phe
    50                  55                  60

Lys Gly Lys Ala Thr Leu Thr Val Asp Lys Ser Ser Ser Thr Ala Phe
65                  70                  75                  80

Met Asp Leu Arg Ile Leu Thr Ser Glu Asp Ser Ala Val Tyr Phe Cys
                85                  90                  95

Ala Arg Lys Thr Thr Asn Tyr Trp Gly Gln Gly Thr Thr Leu Ile Val
            100                 105                 110

Ser Ser
```

<210> SEQ ID NO 103
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 103

```
Gln Ile Gln Leu Gln Gln Ser Gly Ala Glu Leu Met Lys Pro Gly Ala
1               5                   10                  15

Ser Val Arg Met Ser Cys Lys Ala Ser Gly Tyr Thr Phe Ser Ser Tyr
            20                  25                  30

Trp Ile Glu Trp Val Lys Gln Arg Ser Gly His Gly Leu Glu Trp Ile
            35                  40                  45

Gly Glu Ile Phe Pro Gly Gly Ser Thr Ile Tyr Asn Glu Asn Phe
    50                  55                  60

Arg Asp Lys Ala Thr Phe Thr Ala Asp Thr Ser Ser Asn Thr Ala Tyr
65                  70                  75                  80
```

```
Met Gln Leu Ser Ser Leu Thr Ser Glu Asp Ser Ala Val Tyr Phe Cys
                85                  90                  95

Ala Arg Arg Gly Tyr Tyr Asp Ala Ala Trp Phe Asp Tyr Trp Gly Gln
            100                 105                 110

Gly Thr Leu Val Thr Val Ser Ala
        115                 120

<210> SEQ ID NO 104
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Lys Gln Ser Gly Ala Glu Leu Val Arg Pro Gly Thr
1               5                   10                  15

Ser Val Thr Leu Ser Cys Lys Ala Ser Gly Tyr Thr Phe Thr Asp Tyr
            20                  25                  30

Glu Met His Trp Met Lys Gln Thr Pro Val Tyr Gly Leu Glu Trp Ile
        35                  40                  45

Gly Ala Ile Trp Pro Glu Asn Ala Asp Ser Val Tyr Asn Gln Lys Phe
    50                  55                  60

Lys Gly Lys Val Thr Leu Thr Ala Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Thr Arg Glu Gly Gly Asn Tyr Trp Gly Gln Gly Thr Thr Leu Thr Val
            100                 105                 110

Ser Ser

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Gln Gln Ser Gly Thr Glu Leu Val Arg Pro Gly Ala
1               5                   10                  15

Ser Val Lys Leu Ser Cys Thr Ser Ser Asp Phe Asn Ile Lys Asp Thr
            20                  25                  30

Tyr Ile His Trp Val Lys Gln Arg Pro Glu Gln Gly Leu Asp Trp Leu
        35                  40                  45

Gly Arg Ile Asp Pro Ala Asn Gly Asn Thr Lys Tyr Asp Pro Lys Phe
    50                  55                  60

Gln Gly Lys Ala Ala Met Thr Ser Asp Thr Ser Ser Asn Thr Ala Tyr
65                  70                  75                  80

Leu Arg Leu Ser Ser Leu Thr Ser Glu Asp Thr Ala Val Tyr Tyr Cys
                85                  90                  95

Ala Ser Ser Gly Asn Tyr Gly Ala Met Asp Tyr Trp Gly Gln Gly Thr
            100                 105                 110

Ser Val Thr Val Ser Ser
        115
```

```
<210> SEQ ID NO 106
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Gln Ser Gly Asp Glu Leu Met Lys Pro Gly Ala
1               5                   10                  15

Ser Val Lys Ile Ser Cys Lys Val Thr Gly Asn Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Ser Thr Lys Tyr Val Glu Lys Phe
    50                  55                  60

Lys Val Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr His Tyr Pro Gly Trp Leu Val Tyr Trp Gly Gln
            100                 105                 110

Gly Thr Leu Val Thr Val Ser Ala
        115                 120

<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Lys Phe Leu Glu Ser Gly Gly Gly Leu Val Gln Pro Gly Gly
1               5                   10                  15

Ser Leu Arg Leu Ser Cys Ala Val Ser Gly Ile Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Ser Pro Asp Ser Ser Thr Ile Asn Tyr Thr Pro Ser Leu
    50                  55                  60

Lys Asp Lys Phe Val Ile Ser Arg Asp Asn Ala Lys Asn Thr Leu Tyr
65                  70                  75                  80

Leu Gln Met Ser Lys Val Arg Ser Ala Asp Thr Ala Leu Tyr Tyr Cys
                85                  90                  95

Ala Arg Pro Ser Pro Ala Leu Asp Tyr Trp Gly Gln Gly Thr Leu Val
            100                 105                 110

Thr Val Ser Ala
        115

<210> SEQ ID NO 108
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108
```

Gln Ile Gln Leu Val Gln Ser Gly Pro Glu Leu Lys Lys Pro Gly Glu
1               5                   10                  15

Thr Ala Lys Ile Ser Cys Lys Ala Ser Gly Tyr Ala Phe Ser Asn Tyr
            20                  25                  30

Gly Met Asn Trp Val Lys Gln Ala Pro Gly Lys Asp Leu Lys Trp Met
        35                  40                  45

Gly Trp Ile Asp Thr Asp Thr Gly Glu Ala Thr Tyr Thr Asp Asp Phe
50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Glu Tyr Gly Leu Phe Gly Phe Pro Tyr Trp Gly His Gly
            100                 105                 110

Thr Leu Val Thr Val Ser Ala
            115

<210> SEQ ID NO 109
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Ala Met Gly Ile Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
50                  55                  60

Leu Lys Ser Arg Leu Thr Ile Ser Lys Asp Thr Ser Arg Asn Gln Val
65                  70                  75                  80

Phe Leu Lys Ile Ala Ser Val Asp Thr Ala Asp Thr Ala Thr Tyr Phe
                85                  90                  95

Cys Ala Arg Ile Asp Gly Ile Tyr Asp Gly Ser Phe Tyr Ala Met Asp
            100                 105                 110

Tyr Trp Gly Gln Gly Thr Ser Val Thr Val Ser Ser
            115                 120

<210> SEQ ID NO 110
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Lys Gln Ser Gly Pro Gly Leu Val Gln Pro Ser Gln
1               5                   10                  15

Ser Leu Ser Val Ala Cys Thr Val Ser Asp Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
            50                  55                  60

Ser Arg Leu Thr Ile Ser Lys Asp Asn Ser Lys Ser Gln Val Phe Phe
65                  70                  75                  80

Lys Met Asn Ser Leu Gln Thr Thr Asp Thr Ala Ile Tyr Tyr Cys Ala
                85                  90                  95

Arg Asp Tyr Gly Ser Tyr Val Asp Ala Ile Asp Tyr Trp Gly Gln
            100                 105                 110

Gly Thr Ser Val Thr Val Ser Ser
            115                 120

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Gln Met Thr Gln Thr Thr Ser Ser Leu Ser Ala Ser Leu Gly
1               5                   10                  15

Asp Arg Val Thr Ile Ile Cys Ser Ala Ser Gln Val Ile Ser Asn Tyr
            20                  25                  30

Leu Asn Trp Tyr Gln Gln Lys Pro Asp Gly Thr Val Lys Leu Leu Ile
        35                  40                  45

Tyr Phe Thr Ser Ser Leu Arg Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Val Ala Thr Tyr Phe Cys Gln Gln Tyr Ser Lys Leu Pro Trp
                85                  90                  95

Thr Phe Gly Gly Gly Thr Lys Leu Glu Leu Lys
            100                 105

<210> SEQ ID NO 112
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Gly Arg Tyr Thr
            20                  25                  30

Phe Trp Tyr Gln Gln Lys Ser Asn Thr Ala Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Thr Gly Tyr Pro Leu Thr
                85                  90                  95

Phe Gly Ala Gly Thr Lys Leu Glu Leu Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 113

```
Asp Ile Gln Met Thr Gln Thr Pro Ser Ser Leu Ser Ala Ser Leu Gly
1               5                  10                  15

Asp Arg Val Thr Ile Asn Cys Arg Ala Ser Gln Asp Ile Ser Asn Tyr
            20                  25                  30

Phe Asn Trp Tyr Gln Gln Lys Pro Asn Gly Thr Ile Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Lys Ala Thr Tyr Phe Cys His Gln Val Arg Thr Leu Pro Trp
                85                  90                  95

Thr Phe Gly Gly Gly Thr Lys Leu Glu Ile Lys
            100                 105
```

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 114

```
Asp Ile Gln Met Thr Gln Ser Ser Ser Tyr Leu Ser Val Ser Leu Gly
1               5                  10                  15

Gly Ser Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Tyr Gly Thr Thr Asn Leu Glu Thr Gly Val Pro Ser Arg Phe Ser Gly
    50                  55                  60

Ser Gly Ser Gly Arg Asp Tyr Ile Leu Ser Ile Thr Ser Leu Gln Ser
65                  70                  75                  80

Glu Asp Val Ala Ser Tyr Tyr Cys Gln Gln Tyr Trp Asn Thr Pro Phe
                85                  90                  95

Thr Phe Gly Ser Gly Thr Lys Leu Glu Ile Lys
            100                 105
```

<210> SEQ ID NO 115
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 115

```
Ala Val Leu Met Thr Gln Thr Pro Leu Ser Leu Pro Val Ser Leu Gly
1               5                  10                  15
```

Asp Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Arg Asp Phe Thr Leu Lys Ile
65                  70                  75                  80

Ser Arg Val Glu Ala Gly Asp Leu Gly Val Tyr Tyr Cys Phe Gln Gly
                85                  90                  95

Ser His Val Leu Thr Phe Gly Ala Gly Thr Arg Leu Glu Leu Lys
            100                 105                 110

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Val Met Thr Gln Ser Gln Lys Phe Met Ser Thr Ser Val Gly
1               5                   10                  15

Asp Arg Val Ser Ile Thr Cys Lys Ala Ser Gln Phe Val Ser Asp Ala
            20                  25                  30

Val Ala Trp Tyr Gln Gln Lys Pro Gly Gln Ser Pro Lys Leu Leu Ile
        35                  40                  45

Cys Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Arg Thr
65                  70                  75                  80

Glu Asp Leu Ala Val Tyr Tyr Cys Gln Gln His Tyr Ile Val Pro Tyr
                85                  90                  95

Thr Phe Gly Gly Gly Thr Thr Leu Glu Ile Glu
            100                 105

<210> SEQ ID NO 117
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Val Met Thr Gln Ser Gln Lys Phe Met Ser Thr Ser Val Gly
1               5                   10                  15

Asp Arg Val Ser Ile Thr Cys Lys Ala Ser Gln Phe Val Ser Asp Ala
            20                  25                  30

Val Ala Trp Tyr Gln Gln Lys Pro Gly Gln Ser Pro Lys Leu Leu Ile
        35                  40                  45

Cys Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Arg Thr
65                  70                  75                  80

Glu Asp Leu Ala Val Tyr Tyr Cys Gln Gln His Tyr Ile Val Pro Tyr
                85                  90                  95

```
Thr Phe Gly Gly Gly Thr Thr Leu Glu Ile Glu
            100                 105
```

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Ser Asn Leu Glu Thr Gly Ile Pro Ser Arg Phe Ser Gly
    50                  55                  60

Ser Gly Ser Gly Lys Asp Tyr Thr Leu Thr Ile Thr Ser Leu Gln Thr
65                  70                  75                  80

Glu Asp Val Ala Thr Tyr Tyr Cys Gln Gln Tyr Trp Asn Thr Pro Phe
                85                  90                  95

Thr Phe Gly Ser Gly Thr Lys Leu Glu Ile Lys
            100                 105
```

<210> SEQ ID NO 119
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Arg Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Gly Ser Tyr Pro Trp
                85                  90                  95

Thr Phe Gly Gly Gly Thr Lys Leu Glu Leu Lys
            100                 105
```

<210> SEQ ID NO 120
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gln Ile Val Leu Thr Gln Ser Pro Ala Ile Met Ser Ala Ser Pro Gly
```

```
                1               5                  10                  15
Glu Arg Val Thr Leu Thr Cys Ser Ala Ser Ser Ser Leu Ser Ser
            20                  25                  30

Tyr Leu Tyr Trp Tyr Gln Gln Lys Pro Gly Ser Ser Pro Lys Leu Trp
            35                  40                  45

Ile Tyr Gly Ala Ser Asn Leu Ala Ser Gly Val Pro Gly Arg Phe Ser
            50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Leu Thr Phe Gly Ser Gly Thr Lys Leu Glu Leu Lys
                100                 105
```

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Asp Ile Val Met Thr Gln Ser Pro Ser Ser Leu Pro Met Ser Val Gly
1               5                  10                  15

Gln Lys Val Thr Met Ser Cys Lys Ser Ser Gln Ser Leu Leu Asn Ser
            20                  25                  30

Gly Asn Gln Lys Asn Ser Leu Ala Trp Tyr Gln Gln Lys Pro Gly Gln
            35                  40                  45

Ser Pro Lys Leu Leu Val Tyr Leu Ala Ser Thr Arg Glu Ser Gly Val
            50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His His Ser Thr Pro Tyr Thr Phe Gly Gly Gly Thr Lys Leu Glu Leu
                100                 105                 110

Lys
```

<210> SEQ ID NO 122
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Glu Ser Val Leu Thr Gln Ser Pro Ala Leu Met Ser Ala Ser Leu Gly
1               5                  10                  15

Glu Lys Val Thr Met Thr Cys Arg Ala Ser Ser Ser Val Asn His Met
            20                  25                  30

Tyr Trp Tyr Gln Gln Lys Ser Asp Ala Ser Pro Lys Leu Trp Ile Tyr
            35                  40                  45

Tyr Thr Ser Thr Leu Ala Pro Gly Val Pro Ala Arg Phe Ser Gly Ser
            50                  55                  60

Gly Ser Gly Asn Ser Tyr Ser Leu Thr Ile Ser Ser Met Glu Gly Glu
65                  70                  75                  80
```

Asp Ala Ala Thr Tyr Tyr Cys Gln Gln Phe Thr Ile Ser Pro Ser Met
             85                  90                  95

Tyr Thr Phe Gly Gly Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Ser Tyr
            20                  25                  30

Val Ala Trp Tyr Gln Gln Lys Ala Gly Gln Ser Pro Lys Pro Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Glu Phe Thr Leu Thr Ile Ser Asn Val Gln Ser
65                  70                  75                  80

Glu Asp Leu Ala Glu Tyr Phe Cys Gln Gln Tyr Asn Ile Ser Pro Tyr
                85                  90                  95

Thr Phe Gly Gly Gly Thr Lys Leu Glu Ile Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Val Tyr Trp Tyr Gln Gln Lys Ser His Glu Ser Pro Arg Leu Leu Ile
        35                  40                  45

Ile Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Asn Phe Pro Tyr
                85                  90                  95

Thr Phe Gly Gly Gly Thr Lys Leu Glu Ile Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 125

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Ala Ala Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Asn Pro Leu
                85                  90                  95

Thr Phe Gly Ala Gly Thr Lys Leu Glu Ile Lys
            100                 105
```

```
<210> SEQ ID NO 126
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Asn Tyr Tyr Cys Gln Gln Ser Asn
                85                  90                  95

Glu Asp Tyr Thr Phe Gly Gly Gly Thr Lys Leu Glu Ile Lys
            100                 105                 110
```

```
<210> SEQ ID NO 127
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Glu Ser Tyr
            20                  25                  30

Gly Asn Arg Tyr Met Thr Trp Tyr Gln Gln Lys Pro Gly Gln Pro Pro
        35                  40                  45

Lys Leu Leu Ile Tyr Arg Ala Ala Asn Leu Gln Ser Gly Ile Pro Ala
    50                  55                  60
```

```
Arg Phe Ser Gly Ser Gly Ser Arg Thr Asp Phe Thr Leu Thr Ile Asp
 65                  70                  75                  80

Pro Val Glu Ala Asp Asp Val Ala Thr Tyr Tyr Cys Gln Gln Ser Asn
                 85                  90                  95

Glu Asp Pro Trp Thr Phe Gly Gly Gly Thr Lys Val Glu Ile Lys
            100                 105                 110
```

<210> SEQ ID NO 128
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Glu Val Gln Leu Val Glu Ser Gly Gly Gly Leu Val Gln Pro Gly Gly
  1               5                  10                  15

Ser Leu Arg Leu Ser Cys Ala Ala Ser Asp Phe Ser Leu Thr Thr Tyr
             20                  25                  30

Gly Val His Trp Val Arg Gln Ala Pro Gly Lys Gly Leu Glu Trp Leu
         35                  40                  45

Gly Val Ile Trp Ser Gly Gly Ser Thr Asp Tyr Asn Ala Ala Phe Ile
     50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Tyr Gly Ser Thr Tyr Val Asp Ala Ile Asp Tyr Trp Gly Gln
            100                 105                 110

Gly Thr Leu Val Thr Val Ser Ser
            115                 120
```

<210> SEQ ID NO 129
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Glu Val Gln Leu Val Glu Ser Gly Gly Gly Leu Val Gln Pro Gly Gly
  1               5                  10                  15

Ser Leu Arg Leu Ser Cys Ala Ala Ser Asp Phe Ser Leu Thr Thr Tyr
             20                  25                  30

Gly Val His Trp Val Arg Gln Ala Pro Gly Lys Gly Leu Glu Trp Leu
         35                  40                  45

Gly Val Ile Trp Ser Gly Gly Ser Thr Asp Tyr Asn Ala Ala Phe Ile
     50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Tyr Gly Ser Thr Tyr Val Asp Ala Ile Asp Tyr Trp Gly Gln
            100                 105                 110

Gly Thr Leu Val Thr Val Ser Ser Ala Ser Thr Lys Gly Pro Ser Val
            115                 120                 125
```

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Ser Tyr
            20                  25                  30

Gly Asn Arg Tyr Met Thr Trp Tyr Gln Gln Lys Pro Gly Gln Pro Pro
            35                  40                  45

Lys Leu Leu Ile Tyr Arg Ala Ala Asn Leu Gln Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Trp Thr Phe Gly Gln Gly Thr Lys Val Glu Ile Lys
                100                 105                 110

<210> SEQ ID NO 131
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Glu Ser Val Glu Ser Tyr
                 20                  25                  30

Gly Asn Arg Tyr Met Thr Trp Tyr Gln Gln Lys Pro Gly Gln Pro Pro
            35                  40                  45

Lys Leu Leu Ile Tyr Arg Ala Ala Asn Leu Gln Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Trp Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 132
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Asn
            20                  25                  30

Tyr Ile Ser Trp Val Arg Gln Ala Pro Gly Lys Gly Leu Glu Trp Val
        35                  40                  45

Gly Glu Ile Asp Pro Tyr Asp Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Gly Thr Asp Val Met Asp Tyr Trp Gly Gln Gly Thr Leu Val
            100                 105                 110

Thr Val Ser Ser
        115

<210> SEQ ID NO 133
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Asn
            20                  25                  30

Tyr Ile Ser Trp Val Arg Gln Ala Pro Gly Lys Gly Leu Glu Trp Val
        35                  40                  45

Gly Glu Ile Asp Pro Tyr Asp Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Gly Thr Asp Val Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
```

```
                225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Gly Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Trp Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
                100                 105

<210> SEQ ID NO 135
<211> LENGTH: 214
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Asn Tyr Ile Ser
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Ile Asp Pro Tyr Asp Gly Asp Thr Tyr Tyr Ala Asp Ser Val Lys
1               5                   10                  15

Gly

<210> SEQ ID NO 138

```
<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Thr Asp Val Met Asp Tyr
1               5

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Ala Ser Gln Asp Val Ser Thr Ala Val Ala
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Ala Ser Phe Leu Tyr Ser
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Gln Ser Tyr Thr Thr Pro Pro Thr
1               5

<210> SEQ ID NO 142
<211> LENGTH: 34
<212> TYPE: PRT
<213> ORGANISM: Unknown
<220> FEATURE:
<223> OTHER INFORMATION: Description of Unknown: beta-Klotho
      peptide

<400> SEQUENCE: 142

Ser Ser Pro Thr Arg Leu Ala Val Ile Pro Trp Gly Val Arg Lys Leu
1               5                   10                  15

Leu Arg Trp Val Arg Arg Asn Tyr Gly Asp Met Asp Ile Tyr Ile Thr
            20                  25                  30

Ala Ser

<210> SEQ ID NO 143
<211> LENGTH: 16
<212> TYPE: PRT
<213> ORGANISM: Unknown
<220> FEATURE:
```

```
<223> OTHER INFORMATION: Description of Unknown: Fibroblast Growth
      Factor Receptor 1 peptide

<400> SEQUENCE: 143

Lys Leu His Ala Val Pro Ala Ala Lys Thr Val Lys Phe Lys Cys Pro
1               5                   10                  15

<210> SEQ ID NO 144
<211> LENGTH: 14
<212> TYPE: PRT
<213> ORGANISM: Unknown
<220> FEATURE:
<223> OTHER INFORMATION: Description of Unknown: Fibroblast Growth
      Factor Receptor 1 peptide

<400> SEQUENCE: 144

Phe Lys Pro Asp His Arg Ile Gly Gly Tyr Lys Val Arg Tyr
1               5                   10

<210> SEQ ID NO 145
<211> LENGTH: 992
<212> TYPE: PRT
<213> ORGANISM: Homo sapiens

<400> SEQUENCE: 145

Phe Ser Gly Asp Gly Arg Ala Ile Trp Ser Lys Asn Pro Asn Phe Thr
1               5                   10                  15

Pro Val Asn Glu Ser Gln Leu Phe Leu Tyr Asp Thr Phe Pro Lys Asn
                20                  25                  30

Phe Phe Trp Gly Ile Gly Thr Gly Ala Leu Gln Val Glu Gly Ser Trp
            35                  40                  45

Lys Lys Asp Gly Lys Gly Pro Ser Ile Trp Asp His Phe Ile His Thr
    50                  55                  60

His Leu Lys Asn Val Ser Ser Thr Asn Gly Ser Ser Asp Ser Tyr Ile
65                  70                  75                  80

Phe Leu Glu Lys Asp Leu Ser Ala Leu Asp Phe Ile Gly Val Ser Phe
                85                  90                  95

Tyr Gln Phe Ser Ile Ser Trp Pro Arg Leu Phe Pro Asp Gly Ile Val
            100                 105                 110

Thr Val Ala Asn Ala Lys Gly Leu Gln Tyr Tyr Ser Thr Leu Leu Asp
    115                 120                 125

Ala Leu Val Leu Arg Asn Ile Glu Pro Ile Val Thr Leu Tyr His Trp
130                 135                 140

Asp Leu Pro Leu Ala Leu Gln Glu Lys Tyr Gly Gly Trp Lys Asn Asp
145                 150                 155                 160

Thr Ile Ile Asp Ile Phe Asn Asp Tyr Ala Thr Tyr Cys Phe Gln Met
                165                 170                 175

Phe Gly Asp Arg Val Lys Tyr Trp Ile Thr Ile His Asn Pro Tyr Leu
            180                 185                 190

Val Ala Trp His Gly Tyr Gly Thr Gly Met His Ala Pro Gly Glu Lys
    195                 200                 205

Gly Asn Leu Ala Ala Val Tyr Thr Val Gly His Asn Leu Ile Lys Ala
210                 215                 220

His Ser Lys Val Trp His Asn Tyr Asn Thr His Phe Arg Pro His Gln
225                 230                 235                 240

Lys Gly Trp Leu Ser Ile Thr Leu Gly Ser His Trp Ile Glu Pro Asn
                245                 250                 255

Arg Ser Glu Asn Thr Met Asp Ile Phe Lys Cys Gln Gln Ser Met Val
```

```
            260                 265                 270
Ser Val Leu Gly Trp Phe Ala Asn Pro Ile His Gly Asp Gly Asp Tyr
        275                 280                 285

Pro Glu Gly Met Arg Lys Lys Leu Phe Ser Val Leu Pro Ile Phe Ser
290                 295                 300

Glu Ala Glu Lys His Glu Met Arg Gly Thr Ala Asp Phe Phe Ala Phe
305                 310                 315                 320

Ser Phe Gly Pro Asn Asn Phe Lys Pro Leu Asn Thr Met Ala Lys Met
                325                 330                 335

Gly Gln Asn Val Ser Leu Asn Leu Arg Glu Ala Leu Asn Trp Ile Lys
            340                 345                 350

Leu Glu Tyr Asn Asn Pro Arg Ile Leu Ile Ala Glu Asn Gly Trp Phe
        355                 360                 365

Thr Asp Ser Arg Val Lys Thr Glu Asp Thr Thr Ala Ile Tyr Met Met
    370                 375                 380

Lys Asn Phe Leu Ser Gln Val Leu Gln Ala Ile Arg Leu Asp Glu Ile
385                 390                 395                 400

Arg Val Phe Gly Tyr Thr Ala Trp Ser Leu Leu Asp Gly Phe Glu Trp
                405                 410                 415

Gln Asp Ala Tyr Thr Ile Arg Arg Gly Leu Phe Tyr Val Asp Phe Asn
            420                 425                 430

Ser Lys Gln Lys Glu Arg Lys Pro Lys Ser Ser Ala His Tyr Tyr Lys
        435                 440                 445

Gln Ile Ile Arg Glu Asn Gly Phe Ser Leu Lys Glu Ser Thr Pro Asp
    450                 455                 460

Val Gln Gly Gln Phe Pro Cys Asp Phe Ser Trp Gly Val Thr Glu Ser
465                 470                 475                 480

Val Leu Lys Pro Glu Ser Val Ala Ser Ser Pro Gln Phe Ser Asp Pro
                485                 490                 495

His Leu Tyr Val Trp Asn Ala Thr Gly Asn Arg Leu Leu His Arg Val
            500                 505                 510

Glu Gly Val Arg Leu Lys Thr Arg Pro Ala Gln Cys Thr Asp Phe Val
        515                 520                 525

Asn Ile Lys Lys Gln Leu Glu Met Leu Ala Arg Met Lys Val Thr His
    530                 535                 540

Tyr Arg Phe Ala Leu Asp Trp Ala Ser Val Leu Pro Thr Gly Asn Leu
545                 550                 555                 560

Ser Ala Val Asn Arg Gln Ala Leu Arg Tyr Tyr Arg Cys Val Val Ser
                565                 570                 575

Glu Gly Leu Lys Leu Gly Ile Ser Ala Met Val Thr Leu Tyr Tyr Pro
            580                 585                 590

Thr His Ala His Leu Gly Leu Pro Glu Pro Leu Leu His Ala Asp Gly
        595                 600                 605

Trp Leu Asn Pro Ser Thr Ala Glu Ala Phe Gln Ala Tyr Ala Gly Leu
    610                 615                 620

Cys Phe Gln Glu Leu Gly Asp Leu Val Lys Leu Trp Ile Thr Ile Asn
625                 630                 635                 640

Glu Pro Asn Arg Leu Ser Asp Ile Tyr Asn Arg Ser Gly Asn Asp Thr
                645                 650                 655

Tyr Gly Ala Ala His Asn Leu Leu Val Ala His Ala Leu Ala Trp Arg
            660                 665                 670

Leu Tyr Asp Arg Gln Phe Arg Pro Ser Gln Arg Gly Ala Val Ser Leu
        675                 680                 685
```

Ser Leu His Ala Asp Trp Ala Glu Pro Ala Asn Pro Tyr Ala Asp Ser
    690             695                 700

His Trp Arg Ala Ala Glu Arg Phe Leu Gln Phe Glu Ile Ala Trp Phe
705                 710                 715                 720

Ala Glu Pro Leu Phe Lys Thr Gly Asp Tyr Pro Ala Ala Met Arg Glu
                725                 730                 735

Tyr Ile Ala Ser Lys His Arg Arg Gly Leu Ser Ser Ser Ala Leu Pro
            740                 745                 750

Arg Leu Thr Glu Ala Glu Arg Leu Leu Lys Gly Thr Val Asp Phe
        755                 760                 765

Cys Ala Leu Asn His Phe Thr Thr Arg Phe Val Met His Glu Gln Leu
770                 775                 780

Ala Gly Ser Arg Tyr Asp Ser Asp Arg Asp Ile Gln Phe Leu Gln Asp
785                 790                 795                 800

Ile Thr Arg Leu Ser Ser Pro Thr Arg Leu Ala Val Ile Pro Trp Gly
                805                 810                 815

Val Arg Lys Leu Leu Arg Trp Val Arg Arg Asn Tyr Gly Asp Met Asp
            820                 825                 830

Ile Tyr Ile Thr Ala Ser Gly Ile Asp Asp Gln Ala Leu Glu Asp Asp
        835                 840                 845

Arg Leu Arg Lys Tyr Tyr Leu Gly Lys Tyr Leu Gln Glu Val Leu Lys
850                 855                 860

Ala Tyr Leu Ile Asp Lys Val Arg Ile Lys Gly Tyr Tyr Ala Phe Lys
865                 870                 875                 880

Leu Ala Glu Glu Lys Ser Lys Pro Arg Phe Gly Phe Phe Thr Ser Asp
                885                 890                 895

Phe Lys Ala Lys Ser Ser Ile Gln Phe Tyr Asn Lys Val Ile Ser Ser
            900                 905                 910

Arg Gly Phe Pro Phe Glu Asn Ser Ser Arg Cys Ser Gln Thr Gln
        915                 920                 925

Glu Asn Thr Glu Cys Thr Val Cys Leu Phe Leu Val Gln Lys Lys Pro
930                 935                 940

Leu Ile Phe Leu Gly Cys Cys Phe Phe Ser Thr Leu Val Leu Leu Leu
945                 950                 955                 960

Ser Ile Ala Ile Phe Gln Arg Gln Lys Arg Arg Lys Phe Trp Lys Ala
            965                 970                 975

Lys Asn Leu Gln His Ile Pro Leu Lys Lys Gly Lys Arg Val Val Ser
        980                 985                 990

<210> SEQ ID NO 146
<211> LENGTH: 820
<212> TYPE: PRT
<213> ORGANISM: Homo sapiens

<400> SEQUENCE: 146

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg

```
                65                  70                  75                  80
Ile Thr Gly Glu Glu Val Glu Val Gln Asp Ser Val Pro Ala Asp Ser
                    85                  90                  95

Gly Leu Tyr Ala Cys Val Thr Ser Ser Pro Ser Gly Ser Asp Thr Thr
                    100                 105                 110

Tyr Phe Ser Val Asn Val Ser Asp Ala Leu Pro Ser Ser Glu Asp Asp
                    115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                    165                 170                 175

Pro Ser Ser Gly Thr Pro Asn Pro Thr Leu Arg Trp Leu Lys Asn Gly
                    180                 185                 190

Lys Glu Phe Lys Pro Asp His Arg Ile Gly Gly Tyr Lys Val Arg Tyr
                    195                 200                 205

Ala Thr Trp Ser Ile Ile Met Asp Ser Val Val Pro Ser Asp Lys Gly
210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                    245                 250                 255

Ala Gly Leu Pro Ala Asn Lys Thr Val Ala Leu Gly Ser Asn Val Glu
                    260                 265                 270

Phe Met Cys Lys Val Tyr Ser Asp Pro Gln Pro His Ile Gln Trp Leu
                    275                 280                 285

Lys His Ile Glu Val Asn Gly Ser Lys Ile Gly Pro Asp Asn Leu Pro
                    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                    325                 330                 335

Tyr Thr Cys Leu Ala Gly Asn Ser Ile Gly Leu Ser His His Ser Ala
                    340                 345                 350

Trp Leu Thr Val Leu Glu Ala Leu Glu Glu Arg Pro Ala Val Met Thr
                    355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                    405                 410                 415

Lys Ser Ile Pro Leu Arg Arg Gln Val Thr Val Ser Ala Asp Ser Ser
                    420                 425                 430

Ala Ser Met Asn Ser Gly Val Leu Leu Val Arg Pro Ser Arg Leu Ser
                    435                 440                 445

Ser Ser Gly Thr Pro Met Leu Ala Gly Val Ser Glu Tyr Glu Leu Pro
                    450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                    485                 490                 495
```

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
            690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 147
<211> LENGTH: 948
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Tyr Lys Asp Asp Asp Asp Lys Leu Glu Phe Ser Gly Asp Gly Lys
1               5                   10                  15

Ala Ile Trp Asp Lys Lys Gln Tyr Val Ser Pro Val Asn Pro Gly Gln

-continued

```
                20                  25                  30
Leu Phe Leu Tyr Asp Thr Phe Pro Lys Asn Phe Ser Trp Gly Val Gly
             35                  40                  45
Thr Gly Ala Phe Gln Val Glu Gly Ser Trp Lys Ala Asp Gly Arg Gly
         50                  55                  60
Pro Ser Ile Trp Asp Arg Tyr Val Asp Ser His Leu Arg Gly Val Asn
 65                  70                  75                  80
Ser Thr Asp Arg Ser Thr Asp Ser Tyr Val Phe Leu Glu Lys Asp Leu
                 85                  90                  95
Leu Ala Leu Asp Phe Leu Gly Val Ser Phe Tyr Gln Phe Ser Ile Ser
            100                 105                 110
Trp Pro Arg Leu Phe Pro Asn Gly Thr Val Ala Val Asn Ala Lys
         115                 120                 125
Gly Leu Gln Tyr Tyr Arg Ala Leu Leu Asp Ser Leu Val Leu Arg Asn
            130                 135                 140
Ile Glu Pro Ile Val Thr Leu Tyr His Trp Asp Leu Pro Leu Thr Leu
145                 150                 155                 160
Gln Glu Glu Tyr Gly Gly Trp Lys Asn Ala Thr Met Ile Asp Leu Phe
                165                 170                 175
Asn Asp Tyr Ala Thr Tyr Cys Phe Gln Thr Phe Gly Asp Arg Val Lys
            180                 185                 190
Tyr Trp Ile Thr Ile His Asn Pro Tyr Leu Val Ala Trp His Gly Phe
        195                 200                 205
Gly Thr Gly Met His Ala Pro Gly Glu Lys Gly Asn Leu Thr Ala Val
    210                 215                 220
Tyr Thr Val Gly His Asn Leu Ile Lys Ala His Ser Lys Val Trp His
225                 230                 235                 240
Asn Tyr Asp Lys Asn Phe Arg Pro His Gln Lys Gly Trp Leu Ser Ile
                245                 250                 255
Thr Leu Gly Ser His Trp Ile Glu Pro Asn Arg Thr Glu Asn Met Glu
            260                 265                 270
Asp Val Ile Asn Cys Gln His Ser Met Ser Ser Val Leu Gly Trp Phe
        275                 280                 285
Ala Asn Pro Ile His Gly Asp Gly Asp Tyr Pro Glu Phe Met Lys Thr
    290                 295                 300
Ser Ser Val Ile Pro Glu Phe Ser Glu Ala Lys Glu Glu Val Arg
305                 310                 315                 320
Gly Thr Ala Asp Phe Phe Ala Phe Ser Phe Gly Pro Asn Asn Phe Arg
                325                 330                 335
Pro Ser Asn Thr Val Val Lys Met Gly Gln Asn Val Ser Leu Asn Leu
            340                 345                 350
Arg Gln Val Leu Asn Trp Ile Lys Leu Glu Tyr Asp Asn Pro Arg Ile
        355                 360                 365
Leu Ile Ser Glu Asn Gly Trp Phe Thr Asp Ser Tyr Ile Lys Thr Glu
    370                 375                 380
Asp Thr Thr Ala Ile Tyr Met Met Lys Asn Phe Leu Asn Gln Val Leu
385                 390                 395                 400
Gln Ala Ile Lys Phe Asp Glu Ile Gln Val Phe Gly Tyr Thr Ala Trp
                405                 410                 415
Thr Leu Leu Asp Gly Phe Glu Trp Gln Asp Ala Tyr Thr Thr Arg Arg
            420                 425                 430
Gly Leu Phe Tyr Val Asp Phe Asn Ser Glu Gln Lys Glu Arg Lys Pro
        435                 440                 445
```

-continued

Lys Ser Ser Ala His Tyr Tyr Lys Gln Ile Ile Gln Asp Asn Gly Phe
450                     455                     460

Pro Leu Gln Glu Ser Thr Pro Asp Met Lys Gly Gln Phe Pro Cys Asp
465                     470                     475                 480

Phe Ser Trp Gly Val Thr Glu Ser Val Leu Lys Pro Glu Phe Thr Val
                485                     490                     495

Ser Ser Pro Gln Phe Thr Asp Pro His Leu Tyr Val Trp Asn Val Thr
            500                     505                     510

Gly Asn Arg Leu Leu Tyr Arg Val Glu Gly Val Arg Leu Lys Thr Arg
        515                     520                     525

Pro Ser Gln Cys Thr Asp Tyr Val Ser Ile Lys Lys Arg Val Glu Met
    530                     535                     540

Leu Ala Lys Met Lys Val Thr His Tyr Gln Phe Ala Leu Asp Trp Thr
545                     550                     555                 560

Ser Ile Leu Pro Thr Gly Asn Leu Ser Lys Ile Asn Arg Gln Val Leu
                565                     570                     575

Arg Tyr Tyr Arg Cys Val Val Ser Glu Gly Leu Lys Leu Gly Ile Ser
            580                     585                     590

Pro Met Val Thr Leu Tyr His Pro Thr His Ser His Leu Gly Leu Pro
        595                     600                     605

Met Pro Leu Leu Ser Ser Gly Gly Trp Leu Asn Thr Asn Thr Ala Lys
    610                     615                     620

Ala Phe Gln Asp Tyr Ala Gly Leu Cys Phe Lys Glu Leu Gly Asp Leu
625                     630                     635                 640

Val Lys Leu Trp Ile Thr Ile Asn Glu Pro Asn Arg Leu Ser Asp Met
                645                     650                     655

Tyr Asn Arg Thr Ser Asn Asp Thr Tyr Arg Ala Ala His Asn Leu Met
            660                     665                     670

Ile Ala His Ala Gln Val Trp His Leu Tyr Asp Arg Gln Tyr Arg Pro
        675                     680                     685

Val Gln His Gly Ala Val Ser Leu Ser Leu His Ser Asp Trp Ala Glu
    690                     695                     700

Pro Ala Asn Pro Tyr Val Glu Ser His Trp Lys Ala Ala Glu Arg Phe
705                     710                     715                 720

Leu Gln Phe Glu Ile Ala Trp Phe Ala Asp Pro Leu Phe Lys Thr Gly
                725                     730                     735

Asp Tyr Pro Leu Ala Met Lys Glu Tyr Ile Ala Ser Lys Lys Gln Arg
            740                     745                     750

Gly Leu Ser Ser Ser Val Leu Pro Arg Phe Thr Leu Lys Glu Ser Arg
        755                     760                     765

Leu Val Lys Gly Thr Ile Asp Phe Tyr Ala Leu Asn His Phe Thr Thr
    770                     775                     780

Arg Phe Val Ile His Lys Gln Leu Asn Thr Asn Cys Ser Val Ala Asp
785                     790                     795                 800

Arg Asp Val Gln Phe Leu Gln Asp Ile Thr Arg Leu Ser Ser Pro Ser
                805                     810                     815

Arg Leu Ala Val Thr Pro Trp Gly Met Arg Lys Leu Leu Gly Trp Ile
            820                     825                     830

Arg Arg Asn Tyr Arg Asp Met Asp Ile Tyr Val Thr Ala Asn Gly Ile
        835                     840                     845

Asp Asp Leu Ala Leu Glu Asp Asp Gln Ile Arg Lys Tyr Tyr Leu Glu
    850                     855                     860

```
Lys Tyr Val Gln Glu Ala Leu Lys Ala Tyr Leu Ile Asp Lys Val Lys
865                 870                 875                 880

Ile Lys Gly Tyr Tyr Ala Phe Lys Leu Thr Glu Glu Lys Ser Lys Pro
            885                 890                 895

Arg Phe Gly Phe Phe Thr Ser Asp Phe Lys Ala Lys Ser Ser Val Gln
            900                 905                 910

Phe Tyr Ser Lys Leu Ile Ser Ser Ser Gly Phe Ser Ser Glu Asn Arg
            915                 920                 925

Ser Pro Ala Cys Gly Gln Pro Pro Glu Asp Thr Glu Cys Ala Ile Cys
            930                 935                 940

Ser Phe Leu Thr
945
```

<210> SEQ ID NO 148
<211> LENGTH: 949
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Tyr Lys Asp Asp Asp Lys Leu Asp Phe Pro Gly Asp Gly Arg
1               5                   10                  15

Ala Val Trp Ser Gln Asn Pro Asn Leu Ser Pro Val Asn Glu Ser Gln
            20                  25                  30

Leu Phe Leu Tyr Asp Thr Phe Pro Lys Asn Phe Phe Trp Gly Val Gly
            35                  40                  45

Thr Gly Ala Phe Gln Val Glu Gly Ser Trp Lys Lys Asp Gly Lys Gly
50                  55                  60

Leu Ser Val Trp Asp His Phe Ile Ala Thr His Leu Asn Val Ser Ser
65                  70                  75                  80

Arg Asp Gly Ser Ser Asp Ser Tyr Ile Phe Leu Glu Lys Asp Leu Ser
                85                  90                  95

Ala Leu Asp Phe Leu Gly Val Ser Phe Tyr Gln Phe Ser Ile Ser Trp
            100                 105                 110

Pro Arg Leu Phe Pro Asp Gly Thr Val Ala Val Ala Asn Ala Lys Gly
            115                 120                 125

Leu Gln Tyr Tyr Asn Arg Leu Leu Asp Ser Leu Leu Leu Arg Asn Ile
130                 135                 140

Glu Pro Val Val Thr Leu Tyr His Trp Asp Leu Pro Trp Ala Leu Gln
145                 150                 155                 160

Glu Lys Tyr Gly Gly Trp Lys Asn Glu Thr Leu Ile Asp Leu Phe Asn
                165                 170                 175

Asp Tyr Ala Thr Tyr Cys Phe Gln Thr Phe Gly Asp Arg Val Lys Tyr
            180                 185                 190

Trp Ile Thr Ile His Asn Pro Tyr Leu Val Ala Trp His Gly Tyr Gly
            195                 200                 205

Thr Gly Leu His Ala Pro Gly Glu Lys Gly Asn Val Ala Ala Val Tyr
210                 215                 220

Thr Val Gly His Asn Leu Leu Lys Ala His Ser Lys Val Trp His Asn
225                 230                 235                 240

Tyr Asn Arg Asn Phe Arg Pro His Gln Lys Gly Trp Leu Ser Ile Thr
                245                 250                 255

Leu Gly Ser His Trp Ile Glu Pro Asn Arg Ala Glu Ser Ile Val Asp
            260                 265                 270
```

```
Ile Leu Lys Cys Gln Gln Ser Met Val Ser Val Leu Gly Trp Phe Ala
        275                 280                 285

Asn Pro Ile His Gly Asp Gly Asp Tyr Pro Glu Val Met Thr Lys Lys
    290                 295                 300

Leu Leu Ser Val Leu Pro Ala Phe Ser Glu Ala Glu Lys Asn Glu Val
305                 310                 315                 320

Arg Gly Thr Ala Asp Phe Phe Ala Phe Ser Phe Gly Pro Asn Asn Phe
                325                 330                 335

Lys Pro Leu Asn Thr Met Ala Lys Met Gly Gln Asn Val Ser Leu Asn
            340                 345                 350

Leu Arg Gln Val Leu Asn Trp Ile Lys Leu Glu Tyr Gly Asn Pro Arg
        355                 360                 365

Ile Leu Ile Ala Glu Asn Gly Trp Phe Thr Asp Ser Tyr Val Gln Thr
    370                 375                 380

Glu Asp Thr Thr Ala Ile Tyr Met Met Lys Asn Phe Leu Asn Gln Val
385                 390                 395                 400

Leu Gln Ala Ile Arg Leu Asp Gly Val Arg Val Phe Gly Tyr Thr Ala
                405                 410                 415

Trp Ser Leu Leu Asp Gly Phe Glu Trp Gln Asp Ala Tyr Asn Thr Arg
            420                 425                 430

Arg Gly Leu Phe Tyr Val Asp Phe Asn Ser Glu Gln Arg Glu Arg Arg
        435                 440                 445

Pro Lys Ser Ser Ala His Tyr Tyr Lys Gln Val Ile Gly Glu Asn Gly
    450                 455                 460

Phe Thr Leu Arg Glu Ala Thr Pro Asp Leu Gln Gly Gln Phe Pro Cys
465                 470                 475                 480

Asp Phe Ser Trp Gly Val Thr Glu Ser Val Leu Lys Pro Glu Ser Val
                485                 490                 495

Ala Ser Ser Pro Gln Phe Ser Asp Pro His Leu Tyr Val Trp Asn Ala
            500                 505                 510

Thr Gly Asn Arg Met Leu His Arg Val Glu Gly Val Arg Leu Lys Thr
        515                 520                 525

Arg Pro Ala Gln Cys Thr Asp Phe Ile Thr Ile Lys Lys Gln Leu Glu
    530                 535                 540

Met Leu Ala Arg Met Lys Val Thr His Phe Arg Phe Ala Leu Asp Trp
545                 550                 555                 560

Ala Ser Val Leu Pro Thr Gly Asn Leu Ser Glu Val Asn Arg Gln Ala
                565                 570                 575

Leu Arg Tyr Tyr Arg Cys Val Val Thr Glu Gly Leu Lys Leu Asn Ile
            580                 585                 590

Ser Pro Met Val Thr Leu Tyr Tyr Pro Thr His Ala His Leu Gly Leu
        595                 600                 605

Pro Ala Pro Leu Leu His Ser Gly Gly Trp Leu Asp Pro Ser Thr Ala
    610                 615                 620

Lys Ala Phe Arg Asp Tyr Ala Gly Leu Cys Phe Arg Glu Leu Gly Asp
625                 630                 635                 640

Leu Val Lys Leu Trp Ile Thr Ile Asn Glu Pro Asn Arg Leu Ser Asp
                645                 650                 655

Val Tyr Asn Arg Thr Ser Asn Asp Thr Tyr Gln Ala Ala His Asn Leu
            660                 665                 670

Leu Ile Ala His Ala Ile Val Trp His Leu Tyr Asp Arg Gln Tyr Arg
        675                 680                 685
```

```
Pro Ser Gln Arg Gly Ala Leu Ser Leu Ser Leu His Ser Asp Trp Ala
    690                 695                 700
Glu Pro Ala Asn Pro Tyr Val Ala Ser His Trp Gln Ala Ala Glu Arg
705                 710                 715                 720
Phe Leu Gln Phe Glu Ile Ala Trp Phe Ala Glu Pro Leu Phe Lys Thr
                725                 730                 735
Gly Asp Tyr Pro Val Ala Met Arg Glu Tyr Ile Ala Ser Lys Thr Arg
            740                 745                 750
Arg Gly Leu Ser Ser Val Leu Pro Arg Phe Ser Asp Ala Glu Arg
        755                 760                 765
Arg Leu Val Lys Gly Ala Ala Asp Phe Tyr Ala Leu Asn His Phe Thr
770                 775                 780
Thr Arg Phe Val Met His Glu Gln Gln Asn Gly Ser Arg Tyr Asp Ser
785                 790                 795                 800
Asp Arg Asp Val Gln Phe Leu Gln Asp Ile Thr Arg Leu Ala Ser Pro
                805                 810                 815
Ser Arg Leu Ala Val Met Pro Trp Gly Glu Gly Lys Leu Leu Arg Trp
            820                 825                 830
Met Arg Asn Asn Tyr Gly Asp Leu Asp Val Tyr Ile Thr Ala Asn Gly
        835                 840                 845
Ile Asp Asp Gln Ala Leu Gln Asn Asp Gln Leu Arg Gln Tyr Tyr Leu
850                 855                 860
Glu Lys Tyr Val Gln Glu Ala Leu Lys Ala Tyr Leu Ile Asp Lys Ile
865                 870                 875                 880
Lys Ile Lys Gly Tyr Tyr Ala Phe Lys Leu Thr Glu Glu Lys Ser Lys
                885                 890                 895
Pro Arg Phe Gly Phe Phe Thr Ser Asp Phe Lys Ala Lys Ser Ser Ile
            900                 905                 910
Gln Phe Tyr Asn Lys Leu Ile Thr Ser Asn Gly Phe Pro Ser Glu Asn
        915                 920                 925
Gly Gly Pro Arg Cys Asn Gln Thr Gln Gly Asn Pro Glu Cys Thr Val
    930                 935                 940
Cys Leu Leu Leu Leu
945

<210> SEQ ID NO 149
<211> LENGTH: 950
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Tyr Lys Asp Asp Asp Asp Lys Leu Glu Phe Ser Gly Asp Gly Arg
1               5                   10                  15
Ala Val Trp Ser Lys Asn Pro Asn Phe Thr Pro Val Asn Glu Ser Gln
            20                  25                  30
Leu Phe Leu Tyr Asp Thr Phe Pro Lys Asn Phe Phe Trp Gly Val Gly
        35                  40                  45
Thr Gly Ala Leu Gln Val Glu Gly Ser Trp Lys Lys Asp Gly Lys Gly
    50                  55                  60
Pro Ser Ile Trp Asp His Phe Val His Thr His Leu Lys Asn Val Ser
65                  70                  75                  80
Ser Thr Asn Gly Ser Ser Asp Ser Tyr Ile Phe Leu Glu Lys Asp Leu
                85                  90                  95
```

```
Ser Ala Leu Asp Phe Ile Gly Val Ser Phe Tyr Gln Phe Ser Ile Ser
            100                 105                 110

Trp Pro Arg Leu Phe Pro Asp Gly Ile Val Thr Val Ala Asn Ala Lys
            115                 120                 125

Gly Leu Gln Tyr Tyr Asn Thr Leu Leu Asp Ser Leu Val Leu Arg Asn
        130                 135                 140

Ile Glu Pro Ile Val Thr Leu Tyr His Trp Asp Leu Pro Leu Ala Leu
145                 150                 155                 160

Gln Glu Lys Tyr Gly Gly Trp Lys Asn Asp Thr Ile Ile Asp Ile Phe
                165                 170                 175

Asn Asp Tyr Ala Thr Tyr Cys Phe Gln Thr Phe Gly Asp Arg Val Lys
            180                 185                 190

Tyr Trp Ile Thr Ile His Asn Pro Tyr Leu Val Ala Trp His Gly Tyr
        195                 200                 205

Gly Thr Gly Met His Ala Pro Gly Glu Lys Gly Asn Leu Ala Ala Val
        210                 215                 220

Tyr Thr Val Gly His Asn Leu Ile Lys Ala His Ser Lys Val Trp His
225                 230                 235                 240

Asn Tyr Asn Thr His Phe Arg Pro His Gln Lys Gly Trp Leu Ser Ile
                245                 250                 255

Thr Leu Gly Ser His Trp Ile Glu Pro Asn Arg Ser Glu Asn Thr Met
            260                 265                 270

Asp Ile Leu Lys Cys Gln Gln Ser Met Val Ser Val Leu Gly Trp Phe
        275                 280                 285

Ala Ser Pro Ile His Gly Asp Gly Asp Tyr Pro Glu Gly Met Lys Lys
        290                 295                 300

Lys Leu Leu Ser Ile Leu Pro Leu Phe Ser Glu Ala Glu Lys Asn Glu
305                 310                 315                 320

Val Arg Gly Thr Ala Asp Phe Ala Phe Ser Phe Gly Pro Asn Asn
                325                 330                 335

Phe Lys Pro Leu Asn Thr Met Ala Lys Met Gly Gln Asn Val Ser Leu
            340                 345                 350

Asn Leu Arg Glu Ala Leu Asn Trp Ile Lys Leu Glu Tyr Asn Asn Pro
        355                 360                 365

Arg Ile Leu Ile Ala Glu Asn Gly Trp Phe Thr Asp Ser His Val Lys
        370                 375                 380

Thr Glu Asp Thr Thr Ala Ile Tyr Met Met Lys Asn Phe Leu Ser Gln
385                 390                 395                 400

Val Leu Gln Ala Ile Arg Leu Asp Glu Ile Arg Val Phe Gly Tyr Thr
                405                 410                 415

Ala Trp Ser Leu Leu Asp Gly Phe Glu Trp Gln Asp Ala Tyr Thr Ile
            420                 425                 430

Arg Arg Gly Leu Phe Tyr Val Asp Phe Asn Ser Lys Gln Lys Glu Arg
        435                 440                 445

Lys Pro Lys Ser Ser Ala His Tyr Tyr Lys Gln Ile Ile Arg Glu Asn
        450                 455                 460

Gly Phe Ser Leu Lys Glu Ala Thr Pro Asp Val Gln Gly Gln Phe Pro
465                 470                 475                 480

Cys Asp Phe Ser Trp Gly Val Thr Glu Ser Val Leu Lys Pro Glu Ser
                485                 490                 495

Val Ala Ser Ser Pro Gln Phe Ser Asp Pro Tyr Leu Tyr Val Trp Asn
            500                 505                 510
```

-continued

```
Ala Thr Gly Asn Arg Leu Leu His Arg Val Glu Val Arg Leu Lys
            515                 520                 525
Thr Arg Pro Ala Gln Cys Thr Asp Phe Val Asn Ile Lys Lys Gln Leu
530                 535                 540
Glu Met Leu Ala Arg Met Lys Val Thr His Tyr Arg Phe Ala Leu Asp
545                 550                 555                 560
Trp Ala Ser Val Leu Pro Thr Gly Asn Leu Ser Ala Val Asn Arg Gln
                565                 570                 575
Ala Leu Arg Tyr Tyr Arg Cys Val Val Ser Glu Gly Leu Lys Leu Gly
            580                 585                 590
Ile Ser Ala Met Val Thr Leu Tyr Tyr Pro Thr His Ala His Leu Gly
        595                 600                 605
Leu Pro Glu Pro Leu Leu His Ala Gly Gly Trp Leu Asn Pro Ser Thr
610                 615                 620
Val Glu Ala Phe Gln Ala Tyr Ala Gly Leu Cys Phe Gln Glu Leu Gly
625                 630                 635                 640
Asp Leu Val Lys Leu Trp Ile Thr Ile Asn Glu Pro Asn Arg Leu Ser
                645                 650                 655
Asp Ile Tyr Asn Arg Ser Gly Asn Asp Thr Tyr Gly Ala Ala His Asn
            660                 665                 670
Leu Leu Val Ala His Ala Leu Ala Trp Arg Leu Tyr Asp Arg Gln Phe
        675                 680                 685
Arg Pro Ser Gln Arg Gly Ala Val Ser Leu Ser Leu His Ala Asp Trp
690                 695                 700
Ala Glu Pro Ala Asn Pro Tyr Ala Asp Ser His Trp Arg Ala Ala Glu
705                 710                 715                 720
Arg Phe Leu Gln Phe Glu Ile Ala Trp Phe Ala Glu Pro Leu Phe Lys
                725                 730                 735
Thr Gly Asp Tyr Pro Ala Ala Met Arg Glu Tyr Ile Ala Ser Lys His
            740                 745                 750
Arg Arg Gly Leu Ser Ser Ser Ala Leu Pro Arg Leu Thr Glu Ala Glu
        755                 760                 765
Arg Arg Leu Leu Lys Gly Thr Val Asp Phe Cys Ala Leu Asn His Phe
770                 775                 780
Thr Thr Arg Phe Val Met His Glu Gln Leu Ala Gly Ser Arg Tyr Asp
785                 790                 795                 800
Ser Asp Arg Asp Ile Gln Phe Leu Gln Asp Ile Thr Arg Leu Ser Ser
                805                 810                 815
Pro Thr Arg Leu Ala Val Ile Pro Trp Gly Val Arg Lys Leu Leu Arg
            820                 825                 830
Trp Val Arg Arg Asn Tyr Gly Asp Met Asp Ile Tyr Ile Thr Ala Ser
        835                 840                 845
Gly Ile Asp Asp Gln Ala Leu Glu Asp Asp Arg Leu Arg Lys Tyr Tyr
850                 855                 860
Leu Glu Lys Tyr Leu Gln Glu Val Leu Lys Ala Tyr Leu Ile Asp Lys
865                 870                 875                 880
Val Arg Ile Lys Gly Tyr Tyr Ala Phe Lys Leu Ala Glu Glu Lys Ser
                885                 890                 895
Lys Pro Arg Phe Gly Phe Phe Thr Ser Asp Phe Lys Ala Lys Ser Ser
            900                 905                 910
Ile Gln Phe Tyr Asn Lys Met Ile Ser Ser Gly Phe Pro Ser Glu
        915                 920                 925
Asn Ser Ser Ser Arg Cys Ser Gln Thr Gln Lys Asn Thr Glu Cys Thr
```

```
              930                 935                 940
Val Cys Leu Phe Leu Ala
945                 950

<210> SEQ ID NO 150
<211> LENGTH: 950
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Tyr Lys Asp Asp Asp Lys Leu Glu Phe Ser Gly Asp Gly Arg
1               5                   10                  15

Ala Val Trp Ser Lys Asn Pro Asn Phe Thr Pro Val Asn Glu Ser Gln
                20                  25                  30

Leu Phe Leu Tyr Asp Thr Phe Pro Lys Asn Phe Phe Trp Gly Val Gly
            35                  40                  45

Thr Gly Ala Leu Gln Val Glu Gly Ser Trp Lys Lys Asp Gly Lys Gly
        50                  55                  60

Pro Ser Ile Trp Asp His Phe Val His Thr His Leu Lys Asn Val Ser
65                  70                  75                  80

Ser Thr Asn Gly Ser Ser Asp Ser Tyr Ile Phe Leu Glu Lys Asp Leu
                85                  90                  95

Ser Ala Leu Asp Phe Ile Gly Val Ser Phe Tyr Gln Phe Ser Ile Ser
            100                 105                 110

Trp Pro Arg Leu Phe Pro Asp Gly Ile Val Thr Val Ala Asn Ala Lys
        115                 120                 125

Gly Leu Gln Tyr Tyr Asn Ala Leu Leu Asp Ser Leu Val Leu Arg Asn
130                 135                 140

Ile Glu Pro Ile Val Thr Leu Tyr His Trp Asp Leu Pro Leu Ala Leu
145                 150                 155                 160

Gln Glu Lys Tyr Gly Gly Trp Lys Asn Asp Thr Ile Ile Asp Ile Phe
                165                 170                 175

Asn Asp Tyr Ala Thr Tyr Cys Phe Gln Thr Phe Gly Asp Arg Val Lys
            180                 185                 190

Tyr Trp Ile Thr Ile His Asn Pro Tyr Leu Val Ala Trp His Gly Tyr
        195                 200                 205

Gly Thr Gly Met His Ala Pro Gly Glu Lys Gly Asn Leu Ala Ala Val
210                 215                 220

Tyr Thr Val Gly His Asn Leu Ile Lys Ala His Ser Lys Val Trp His
225                 230                 235                 240

Asn Tyr Asn Thr His Phe Arg Pro His Gln Lys Gly Trp Leu Ser Ile
                245                 250                 255

Thr Leu Gly Ser His Trp Ile Glu Pro Asn Arg Ser Glu Asn Thr Met
            260                 265                 270

Asp Ile Leu Lys Cys Gln Gln Ser Met Val Ser Val Leu Gly Trp Phe
        275                 280                 285

Ala Asn Pro Ile His Gly Asp Gly Asp Tyr Pro Glu Gly Met Lys Lys
        290                 295                 300

Lys Leu Leu Ser Ile Leu Pro Leu Phe Ser Glu Ala Glu Lys Asn Glu
305                 310                 315                 320

Val Arg Gly Thr Ala Asp Phe Phe Ala Phe Ser Phe Gly Pro Asn Asn
                325                 330                 335
```

```
Phe Lys Pro Leu Asn Thr Met Ala Lys Met Gly Gln Asn Val Ser Leu
            340                 345                 350

Asn Leu Arg Glu Ala Leu Asn Trp Ile Lys Leu Glu Tyr Asn Asn Pro
            355                 360                 365

Gln Ile Leu Ile Ala Glu Asn Gly Trp Phe Thr Asp Ser His Val Lys
        370                 375                 380

Thr Glu Asp Thr Thr Ala Ile Tyr Met Met Lys Asn Phe Leu Ser Gln
385                 390                 395                 400

Val Leu Gln Ala Ile Arg Leu Asp Glu Ile Arg Val Phe Gly Tyr Thr
                405                 410                 415

Ala Trp Ser Leu Leu Asp Gly Phe Glu Trp Gln Asp Ala Tyr Thr Ile
            420                 425                 430

Arg Arg Gly Leu Phe Tyr Val Asp Phe Asn Ser Lys Gln Lys Glu Arg
            435                 440                 445

Lys Pro Lys Ser Ser Ala His Tyr Tyr Lys Gln Ile Ile Arg Glu Asn
        450                 455                 460

Gly Phe Ser Leu Lys Glu Ala Thr Pro Asp Val Gln Gly Gln Phe Pro
465                 470                 475                 480

Cys Asp Phe Ser Trp Gly Val Thr Glu Ser Val Leu Lys Pro Glu Ser
            485                 490                 495

Val Ala Ser Ser Pro Gln Phe Ser Asp Pro Tyr Leu Tyr Val Trp Asn
            500                 505                 510

Ala Thr Gly Asn Arg Leu Leu His Arg Val Glu Gly Val Arg Leu Lys
            515                 520                 525

Thr Arg Pro Ala Gln Cys Thr Asp Phe Val Asn Ile Lys Lys Gln Leu
530                 535                 540

Glu Met Leu Ala Arg Met Lys Val Thr His Tyr Arg Phe Ala Leu Asp
545                 550                 555                 560

Trp Ala Ser Val Leu Pro Thr Gly Asn Leu Ser Ala Val Asn Arg Gln
            565                 570                 575

Ala Leu Arg Tyr Tyr Arg Cys Val Val Ser Glu Gly Leu Lys Leu Gly
            580                 585                 590

Ile Ser Ala Met Val Thr Leu Tyr Tyr Pro Thr His Ala His Leu Gly
        595                 600                 605

Leu Pro Glu Pro Leu Leu His Ala Gly Gly Trp Leu Asn Pro Ser Thr
610                 615                 620

Val Glu Ala Phe Gln Ala Tyr Ala Gly Leu Cys Phe Gln Glu Leu Gly
625                 630                 635                 640

Asp Leu Val Lys Leu Trp Ile Thr Ile Asn Glu Pro Asn Arg Leu Ser
                645                 650                 655

Asp Ile Tyr Asn Arg Ser Gly Asn Asp Thr Tyr Gly Ala Ala His Asn
            660                 665                 670

Leu Leu Val Ala His Ala Leu Ala Trp Arg Leu Tyr Asp Arg Gln Phe
            675                 680                 685

Arg Pro Ser Gln Arg Gly Ala Val Ser Leu Ser Leu His Ala Asp Trp
        690                 695                 700

Ala Glu Pro Ala Asn Pro Tyr Ala Asp Ser His Trp Arg Ala Ala Glu
705                 710                 715                 720

Arg Phe Leu Gln Phe Glu Ile Ala Trp Phe Ala Glu Pro Leu Phe Lys
                725                 730                 735

Thr Gly Asp Tyr Pro Ala Ala Met Arg Glu Tyr Ile Ala Ser Lys His
            740                 745                 750

Arg Arg Gly Leu Ser Ser Ser Ala Leu Pro Arg Leu Thr Glu Ala Glu
```

```
                755                 760                 765
Arg Arg Leu Leu Lys Gly Thr Val Asp Phe Cys Ala Leu Asn His Phe
770                 775                 780

Thr Thr Arg Phe Val Met His Glu Gln Leu Ala Gly Ser Arg Tyr Asp
785                 790                 795                 800

Ser Asp Arg Asp Ile Gln Phe Leu Gln Asp Ile Thr Arg Leu Ser Ser
                805                 810                 815

Pro Thr Arg Leu Ala Val Ile Pro Trp Gly Val Arg Lys Leu Leu Arg
                820                 825                 830

Trp Val Arg Arg Asn Tyr Gly Asp Met Asp Ile Tyr Ile Thr Ala Ser
                835                 840                 845

Gly Ile Asp Asp Gln Ala Leu Glu Asp Asp Arg Leu Arg Lys Tyr Tyr
                850                 855                 860

Leu Glu Lys Tyr Leu Gln Glu Val Leu Lys Ala Tyr Leu Ile Asp Lys
865                 870                 875                 880

Val Arg Ile Lys Gly Tyr Tyr Ala Phe Lys Leu Ala Glu Glu Lys Ser
                885                 890                 895

Lys Pro Arg Phe Gly Phe Phe Thr Ser Asp Phe Lys Ala Lys Ser Ser
                900                 905                 910

Ile Gln Phe Tyr Asn Lys Met Ile Ser Ser Gly Phe Pro Ser Glu
                915                 920                 925

Asn Ser Ser Arg Cys Ser Gln Thr Gln Lys Asn Thr Glu Cys Thr
930                 935                 940

Val Cys Leu Phe Leu Val
945                 950

<210> SEQ ID NO 151
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
            35                  40                  45

Gln His Gly Lys Gly Ala Ser Ile Trp Asp Thr Phe Thr His His Pro
        50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
        130                 135                 140

Glu Arg Leu Arg Glu Leu Gly Val Gln Pro Val Val Thr Leu Tyr His
145                 150                 155                 160
```

```
Trp Asp Leu Pro Gln Arg Leu Gln Asp Ala Tyr Gly Gly Trp Ala Asn
                165                 170                 175
Arg Ala Leu Ala Asp His Phe Arg Asp Tyr Ala Glu Leu Cys Phe Arg
            180                 185                 190
His Phe Gly Gly Gln Val Lys Tyr Trp Ile Thr Ile Asp Asn Pro Tyr
        195                 200                 205
Val Val Ala Trp His Gly Tyr Ala Thr Gly Arg Leu Ala Pro Gly Ile
    210                 215                 220
Arg Gly Ser Pro Arg Leu Gly Tyr Leu Val Ala His Asn Leu Leu Leu
225                 230                 235                 240
Ala His Ala Lys Val Trp His Leu Tyr Asn Thr Ser Phe Arg Pro Thr
                245                 250                 255
Gln Gly Gly Gln Val Ser Ile Ala Leu Ser Ser His Trp Ile Asn Pro
            260                 265                 270
Arg Arg Met Thr Asp His Ser Ile Lys Glu Cys Gln Lys Ser Leu Asp
        275                 280                 285
Phe Val Leu Gly Trp Phe Ala Lys Pro Val Phe Ile Asp Gly Asp Tyr
    290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                325                 330                 335
Cys Phe Gly Pro Thr Leu Ser Phe Gln Leu Leu Asp Pro His Met Lys
            340                 345                 350
Phe Arg Gln Leu Glu Ser Pro Asn Leu Arg Gln Leu Leu Ser Trp Ile
        355                 360                 365
Asp Leu Glu Phe Asn His Pro Gln Ile Phe Ile Val Glu Asn Gly Trp
    370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                405                 410                 415
Val Asp Val Ile Gly Tyr Thr Ala Trp Ser Leu Met Asp Gly Phe Glu
            420                 425                 430
Trp His Arg Gly Tyr Ser Ile Arg Arg Gly Leu Phe Tyr Val Asp Phe
        435                 440                 445
Leu Ser Gln Asp Lys Met Leu Leu Pro Lys Ser Ser Ala Leu Phe Tyr
    450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                485                 490                 495
Asn Tyr Ile Gln Val Asp Thr Thr Leu Ser Gln Phe Thr Asp Leu Asn
            500                 505                 510
Val Tyr Leu Trp Asp Val His His Ser Lys Arg Leu Ile Lys Val Asp
        515                 520                 525
Gly Val Val Thr Lys Lys Arg Lys Ser Tyr Cys Val Asp Phe Ala Ala
    530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                565                 570                 575
Gln Val Asn His Thr Ile Leu Gln Tyr Tyr Arg Cys Met Ala Ser Glu
```

```
                580             585             590
Leu Val Arg Val Asn Ile Thr Pro Val Val Ala Leu Trp Gln Pro Met
            595                 600             605

Ala Pro Asn Gln Gly Leu Pro Arg Leu Leu Ala Arg Gln Gly Ala Trp
610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
                660                 665                 670

Ala His Ala Leu Ala Trp His Val Tyr Asn Glu Lys Phe Arg His Ala
                675                 680                 685

Gln Asn Gly Lys Ile Ser Ile Ala Leu Gln Ala Asp Trp Ile Glu Pro
                690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
                740                 745                 750

Leu Pro Tyr Phe Thr Glu Asp Glu Lys Lys Leu Ile Gln Gly Thr Phe
                755                 760                 765

Asp Phe Leu Ala Leu Ser His Tyr Thr Thr Ile Leu Val Asp Ser Glu
                770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
                820                 825                 830

Leu Pro Met Tyr Ile Ile Ser Asn Gly Ile Asp Asp Gly Leu His Ala
                835                 840                 845

Glu Asp Asp Gln Leu Arg Val Tyr Tyr Met Gln Asn Tyr Ile Asn Glu
                850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
                900                 905                 910

Lys Ile Ile Asp Ser Asn Gly Phe Pro Gly Pro Glu Thr Leu Glu Arg
                915                 920                 925

Phe Cys Pro Glu Glu Phe Thr Val Cys Thr Glu Cys Ser Phe His
                930                 935                 940

Thr Arg Lys Ser Leu Leu Ala Phe Ile Ala Phe Leu Phe Ala Ser
945                 950                 955                 960

Ile Ile Ser Leu Ser Leu Ile Phe Tyr Tyr Ser Lys Lys Gly Arg Arg
                965                 970                 975

Ser Tyr Lys Leu Glu Asp Tyr Lys Asp Asp Asp Lys
                980                 985

<210> SEQ ID NO 152
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Thr Tyr Ile Ser
1               5

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Ile Asp Pro Tyr Asp Gly Ala Thr Asp Tyr Ala Asp Ser Val Lys
1               5                   10                  15

Gly

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Glu His Phe Asp Ala Trp Val His Tyr Tyr Val Met Asp Tyr
1               5                   10

<210> SEQ ID NO 155
<211> LENGTH: 455
<212> TYPE: PRT
<213> ORGANISM: Homo sapiens

<400> SEQUENCE: 155

Phe Pro Cys Asp Phe Ser Trp Gly Val Thr Glu Ser Val Leu Lys Pro
1               5                   10                  15

Glu Ser Val Ala Ser Ser Pro Gln Phe Ser Asp Pro His Leu Tyr Val
                20                  25                  30

Trp Asn Ala Thr Gly Asn Arg Leu Leu His Arg Val Glu Gly Val Arg
            35                  40                  45

Leu Lys Thr Arg Pro Ala Gln Cys Thr Asp Phe Val Asn Ile Lys Lys
    50                  55                  60

Gln Leu Glu Met Leu Ala Arg Met Lys Val Thr His Tyr Arg Phe Ala
65                  70                  75                  80

Leu Asp Trp Ala Ser Val Leu Pro Thr Gly Asn Leu Ser Ala Val Asn
                85                  90                  95

Arg Gln Ala Leu Arg Tyr Tyr Arg Cys Val Val Ser Glu Gly Leu Lys
                100                 105                 110

Leu Gly Ile Ser Ala Met Val Thr Leu Tyr Tyr Pro Thr His Ala His
            115                 120                 125

Leu Gly Leu Pro Glu Pro Leu Leu His Ala Asp Gly Trp Leu Asn Pro
    130                 135                 140

Ser Thr Ala Glu Ala Phe Gln Ala Tyr Ala Gly Leu Cys Phe Gln Glu
145                 150                 155                 160
```

Leu Gly Asp Leu Val Lys Leu Trp Ile Thr Ile Asn Glu Pro Asn Arg
            165                 170                 175

Leu Ser Asp Ile Tyr Asn Arg Ser Gly Asn Asp Thr Tyr Gly Ala Ala
            180                 185                 190

His Asn Leu Leu Val Ala His Ala Leu Ala Trp Arg Leu Tyr Asp Arg
            195                 200                 205

Gln Phe Arg Pro Ser Gln Arg Gly Ala Val Ser Leu Ser Leu His Ala
            210                 215                 220

Asp Trp Ala Glu Pro Ala Asn Pro Tyr Ala Asp Ser His Trp Arg Ala
225                 230                 235                 240

Ala Glu Arg Phe Leu Gln Phe Glu Ile Ala Trp Phe Ala Glu Pro Leu
                245                 250                 255

Phe Lys Thr Gly Asp Tyr Pro Ala Ala Met Arg Glu Tyr Ile Ala Ser
                260                 265                 270

Lys His Arg Arg Gly Leu Ser Ser Ala Leu Pro Arg Leu Thr Glu
            275                 280                 285

Ala Glu Arg Arg Leu Leu Lys Gly Thr Val Asp Phe Cys Ala Leu Asn
        290                 295                 300

His Phe Thr Thr Arg Phe Val Met His Glu Gln Leu Ala Gly Ser Arg
305                 310                 315                 320

Tyr Asp Ser Asp Arg Asp Ile Gln Phe Leu Gln Asp Ile Thr Arg Leu
                325                 330                 335

Ser Ser Pro Thr Arg Leu Ala Val Ile Pro Trp Gly Val Arg Lys Leu
                340                 345                 350

Leu Arg Trp Val Arg Arg Asn Tyr Gly Asp Met Asp Ile Tyr Ile Thr
            355                 360                 365

Ala Ser Gly Ile Asp Asp Gln Ala Leu Glu Asp Arg Leu Arg Lys
        370                 375                 380

Tyr Tyr Leu Gly Lys Tyr Leu Gln Glu Val Leu Lys Ala Tyr Leu Ile
385                 390                 395                 400

Asp Lys Val Arg Ile Lys Gly Tyr Tyr Ala Phe Lys Leu Ala Glu Glu
                405                 410                 415

Lys Ser Lys Pro Arg Phe Gly Phe Phe Thr Ser Asp Phe Lys Ala Lys
                420                 425                 430

Ser Ser Ile Gln Phe Tyr Asn Lys Val Ile Ser Ser Arg Gly Phe Pro
            435                 440                 445

Phe Glu Asn Ser Ser Ser Arg
    450                 455

<210> SEQ ID NO 156
<211> LENGTH: 36
<212> TYPE: DNA
<213> ORGANISM: Mus sp.

<400> SEQUENCE: 156
gttaccggct tctccggaga cgggaaagca atatgg                                    36

<210> SEQ ID NO 157
<211> LENGTH: 52
<212> TYPE: PRT
<213> ORGANISM: Homo sapiens

<400> SEQUENCE: 157

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                    20                  25                  30

Gly Gly Leu Gln Arg Ser Val Ile Leu Ser Ala Leu Ile Leu Leu Arg
                35                  40                  45

Ala Val Thr Gly
    50

<210> SEQ ID NO 158
<211> LENGTH: 938
<212> TYPE: PRT
<213> ORGANISM: Mus sp.

<400> SEQUENCE: 158

Phe Ser Gly Asp Gly Lys Ala Ile Trp Asp Lys Lys Gln Tyr Val Ser
1               5                   10                  15

Pro Val Asn Pro Ser Gln Leu Phe Leu Tyr Asp Thr Phe Pro Lys Asn
                20                  25                  30

Phe Ser Trp Gly Val Gly Thr Gly Ala Phe Gln Val Glu Gly Ser Trp
            35                  40                  45

Lys Thr Asp Gly Arg Gly Pro Ser Ile Trp Asp Arg Tyr Val Tyr Ser
    50                  55                  60

His Leu Arg Gly Val Asn Gly Thr Asp Arg Ser Thr Asp Ser Tyr Ile
65                  70                  75                  80

Phe Leu Glu Lys Asp Leu Leu Ala Leu Asp Phe Leu Gly Val Ser Phe
                85                  90                  95

Tyr Gln Phe Ser Ile Ser Trp Pro Arg Leu Phe Pro Asn Gly Thr Val
            100                 105                 110

Ala Ala Val Asn Ala Gln Gly Leu Arg Tyr Tyr Arg Ala Leu Leu Asp
        115                 120                 125

Ser Leu Val Leu Arg Asn Ile Glu Pro Ile Val Thr Leu Tyr His Trp
130                 135                 140

Asp Leu Pro Leu Thr Leu Gln Glu Glu Tyr Gly Gly Trp Lys Asn Ala
145                 150                 155                 160

Thr Met Ile Asp Leu Phe Asn Asp Tyr Ala Thr Tyr Cys Phe Gln Thr
                165                 170                 175

Phe Gly Asp Arg Val Lys Tyr Trp Ile Thr Ile His Asn Pro Tyr Leu
            180                 185                 190

Val Ala Trp His Gly Phe Gly Thr Gly Met His Ala Pro Gly Glu Lys
        195                 200                 205

Gly Asn Leu Thr Ala Val Tyr Thr Val Gly His Asn Leu Ile Lys Ala
210                 215                 220

His Ser Lys Val Trp His Asn Tyr Asp Lys Asn Phe Arg Pro His Gln
225                 230                 235                 240

Lys Gly Trp Leu Ser Ile Thr Leu Gly Ser His Trp Ile Glu Pro Asn
                245                 250                 255

Arg Thr Asp Asn Met Glu Asp Val Ile Asn Cys Gln His Ser Met Ser
            260                 265                 270

Ser Val Leu Gly Trp Phe Ala Asn Pro Ile His Gly Asp Gly Asp Tyr
        275                 280                 285

Pro Glu Phe Met Lys Thr Gly Ala Met Ile Pro Glu Phe Ser Glu Ala
    290                 295                 300

Glu Lys Glu Glu Val Arg Gly Thr Ala Asp Phe Phe Ala Phe Ser Phe
305                 310                 315                 320

Gly Pro Asn Asn Phe Arg Pro Ser Asn Thr Val Val Lys Met Gly Gln
                325                 330                 335

```
Asn Val Ser Leu Asn Leu Arg Gln Val Leu Asn Trp Ile Lys Leu Glu
            340                 345                 350

Tyr Asp Asp Pro Gln Ile Leu Ile Ser Glu Asn Gly Trp Phe Thr Asp
            355                 360                 365

Ser Tyr Ile Lys Thr Glu Asp Thr Thr Ala Ile Tyr Met Met Lys Asn
    370                 375                 380

Phe Leu Asn Gln Val Leu Gln Ala Ile Lys Phe Asp Glu Ile Arg Val
385                 390                 395                 400

Phe Gly Tyr Thr Ala Trp Thr Leu Leu Asp Gly Phe Glu Trp Gln Asp
                405                 410                 415

Ala Tyr Thr Thr Arg Arg Gly Leu Phe Tyr Val Asp Phe Asn Ser Glu
            420                 425                 430

Gln Lys Glu Arg Lys Pro Lys Ser Ser Ala His Tyr Tyr Lys Gln Ile
            435                 440                 445

Ile Gln Asp Asn Gly Phe Pro Leu Lys Glu Ser Thr Pro Asp Met Lys
        450                 455                 460

Gly Arg Phe Pro Cys Asp Phe Ser Trp Gly Val Thr Glu Ser Val Leu
465                 470                 475                 480

Lys Pro Glu Phe Thr Val Ser Ser Pro Gln Phe Thr Asp Pro His Leu
                485                 490                 495

Tyr Val Trp Asn Val Thr Gly Asn Arg Leu Leu Tyr Arg Val Glu Gly
            500                 505                 510

Val Arg Leu Lys Thr Arg Pro Ser Gln Cys Thr Asp Tyr Val Ser Ile
            515                 520                 525

Lys Lys Arg Val Glu Met Leu Ala Lys Met Lys Val Thr His Tyr Gln
    530                 535                 540

Phe Ala Leu Asp Trp Thr Ser Ile Leu Pro Thr Gly Asn Leu Ser Lys
545                 550                 555                 560

Val Asn Arg Gln Val Leu Arg Tyr Tyr Arg Cys Val Val Ser Glu Gly
                565                 570                 575

Leu Lys Leu Gly Val Phe Pro Met Val Thr Leu Tyr His Pro Thr His
            580                 585                 590

Ser His Leu Gly Leu Pro Leu Pro Leu Leu Ser Ser Gly Gly Trp Leu
            595                 600                 605

Asn Met Asn Thr Ala Lys Ala Phe Gln Asp Tyr Ala Glu Leu Cys Phe
        610                 615                 620

Arg Glu Leu Gly Asp Leu Val Lys Leu Trp Ile Thr Ile Asn Glu Pro
625                 630                 635                 640

Asn Arg Leu Ser Asp Met Tyr Asn Arg Thr Ser Asn Asp Thr Tyr Arg
                645                 650                 655

Ala Ala His Asn Leu Met Ile Ala His Ala Gln Val Trp His Leu Tyr
            660                 665                 670

Asp Arg Gln Tyr Arg Pro Val Gln His Gly Ala Val Ser Leu Ser Leu
            675                 680                 685

His Cys Asp Trp Ala Glu Pro Ala Asn Pro Phe Val Asp Ser His Trp
        690                 695                 700

Lys Ala Ala Glu Arg Phe Leu Gln Phe Glu Ile Ala Trp Phe Ala Asp
705                 710                 715                 720

Pro Leu Phe Lys Thr Gly Asp Tyr Pro Ser Val Met Lys Glu Tyr Ile
                725                 730                 735

Ala Ser Lys Asn Gln Arg Gly Leu Ser Ser Ser Val Leu Pro Arg Phe
            740                 745                 750
```

```
Thr Ala Lys Glu Ser Arg Leu Val Lys Gly Thr Val Asp Phe Tyr Ala
        755                 760                 765
Leu Asn His Phe Thr Thr Arg Phe Val Ile His Lys Gln Leu Asn Thr
    770                 775                 780
Asn Arg Ser Val Ala Asp Arg Asp Val Gln Phe Leu Gln Asp Ile Thr
785                 790                 795                 800
Arg Leu Ser Ser Pro Ser Arg Leu Ala Val Thr Pro Trp Gly Val Arg
                805                 810                 815
Lys Leu Leu Ala Trp Ile Arg Arg Asn Tyr Arg Asp Arg Asp Ile Tyr
            820                 825                 830
Ile Thr Ala Asn Gly Ile Asp Asp Leu Ala Leu Glu Asp Asp Gln Ile
        835                 840                 845
Arg Lys Tyr Tyr Leu Glu Lys Tyr Val Gln Glu Ala Leu Lys Ala Tyr
    850                 855                 860
Leu Ile Asp Lys Val Lys Ile Lys Gly Tyr Tyr Ala Phe Lys Leu Thr
865                 870                 875                 880
Glu Glu Lys Ser Lys Pro Arg Phe Gly Phe Phe Thr Ser Asp Phe Arg
                885                 890                 895
Ala Lys Ser Ser Val Gln Phe Tyr Ser Lys Leu Ile Ser Ser Ser Gly
            900                 905                 910
Leu Pro Ala Glu Asn Arg Ser Pro Ala Cys Gly Gln Pro Ala Glu Asp
        915                 920                 925
Thr Asp Cys Thr Ile Cys Ser Phe Leu Val
    930                 935

<210> SEQ ID NO 159
<211> LENGTH: 53
<212> TYPE: PRT
<213> ORGANISM: Homo sapiens

<400> SEQUENCE: 159

Met Glu Lys Lys Leu His Ala Val Pro Ala Ala Lys Thr Val Lys Phe
1               5                   10                  15
Lys Cys Pro Ser Ser Gly Thr Pro Asn Pro Thr Leu Arg Trp Leu Lys
            20                  25                  30
Asn Gly Lys Glu Phe Lys Pro Asp His Arg Ile Gly Gly Tyr Lys Val
        35                  40                  45
Arg Tyr Ala Thr Trp
    50

<210> SEQ ID NO 160
<211> LENGTH: 34
<212> TYPE: PRT
<213> ORGANISM: Homo sapiens

<400> SEQUENCE: 160

Ser Ser Pro Thr Arg Leu Ala Val Ile Pro Trp Gly Val Arg Lys Leu
1               5                   10                  15
Leu Arg Trp Val Arg Arg Asn Tyr Gly Asp Met Asp Ile Tyr Ile Thr
            20                  25                  30
Ala Ser

<210> SEQ ID NO 161
<211> LENGTH: 34
<212> TYPE: PRT
<213> ORGANISM: Macaca fascicularis

<400> SEQUENCE: 161
```

```
Ser Ser Pro Thr Arg Leu Ala Val Ile Pro Trp Gly Val Arg Lys Leu
1               5                   10                  15

Leu Arg Trp Val Arg Arg Asn Tyr Gly Asp Met Asp Ile Tyr Ile Thr
            20                  25                  30

Ala Ser

<210> SEQ ID NO 162
<211> LENGTH: 34
<212> TYPE: PRT
<213> ORGANISM: Rattus sp.

<400> SEQUENCE: 162

Ser Ser Pro Ser Arg Leu Ala Val Thr Pro Trp Gly Met Arg Lys Leu
1               5                   10                  15

Leu Gly Trp Ile Arg Arg Asn Tyr Arg Asp Met Asp Ile Tyr Val Thr
            20                  25                  30

Ala Asn

<210> SEQ ID NO 163
<211> LENGTH: 34
<212> TYPE: PRT
<213> ORGANISM: Mus sp.

<400> SEQUENCE: 163

Ser Ser Pro Ser Arg Leu Ala Val Thr Pro Trp Gly Val Arg Lys Leu
1               5                   10                  15

Leu Ala Trp Ile Arg Arg Asn Tyr Arg Asp Arg Asp Tyr Ile Thr
            20                  25                  30

Ala Asn

<210> SEQ ID NO 164
<211> LENGTH: 34
<212> TYPE: PRT
<213> ORGANISM: Unknown
<220> FEATURE:
<223> OTHER INFORMATION: Description of Unknown: Rabbit
      polypeptide

<400> SEQUENCE: 164

Ala Ser Pro Ser Arg Leu Ala Val Met Pro Trp Gly Glu Gly Lys Leu
1               5                   10                  15

Leu Arg Trp Met Arg Asn Asn Tyr Gly Asp Leu Asp Val Tyr Ile Thr
            20                  25                  30

Ala Asn

<210> SEQ ID NO 165
<211> LENGTH: 17
<212> TYPE: PRT
<213> ORGANISM: Mus sp.

<400> SEQUENCE: 165

Phe Ser Gly Asp Gly Lys Ala Ile Trp Asp Lys Lys Gln Tyr Val Ser
1               5                   10                  15

Pro

<210> SEQ ID NO 166
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 166

Phe Ser Glu Thr Gly Lys Gln Tyr Gly Ile Lys Asn Ser Thr
1               5                   10